United States Patent [19]

Fenn

[11] Patent Number: 5,441,532
[45] Date of Patent: Aug. 15, 1995

[54] ADAPTIVE FOCUSING AND NULLING HYPERTHERMIA ANNULAR AND MONOPOLE PHASED ARRAY APPLICATORS

[75] Inventor: Alan J. Fenn, Wayland, Mass.

[73] Assignee: Massachusetts Institute of Technology, Cambridge, Mass.

[21] Appl. No.: 846,808

[22] Filed: Mar. 4, 1992

Related U.S. Application Data

[63] Continuation-in-part of Ser. No. 722,612, Jun. 26, 1991, Pat. No. 5,251,645.

[51] Int. Cl.⁶ ............................................... A61N 5/00
[52] U.S. Cl. .................................... 607/101; 607/156; 128/653.1
[58] Field of Search ................................ 607/100–102, 607/154, 156; 128/653.1

[56] References Cited

U.S. PATENT DOCUMENTS

| | | | |
|---|---|---|---|
| 3,095,880 | 7/1963 | Haagensen . | |
| 3,800,802 | 4/1974 | Berry et al. | 128/422 |
| 3,895,639 | 7/1975 | Rodler | 128/422 |
| 4,140,130 | 2/1979 | Storm, III | 128/404 |
| 4,186,729 | 2/1980 | Harrison | 128/1.3 |
| 4,271,848 | 6/1981 | Turner et al. | 128/804 |
| 4,397,313 | 8/1983 | Vaguine | 128/399 |
| 4,397,314 | 8/1983 | Vaguine | 128/399 |
| 4,403,618 | 9/1983 | Turner et al. | 128/804 |
| 4,434,341 | 2/1984 | Busby | 219/10.55 |
| 4,448,198 | 5/1984 | Turner | 128/422 |
| 4,462,412 | 7/1984 | Turner | 128/804 |
| 4,586,516 | 5/1986 | Turner | 128/804 |
| 4,589,423 | 5/1986 | Turner | 128/804 |
| 4,632,127 | 12/1986 | Sterzer | 128/804 |
| 4,638,813 | 1/1987 | Turner | 128/804 |
| 4,669,475 | 6/1987 | Turner | 128/399 |
| 4,672,980 | 6/1987 | Turner | 128/804 |
| 4,702,262 | 10/1987 | Andersen et al. | 128/804 |
| 4,719,919 | 1/1988 | Marchosky et al. | 128/401 |
| 4,798,215 | 1/1989 | Turner | 128/804 |
| 4,860,752 | 8/1989 | Turner | 128/422 |
| 4,869,247 | 9/1989 | Howard, III et al. | 128/303.1 |
| 4,934,365 | 6/1990 | Morgenthaler | 128/399 |
| 4,951,688 | 8/1990 | Keren | 128/804 |
| 4,974,587 | 12/1990 | Turner et al. | 128/399 |
| 4,989,601 | 2/1991 | Marchosky et al. | 128/399 |
| 5,101,836 | 4/1992 | Lee | 128/804 |
| 5,251,645 | 10/1993 | Fenn | 607/154 |

FOREIGN PATENT DOCUMENTS

| | | | |
|---|---|---|---|
| 0167670A1 | 12/1984 | European Pat. Off. . | |
| 0256524 | 8/1987 | European Pat. Off. . | |
| 3431314 | 3/1986 | Germany | 607/154 |
| 3831016A1 | 3/1990 | Germany . | |
| 624409 | 9/1943 | United Kingdom . | |
| WO80/01461 | 7/1980 | WIPO . | |

OTHER PUBLICATIONS

Zhang, Y., et al., "Heating Patterns Generated by Phase Modulation of a Hexagonal Array of Interstitial Anten-
(List continued on next page.)

Primary Examiner—Lee S. Cohen
Attorney, Agent, or Firm—Palmer & Dodge

[57] ABSTRACT

An R.F. hyperthermia phased array applicator uses adaptive nulling and focusing with non-invasive electric field probes to control the electric field intensity at selected positions in and around a target body to provide improved heating of solid tumors during hyperthermia treatment. A gradient search or matrix inversion algorithm is used to control the amplitude and phase weighting for the phased array transmit elements of the hyperthermia applicator. A 915 MHz monopole phased array hyperthermia applicator for heating brain tumors has an enclosed vessel including a plurality of monopole transmit antenna elements disposed as a circular arc array on a ground plane which has an aperture for positioning the tumor in proximity to the monopole antenna elements. Adaptive focusing with non-invasive electric field probes is used to maximize the electric field at the tumor site. Parallel plate microwave waveguides are used to direct R.F. energy from the monopole phased array to the tumor site. A microwave transmit and receive module generates amplitude and phase controlled transmit signals for exciting the monopole antenna elements, and receives passive microwave signals from the monopole antenna elements for taking non-invasive radiomerry temperature measurements of the tumor site.

56 Claims, 61 Drawing Sheets

OTHER PUBLICATIONS nas", *IEEE Transactions on Biomedical Engineering*, 38(1): 92–97, (1991).

Boag, A., et al., "Optimal Excitation of Multiapplicator Systems for Deep Regional Hyperthermia", *IEEE Transactions on Biomedical Engineering*, 37(10): 987–995, (1990).

Sathiaseelan, V., "Potential for patient-specific optimization of deep heating patterns through manipulation of amplitude and phase", *Strahlenther Onkol*, 165(10): 743–745, (1989).

Loane, Joseph T. III, "Gain Optimization of a Near-Field Focusing Array for Hyperthermia Applications", *IEEE Transactions on Microwave Theory and Techniques*, 37(10): 1629–1635, (1989).

Roemer, R. B., et al., "Feedback Control and Optimization of Hyperthermia Heating Patterns: Present Status and Future Needs", *IEEE Eighth Annual Conference of the Engineering in Medicine and Biology Society*, 1496–1499, (1986).

Babbs, C. F., et al., "A Predictive-Adaptive, Multipoint Feedback Controller for Local Heat Therapy of Solid Tumors", *IEEE Transactions on Microwave Theory and Techniques*, MTT–34(5): 604–611, (1986).

Knudsen, Morten, et al., "Optimal Temperature Control With Phased Array Hyperthermia System", *IEEE Transactions on Microwave Theory and Techniques*, MTT–34(5): 597–603, (1986).

Morita, Nagayoshi, et al., "An Optimal Excitation Method in Multi-Applicator Systems for Forming a Hot Zone Inside the Human Body", *IEEE Transactions on Microwave Theory and Techniques*, MTT–34(5): 532–538, (1986).

De Wagter, Carlos, "Optimization of Simulated Two-Dimensional Temperature Distributions Induced by Multiple Electromagnetic Applicators", *IEEE Transactions on Microwave Theory and Techniques*, MTT34(5): 589–596, (1986).

Sathiaseelan, V., et al., "Theoretical Analysis and Clinical Demonstration of the Effect of Power Pattern Control Using the Annular Phased-Array Hyperthermia System", *IEEE Transactions on Microwave Theory and Techniques*, MTT34(5): 514–519, (1986).

Paglione et al., "Instrumentation for Invasive and Non-Invasive Microwave Hyperthermia of Brain Tumors," *IEEE MTT-S Digest*, 767–769, (1986).

Marchosky et al., "Hyperthermia Treatment of Brain Tumors," *Missouri Medicine*, 29–33, (1983).

Kachmar, "Brain Tumors Succumb to New Microwave Probes," *Microwaves & RF*, 30–46, (1983).

Marchosky et al., "Hyperthermia Catheter Implantation and Therapy in the Brain," *J. Neurosurg*, vol. 72, 975–979, (1990).

"Cook VH8500 Hyperthermia Catheters," Cook Incorporated, (1990).

"Cook VH8500 Hyperthermia System," Cook Incorporated, (1990).

Alan J. Fenn, "Theoretical and Experimental Study of Monopole Phased Array Antennas," *IEEE Transactions on Antennas and Propagation*, 33(10), 1118–1126, (1985).

Jorge G. Pereira et al., "Optimal Microwave Source Distribution for Heating Off-Center Tumors in Biological Spheres," *Annual International Conference of the IEEE Engineering in Medicine and Biology Society*, 13(2), 978–979, (1991).

Aumann et al., "Intermediate Frequency Transmit/-Receive Modules for Low-Sidelobe Phased Array Application," *IEEE National Radar Conference*, 33–37, (1988).

Johnson et al. An Experimental Adaptive Nulling Receiver Utilizing the Sample Matrix Inversion Algorithm with Channel Equalization (1991) IEEE, vol. 39, No. 5, pp. 798–808.

Ebinni et al. Multiple-Focus Ultrasound Phased-Array Pattern Synthesis; Optimal Driving-Signal Distributions for Hyperthermia (1989) IEEE, vol. 36, No. 5, pp. 540–548.

Wong, et al. Computationally Efficient Algorithms for Control of Ultrasound Phased-Array Hyperthermia Applicators Based on a Pseudoinverse Method (1990) IEEE, vol. 37, No. 3, pp. 274–277.

Ebinni et al. Acoustic Feedback for Hyperthermia Phased-Array Applicators: Aberration Correction, Motion Compensation and Multiple Focusing in the in the Presence of Tissue Inhomogeneities (1991) IEEE, vol. 2, pp. 1343–1346.

Ebinni et al. Experimental Evaluation of a Prototype Cylindrical Section Ultrasound Hyperthermia Phased-Array Applicator (1991) IEEE, vol. 38, No. 5, pp. 510–520.

PCT International Search Report for PCT/US92/05464 (the PCT application corresponding to the present U.S. application).

Von Hippel et al, "Dielectric Analysis of Biomaterials" NTIS, Oct. 1973, 27 pp.

$R = \dfrac{1}{k\Delta\ell}$ [°C / W], k = THERMAL CONDUCTIVITY $C = \rho C_p (\Delta\ell)^3$ [J/°C], $\rho$ = DENSITY, $C_p$ = SPECIFIC HEAT $P = \text{SAR}\, \rho\, (\Delta\ell)^3$ [W], SAR $= \dfrac{\sigma}{2\rho}|E|^2$ (Specific Absorption Rate)

$\sigma$ = ELECTRICAL CONDUCTIVITY $|E|$ = MAGNITUDE OF ELECTRIC FIELD

| PARAMETER | PHANTOM MUSCLE TISSUE | DISTILLED WATER |
|---|---|---|
| DIELECTRIC CONSTANT @ 100 MHz | 73.5 | 80.0 |
| ELECTRICAL CONDUCTIVITY @ 100 MHz | 0.5 S/m | 0.0001 S/m |
| DENSITY | 970.0 kg/m$^3$ | 1000.0 kg/m$^3$ |
| SPECIFIC HEAT | 3516.0 J/kg °C | 4200.0 J/kg °C |
| THERMAL CONDUCTIVITY | 0.544 W/m °C | 0.6019 W/m °C |

Table 1

Fig. 16(b)

EXPERIMENTAL CONFIGURATION

| POSITION | COMMENT | PROBE |
|----------|------------|--------|
| 1 | TUMOR SITE | EP-500 |
| 2 | NULL SITE | EP-100 |
| 3 | REF. SITE | EP-400 |

| POSITION | COMMENT | PROBE |
|---|---|---|
| 1 | TUMOR SITE | EP-500 |
| 2 | NULL SITE | EP-100 |
| 3 | REF. SITE | EP-400 |

EXPERIMENTAL CONFIGURATION

| POSITION | COMMENT | PROBE |
|---|---|---|
| 1 | TUMOR SITE | EP-500 |
| 2 | NULL SITE | EP-100 |
| 3 | NULL SITE | EP-100 |

ADAPTIVE FOCUSING AND NULLING HYPERTHERMIA ANNULAR AND MONOPOLE PHASED ARRAY APPLICATORS

GOVERNMENT SUPPORT

The invention described herein was supported in whole or in part by Contract No. F19628-90-C-0002 from the United States Air Force.

RELATED APPLICATIONS

This application is a continuation-in-part of U.S. Ser. No. 07/722,612 filed on Jun. 26, 1991, now U.S. Pat. No. 5,251,645.

COPYRIGHT

Appendices A–D of the disclosure of this patent document contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The successful treatment of deep-seated malignant tumors within a patient is often a difficult task. The objective of the treatment is to reduce in size or completely remove the tumor mass by one or more modalities available at the treatment facility. Common treatment modalities are surgery, chemotherapy, and x-ray therapy. One treatment modality used alone or in conjunction with one of the above modalities is "tissue heating", or hyperthermia. Hyperthermia can be considered as a form of high fever localized within the body. A controlled thermal dose distribution is required for hyperthermia to have a therapeutic value. Typical localized-hyperthermia temperatures required for therapeutic treatment of cancer are in the 43°–45° C. range. Normal tissue should be kept at temperatures below 43° C. during the treatment. Typically, hyperthermia is induced in the body by radio-frequency (RF) waves, acoustic (ultrasound) waves, or a combination of both. One of the most difficult aspects of implementing hyperthermia, with either RF or ultrasound waves, is producing sufficient heating at depth. Multiple-applicator RF hyperthermia arrays are commonly used to provide a focused near-field main beam at the tumor position. Ideally, a focal region should be concentrated at the tumor site with minimal energy delivered to surrounding normal tissue.

In RF hyperthermia systems, the hyperthermia antenna beamwidth is proportional to the RF wavelength in the body. A small focal region suggests that the RF wavelength be as small as possible. However, due to propagation losses in tissue, the RF depth of penetration decreases with increasing transmit frequency. One of the major side-effects in heating a deep-seated tumor with a hyperthermia antenna is the formation of undesired "hot spots" in surrounding tissue. This additional undesired heating often produces pain, burns, and blistering in the patient, which requires terminating the treatment immediately. The patient does not receive anesthetics during the hyperthermia treatment in order to provide direct verbal feedback of any pain. Thus, techniques for reducing hot spots while maximizing energy delivered to the tumor site are desired in hyperthermia treatment.

RF hyperthermia systems with electric field transmitting arrays, i.e., antenna arrays, in the frequency band of 60–2000 Mhz have been used to localize heating of malignant tumors within a target body. Phase control alone of the transmitting antennas of such an array has been used to synthesize therapeutic RF radiation patterns within a target body. Theoretical studies of adaptive control of individual antenna phase and power (transmit weights) has been used to maximize the tumor temperature (or RF power delivered to the tumor) while minimizing the surrounding tissue temperature (or RF power delivered to the surrounding tissue). Invasive temperature measuring techniques have been used to optimize the radiation pattern within a target body.

One commercially available hyperthermia annular phased-array antenna system is the Model BSD-2000, SIGMA-60 applicator, available from BSD Medical Corporation, Salt Lake City, Utah. This phased-array system fully surrounds the patient, placing the patient at the center of an annular array of dipole transmit antennas. By fully surrounding the patient with an annular phased-array, it is possible to obtain constructive interference (or signal enhancement) deep within the target volume. This hyperthermia system uses a 60 cm array diameter with eight uniformly spaced dipole elements operating over the frequency band 60–120 MHz. The eight dipoles are fed as four active pairs of elements. There are four high-power amplifiers which drive the dipole pairs with up to 500 W average power per channel. Each of the four active channels has an electronically controlled variable-phase shifter for focusing the array. Temperature and electric-field probe sensors (both invasive and non-invasive) are used to monitor the treatment. A cool-water (5°–40° C.) bolus between the patient and the phased-array is used to prevent excess heating of the skin surface. The water bolus is filled with circulating distilled water, which has a very low propagation loss.

SUMMARY OF THE INVENTION

In accordance with the invention, adaptive nulling and/or focusing with non-invasive auxiliary probes is used to reduce or enhance the field intensity at selected positions in and around the target body while maintaining a desired focus at a tumor thereby avoiding or reducing the occurrences of "hot spots" while enhancing heating of the tumor during ultrasonic or R.F. hyperthermia treatment.

In general, in one aspect, the invention features a hyperthermia applicator having electric field radiators each coupled to a source of electric radiation through a controllable transmit weighting network to control the phase and amplitude of the electric field radiation transmitted by each radiator. The transmit weighting networks respond to feedback signals from a controller coupled to electric field probes which receive the electric field radiation from the radiators. The controller adjusts the feedback signals in response to the received electric field radiation so that the electric field radiation is minimized at the electric field probes.

Preferred embodiments include a phased array of electric field radiators, and an annular array of electric field radiators for surrounding the target. The electric field probes include probes placed non-invasively around the perimeter of the target where the electric field energy is to be minimized. In one embodiment, the target is modeled as an ellipse and the electric field probes are placed at the front, back, and on both sides of the ellipse.

In another aspect, the invention also features a secondary electric field probe, and the controller adjusts the feedback signals in response to the electric field radiation received by the secondary electric field probe so that the electric field radiation is maximized at the secondary probe. Embodiments include placing the secondary probe at the desired focus of the electric field radiation.

In yet another aspect, the invention features the controller performing either a matrix inversion algorithm or a gradient search algorithm to adjust the feedback signals controlling the transmit weighting networks in response to the electric field energy received by the electric field probes.

In general, in another aspect, the invention features a hyperthermia applicator for heating a target inside a body, having electric field radiators each coupled to a source of electric radiation through a controllable transmit weighting network to control the phase and amplitude of the electric field radiation transmitted by each radiator. The transmit weighting networks respond to feedback signals from a controller coupled to electric field probes placed outside the body which receive the electric field radiation from the radiators. The controller adjusts the feedback signals in response to the electric field radiation received outside the body so that the electric field radiation is controlled at the target inside the body.

Preferred embodiments include a phased-array of electric field radiators, an annular array of electric field radiators for surrounding the target, and an array of monopole antenna elements for positioning nearby the target.

In preferred embodiments of the monopole array, the monopole antenna elements are perpendicularly mounted to one side of an RF reflecting groundplane. An RF reflecting screen is mounted perpendicular to the groundplane surface behind the monopole antenna elements to reflect RF energy from the monopole antenna elements toward the target. The ground plane includes an aperture for positioning the target on the same side of the ground plane as the monopole antenna elements. An enclosure surrounds the monopole antenna elements and provides a vessel for enclosing a bolus of fluid, such as deionized water, between the monopole antenna elements and the body. In other preferred embodiments another ground plane is provided above the monopole antenna elements to form a waveguide between the antenna elements and the target body. Further, multiple waveguides and monopole antenna arrays can be stacked.

In other preferred embodiments of the monopole array, the monopole array antenna elements resonate between 800 and 1000 MHz and are arranged in a circular arc having a radius of between 5 and 20 cm. The body is a cranium and the target is a brain tumor. The radius of the monopole array circular arc is either the distance from the monopole antenna array to the center of the cranium, or to the target tumor.

In still other preferred embodiments, the electric field probes are non-invasively placed along the perimeter of the body between the elements of the phased-array and the target. The controller adjusts the feedback signal, with a gradient search or matrix inversion algorithm, to minimize the difference in the electric field detected by adjacent electric field probes and thereby provide uniform electric field radiation into the body.

In yet other preferred embodiments, the electric field probes are formed into an array non-invasively placed between the phased array and the target. The controller adjusts the feedback signal, with a gradient search or matrix inversion algorithm, to provide a particular electric field pattern across the electric field probe array and thereby focus radiation into the target. The electric field probe array elements are placed symmetrically with respect to a bisector line which runs from the target to the phased array to bisect the phased array. The controller adjusts the feedback signal to balance the electric field pattern with respect to the bisector line, and to minimize the difference in the electric field detected along the bisector line.

Thus, the present invention offers the advantages of allowing effective hyperthermia treatment to be applied to deep-seated tumors within the body while reducing or eliminating hot-spot formation on the surface of the body which interferes with the treatment. Another advantage is that hot spots are eliminated quickly by sensing and adjusting the E-field radiation in the vicinity of the expected hot spot rather than by measuring the temperature rise of the tissue after heating has already occurred. Still another advantage is that the E-field sensing probes may be located on the surface of the target rather than having to be invasively placed within the target body. A further advantage is that the E-field radiation can be focused on a target inside a body using E-field sensing probes non-invasively placed outside the body to maximize heating of the target tissue.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout different views. The drawings are not necessarily to scale, emphasis instead being placed upon illustrating the principles of the invention.

FIG. 16(b) is a table of values used in the simulation model of FIG. 16(a).

DETAILED DESCRIPTION OF THE PREFERRED EMBODIMENT

Apparatus

Figure 1:
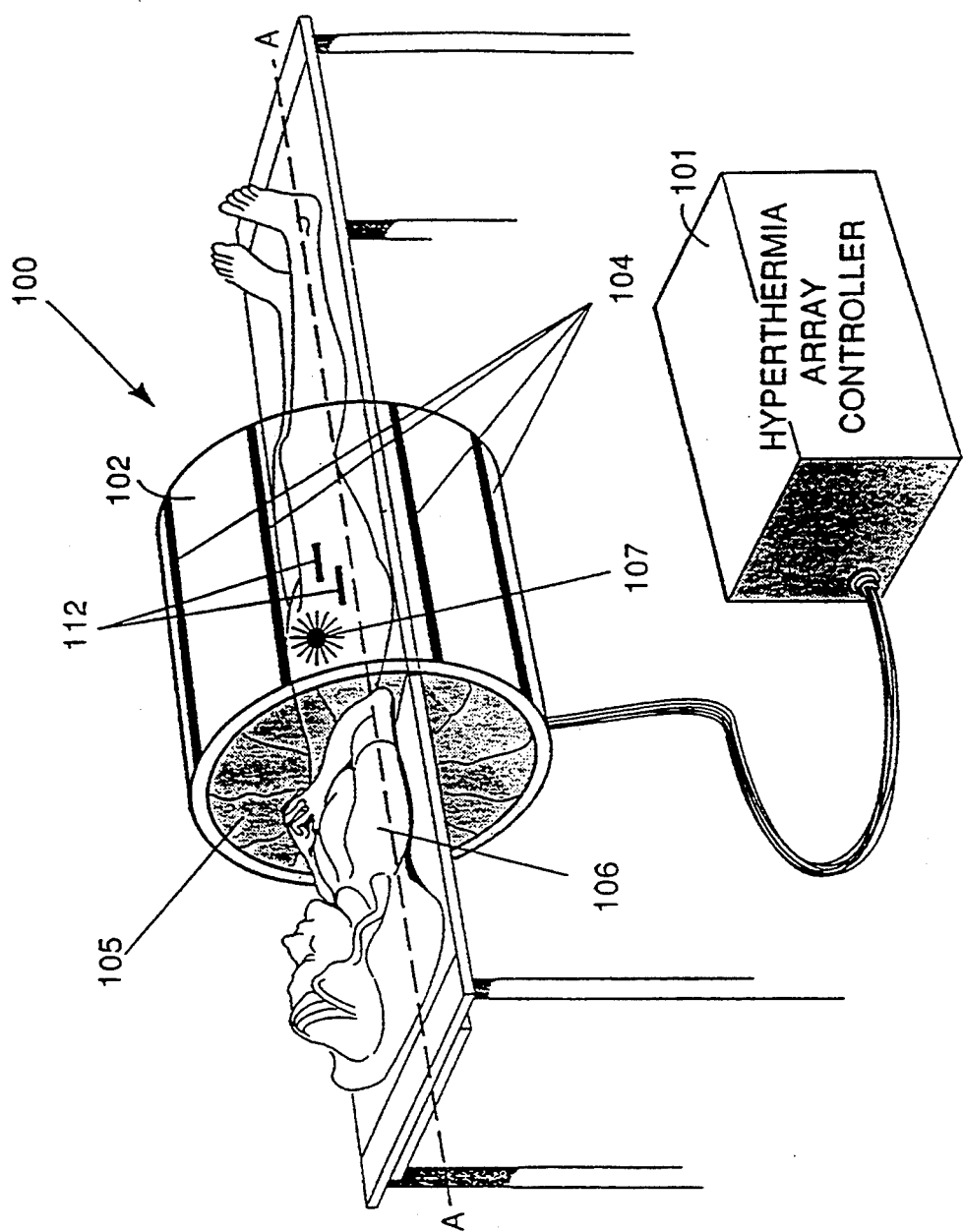
FIG. 1 is a perspective view of an RF annular array hyperthermia system featuring the adaptive nulling of this invention.

Referring to FIG. 1, there is shown a hyperthermia annular phased-array system 100 having improved "hot spot" characteristics achieved by utilizing the focused near-field adaptive nulling apparatus of this invention. An annular hyperthermia phased-array applicator 102, energized by a hyperthermia array controller 101, has a plurality of dipole transmit antenna elements 104 placed around a patient to be treated, or target body 106. The dipole antenna elements are uniformly disposed around the patient. Each dipole antenna element is oriented parallel to the other dipole antennas and parallel to a longitudinal axis A—A passing through the center of a cylinder defined by applicator 102. The patient is positioned within the hyperthermia phased array applicator 102 such that the deep-seated tumor to be treated 107 is at the approximate center, or focus, of the phased array applicator. A water-bolus 105 is provided between the patient and the phased array applicator to control the temperature of the patient's skin. Phased-array applicator 102 therapeutically illuminates the target body 106 with electric field (E-field) energy radiated by dipole antenna elements 104 focused on tumor 107 deep within the body.

An example of a deep-seated tumor is cancer of the prostate. The tumor volume often has a decreased blood flow which aids in heating the tumor, compared to normal tissue for which heat is carried away by normal blood flow. In practice, undesired high-temperature regions away from the focus can also occur on the skin and inside the volume of the target body. For example, scar tissue, which has a decreased blood flow rate, will tend to heat up more rapidly than normal tissue having normal blood flow.

In the adaptive hyperthermia array of this invention, electric-field nulls are used to reduce the power delivered to potential hot spots. Computer simulations, described herein, establish that non-invasive field probes, or sensors, 112 placed on the surface of the target can be used to eliminate hot spots interior to the target tissue. With the adaptive hyperthermia phased-array described herein, RF energy nulls are adaptively formed to reduce the electric field energy delivered to these potential hot spots. As will be shown, the energy nulls achieved by the adaptive nulling apparatus of this invention are both invasive to the target, i.e., extend into the target body, and non-invasive to the target, i.e., on the surface of the target.

Figure 2:
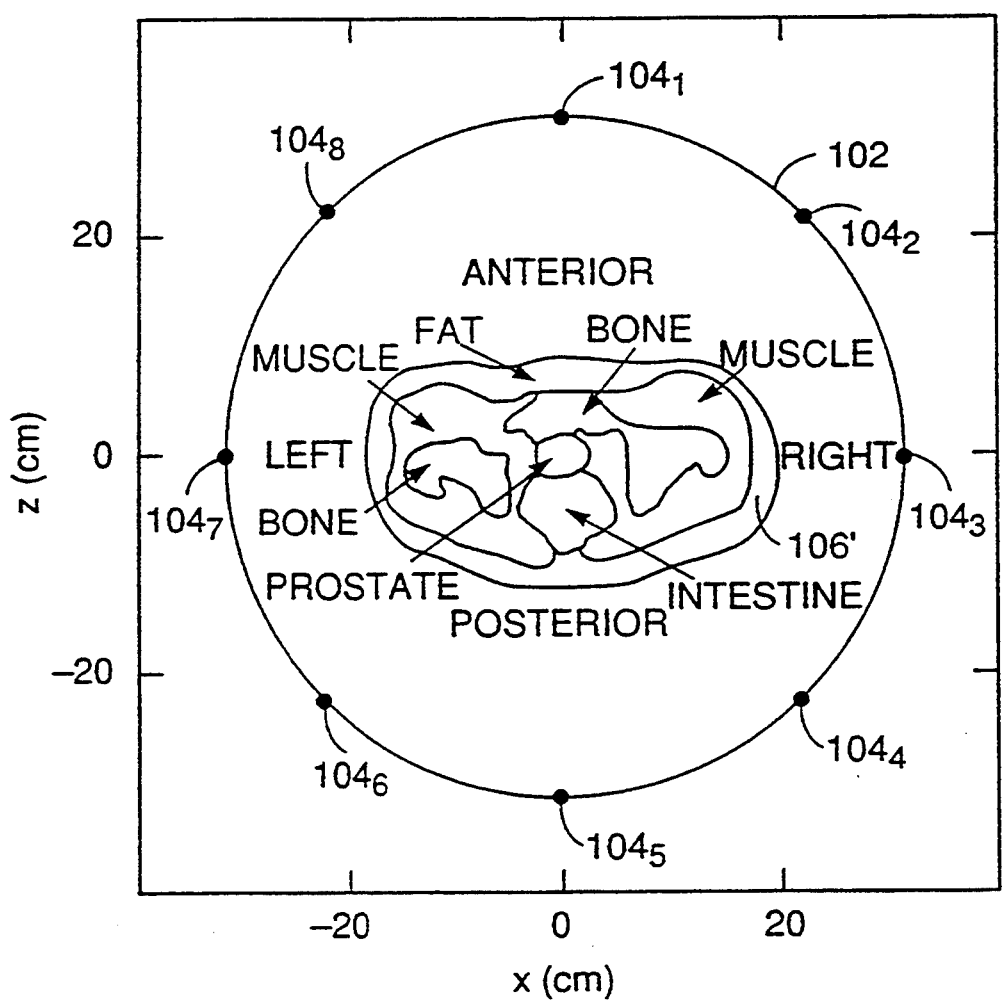
FIG. 2 is a cross-sectional representation of the annular array of FIG. 1.

Referring to FIG. 2, there is shown a schematic cross-sectional representation of an embodiment of an eight-element hyperthermia phased-array applicator 102 of FIG. 1. Phased-array applicator 102 has transmit antennas $104_1$ through $104_8$, arranged symmetrically surrounding a human body target $106'$ at the prostate level.

Figure 3:
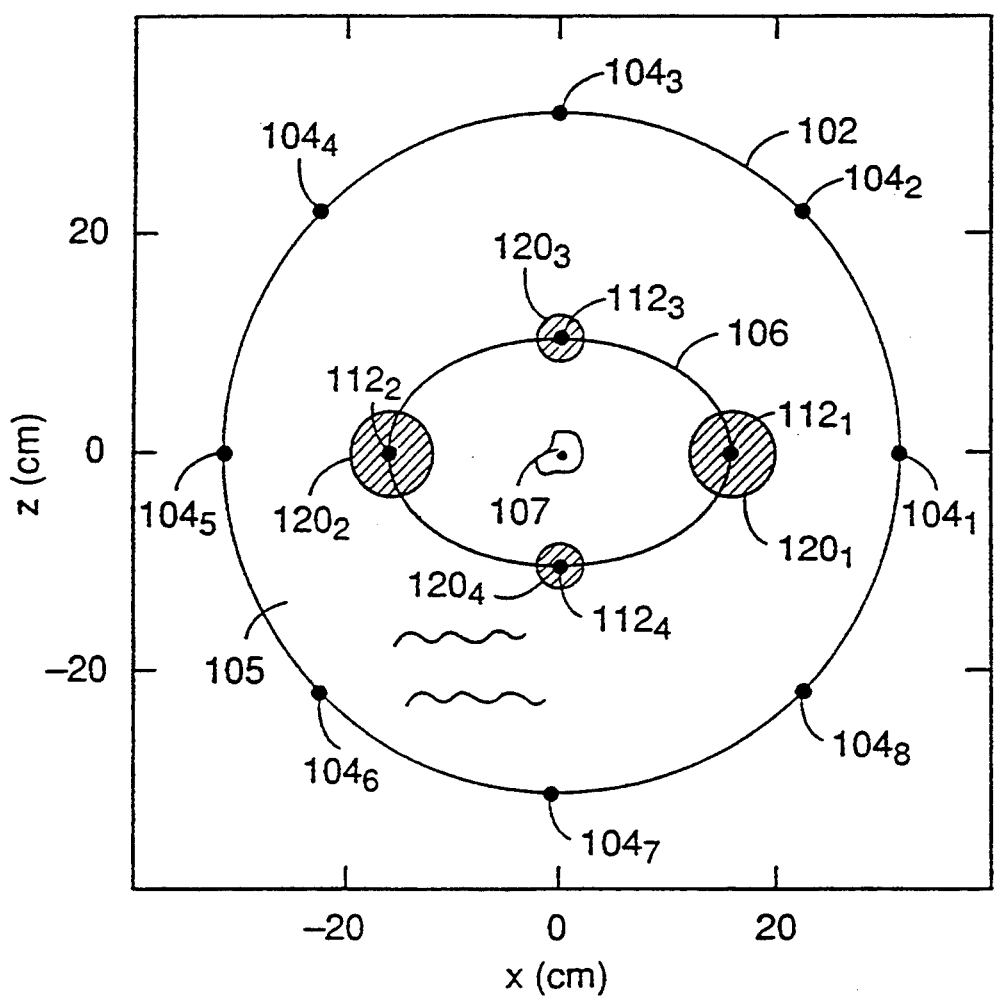
FIG. 3 is an analytical model of the cross-sectional representation of FIG. 2.

An analytical model of the embodiment of FIG. 2 is shown in FIG. 3. Here, an elliptical phantom target 106 is used to model the prostate-level cross section of the human body $106'$. The center 107 of the elliptical phantom models the location of the prostate tumor to receive hyperthermia treatment, i.e., the focus of RF energy for the phased array applicator 102. Water bolus 105 is assumed to surround the target body 106, and is treated as a homogeneous medium for analysis purposes.

Four auxiliary RF E-field probes, or sensors, $112_1$ through $112_4$, i.e., receiving antennas, are placed around the perimeter of the target to model non-invasive probes placed on the skin of the human body target. Each auxiliary probe $112_1$ through $112_4$ has a corresponding null zone $120_1$ through $120_4$, respectively, centered at each auxiliary probe and extending into the elliptical target region 106. Each null zone indicates an area in which undesired "hot spots" are reduced or eliminated. The width of each null zone is directly related to the strength of each null. The strength of each null (sometimes referred to as the amount of cancellation) is directly related to the signal-to-noise ratio at the probe position ($SNR_P$). A low $SNR_P$ indicates a large amount of nulling (strong null), and a high $SNR_P$ indicates a small amount of nulling (weak null). The resolution, or minimum spacing, between the focus 107 and any null position is normally equal to the half-power beamwidth of the transmit antenna. Resolution may be enhanced somewhat by using weak nulls whenever the separation between the null and focus is closer than the half-power beamwidth.

Figure 4:
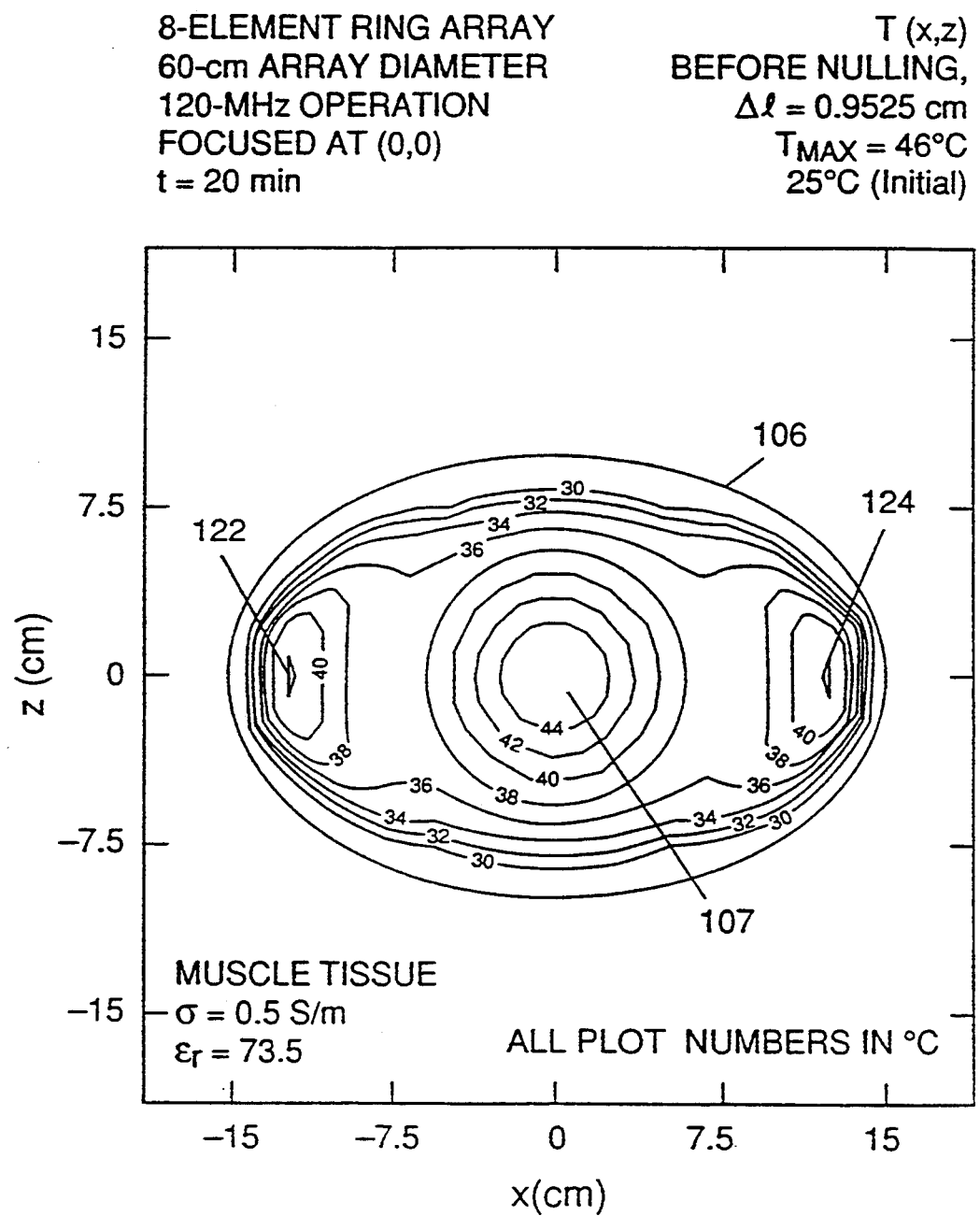
FIG. 4 is a simulated thermal profile of the analytical model of FIG. 3 without the adaptive nulling of this invention.

Referring to FIG. 4, there is shown the results of a simulation of the thermal distribution inside the target body 106 for the hyperthermia ring array applicator 102 of the analytical model of FIG. 3, without adaptive nulling, transmitting into the target body. For simulation purposes, target body 106 is assumed to be a homogeneous elliptical region, and the RF energy from the array is focused at the center of the ellipse 107, simulating the tumor site. No adaptive nulling is used. The contour lines of the thermal distribution represent isotherms having the indicated temperature in degrees Celsius (°C.), and are spaced at 2° C. intervals. The simulation shows that the focus is expected to have a temperature of approximately 46° C., while two undesired "hot spots" 122 and 124 to the left and right of the focus, respectively, are expected to have temperatures of approximately 42° C.

Figure 5:
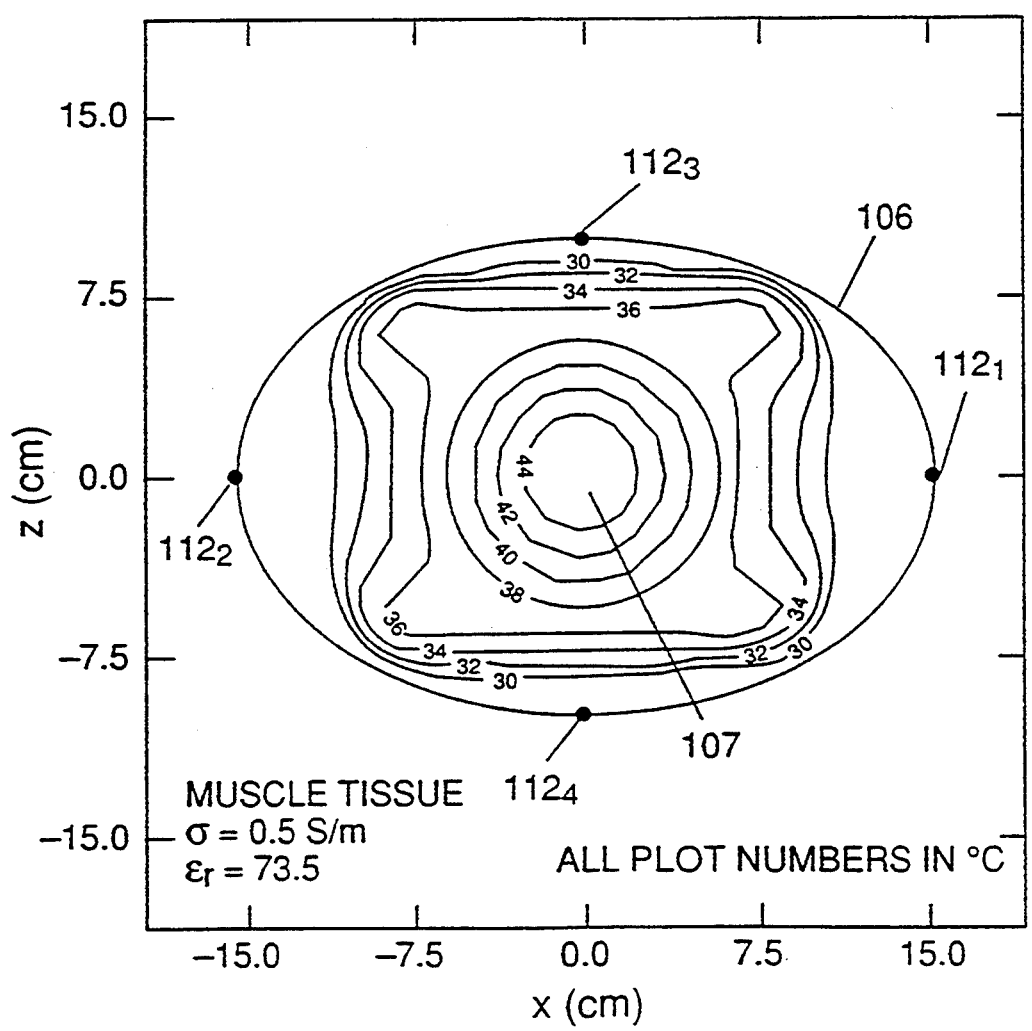
FIG. 5 is a simulated thermal profile of the analytical model of FIG. 3 with the adaptive nulling of this invention.

FIG. 5 shows a simulated thermal distribution for the model of FIG. 3 where the adaptive nulling methods of this invention are applied. Comparison of FIG. 5 with FIG. 4 show that the "hot spots" 122 and 124 are essentially eliminated, no new "hot spots" have been produced within the target body, and the peak temperature induced at the focus is still approximately 46° C.

Figure 6:
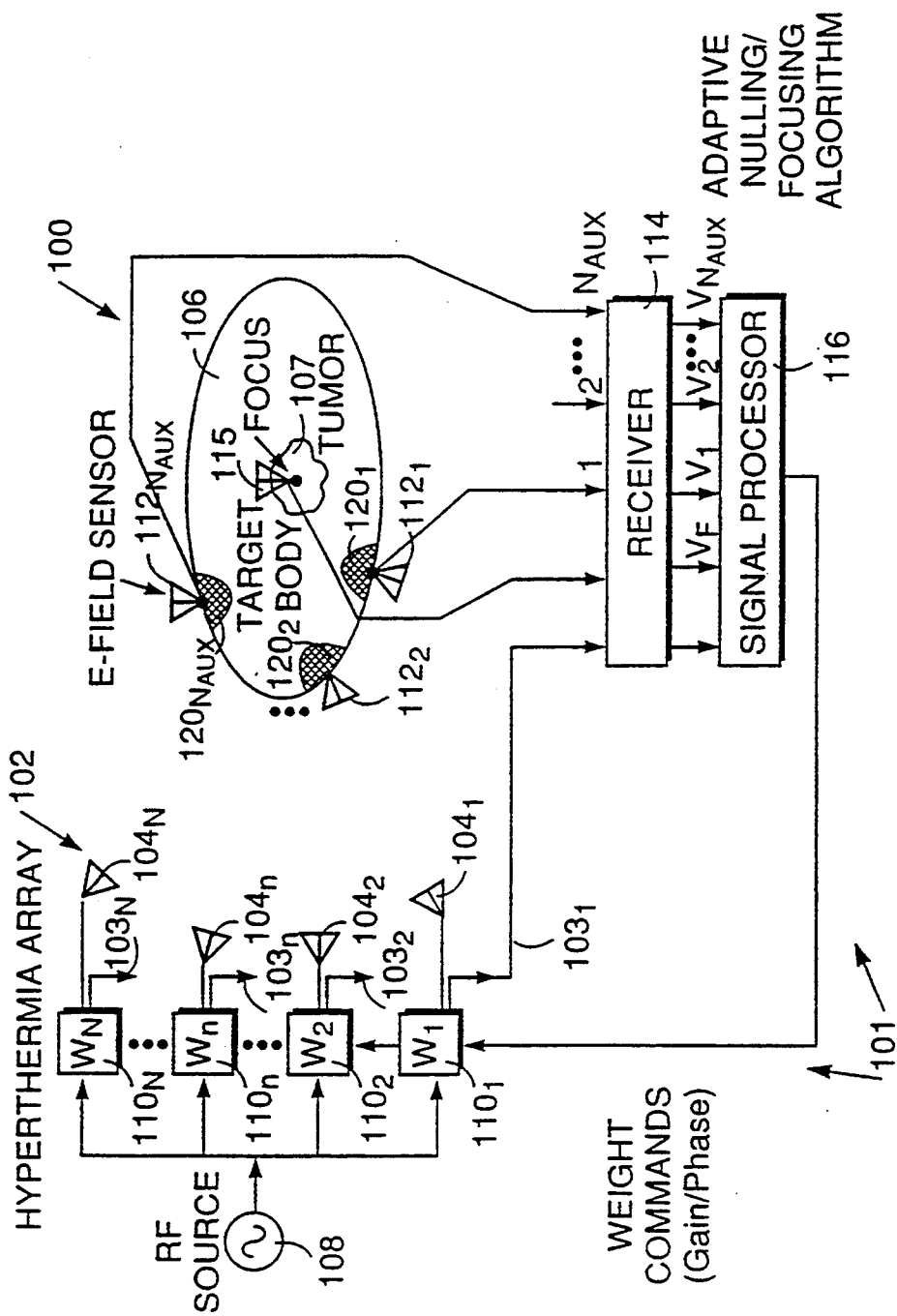
FIG. 6 is a schematic diagram of the adaptive hyperthermia array and array controller of FIG. 1.

Referring to FIG. 6, a generalized schematic of the non-invasive adaptive-nulling hyperthermia system of FIG. 3 includes hyperthermia transmitting phased array applicator 102 having a plurality of transmitting antenna elements $104_n$, where n=1, . . . , N, surrounding target body 106 for focusing RF energy at focus 107 within the target body. Phased array applicator 102 is energized by an RF energy source 108 which is distributed to and drives each transmit antenna element $104_n$ through a corresponding transmit weighting function $110_n$, each having a corresponding weight $w_n$. Each weighting function $w_n$ may affect the gain and phase of the RF energy fed to its corresponding antenna $104_n$ in the array, i.e., $w_n$ represents a complex weighting function. Each weighting function $110_n$ may be implemented by a voltage controlled RF amplifier and a voltage controlled RF phase shifter. An amplitude control voltage representing the amplitude component of transmit weight $w_n$ is fed to the voltage controlled amplifier, and a phase control voltage representing the phase of transmit weight $w_n$ is fed to the voltage controlled phase shifter.

Target body 106 has a plurality of E-field auxiliary probes $112_m$, where $m=1, \ldots, N_{aux}$, i.e., receiving antennas, positioned at various locations on the surface of the body for sampling the E-field at each particular location. Another receiving probe 115 may be placed at the desired focus 107 of the array.

Receiving probes $112_m$ and 115 each drive an input to an RF receiver 114. The transmit amplitude and phase weights of each weighting function $w_n$ are fed to the receiver 114 through lines $103_n$ and are used to find the transmit level of each transmit element $104_n$. The outputs of receiver 114 represent the auxiliary probe-received complex voltages $v_1, v_2, \ldots, v_{N_{aux}}$, the focus probe-received complex voltage $v_F$, and the transmit level of the phased array. The receiver outputs drive the inputs of a signal processor 116, which applies a nulling algorithm to adjust the weighting functions $w_n$ and thereby null, or minimize, the RF signal received by each receiving probe $112_m$, i.e., minimize the $SNR_P$ at each probe.

To generate the desired field distribution in a clinical adaptive hyperthermia system, the receiving probes are positioned as close as possible to the focus (tumor site) and to where high temperatures are to be avoided (such as near the spinal cord and scar tissue). For an annular array configuration the receiving probes can be located non-invasively on the surface (skin) of the target. Initially, the hyperthermia array is focused to produce the required field intensity at the tumor. An invasive probe may be used to achieve the optimum focus at depth. To avoid undesired hot spots, it is necessary to minimize the power received at the desired null positions and to constrain the array transmit weights $w_n$ to deliver a required amount of transmitted or focal region power.

Signal processor 116 performs either a sample matrix inversion (SMI) algorithm or a gradient search algorithm on the signals output from receiver 114 and updates the adaptive array weights $w_n$ (with gain g and phase $\phi$) to rapidly (within seconds) form the nulls at the auxiliary probes before a significant amount of target heating takes place. With this adaptive system, it is possible to avoid unintentional hot spots in the proximity of the auxiliary probes and maintain a therapeutic thermal dose distribution at the focus (tumor).

Signal processor 116 may also perform a maximizing algorithm to maximize energy at the focus 107. The focus probe 115 is invasively placed at the desired focus 107, and used to generate a maximum signal, or signal-to-noise ratio ($SNR_F$), at the tumor site. RF receiver 114 makes an amplitude and phase measurement on the output signal from invasive probe 115 for each transmit antenna element $104_n$ radiating one at a time. Signal processor 116 processes these measurements and feeds back weight command signals to the transmit weighting functions $110_n$ to calibrate or phase align the transmit channels to thereby maximize the $SNR_F$, or RF power, at the invasive focal point probe. If receiver 114 makes amplitude-only measurements from invasive focus probe 115, then a gradient search technique may be applied by the signal processor with all elements transmitting simultaneously to maximize the $SNR_F$ at the invasive focal point probe.

Theoretical Formulation of Nulling Algorithms

Figure 7:
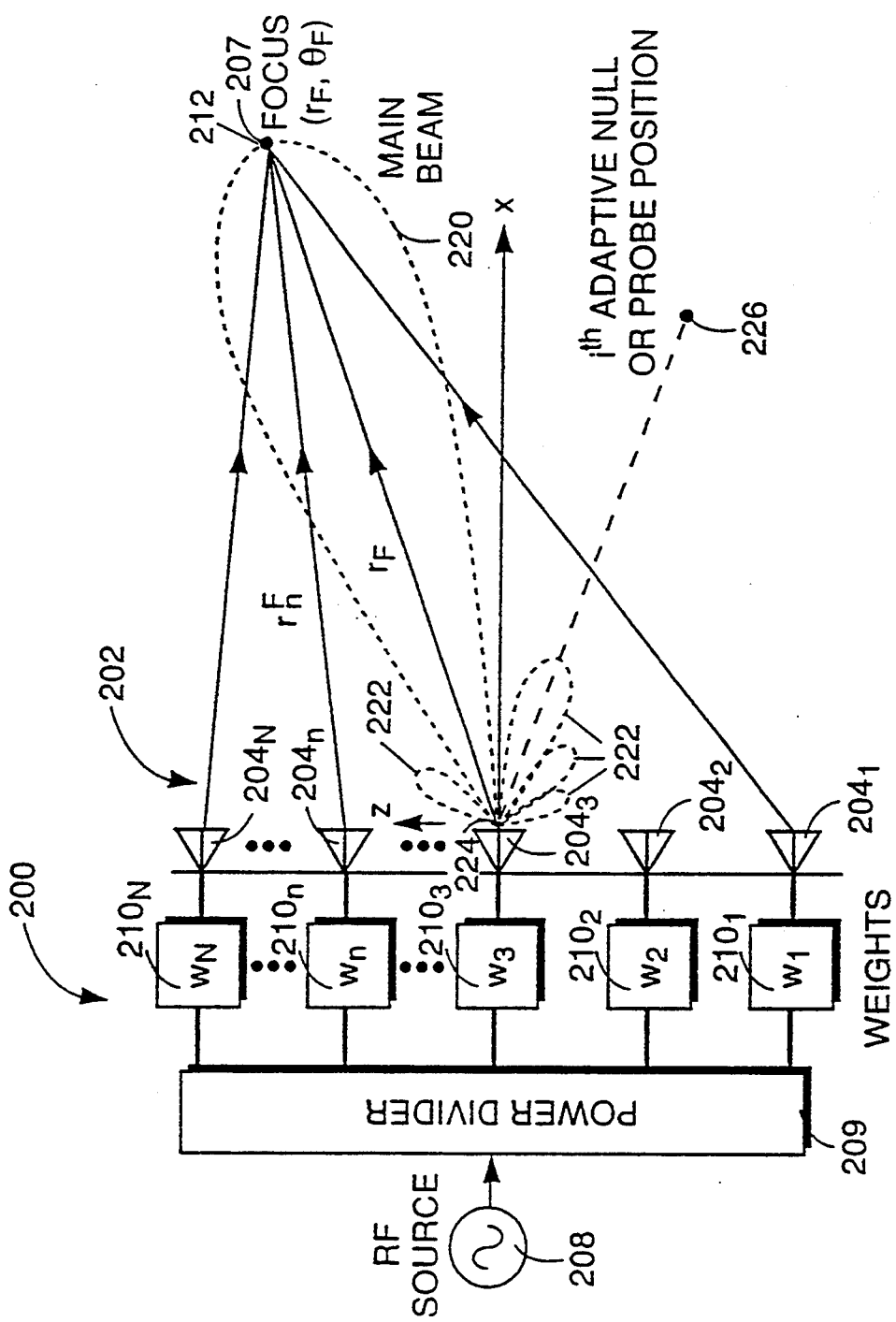
FIG. 7 is a schematic diagram of an analytical model of an adaptive array for simulating the hyperthermia array of FIG. 1.

FIG. 7 shows an analytical model of a hyperthermia phased-array antenna system 200, paralleling the generalized hyperthermia phased-array antenna system 100 of FIG. 6, illustrating the principles of the near-field adaptive nulling technique of this invention. The phased-array antenna system 200 includes a hyperthermia transmitting antenna array 202 having a plurality of transmitting antennas $204_n$, where $n=1, \ldots, N$ for focusing RF energy at a desired focus 207 in the near field of the antenna. Antenna array 202 is energized by an RF energy source 208 which drives a power divider 209. Power divider 209 has one output for driving each antenna $204_n$ a corresponding transmit weighting function $210_n$, each having a corresponding transmit weight $w_n$. It is assumed here that each weighting function $w_n$ may affect the phase of the RF energy fed to its corresponding antenna $204_n$ in the array. A calibration E-field probe 212, or focus probe antenna, is positioned at focus 207 for sampling the E-field at that location.

It is assumed that the hyperthermia phased-array antenna 200 is focused (as it normally is) in the near field and that a main beam 220 and possibly sidelobes 222 are formed in the target. In general, phase and amplitude focusing is possible. It is assumed that phase focusing alone is used to produce the desired quiescent main beam, i.e., weighting functions $w_n$ affects only the phase of the RF signal driving each antenna. The signal received by the calibration probe can be maximized by adjusting the phase weighting functions $w_n$ so that the observed transmit antenna element-to-element phase variation is removed, i.e., all transmit antennas appear to be in-phase when observed from the focus.

One way to achieve phase coherence at the focus in a numerical simulation is to choose a reference path length as the distance from the focus to the phase center 224 of the array. This distance is denoted $r_F$ and the distance from the focus to the nth array transmit antenna element is denoted $r_n^F$. The voltage received at the calibration probe 212 (located at focus 207) due to the nth array element may be computed using the "method of moments", as described below. To maximize the received voltage at the calibration probe output, it is necessary to apply the phase conjugate of the signal observed at the calibration probe, due to each array transmit antenna element, to the corresponding element at the transmit array. The resulting near-field radiation pattern will have a main beam and sidelobes. The main beam will be pointed at the array focal point, and sidelobes will exist at angles away from the main beam. Auxiliary probes can then be placed at the desired null positions in the quiescent sidelobe region. These sidelobes occur where tissue hot spots are likely to occur, and they are nulled by one of the adaptive nulling algorithms described below.

Adaptive Transmit Array Formulation

Considering again the hyperthermia array and probe geometry shown in FIG. 7, the hyperthermia transmit antenna array 202 typically contains N identical transmit antenna elements 204. The number of adaptive channels is denoted M, and for a fully adaptive array $M=N$. The ideal transmit weights $w_n$ (a complex voltage gain vector) are assumed in the computer simulation, with $w=(w_1, w_2, \ldots, w_N)^T$ denoting the adaptive channel weight vector as shown in FIG. 6. (Superscript T means transpose). To generate adaptive nulls, the transmit weights (phase and gain) are controlled by either the Sample Matrix Inversion (SMI) algorithm or a gradient search algorithm. The SMI algorithm has the flexibility to operate in either open- or closed-loop feedback modes; the gradient search algorithm operates only in a feedback mode.

Sample Matrix Inversion (SMI) Algorithm

For the SMI algorithm, the fundamental quantities required to fully characterize the incident field for adaptive nulling purposes are the adaptive channel cross correlations. To implement this algorithm it is necessary to know the complex received voltage at each of the auxiliary probes. For example, the moment-method formulation (described below) allows computation of complex-received voltage at each of the auxiliary probes.

Figure 8:
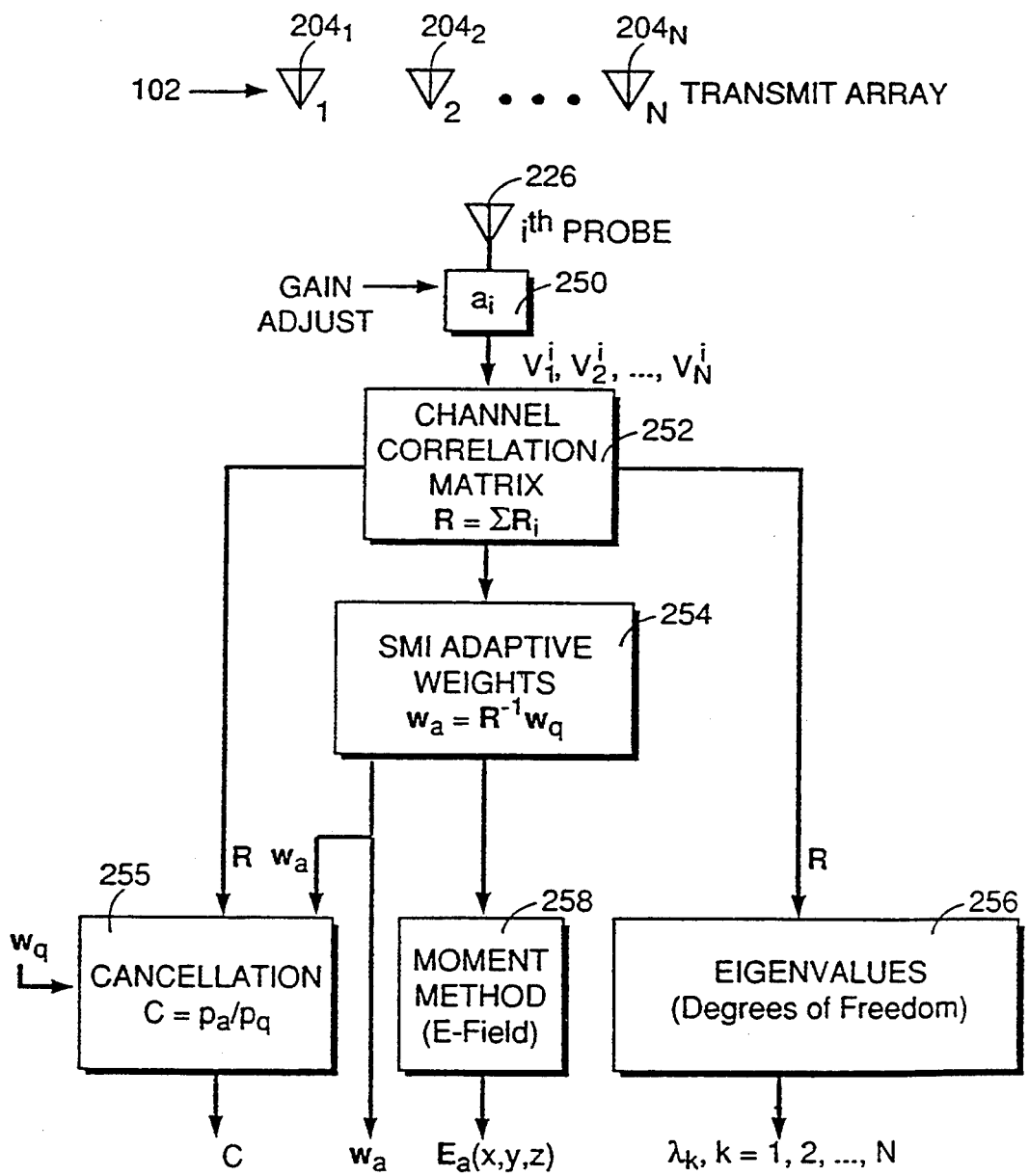
FIG. 8 is a block diagram detailing the sample matrix inversion algorithm derived from the adaptive hyperthermia array model of FIG. 7.

FIG. 8 is a block diagram showing the SMI algorithm applied to the adaptive hyperthermia phased-array of FIG. 7, and the derivation of performance measures to quantify computer simulation results. Four performance measures are used to quantify the computer simulations: electric-field distribution $E(x,y,z)$, channel correlation matrix eigenvalues $\lambda_k$, $k=1, \ldots, N$, adaptive transmit weights $W_a$, and interference cancellation C. The calculation of these performance measures is described in detail below.

Assuming a spherical wavefront is incident at an ith probe antenna 226 due to each of the N array transmit antenna elements $204_n$ (radiating one at a time with a unity-amplitude reference signal), the result is a set of probe-received complex voltages denoted $v_1^i, v_2^i, \ldots, v_N^i$ after a gain adjustment 250. The cross correlation $R_{mn}^i$ of the received voltages due to the mth and nth transmit antenna (adaptive transmit channel) at the ith probe is given by $$R_{mn}^i = E(v_m v_n^*), \quad (1)$$

where * means complex conjugate and $E(\cdot)$ means mathematical expectation. (Note: for convenience, in Equation (1) the superscript i in $v_m$ and in $v_n$ has been omitted.) Because $v_m$ and $v_n$ represent voltages of the same waveform but at different times, $R_{mn}^i$ is also referred to as an autocorrelation function.

In the frequency domain, assuming the transmit waveform has a band-limited white noise power spectral density (as commonly assumed in radar system analysis), Equation (1) can be expressed as the frequency average $$R_{mn}^i = \frac{1}{B} \int_{f_1}^{f_2} v_m(f) v_n^*(f) df, \quad (2)$$

where $B = f_2 - f_1$ is the nulling bandwidth, or bandwidth of frequencies applied by the hyperthermia treatment, and f is the transmit frequency of the hyperthermia array. It should be noted that $v_m(f)$ takes into account the transmit wavefront shape, which is spherical for the hyperthermia application. For the special case of a continuous wave (CW) transmit waveform, as normally used in hyperthermia, the cross correlation reduces to $$R_{mn}^i = v_m(f_o) v_n^*(f_o) \quad (3)$$

where $f_o$ is the transmit frequency of the hyperthermia array.

Next, the channel correlation matrix, or interference covariance matrix, denoted R is determined 252. (Note: in hyperthermia, interference is used to refer to the signals received at the auxiliary probes. The undesired "hot spots" can be thought of as interfering with the therapy.) If there are $N_{aux}$ independent desired null positions or auxiliary probes, the $N_{aux}$-probe channel correlation matrix is the sum of the channel correlation matrices observed at the individual probes. That is, $$R = \sum_{i=1}^{N_{aux}} R_i + I, \quad (4)$$

where $R_i$ is the sample channel correlation matrix observed at the ith probe and I is the identity matrix used to represent the thermal noise level of the receiver for simulation purposes.

Prior to generating an adaptive null, the adaptive channel weight vector, w, is chosen to synthesize a desired quiescent radiation pattern. When nulling is desired, the optimum set of transmit weights to form an adaptive null (or nulls), denoted $w_a$, is computed 254 by $$w_a = R^{-1} w_q, \quad (5)$$

where $^{-1}$ means inverse and $w_q$ is the quiescent weight vector. During array calibration, the normalized quiescent transmit weight vector, with transmit element $204_1$ radiating, is chosen to be $w_q = (1,0,0, \ldots, 0)^T$, i.e., the transmit channel weight of element $204_1$ is unity and the remaining transmit channel weights are zero. Similar weight settings are used to calibrate the remaining transmit elements. For a fully adaptive annular array focused at the origin in homogeneous tissue, the normalized quiescent weight vector is simply $w_q = (1,1,1, \ldots, 1)^T$. Commonly, the weight vector is constrained to deliver a required amount of power to the hyperthermia array or to the tumor. For simplicity in the computer simulation used to analyze the hyperthermia array, the weights are constrained such that $$\sum_{n=1}^{N} |w_n|^2 = 1, \quad (6)$$

where $w_n$ is the transmit weight for the nth element. It should be noted that in the computer simulations, the electric field due to the normalized weight vector is scaled appropriately to deliver the required amount of power to the tissue so that a desired focal-region temperature level is achieved after t minutes. The summation of power received at the probes is given by $$p = w^\dagger R w, \quad (7)$$

where $\dagger$ means complex conjugate transpose. The signal-plus-noise-to-noise ratio for the auxiliary probe array, denoted $SNR_P$, is computed as the ratio of the auxiliary probe array output power (defined in Equation (7)) with the transmit signal present, to the probe array output power with only receiver noise present, that is, $$INR = \frac{w^\dagger R w}{w^\dagger w}. \quad (8)$$

Next, the adaptive array cancellation ratio indicative of the null strength, denoted C, is determined 255. C is defined here as the ratio of the summation of probe-received power after adaptation to the summation of probe-received power before adaptation (quiescent); that is, $$C = \frac{p_a}{p_q}. \quad (9)$$

A large amount of cancellation indicated by a large value for C indicates a strong null, while a small amount of cancellation indicated by a small value for C indicates a weak null. Substituting Equation (7) into Equation (9) yields $$C = \frac{w_a^\dagger R w_a}{w_q^\dagger R w_q}. \quad (10)$$

Figure 9:
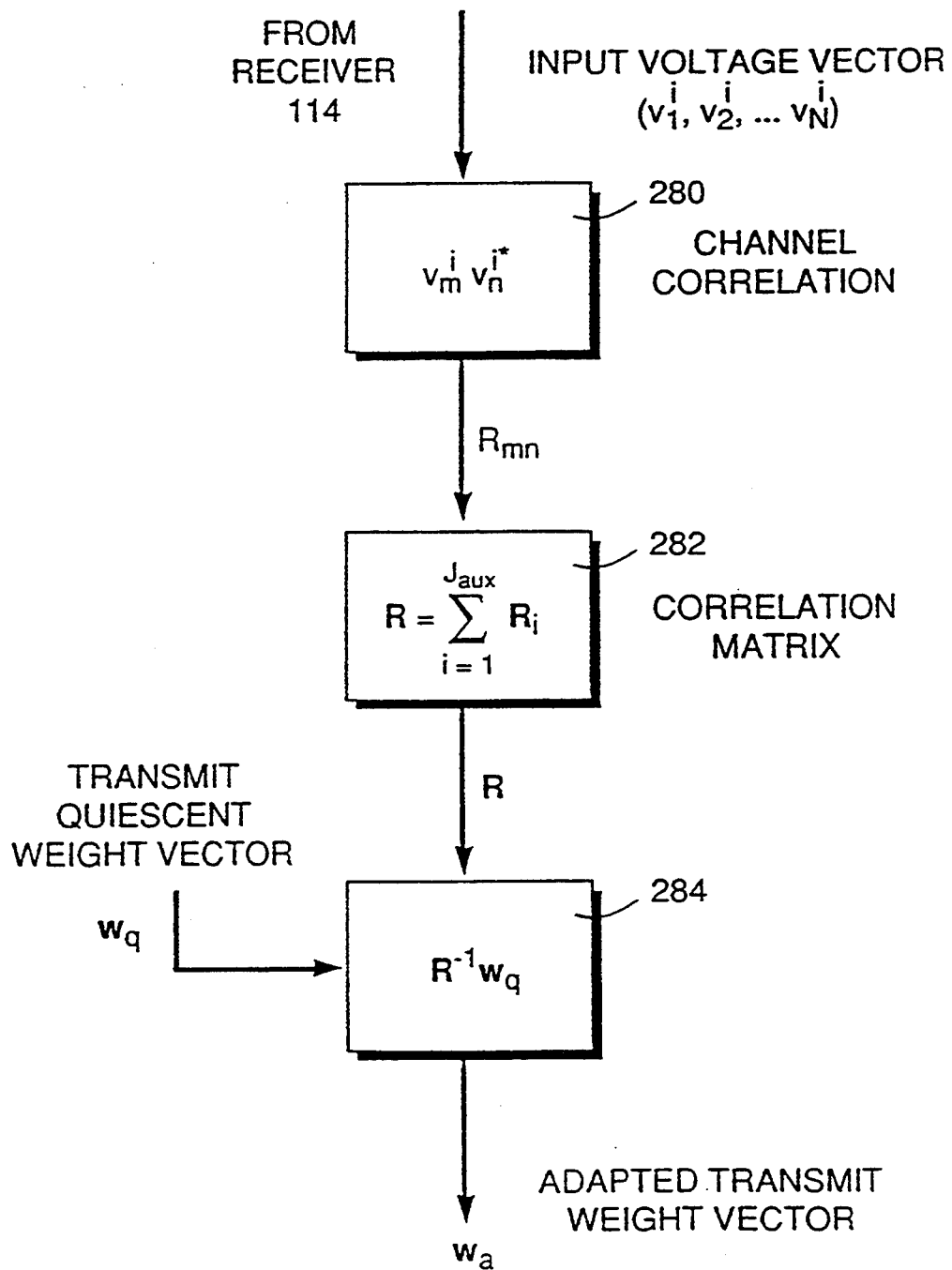
FIG. 9 is a block diagram of the sample matrix inversion algorithm performed by the hyperthermia array controller of FIG. 6.

Next, the channel correlation matrix defined by the elements in Equations (2) or (3) is Hermitian (that is, $R = R^\dagger$), which, by the spectral theorem, can be decomposed 256 in eigenspace as $$R = \sum_{k=1}^{M} \lambda_k e_k e_k^\dagger. \quad (11)$$

where $\lambda_k$, $k = 1, 2, \ldots, M$ are the eigenvalues of R, and $e_k$, $k = 1, 2, \ldots, M$ are the associated eigenvectors of R. The channel correlation matrix eigenvalues ($\lambda_1, \lambda_2, \ldots, \lambda_M$) are a convenient quantitative measure of the use of the adaptive array degrees of freedom. The amplitude spread between the largest and smallest eigenvalues is a quantitative measure of the dynamic range of the interference (hot spot) signals. FIG. 9 is a block diagram of the sample matrix inversion algorithm implemented by the signal processor 116 of FIG. 6. Receiver 114 generates probe-received complex voltage vector $v_1{}^i, v_2{}^i, \ldots, v_N{}^i$ for the ith auxiliary probe. The signal processor generates 280 the transmit channel correlations $R_{mn}{}^i$ defined by equation (3), and sums 282 them to form the channel correlation matrix R defined by equation (4). Next, the signal processor multiplies 284 the inverse of the channel correlation matrix $R^1$ by the quiescent transmit weight vector $w_q$ to form the new adapted transmit weight vector $w_1$ containing the adapted transmit weights fed back to the transmit weight networks $110_n$ of FIG. 6.

Gradient Search Algorithm

Under conditions where only the probe received voltage amplitude is measured, it is appropriate to consider a gradient search algorithm to minimize the interference power at selected positions. The gradient search is used to control the transmit weights $w_n$ iteratively such that the RF signal received by the probe array is minimized. The transmit array weights (gain and phase) are adaptively changed in small increments and the probe array output power is monitored to determine weight settings that reduce the output power most rapidly to a null.

Consider J sets of N transmit weights that are applied to adaptive hyperthermia phased array applicator 102 of FIG. 6. In terms of adaptive nulling, the optimum transmit weight settings (from the collection of J sets of N transmit weights) occur when the $SNR_P$ is minimized. Equivalently, the total interference power received by the auxiliary probe array, denoted $p^{rec}$, is to be minimized. For notational convenience let a figure of merit F denote either the $SNR_P$ or $p^{rec}$ and employ a gradient search to find the optimum transmit weights to minimize F, that is, $$F_{opt} = \min(F_j) j = 1, 2, \ldots, J. \quad (12)$$

The transmit weight settings for which $F_{opt}$ occurs yields the closest approximation to the optimal transmit weights determined by using the sample matrix inverse approach described above.

Figure 10:
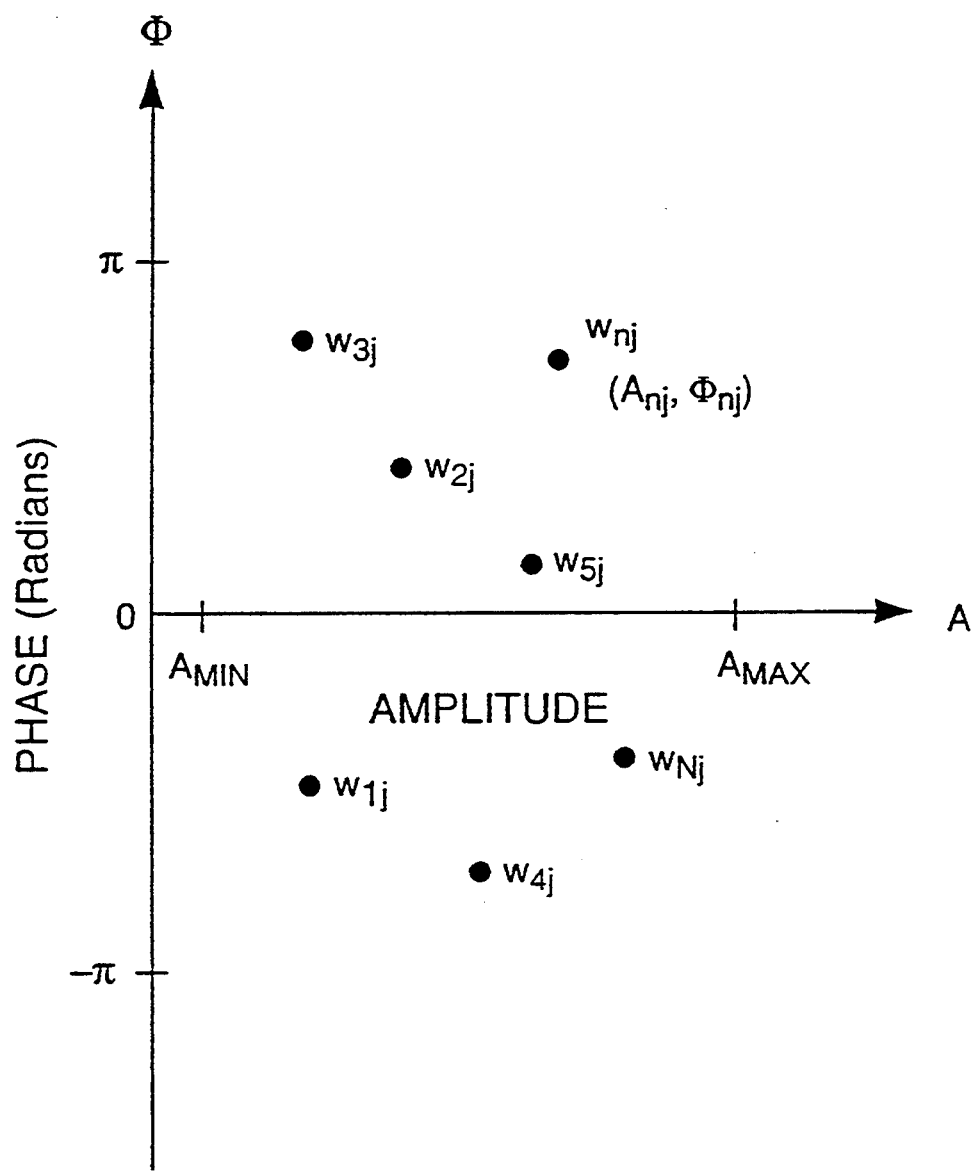
FIG. 10 is a scatter diagram of transmit weights used in deriving the gradient search adaptive hyperthermia algorithm.

FIG. 10 shows an amplitude and phase scatter diagram for the N complex transmit weights $w_n$ at the jth configuration, i.e., the jth set of weights tried. The nth transmit weight in the jth configuration of transmit weights is denoted $$w_{nj} = A_{nj} e^{j\Phi_{nj}}. \quad (13)$$

where $A_{nj}$ is the transmit weight amplitude distributed over the range $A_{min}$ to $A_{max}$ and $\Phi_{nj}$ is the transmit weight phase distributed over the range $-\pi$ to $\pi$ radians.

Figure 11:
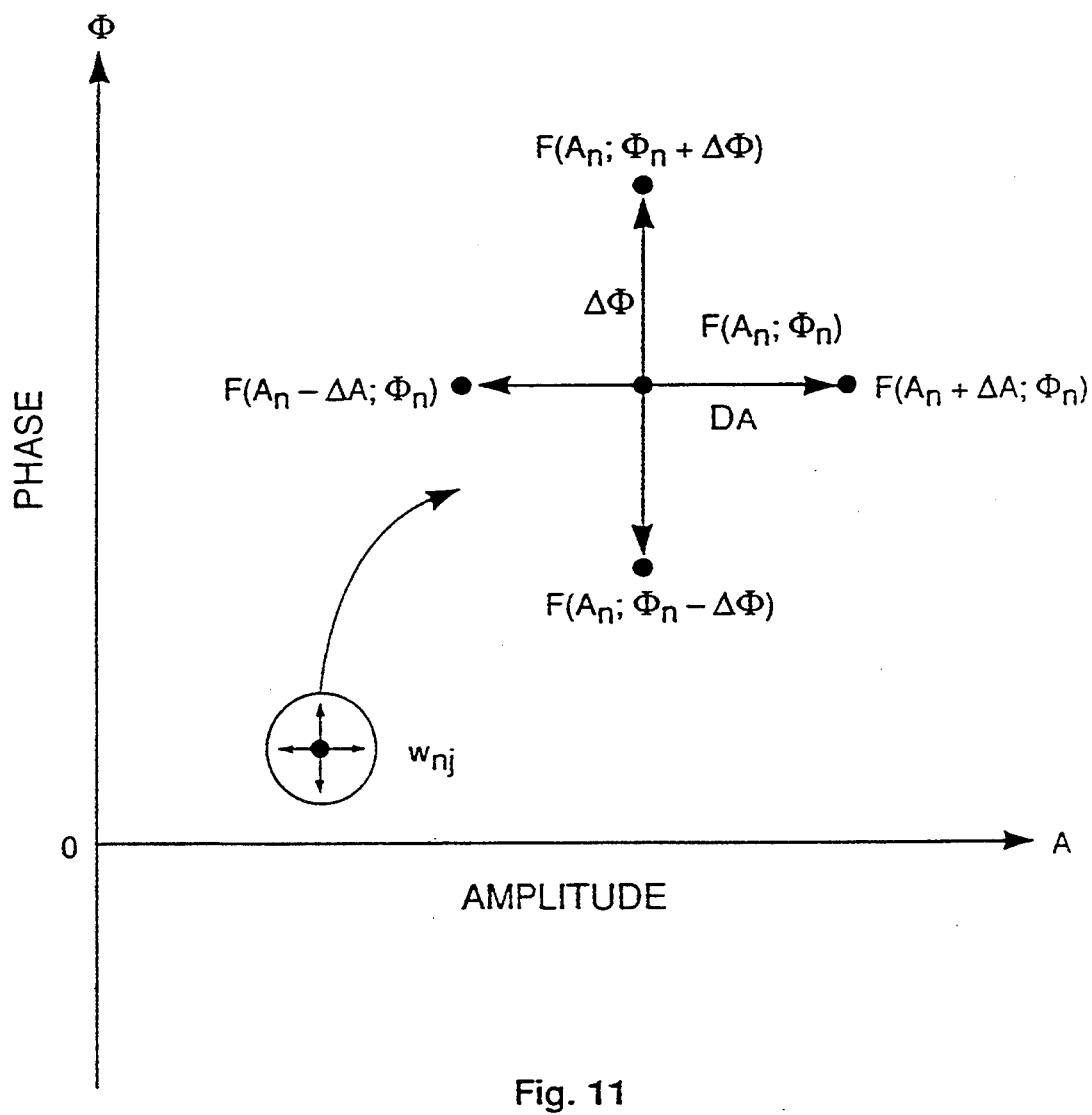
FIG. 11 is a diagram showing the derivation of the gradient search directions.

Referring also to FIG. 11, it is desired to find the values of amplitude and phase for each of the N transmit weights such that the figure of merit F ($SNR_P$ or $p^{rec}$) is minimized. When the figure of merit is minimized, adaptive radiation pattern nulls will be formed at the auxiliary probe positions.

Assuming an initial setting of the N transmit weights such as those selected to focus the radiation pattern on a tumor, the weights are adjusted by dithering them until the optimum figure of merit is achieved. It is desired to find the collective search directions for the N transmit weights such that F decreases most rapidly. That is, weights are selected so that the directional derivative is minimized at $(A_j, \Phi_j)$, where $A_j$ and $\Phi_j$ are vectors representing the transmit amplitude weights and transmit phase weights, respectively, for the jth configuration.

The directional derivative of $F_j$ is expressed in terms of the amplitude and phase changes of the transmit weights as $$D(F_j) = \sum_{n=1}^{N} \left( \frac{\partial F_j}{\partial A_{nj}} r_{A_{nj}} + \frac{\partial F_j}{\partial \Phi_{nj}} r_{\Phi_{nj}} \right) \quad (14)$$

where $\partial$ means partial derivative, and $r_{A_{nj}}, r_{\Phi_{nj}}$ are the (A, $\Phi$) directions for which $F_j$ is decreasing most rapidly. The directions $r_{A_{nj}}, r_{\Phi_{nj}}$ are constrained by $$\sum_{i=1}^{N} (r_{A_{nj}}^2 + r_{\Phi_{nj}}^2) = 1. \quad (15)$$

It is desired to minimize $D(F_j)$ subject to the above constraint equation.

Using Lagrange multipliers it is possible to construct the Lagrangian function $$L_j = \sum_{n=1}^{N} \left( \frac{\partial F_j}{\partial A_{nj}} r_{A_{nj}} + \frac{\partial F_j}{\partial \Phi_{nj}} r_{\Phi_{nj}} \right) + \quad (16)$$

-continued $$G\left[1 - \sum_{n=1}^{N}(r_{Anj}^2 + r_{\Phi nj}^2)\right]$$

where G is a constant to be determined. The requirement that $L_j$ be an extremum implies $$\frac{\partial L_j}{\partial r_{Anj}} = \frac{\partial F_j}{\partial A_{nj}} - 2Gr_{Anj} = 0, n = 1, 2, \ldots, N \quad (17)$$

and $$\frac{\partial L_j}{\partial r_{\Phi nj}} = \frac{\partial F_j}{\partial \Phi_{nj}} - 2Gr_{\Phi nj} = 0, n = 1, 2, \ldots, N \quad (18)$$

or that $$r_{Anj} = \frac{1}{2G} \frac{\partial F_j}{\partial A_{nj}} \quad (19)$$

and $$r_{\Phi nj} = \frac{1}{2G} \frac{\partial F_j}{\partial \Phi_{nj}}. \quad (20)$$

Squaring equations (19) and (20) and invoking equation (15) yields $$\sum_{i=1}^{N}(r_{Anj}^2 + r_{\Phi nj}^2) = 1 = \frac{1}{4G^2} \sum_{n=1}^{N}\left[\left(\frac{\partial F_j}{\partial A_{nj}}\right)^2 + \left(\frac{\partial F_j}{\partial \Phi_{nj}}\right)^2\right] \quad (21)$$

thus, $$G = \pm \frac{1}{2} \sqrt{\sum_{n=1}^{N}\left[\left(\frac{\partial F_j}{\partial A_{nj}}\right)^2 + \left(\frac{\partial F_j}{\partial \Phi_{nj}}\right)^2\right]}. \quad (22)$$

Substituting this expression for G in equations (19) and (20) gives $$r_{Anj} = -\frac{\frac{\partial F_j}{\partial A_{nj}}}{\sqrt{\sum_{n=1}^{N}\left[\left(\frac{\partial F_j}{\partial A_{nj}}\right)^2 + \left(\frac{\partial F_j}{\partial \Phi_{nj}}\right)^2\right]}} \quad (23)$$

and $$r_{\Phi nj} = -\frac{\frac{\partial F_j}{\partial \Phi_{nj}}}{\sqrt{\sum_{n=1}^{N}\left[\left(\frac{\partial F_j}{\partial A_{nj}}\right)^2 + \left(\frac{\partial F_j}{\partial \Phi_{nj}}\right)^2\right]}}. \quad (24)$$

The minus sign was chosen corresponding to the direction of maximum function decrease. This choice of minus sign in equation (22) enforces nulls in the hyperthermia array radiation pattern. Alternatively, if the positive sign in equation (22) is selected, then the gradient directions can be used to maximize the figure of merit for the purposes of focusing at an invasive probe at the tumor site, i.e., maximize the $SNR_F$. This may be used, for example, to determine the quiescent transmit weight vector $w_q$. Thus, two gradient searches may be performed to optimize the radiation pattern of the hyperthermia array. The first to produce a peak or focused radiation pattern at the tumor, and the second to form the desired nulls at the auxiliary probes. Furthermore, these two gradient searches may be implemented as a single, combined gradient search constrained to maximize the radiation pattern at the focus and minimize the radiation pattern at the desired nulls. The combined gradient search is implemented by minimizing the figure of merit defined as the ratio of the power received at the auxiliary probes to the power received by the probe at the focus.

The partial derivatives $$\frac{\partial F_j}{\partial A_{nj}}, \frac{\partial F_j}{\partial \Phi_{nj}}; n = 1, 2, \ldots, N \quad (25)$$

represent the gradient directions for maximum function decrease. Since the figure of merit F cannot be expressed here in analytical form, the partial derivatives are numerically evaluated by using finite differences. Thus, we write $$\frac{\partial F_j}{\partial A_{nj}} = \frac{\Delta F_{Anj}}{2\Delta A_{nj}} \quad (26)$$

and $$\frac{\partial F_j}{\partial \Phi_{nj}} = \frac{\Delta F_{\Phi nj}}{2\Delta \Phi_{nj}} \quad (27)$$

where as shown in FIG. 2 the figure of merit differences are $$\Delta F_{Anj} = F_j(A_{nj} + \Delta A_{nj}; \Phi_{nj}) - F_j(A_{nj}; \Phi_{nj}) \quad (28)$$

and $$\Delta F_{\Phi nj} = F_j(A_{nj}; \Phi_{nj} + \Delta \Phi_{nj}) - F_j(A_{nj}; \Phi_{nj} - \Delta \Phi_{nj}) \quad (29)$$

and $\Delta A_{nj}$ and $\Delta \Phi_{nj}$ are assumed to be small increments. We will assume that the increments $\Delta A_{nj}$ and $\Delta \Phi_{nj}$ are independent of the configuration number and element number, that is, $$\Delta A_{nj} = \Delta A \quad (30)$$

and $$\Delta \Phi_{nj} = \Delta \Phi. \quad (31)$$

Substituting equations (26), (27), (30) and (31) in equations (23) and (24) gives the desired result for the search directions $$r_{Anj} = -\frac{\frac{\Delta F_{Anj}}{\Delta A}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}} \quad (32)$$

and $$r_{\Phi nj} = -\frac{\frac{\Delta F_{\Phi nj}}{\Delta \Phi}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}. \quad (33)$$

Equations (32) and (33) are used to compute the new amplitude and phase settings of the (j+1)th transmit weight configuration according to $$A_{n,j+1} = A_{nj} + \Delta A r_{Anj} \quad (34)$$

and $$\Phi_{n,j+1} = \Phi_{nj} + \Delta \Phi r_{101\ nj}. \quad (35)$$

In practice, it may be necessary to keep one of the transmit weights fixed (in amplitude and in phase) during the gradient search to guarantee convergence.

Figure 12:
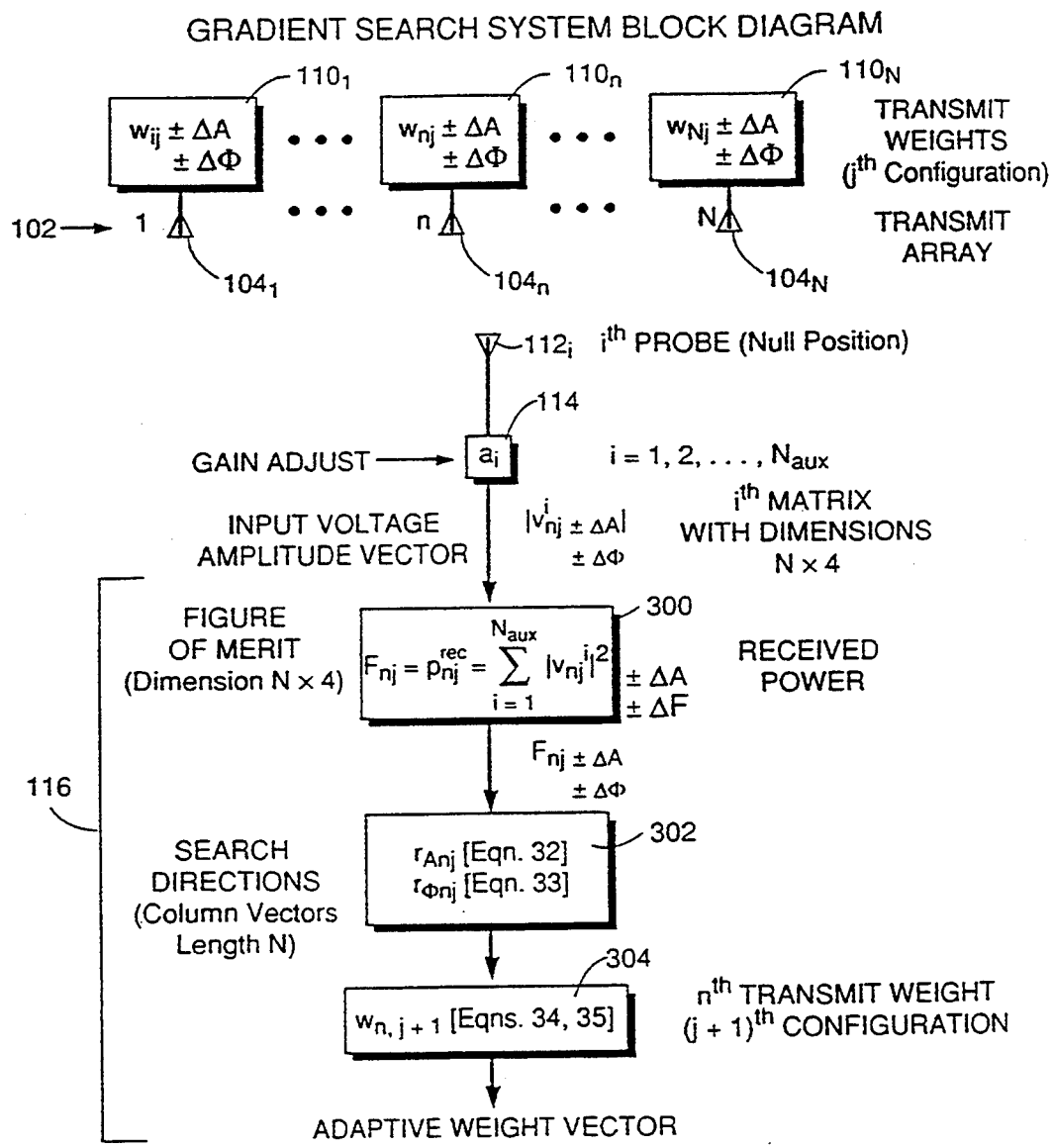
FIG. 12 is a block diagram of the gradient search performed by the hyperthermia array controller of FIG. 6.

FIG. 12 is a block diagram of the gradient search algorithm implemented by the signal processor 116 of FIG. 6. Each of the N transmit antennas $104_n$ of phased array applicator 102 (FIG. 6) is driven through its corresponding weighting network $110_n$ which applies complex transmit weights $w_{nj}$ at the jth configuration of the weights. The transmit antennas induce a voltage across the ith probe antenna $112_i$ at the corresponding input to receiver 114 (FIG. 6). Receiver 114 amplifies the signal received from the ith probe by gain $a_i$ to produce voltage amplitude vector $|v_1{}^j|, |v_2{}^j|, \ldots, |v_N{}^j|$ at the receiver output.

The voltage amplitude vector is input to signal processor 116 which performs the gradient search. For any initial configuration (j=1) of the transmit weights $W_{nj}$, the signal processor causes each weight to be dithered by a small amount in amplitude, $\Delta A_{nj}$, and phase, $\Delta \Phi_{nj}$. Each transmit weight is dithered independent of the other transmit weights, which remain in their jth configuration state. Received voltage vectors $|v_1{}^j|, |v_2{}^j|, \ldots, |v_N{}^j|$, i.e. are stored and used to calculate the resulting figure of merit $F_{nj}$ 300 for each dithered condition, the figure of merit being the power received by the auxiliary prove array. The figure of merit is a rectangular matrix of dimension N×4, where the dimensionality of four is due to the plus and minus dithering of both of the amplitude and phase. The figure of merit differences $\Delta F_{Anj}$ and $\Delta F_{\Phi nj}$ caused by dithering the amplitude and phase, respectively, are calculated according to equations (28) and (29). The gradient search directions $r_{Anj}$ and $r_{\Phi nj}$, based upon minimizing the auxiliary probe array received power, are then determined 302 from the figure of merit differences according to equations (32) and (33), respectively. The resulting search directions are used to update 304 transmit weights $W_{nj}$ to the (j+1)th configuration transmit weights $W_{n,(j+1)}$ according to equations (34) and (35). The transmit weights $W_{n,0+1}$ are sent to update the transmit weighting networks $110_n$, and the process is repeated. The final adaptive weight vector $w_a$ is achieved when the (j+1)th transmit weight configuration has converged. Convergence is expected to occur within several hundred iterations depending on the dither step size $\Delta A$ and $\Delta \Phi$.

It is understood that other forms of gradient searches exist which can be used to update the transmit weights toward convergence. Another such gradient search approach, where the step sizes $\Delta A$ and $\Delta \Phi$ are computed at each iteration, is described by D. J. Farina and R. P. Flam, "A Self-normalizing Gradient Search Adaptive Array Algorithm", IEEE Transactions on Aerospace and Electronic Systems, November 1991, Vol. 27, No. 6, pp 901-905.

COMPUTER SIMULATION OF ADAPTIVE NULLING HYPERTHERMIA

Moment-Method Formulation

Referring again to FIG. 8, a method of moments formulation 258 is used to compute the probe-received voltages in Equation (2) due to the transmitting hyperthermia phased-array antenna in an infinite homogeneous conducting medium. The medium is described by the three parameters $\mu$, $\epsilon$, and $\sigma$, which are discussed below. The formulation given here is analogous to that developed under array-receiving conditions for an adaptive radar. The software used to analyze a hyperthermia array is based on the receive-array analogy but the theory presented below is given in the context of a transmit array.

An antenna analysis code (WIRES) originally developed by J. H. Richmond is capable of analyzing antenna or radar cross section problems. See, J. H. Richmond, "Computer program for thin-wire structures in a homogeneous conducting medium", Ohio State University, ElectroScience Laboratory, Technical Report 2902-12, August 1973; and, J. H. Richmond, "Radiation and scattering by thin-wire structures in a homogeneous conducting medium (computer program description)", IEEE Trans. Antennas Propagation, Vol. AP-22, no. 2, p. 365, March 1974. WIRES was modified to analyzing the near-field and far-field adaptive nulling performance of thin-wire phased arrays in free space. A new version of the thin-wire code that can analyze adaptive hyperthermia arrays in an infinite homogeneous conducting medium was written to conduct the adaptive hyperthermia simulation discussed below. The new version of the thin-wire code is attached as Appendix A.

WIRES is a moment-method code that uses the electric field integral equation (EFIE) to enforce the boundary condition of the tangential electric field being zero at the surface of the antenna of interest. The moment-method basis and testing functions used in this code are piecewise sinusoidal.

Appendix B lists sample input and output files for the adaptive hyperthermia simulation. The first data file was used to generate the E-field results for a four auxiliary probe system, and the second data file was used to generate the E-field results for a two auxiliary probe system. The corresponding output files give the values for the array mutual coupling, quiescent and adaptive transmit weights, channel correlation matrix, eigenvalues, and cancellation.

Figure 13:
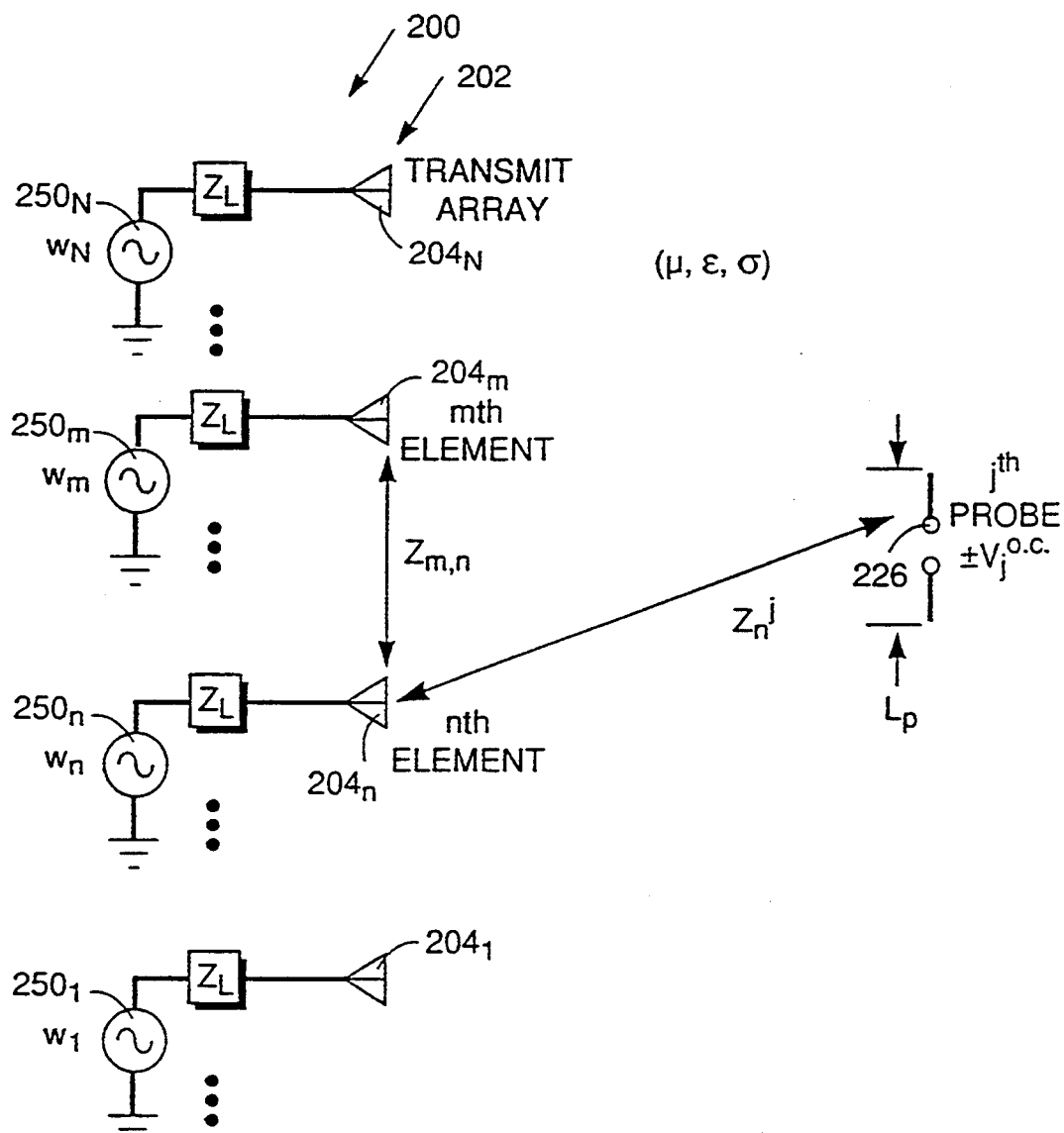
FIG. 13 is a schematic diagram of the analytical model of FIG. 7 redrawn to simplify derivation of method of moments analysis.

Referring to FIG. 13, there is shown the hyperthermia phased-array antenna system 200 of FIG. 7, redrawn to simplify the following method of moments analysis. The RF source 208, power divider 209 and weights $210_n$ of FIG. 7, are modeled as a plurality of RF signal generators $250_1$ through $250_N$, feeding its corresponding transmit antenna element $204_1$ through $204_N$. Each generator $250_1$ through $250_N$ has a corresponding amplitude and phase weight denoted by $w_1$ through $w_N$, and a known output impedance $Z_L$. The jth probe 226 (i.e., the same as the ith probe 226 of FIG. 7, with different notation) is modeled as a dipole antenna having an overall length $L_p$ and an open-circuit voltage $v_j{}^{o.c.}$ induced by the RF energy transmitted from the antenna array 200.

The open-circuit voltage at the jth probe antenna 226 is computed from the array terminal currents and from $Z_{nj}$, the open-circuit mutual impedance between the nth array element and the gth probe antenna. Let $v_{nj}{}^{o.c.}$ represent the open-circuit voltage at the jth probe due to the nth transmit-array element. Here, the jth probe can denote either the focal point calibration probe (calibration probe 212 of FIG. 7) or one of the auxiliary probes used to null a sidelobe. The number of auxiliary probes is denoted by $N_{aux}$.

Figure 14:
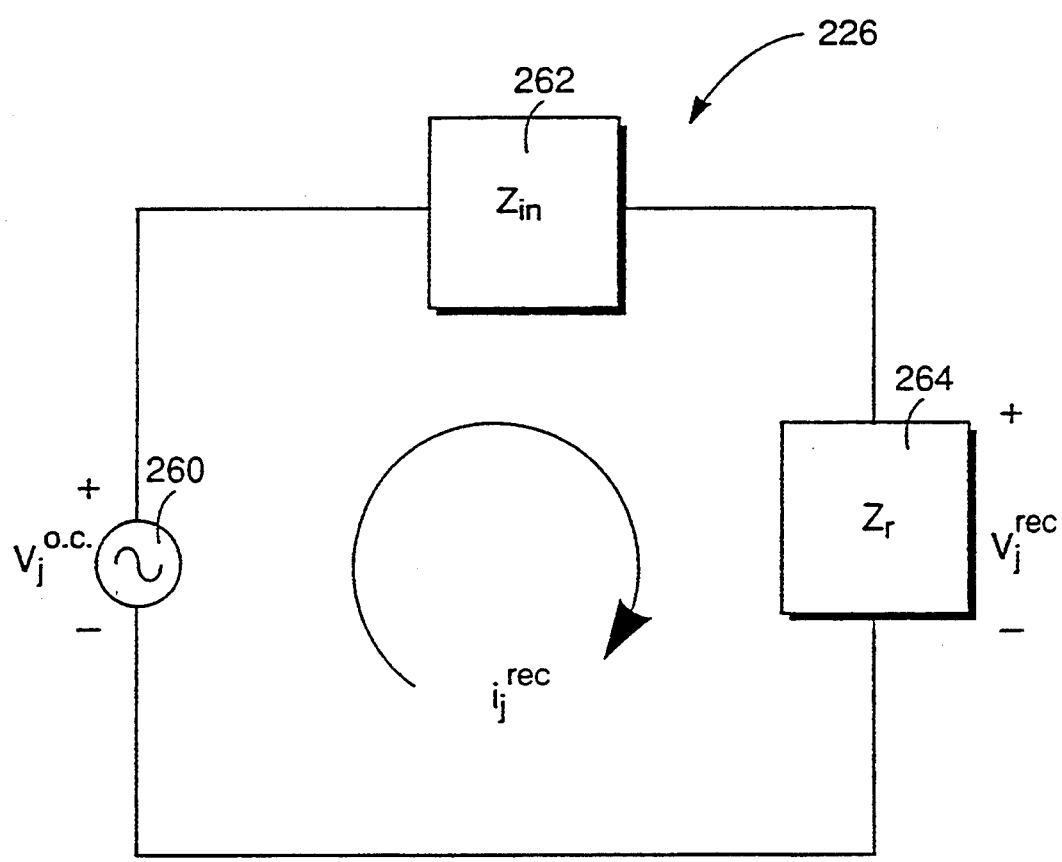
FIG. 14 is a schematic diagram of an equivalent circuit model for simulating an auxiliary probe.

Referring also to FIG. 14, the jth probe 226 is modeled as a voltage source 260, having an output voltage $v_j^{o.c.}$, driving a first impedance 262, representing the input impedance $Z_{IN}$ of the jth probe, in series with a second impedance 264, representing the termination impedance $Z_r$ of the jth probe. The jth probe receive current $I_j^{rec}$ flows through these two impedances. The output voltage of the jth probe $v_j^{rec}$ appears across the termination impedance $Z_r$.

Referring again to FIG. 13, next, let Z denote the open-circuit mutual impedance matrix (with dimensions N X N for the N-element array). The open-circuit mutual impedance between array elements $204_m$ and $204_n$ is denoted $Z_{m,n}$. It is assumed that multiple interaction between the hyperthermia array and the auxiliary probe can be neglected. Thus, the hyperthermia array terminal current vector i can be computed in terms of the transmit weights w as $$i = [Z + Z_L I]^{-1} w. \tag{36}$$

Next let $Z_n^j$ be the open-circuit mutual impedance between the jth probe and the nth array element. The induced open-circuit voltage $v_{nj}^{o.c.}$ at the jth receive probe, due to the nth array element transmit current $i_n$, can then be expressed as $$v_{nj}^{o.c.} = Z_n^j \cdot i_n \tag{37}$$

In matrix form, the induced open-circuit probe-voltage matrix $v_{probe}^{o.c.}$ is $$v_{probe}^{o.c.} = Z_{probe,array} i \tag{38}$$

or $$v_{probe}^{o.c.} = Z_{probe,array}[Z + Z_L I]^{-1} w \tag{39}$$

where $Z_{probe,array}$ is a rectangular matrix of order $N_{aux}$ X N for the open-circuit mutual impedance between the probe array and the hyperthermia array. Note that the jth row of the matrix $Z_{probe,array}$ is written as $(Z_1^j, Z_2^j, \ldots, Z_N^j)$, where $j = 1, 2, \ldots, N_{aux}$. The receive voltage matrix is then computed by the receiving circuit equivalence theorem for an antenna. The receive-antenna equivalent circuit is depicted in FIG. 14, where it is readily determined that $$v_{probe}^{rec} = v_{probe}^{o.c.} \frac{Z_r}{Z_{in} + Z_r} \tag{40}$$

where $Z_{in}$ is the input impedance of the probe. It should be noted that the $v_{probe}^{rec}$ matrix is a column vector of length $N_{aux}$ and $V_j^{rec}$ is the jth element of the matrix. The probe-receive current matrix is given by $$i_{probe}^{rec} = v_{probe}^{o.c.} \frac{1}{Z_{in} + Z_r} \tag{41}$$

The jth element of the column vector $i_{probe}^{rec}$ is denoted $i_j^{rec}$, $j = 1, 2, \ldots, N_{aux}$. Finally, the power received by the jth probe is $$p_j^{rec} = \tfrac{1}{2} Re(v_j^{rec} \cdot i_j^{rec*}) \tag{42}$$

where Re means real part. Substituting Equations (40) and (41) into Equation (42) yields $$p_j^{rec} = \frac{1}{2} |v_j^{o.c.}|^2 \frac{Re(Z_r)}{|Z_{in} + Z_r|^2} \tag{43}$$

total interference power received by the auxiliary probe array is given by $$p^{rec} = \sum_{j=1}^{J_{aux}} p_j^{rec} \tag{44}$$

The incident electric field E is related to the open-circuit voltage $v^{o.c.}$ by the effective height h of the probe antenna as $$v^{o.c.} = hE \tag{45}$$

If the length $L_p$ of the probe antenna 226 is approximately $0.1\lambda$ or less, the current distribution is triangular and the effective height is $h = 0.5 L_p$. Thus, for a short-dipole probe the open-circuit voltage can be expressed as $$v^{o.c.} = \frac{L_p}{2} E \tag{46}$$

It then follows from Equation (46) that the E field for a short-dipole probe at position (x,y,z) is given by $$E(x,y,z) = \frac{2 v^{o.c.}(x,y,z)}{L_p} \tag{47}$$

Finally, the quiescent and adapted E-field radiation patterns are computed using the quiescent and adapted weight vectors $w_q$ and $w_a$, respectively, in Equations (39) and (47). The moment-method expansion and testing functions are assumed to be sinusoidal. The open-circuit mutual impedances in Equation (39) between thin-wire dipoles in a homogeneous conducting medium are computed based on subroutines from the moment-method computer code developed by J. H. Richmond. In evaluating $Z_n^j$ for the jth auxiliary probe, double precision computations are used.

As mentioned previously, the array is calibrated (phased focused) initially using a short dipole at the focal point. To accomplish this numerically, having computed $v_{focus}^{rec}$, the transmit array weight vector w will have its phase commands set equal to the conjugate of the corresponding phases in $v_{focus}^{rec}$. Transmit antenna radiation patterns are obtained by scanning (moving) a dipole probe with half-length 1 in the near-field and computing the receive probe-voltage response.

The received voltage matrix for the jth probe (denoted $v_j^{rec}$) is computed at K frequencies across the nulling bandwidth. Thus, $v_j^{rec}(f_1), v_j^{rec}(f_2), \ldots, v_j^{rec}(f_K)$ are needed. For the purposes of this computer simulation, the impedance matrix is computed at K frequencies and is inverted K times. The probe channel correlation matrix elements are computed by evaluating Equation (2) numerically, using Simpson's rule numerical integration. For multiple auxiliary probes, the channel correlation matrix is evaluated using Equation (4). Adaptive array radiation patterns are computed by superimposing the quiescent radiation pattern with the weighted sum of auxiliary-channel-received voltages.

Wave Propagation in Conducting Media

To gain insight into the effect of a lossy medium, e.g., the target body, on the propagation of an electromagnetic wave, it is useful to review certain fundamental equations which govern the field characteristics. In a conducting medium, Maxwell's curl equations in time-harmonic form are $$\nabla \times H = J + j\omega\epsilon E \tag{48}$$

and $$\nabla \times E = -j\omega\mu H \tag{49}$$

where E and H are the electric and magnetic fields, respectively, J is the conduction current density, $\omega = 2\pi f$ is the radian frequency, $\epsilon$ is the permittivity of the medium, and $\mu$ is the permeability of the medium. The permittivity is expressed as $\epsilon = \epsilon_r \epsilon_o$, where $\epsilon_r$ is the dielectric constant (relative permittivity) and $\epsilon_o$ is the permittivity of free space. Similarly, $\mu = \mu_r \mu_o$, where $\mu_r$ is the relative permeability and $\mu_o$ is the permeability of free space. For a medium with electrical conductivity $\sigma$, J and E are related as $$J = \sigma E \tag{50}$$

Substituting Equation (50) into Equation (48) yields $$\nabla = H = (\sigma + j\omega\epsilon)E \tag{51}$$

From Equations (48) and (49), the vector wave equation in terms of E is derived as $$\nabla^2 E - \gamma^2 E = 0 \tag{52}$$

It is readily shown that $$\gamma = \pm \sqrt{j\omega\mu(\sigma + j\omega\epsilon)} = \pm j\omega \sqrt{\mu\epsilon} \sqrt{1 - j\frac{\sigma}{\omega\epsilon}} \tag{53}$$

The quantity $\sigma/\omega\epsilon$ is referred to as the loss tangent. It is common to express the complex propagation constant as $$\gamma = \alpha + j\beta \tag{54}$$

where $\alpha$ is the attenuation constant and $\beta$ is the phase constant. The constants $\alpha$ and $\beta$ are found by setting Equation (53) equal to Equation (54) and then squaring both sides, equating the real and imaginary parts, and solving the pair of simultaneous equations, with the result $$\alpha = \frac{\omega\sqrt{\mu\epsilon}}{\sqrt{2}} \left[ \sqrt{1 + \left(\frac{\sigma}{\omega\epsilon}\right)^2} - 1 \right]^{\frac{1}{2}} \tag{55}$$

and $$\beta = \frac{\omega\sqrt{\mu\epsilon}}{\sqrt{2}} \left[ \sqrt{1 + \left(\frac{\sigma}{\omega\epsilon}\right)^2} + 1 \right]^{\frac{1}{2}} \tag{56}$$

The wavelength $\lambda$ in the lossy dielectric is then computed from $$\lambda = \frac{2\pi}{\beta} \tag{57}$$

The intrinsic wave impedance $\eta$ is given by $$\eta = \sqrt{\frac{j\omega\mu}{\sigma + j\omega\epsilon}} = \sqrt{\frac{\mu}{\epsilon}} \frac{1}{\sqrt{1 - j\frac{\sigma}{\omega\epsilon}}} \tag{58}$$

The instantaneous power density of the electromagnetic field is given by Poynting's vector, denoted P, $$P = \tfrac{1}{2} E \times H^* \tag{59}$$

which has units of (W/m²). The time-average power flow density is equal to the real part of the complex Poynting's vector. The time-average power dissipation per unit volume $P_d$ (W/m³) is derived from Maxwell's equations, with the result $$P_d = \tfrac{1}{2} E \cdot J^* = \tfrac{1}{2}\sigma|E|^2 \tag{60}$$

The specific absorption rate (SAR) is the power dissipated or absorbed per unit mass (W/kg) of the medium (tissue), or $$SAR = \frac{P_d}{\rho} = \frac{\sigma}{2\rho}|E|^2 \tag{61}$$

where $\rho$ is the density of the medium in kg/m³.

It is convenient to have a simple equation for computing the propagation loss between any two points in the near field of an isolated transmitting antenna. Thus, mutual coupling effects are ignored for the time being. Consider a time-harmonic source radiating a spherical wave into an infinite homogeneous conducting medium. For an isotropic radiator, and suppressing the $e^{j\omega t}$ time dependence, the electric field as a function of range r can be expressed as $$E(r) = E_o \frac{e^{-\gamma r}}{r} \tag{62}$$

where $E_o$ is a constant.

For a source at the origin, the amplitude of the electric field at range $r_1$ is given by and at range $r_2$ by $$|E(r_1)| = E_o \frac{e^{-\alpha r_1}}{r_1} \tag{63}$$

$$|E(r_2)| = E_o \frac{e^{-\alpha r_2}}{r_2} \tag{64}$$

The total propagation loss between ranges $r_1$ and $r_2$ is found by taking the ratio of Equations (64) and (63), or $$\frac{|E(r_2)|}{|E(r_1)|} = \frac{r_1}{r_2} e^{-\alpha(r_2 - r_1)} \tag{65}$$

The field attenuation $A_{60}$ in dB from range $r_1$ to range $r_2$ due to the lossy dielectric is simply $$A_{60} = 20\log_{10}(e^{-\alpha(r_{+2} - r_1)}) \tag{66}$$

Similarly, the 1/r attenuation loss $A_r$ in dB is $$A_r = 20\log_{10}\frac{r_1}{r_2} \tag{67}$$

Thermal Modeling of an Inhomogeneous Target

A thermal analysis computer program called the transient thermal analyzer (TTA), developed by Arthur D. Little, Inc., has been used to accomplish the thermal modeling of homogeneous muscle tissue surrounded by a constant-temperature water bolus.

The TTA program uses the finite-difference technique to solve a set of nonlinear energy balance equations. Consider a system of interconnected nodes that model an inhomogeneous volume for which the temperature $T_i$ of the ith node is to be determined. The heat-balance equation, which is solved by TTA, is expressed as $$\sum_{i=1}^{N} Q_{i,j} - P_i(t) + M_i \frac{dT_i}{dt} = 0 \tag{68}$$

where $Q_{ij}$ is the net outward heat flow from node i in the direction of node j, $P_i(t)$ is the power into node i at time t, and $M_i$ is the thermal mass (mass times specific heat) of node i.

Figure 15:
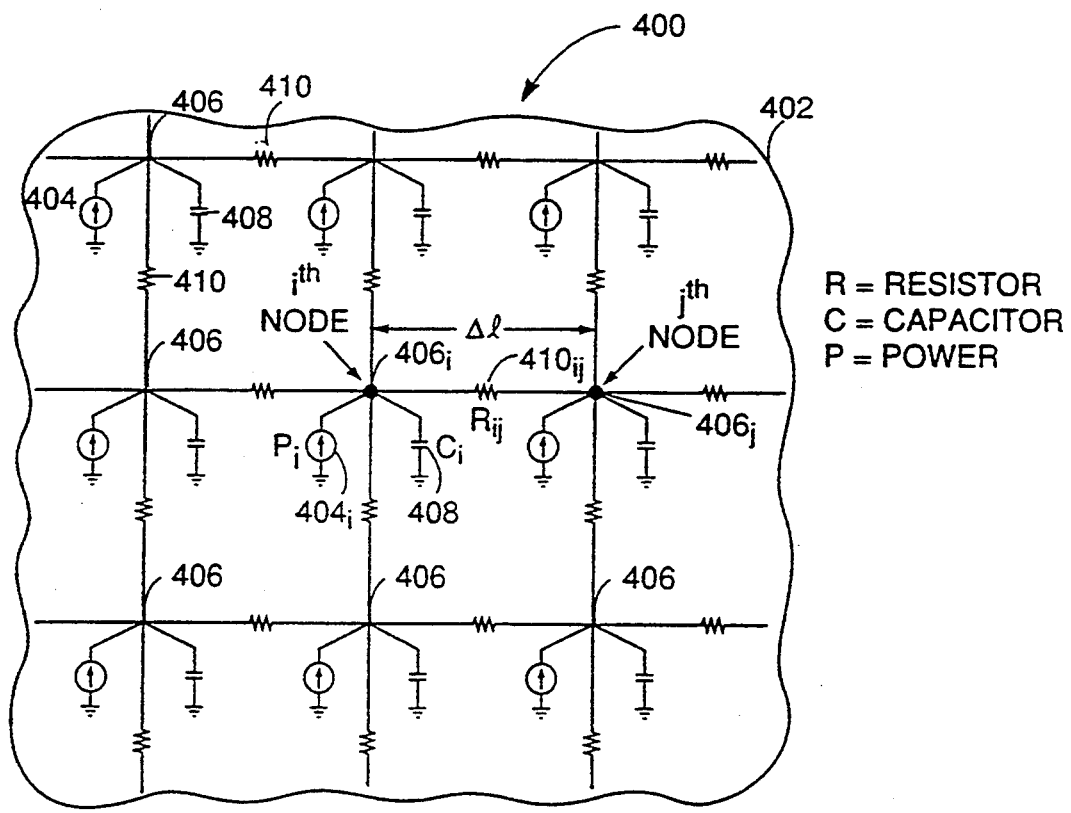
FIG. 15 is a schematic diagram of a thermal conductivity model for simulating hyperthermia heating within a target.

FIG. 15 shows an electric circuit analog 400 which is used to model the two-dimensional thermal characteristics of the material volume 402 which simulates the target body as a plurality of uniformly distributed nodes 406 spaced $\Delta 1$ apart. With reference to the ith node $406_i$, but applying generally to the other nodes, power $P_i$ in watts is delivered $404_i$ to the ith node. Capacitor $408_i$, having thermal capacitance denoted $C_i$ (with units Joules/°C.), is used to model the thermal capacitance at the ith node. Resistor $410_{ij}$, having heat resistance denoted $R_{ij}$ (with units °C./W), is used to model the heat resistance between ith node $406_i$ and the jth node $406_j$.

With a spacing of $\Delta 1$ between nodes (assuming cubic cells), the values of $R_{ij}$, $C_i$ and $P_i$ are computed as $$R_{i,j} = \frac{1}{k_{i,j}\Delta l} \tag{69}$$

where $k_{ij}$ is the thermal conductivity (with units W/m°C.) between nodes i and j;

$$C_i = \rho_i C_{pi}(\Delta 1)^3 \tag{70}$$

where $C_{pi}$ is the specific heat at the ith node and $\rho_i$ is the density (kg/m$^3$) at the ith node; and $$P_i = (SAR)_i \rho_i (\Delta 1)^3 \tag{71}$$

where $(SAR)_i$ is the SAR for the ith node, which is given by $$(SAR)_i = \frac{\sigma_i}{2\rho_i} |E_i|^2 \tag{72}$$

where $\sigma_i$ is the electrical conductivity of the ith node and $|E_i|$ is the magnitude of the electric field delivered by the hyperthermia array to the ith node. It should be noted that in substituting Equation (72) into Equation (71), the density $\rho_i$ cancels. Thus, an equivalent approach to computing the power delivered to the ith node is written in terms of the time-average power dissipated per unit volume of the ith node (denoted $P_{di}$) as $$P_i = P_{di}(\Delta 1)^3 \tag{73}$$

Figure 16A:
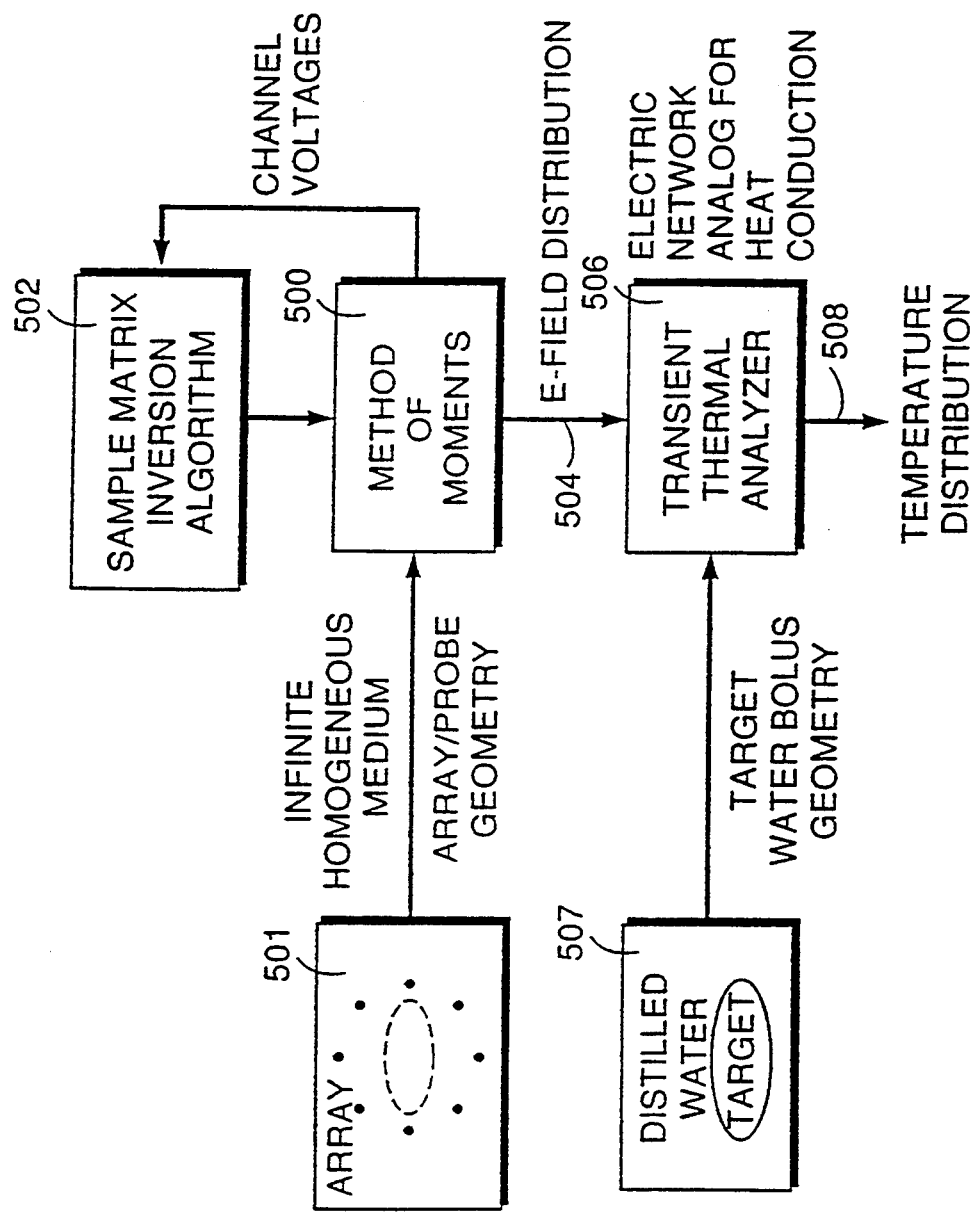
FIG. 16(a) is a block diagram detailing the simulation model of the hyperthermia array of FIG. 1.

FIG. 16 is a block diagram showing how TTA is used in the hyperthermia simulation described herein. First, the method of moments 500, controlled by the SMI nulling algorithm 502, is used to compute the electric field radiation pattern throughout a homogeneous region, simulating muscle tissue, inside an annular phased array 501. These E-field simulations assume that the signal received by a short-dipole probe within the region is due to a transmitting phased array embedded in an infinite homogeneous lossy dielectric (muscle tissue).

The resulting E-Field power distribution is then read 504 into the TTA program 506, which computes the temperature distribution inside an elliptical muscle-tissue target surrounded with a constant-temperature water bolus 507. Because the RF wavelengths in the target and water bolus are similar, the E-field simulations are believed to give a reasonable approximation to the field distribution inside the elliptical target. The computed temperature distribution is output 508 from the TTA for further analysis or display.

The E-field calculation in the assumed infinite homogeneous medium introduces additional field attenuation not present in a clinical hyperthermia system with an annular array transmitting through a water bolus into a patient. As mentioned earlier, the water bolus has very little RF propagation loss. In addition, the transmit array weights are normalized according to Equation (6). Thus, no attempt is made to compute the absolute E-field strength in volts/meter in the elliptical target. Instead, the peak power in the elliptical target is adjusted (by a scale factor) to produce a desired maximum focal-region temperature ($T_{max}$) after t minutes. It should be noted that an approximate absolute scale factor could be computed by making an initial computer simulation with an infinite homogeneous water bolus and then matching the target boundary field to the infinite homogeneous muscle tissue simulation.

The computer simulation model is related, in part, to the hyperthermia annular phased-array antenna system shown in FIG. 1. The simulated array is assumed to have a 60-cm array diameter with eight uniformly spaced dipole elements which operate over the frequency band 60–120 MHz. The eight elements of the array are assumed to be fully adaptive, whereby seven independent nulls can be formed while simultaneously focusing on a tumor.

It is further assumed for the purpose of this simulation that the adaptive radiation pattern null-width characteristics in a homogeneous target are similar to the characteristics observed in an inhomogeneous target. The null-width characteristics are directly related to the RF wavelength, and, only a 5 percent change in wavelength occurs between the assumed muscle tissue and water bolus. With this assumption, the transmit array may be simulated as embedded in homogeneous tissue, which allows direct use of the thin-wire moment-method formulation discussed above.

After computing the two-dimensional E-field distribution in the homogeneous medium, we then consider only an elliptical portion of the homogeneous region and use the ellipse as the homogeneous target. In the thermal analysis, the elliptical target is surrounded with a constant 10° C. water bolus. The E-field amplitude is scaled to produce a 46° C. peak temperature, at time t=20 minutes, at the center of the elliptical phantom. The initial temperature of the phantom is assumed to be 25° C. (room temperature).

All computer simulations assume a 120 MHz operating frequency with initially four auxiliary nulling probes, i.e., $N_{aux}=4$. The parameters used in the electrical and thermal analyses are summarized in Table 1. These parameters are for a frequency of 100 MHz, but is assumed that similar values of the parameters will exist at 120 MHz. It should be noted that although the relative dielectric constants of phantom muscle tissue and distilled water are very similar, the electrical conductivities are vastly different. The relevant thermal characteristics—density, specific heat, and thermal conductivity—are very similar for phantom muscle tissue and distilled water.

SIMULATION RESULTS

Electric Field for Array in Homogeneous Tissue

Substituting the values f=120 MHz, $\sigma=0.5$ S/m, and $\epsilon_r=73.5$ into Equation (53) yields $\gamma_m=10.0+j23.8$ for the muscle tissue. With $\beta_m=23.8$ radians/m, the wavelength in the phantom muscle tissue is $\lambda_m=26.5$ cm. The attenuation constant for the muscle tissue is $\alpha_m=10.0$ radians/m. Similarly, for distilled water $\gamma_w=0.0021+j22.5$, so the wavelength is $\lambda_w=27.9$ cm. The attenuation constant for the distilled water medium is $\alpha_w=0.0021$ radians/m. The propagation loss in the phantom muscle tissue is $20\log_{10}e^{-10.0}$, or $-0.87$ dB/cm. Similarly, the propagation loss in the distilled water is found to be $-0.0002$ dB/cm. Thus, the total loss due to propagation through 15 cm of distilled water is 0.003 dB. For 15 cm of muscle tissue the corresponding loss is 13.1 dB. The wave impedance in the muscle tissue is computed from Equation (58) as $\eta_m=33.9+j14.2$ Ω, and similarly in the distilled water $\eta_w=42.1+j0.004$ Ω.

Figure 17:
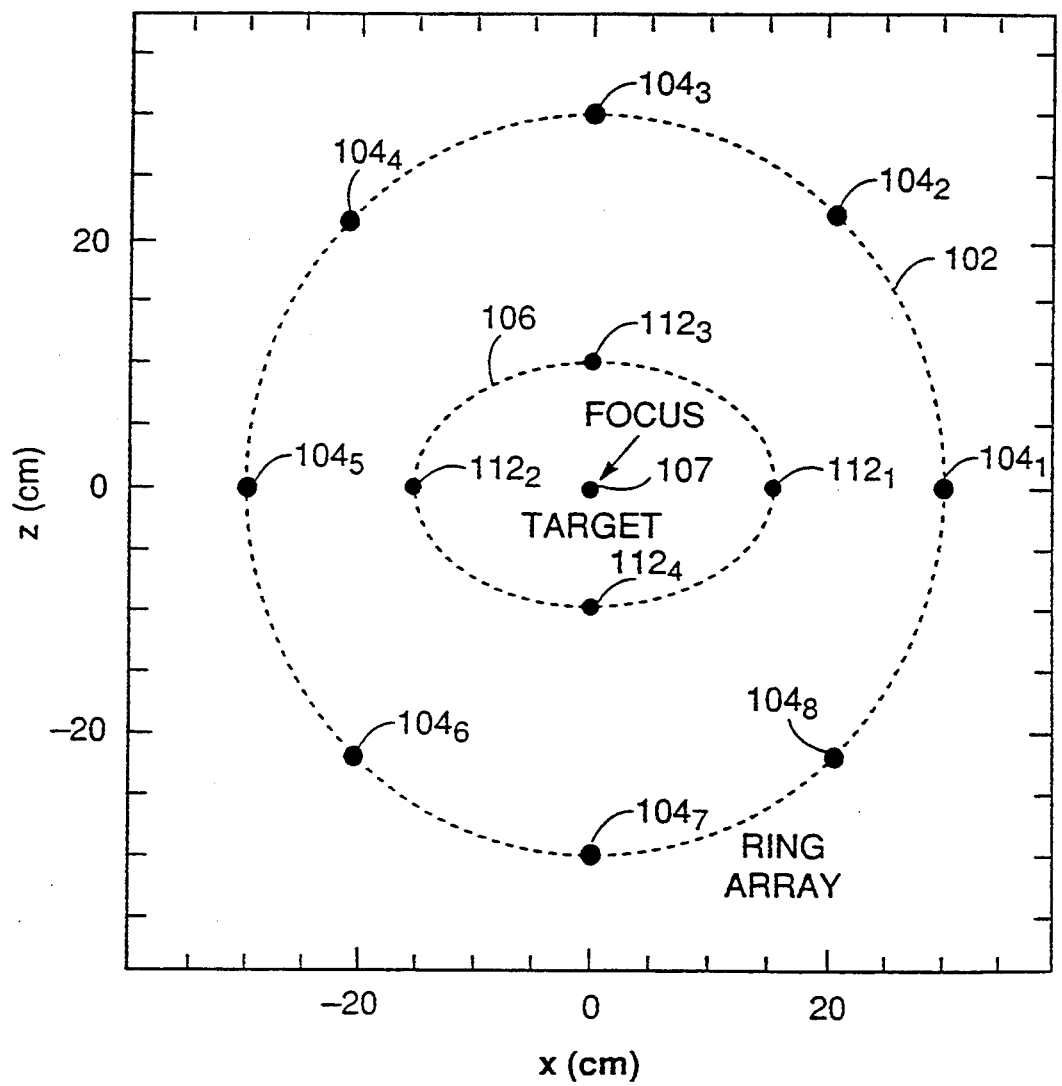
FIG. 17 is a schematic diagram of the transmit antenna array and auxiliary probe array geometries for the simulation model of FIG. 16(a).

FIG. 17 shows the geometry used in the simulations, which parallels the array shown in FIG. 3. A 60-cm-diameter ring phased array applicator 102 of eight perfectly conducting center-fed dipoles, $104_1$ through $104_8$, uniformly surrounds a fictitious elliptical target zone 106 with major axis 30 cm and minor axis 20 cm. The length of each dipole array element $104_n$ at 120 MHz in the infinite homogeneous muscle tissue is $\lambda/2$, or 13.25 cm. The array focus 107 is assumed at the origin (x=0, y=0, z=0) and four auxiliary short-dipole probes, $112_1$ through $112_4$, with length 1.27 cm (0.05λ) are positioned at (x,y,z) coordinates at (15 cm, 0, 0), (−15 cm, 0, 0), (0, 0, 10 cm), and (0, 0, −10 cm), respectively, i.e., the auxiliary E-field probes are located every 90° in azimuth on the perimeter of the target. In rectangular coordinates, each dipole is oriented along the y direction and the feed terminals of each dipole are located at y=0.

The moment-method computer simulations were run on a Sun 3/260 workstation. The total CPU time for a complete moment-method run is 19.2 minutes. This CPU time includes computing the quiescent and adaptive radiation patterns on a 41 by 41 grid of points. The CPU time without radiation pattern calculations is 33 seconds.

Figure 18:
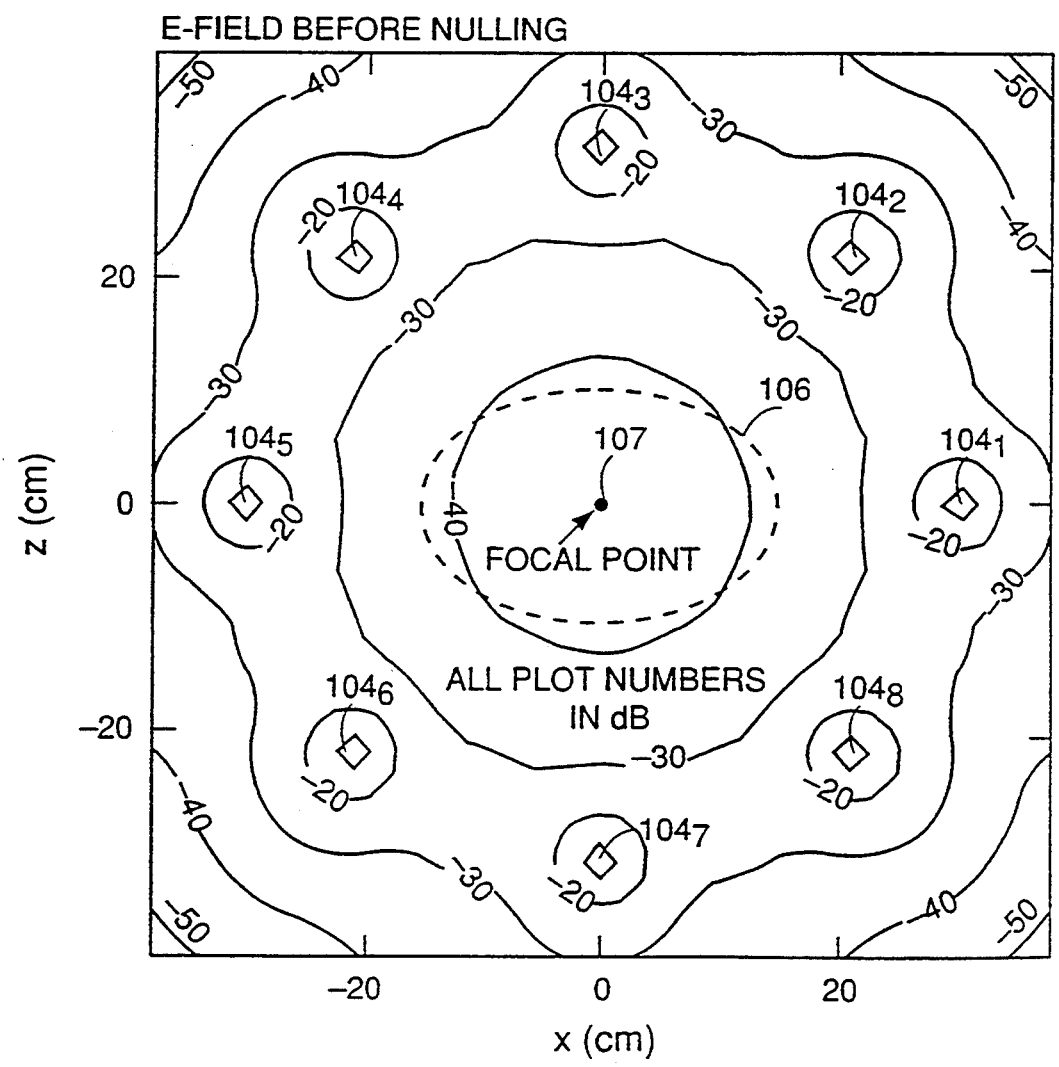
FIG. 18 is a diagram of the simulated E-field for the simulation model of FIG. 16(a) prior to adaptive nulling.

FIG. 18 shows the two-dimensional radiation pattern in the plane y=0, before nulling, at 120 MHz with uniform amplitude and phase illumination. The calculated data are collected on a 41 by 41 grid of points over a square region, with side length 76.2 cm, centered at the focus 107. The spacing between data points is 1905 cm, or 0072λ, and the contour levels are displayed in 10-dB steps. The E-field data are computed for the case of a 1.27-cm short-dipole observation probe. The positions of the eight dipole radiators $104_1$ through $104_8$ are clearly evident by the −20 dB contours surrounding each element. The radiation pattern is symmetric because of the symmetry of the array and the assumed homogeneous medium.

Figure 19:
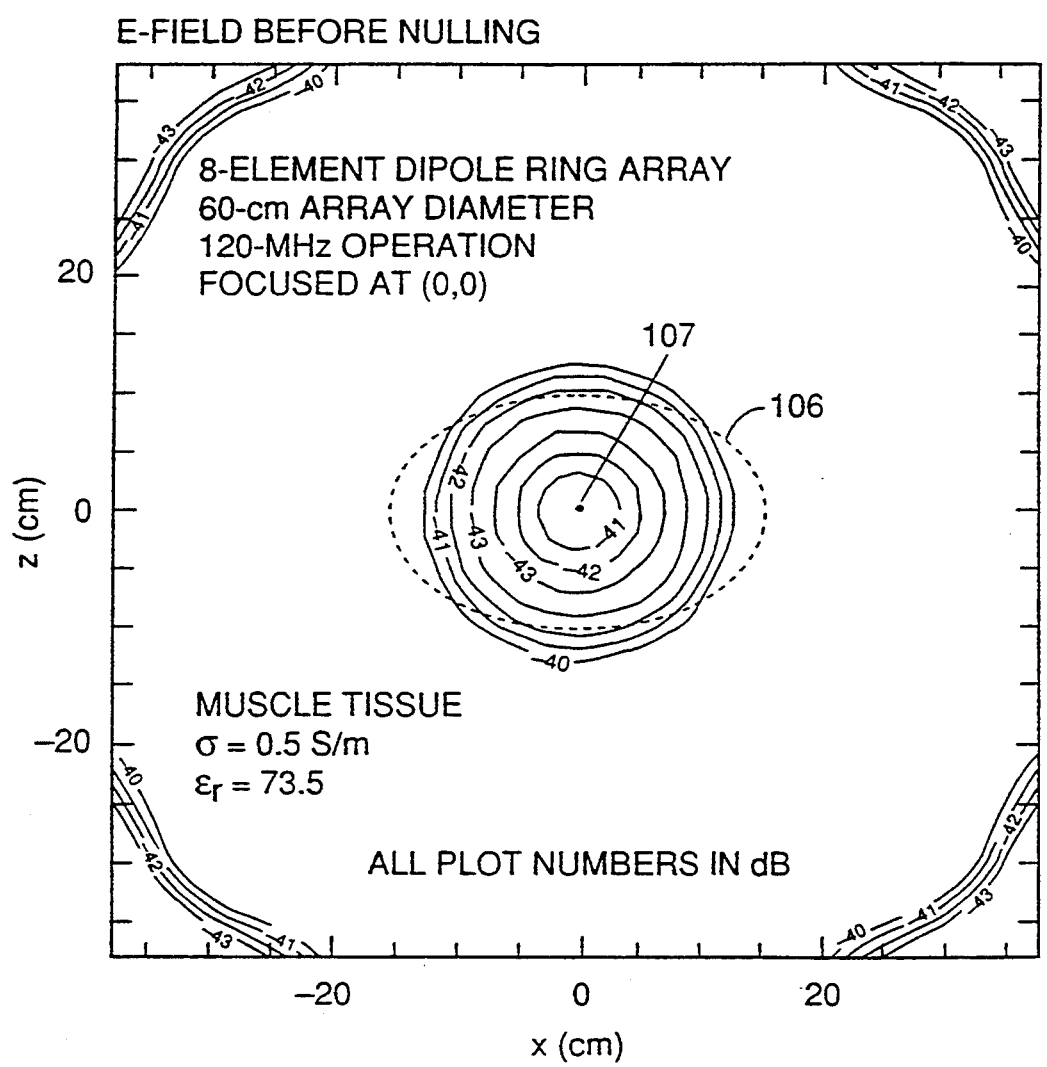
FIG. 19 is a diagram of the simulated profile in 1 dB steps for the E-field of FIG. 18.

FIG. 19 shows finer contour levels (1-dB steps) for the quiescent radiation pattern of FIG. 18. Here, it is evident that the focused main beam of the ring array is increasing in amplitude as the observation point moves closer to the focus. Away from the main beam region, the pattern amplitude is seen to increase as the observation position moves toward the array perimeter.

Figure 20:
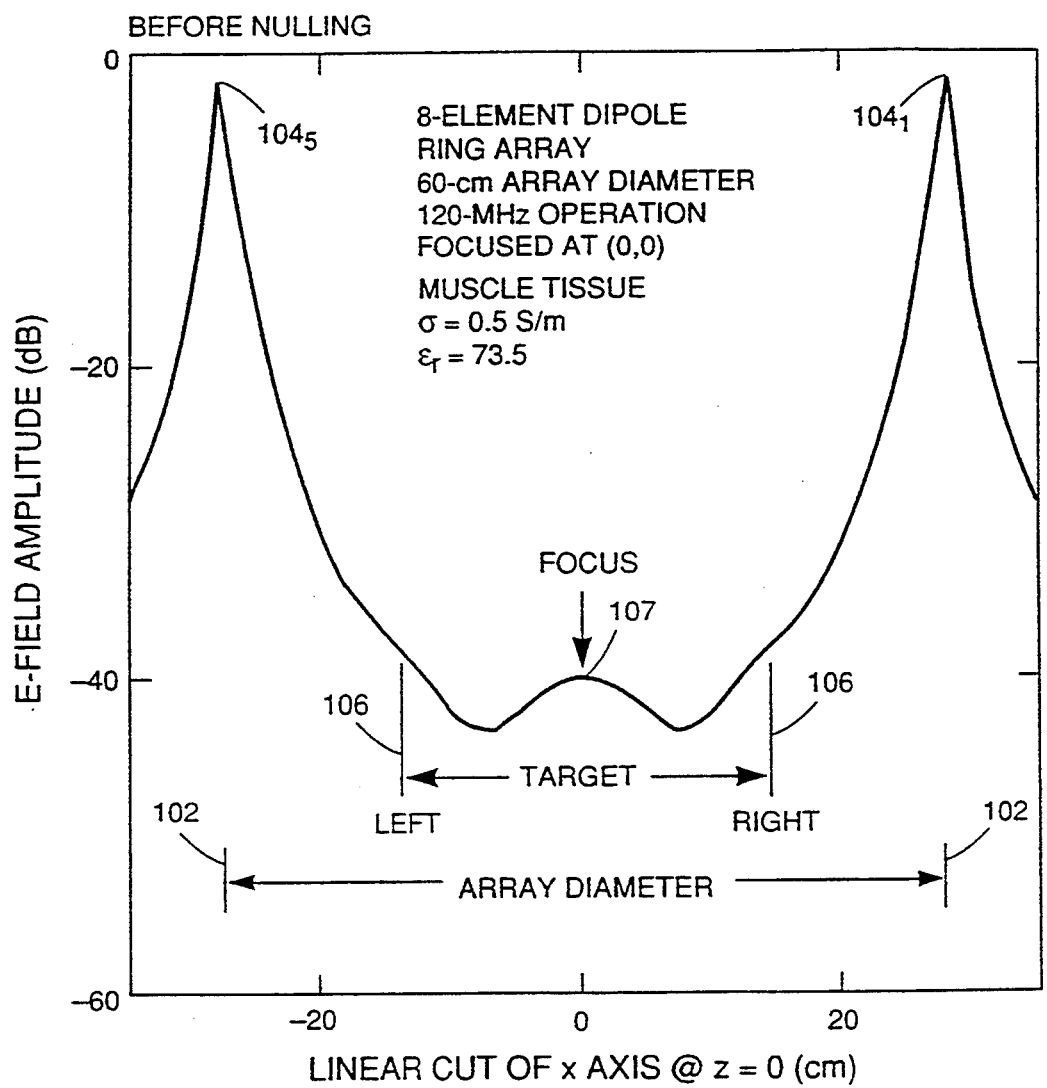
FIGS. 20 and 21 are diagrams of the simulated E-field profile of FIG. 19 taken along the x- and z-axes, respectively.
Figure 21:
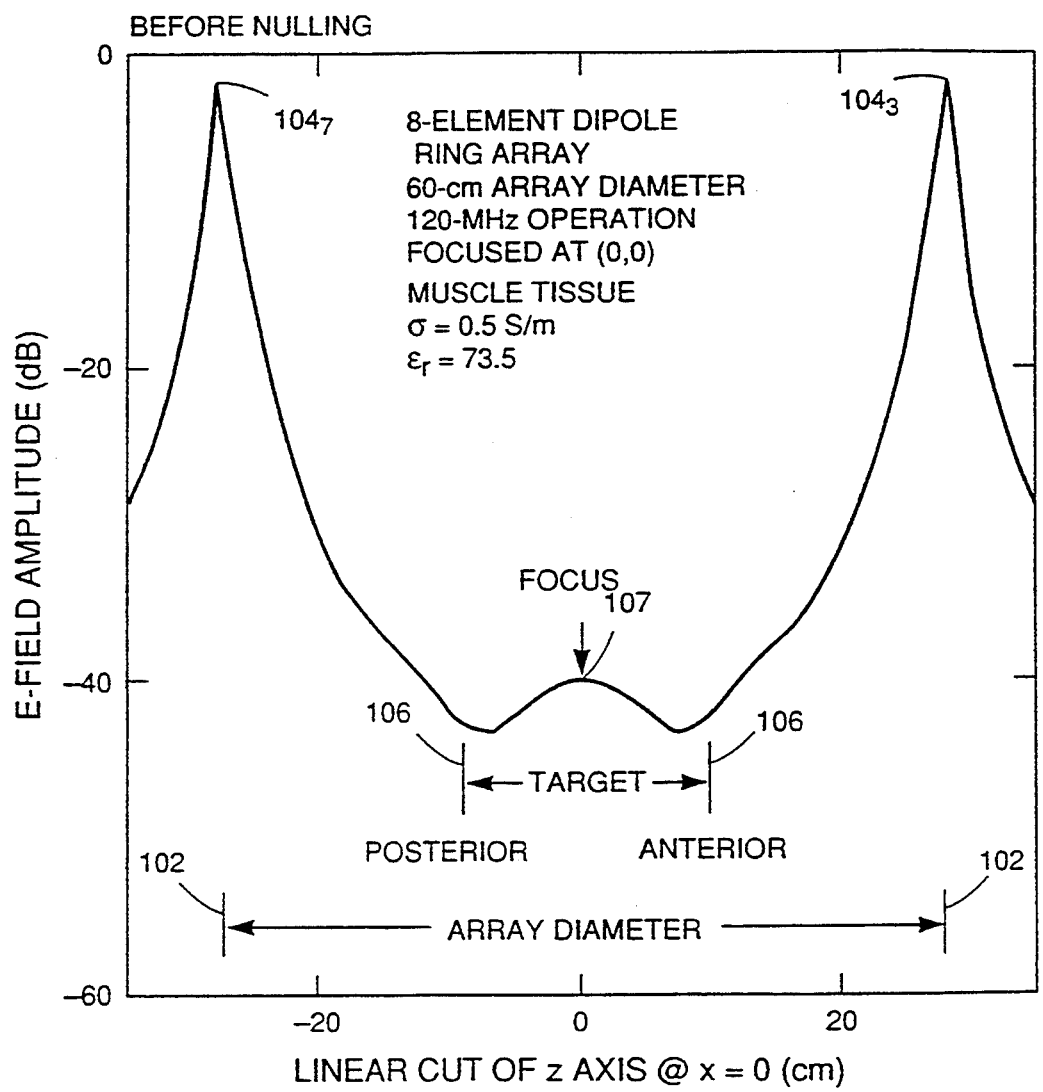

FIG. 20 shows the quiescent radiation pattern of FIG. 18 cut at z=0. The large amplitude that occurs at ±30 cm, i.e., at the position of the phased array applicator 102, is due to the E-field probe's close proximity to the transmitting elements $104_1$ and $104_5$. The large attenuation that occurs from the array diameter to the focus is due to the 1/r attenuation loss and the loss in the uniform homogeneous muscle tissue. FIG. 21 shows the radiation pattern of FIG. 18 cut at x=0. Here, the pattern is identical to the pattern of FIG. 20 due to the symmetry of the array. In both FIGS. 20 and 21 the boundary of the fictitious elliptical target zone 106 is indicated. The target zone of FIG. 20 is larger than that of FIG. 21 since the major axis of elliptical target 106 lies along the x-axis, and the minor axis of target 106 lies along the z-axis.

The increasing radiation pattern amplitude near the left and right sides of the elliptical target of FIG. 20 is shown to produce hot spots in the thermal distribution. Because the top (anterior) and bottom (posterior) of the elliptical target of FIG. 21 are not as strongly illuminated as to the left and right sides of the elliptical target of FIG. 20, no quiescent hot spots occur at the top or bottom.

Further, FIG. 20 shows that the ring-array half-power beamwidth in the target region is approximately 13 cm, or approximately one-half the wavelength (26.5 cm) in the phantom muscle tissue. The adaptive nulling resolution or closest allowed spacing between a strong adaptive null and the main beam has been shown to be equal to the half-power beamwidth of the antenna. Thus, the closest allowed null position is 13 cm from the focus. Since the target width is 30 cm across the major axis, two nulls can be formed at (x=±15 cm, z=0) at the left and right side of the target without disturbing the focus. However, if two strong nulls are formed at the posterior and anterior (x=0, z=±10 cm) of the target the focus will be compromised. In practice, the water bolus surrounding the target would restrict the placement of short-dipole probes $112_n$ to the surface of the target. Thus, only weak nulls can be formed at (x=0, z=±10 cm) so that the focus will not be affected by the adaptive nulling process. That is, the effect of the two minor axis nulls is to keep the z=±10 cm E-field from increasing beyond the quiescent values.

Next, adaptive radiation patterns are computed with four auxiliary dipole probes $112_1$ through $112_4$ positioned as shown in FIG. 17. The value of the receiving gain for auxiliary dipole probes $112_1$ and $112_2$ is adjusted to produce a SNR>35 dB. This amount of SNR results in greater than 35 dB of nulling in the direction of auxiliary dipole probes $112_1$ and $112_2$. In contrast, the gain values for auxiliary dipole probes $112_3$ and $112_4$ are turned down to produce about a 3 dB SNR. Thus, only about 3 dB of nulling will occur at probe positions $112_3$ and $112_4$ as the adaptive algorithm reduces the interference to the noise level of the receiver. The reason for choosing these null strengths will become apparent with the data that follow.

Figure 22:
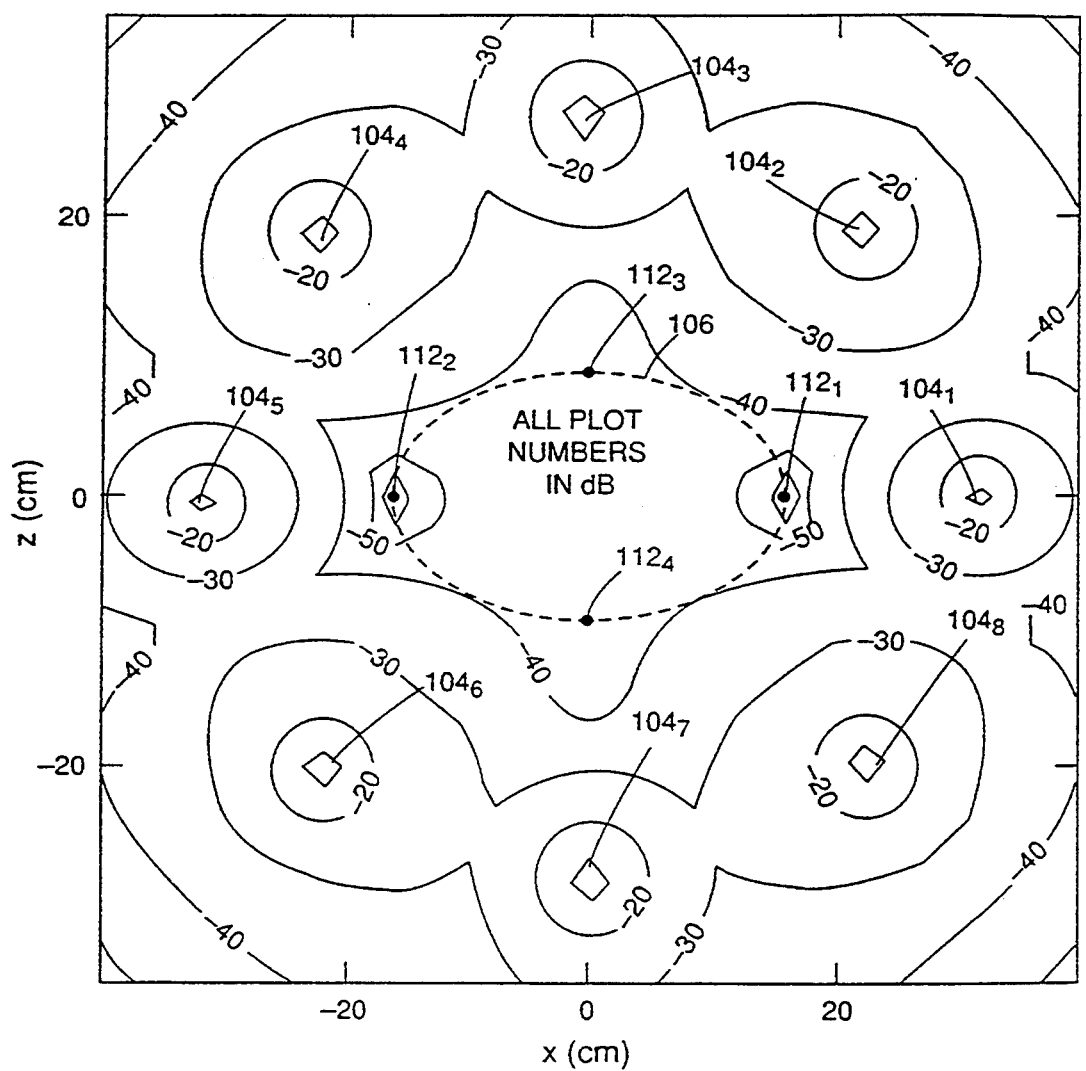
FIG. 22 is a diagram of the simulated E-field for the simulation model of FIG. 16(a) after adaptive nulling.

FIG. 22 shows the two-dimensional radiation pattern after nulling with four auxiliary probes $112_1$ through $112_4$. Two strong adaptive nulls at $x = \pm 15$ cm occur as expected, and weak nulling occurs at $z = \pm 10$ cm, also as expected.

Figure 23:
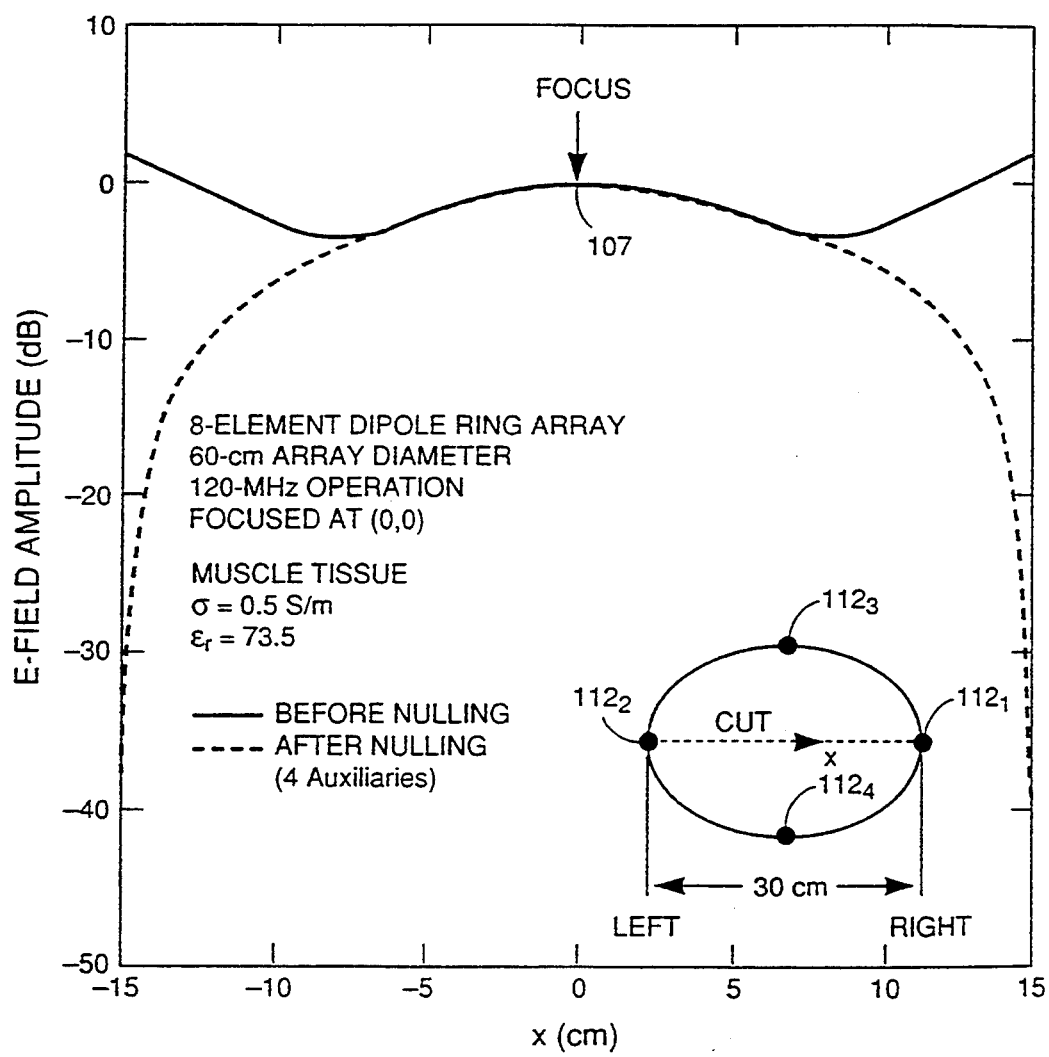
FIGS. 23 and 24 are diagrams of the simulated E-field of FIGS. 18 and 22 taken along the x- and z-axes, respectively.
Figure 24:
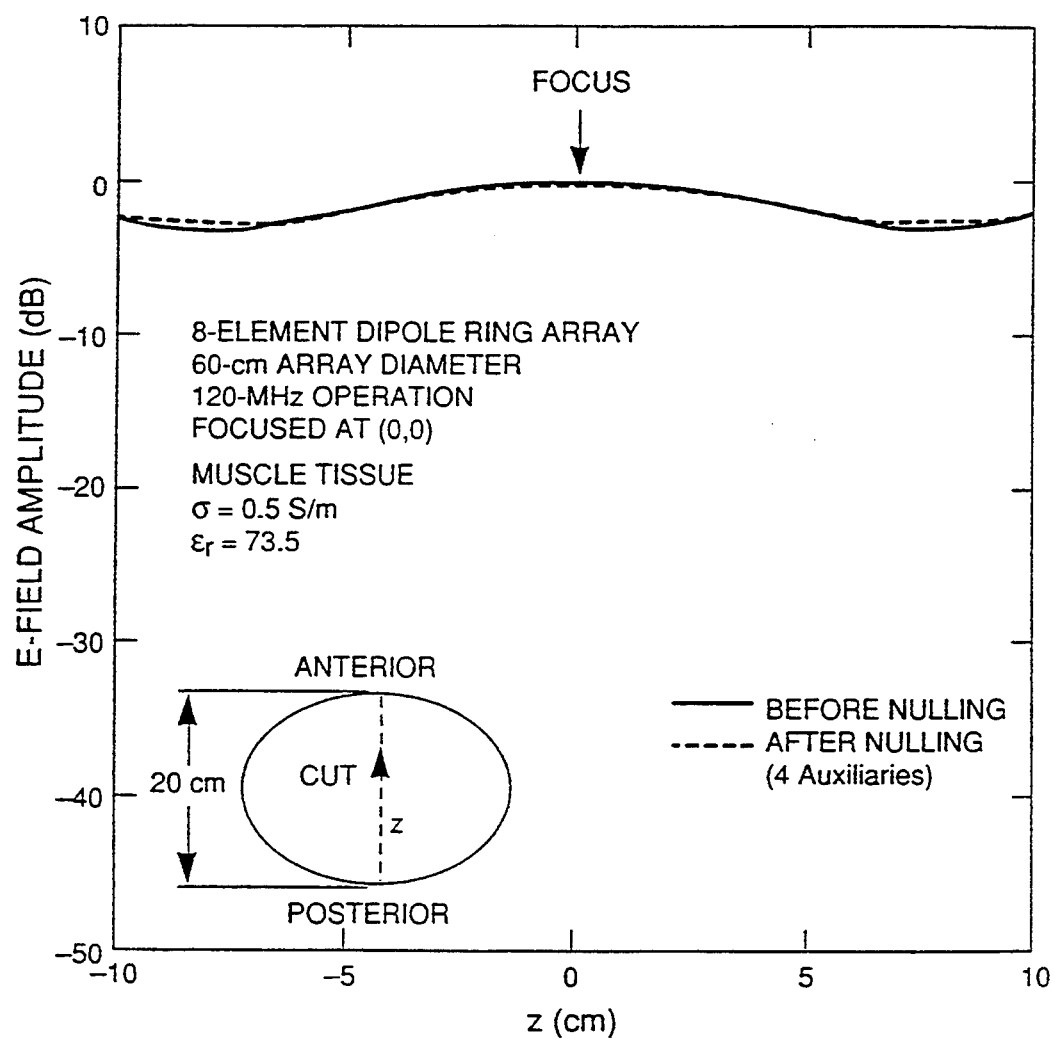

The two strong nulls in the $z=0$ cut are quantified in FIG. 23, where greater than 35 dB of interference nulling or pattern reduction occurs at $x = \pm 15$ cm. The peak level at the focus 107 is adjusted to 0 dB for both the quiescent and adaptive patterns. Two weak adaptive nulls are seen in the $x=0$ radiation pattern cut shown in FIG. 24. The weak nulls in effect in the adaptive patterns reduce variation from the quiescent radiation pattern.

Figure 25A:
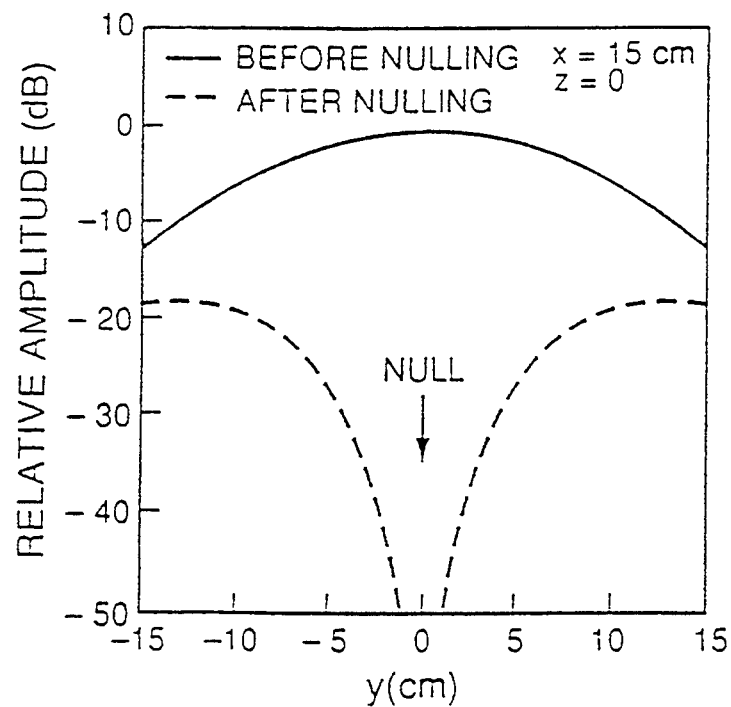
FIG. 25(a) is a diagram of the simulated E-field before and after adaptive nulling taken longitudinally in the y direction along the x=15, z=0 cm line of the geometry shown in FIG. 25(b).
Figure 25B:
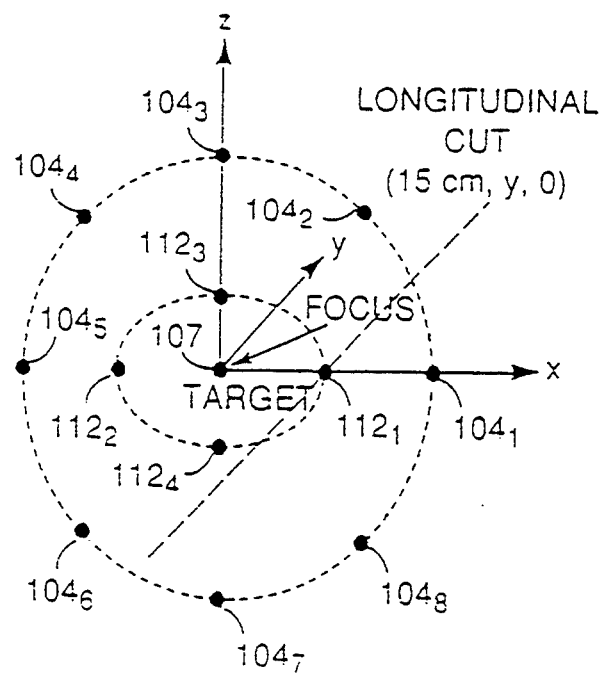

FIG. 25(a) shows the two-dimensional radiation pattern before and after nulling taken longitudinally along a line parallel to the y-axis and passing through probe $112_1$ as shown in FIG. 25(b), i.e., $x=15$ cm, $z=0$. This radiation pattern clearly shows that a strong adaptive null also extends in the y direction from the E-field probe being nulled.

Figures 26A, 26B:
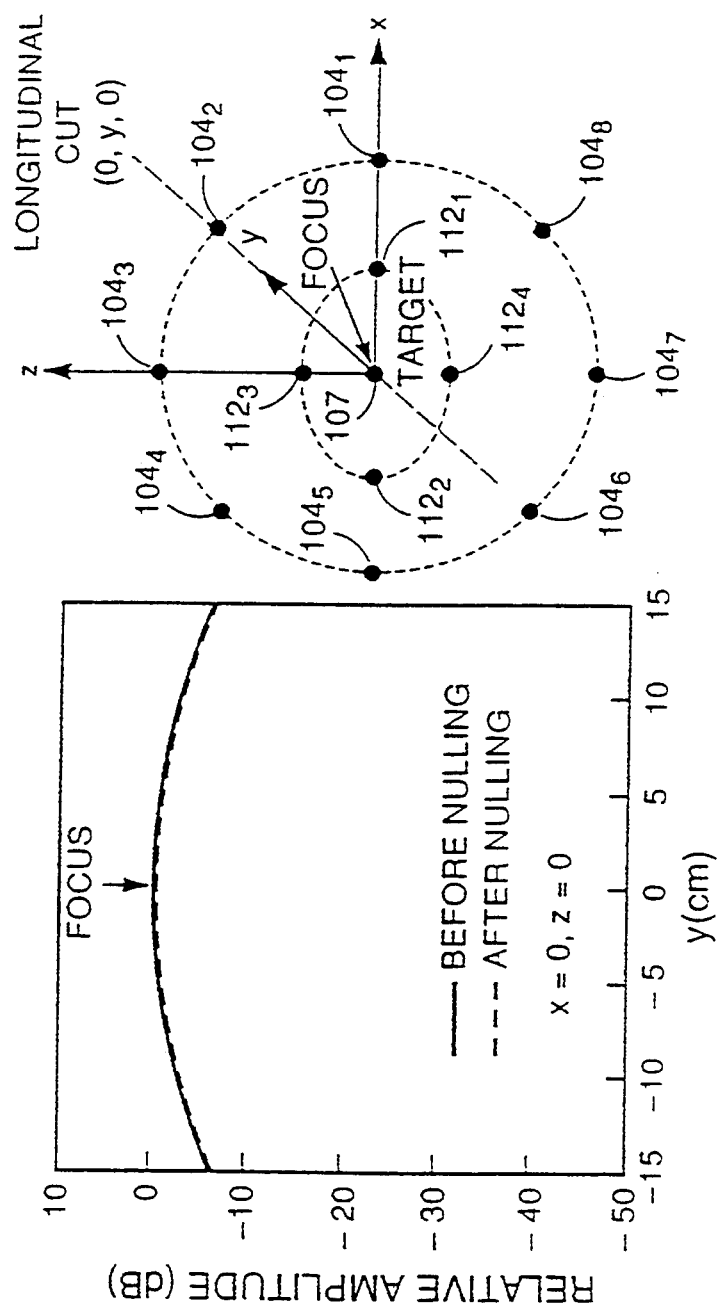
FIG. 26(a) is a diagram of the simulated E-field before and after adaptive nulling taken longitudinally along the y axis (x=0, z=0 cm) of the geometry shown in FIG. 26(b).

FIG. 26(a) shows the two-dimensional radiation pattern before and after nulling taken along the y-axis and passing through the focus 107 as shown in FIG. 26(b), i.e., $x=0$, $z=0$. This radiation pattern clearly shows that the E-field at the focus remains virtually the same in the y direction before and after adaptive nulling at the E-field probes $112_1$ through $112_4$.

Figure 27:
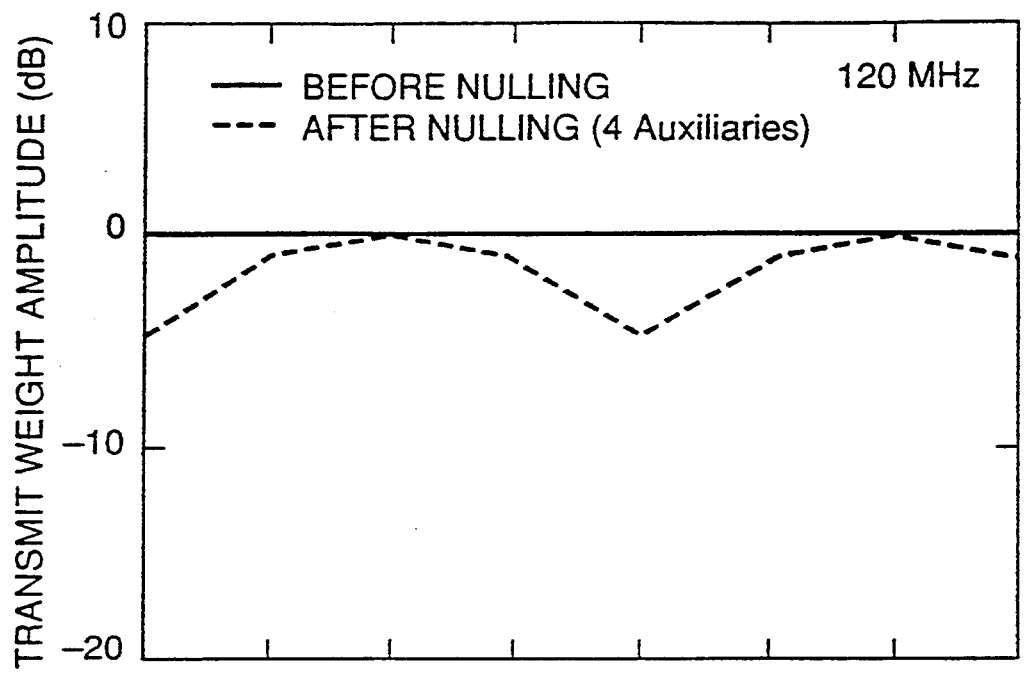
FIGS. 27(a) and 27(b) are graphs showing the transmit weight amplitude and phase, respectively, before and after adaptive nulling.
Figure 27:
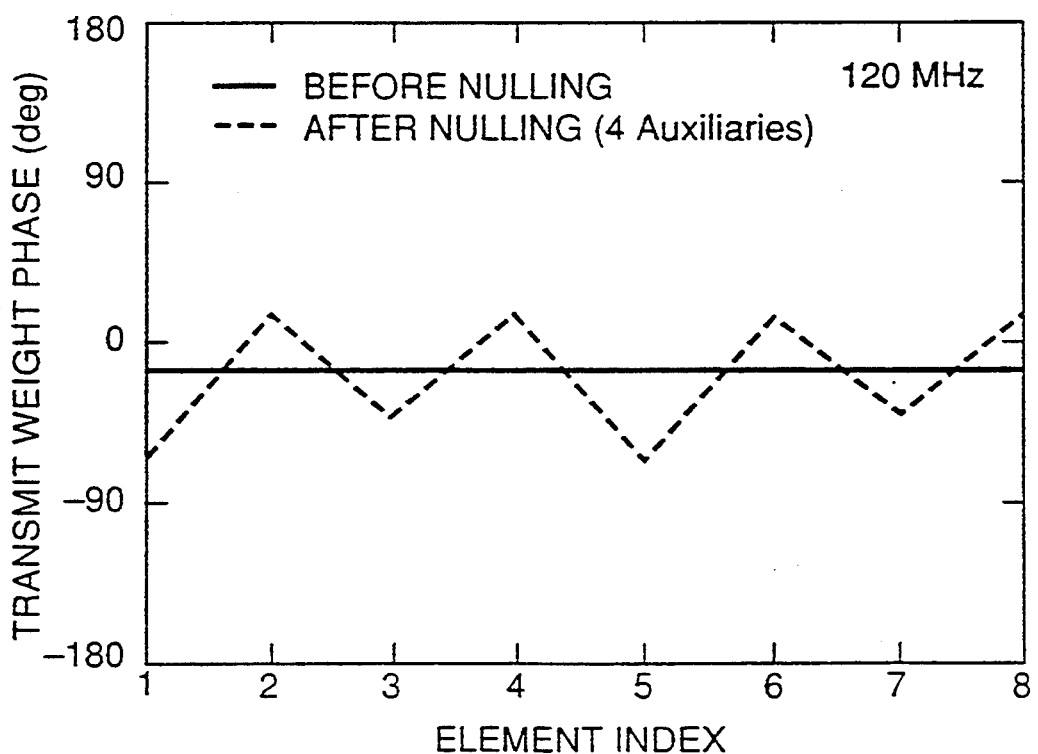

FIG. 27(a) shows the transmit array amplitude weights before (solid line) and after (broken line) nulling, and FIG. 27(b) shows the transmit array phase weights before (solid line) and after (broken line) nulling. As shown, the adaptive transmit weights exhibit a 5-dB dynamic range in FIG. 27(a).

Figure 28:
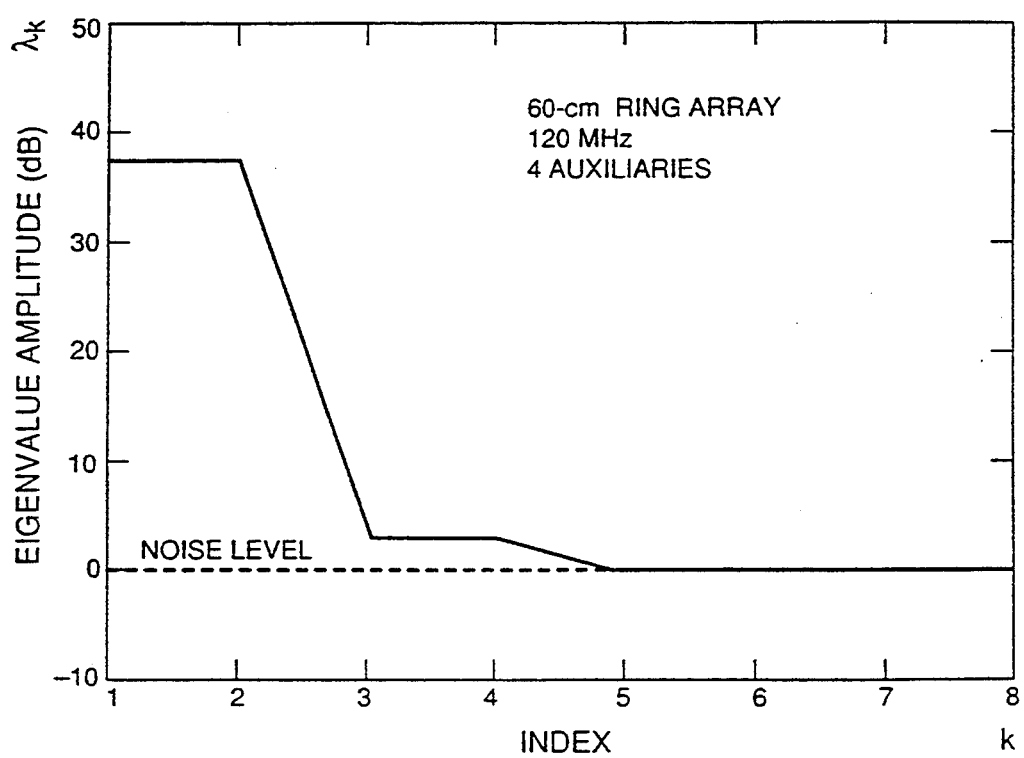
FIG. 28 is a graph showing the channel correlation matrix eigenvalues.

FIG. 28 shows the channel correlation matrix eigenvalues before (solid line) and after (broken line) nulling. There are two large eigenvalues, $\lambda_1$ and $\lambda_2$, and two weak (non-zero) eigenvalues, $\lambda_3$ and $\lambda_4$, shown in FIG. 28. These eigenvalues are directly associated with the two high-SNR auxiliary probes $112_1$ and $112_2$, and the two weak-SNR auxiliary probes $112_3$ and $112_4$, respectively. Note that the 0-dB level in FIG. 28 is equal to the receiver noise level. The probe-array output power before and after adaptive nulling is 31.4 dB and 0.9 dB, respectively, as calculated from equation (10). This difference in power before and after nulling indicates that the adaptive cancellation is $-30.5$ dB.

Temperature Distribution in Elliptical Phantom

To simulate the temperature distribution in the target body resulting from the calculated E-fields, the transient thermal analysis (TTA) software is used to compute the temperature distribution in an elliptical phantom surrounded with a constant-temperature water bolus. The 41×41 two-dimensional E-field radiation pattern data of FIGS. 18 through 24 are used as the power source for the thermal node network. Two node spacings are considered. First, the node spacing $\Delta x = \Delta z = \Delta 1 = 1.905$ cm (coarse grid) is used to obtain thermal data. Then, the node spacing is decreased by a factor of two to $\Delta 1 = 0.9525$ cm (fine grid) to check convergence. The coarser spacing is shown to be adequate.

Figure 29:
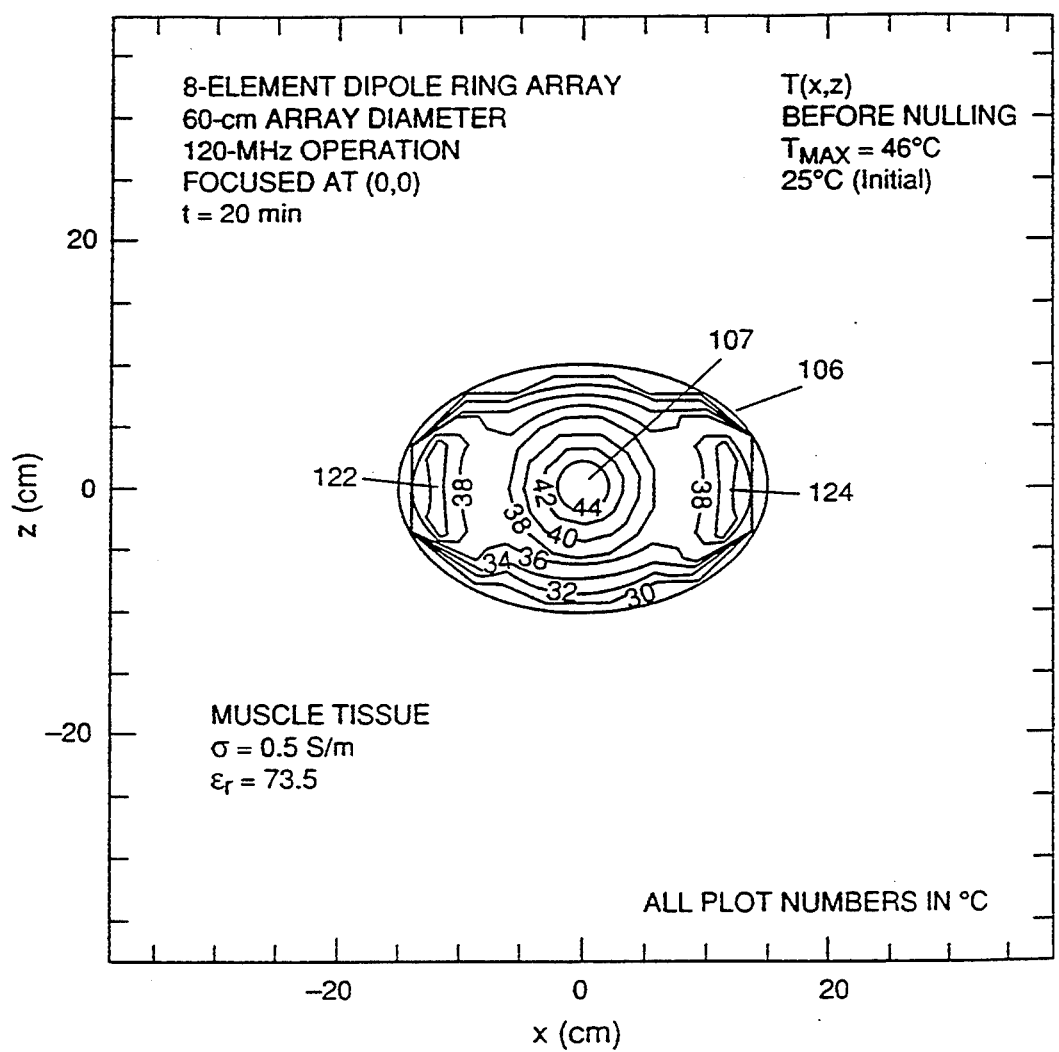
FIG. 29 is a diagram of the simulated target temperature profile for the E-field of FIG. 18 prior to adaptive nulling.
Figure 30:
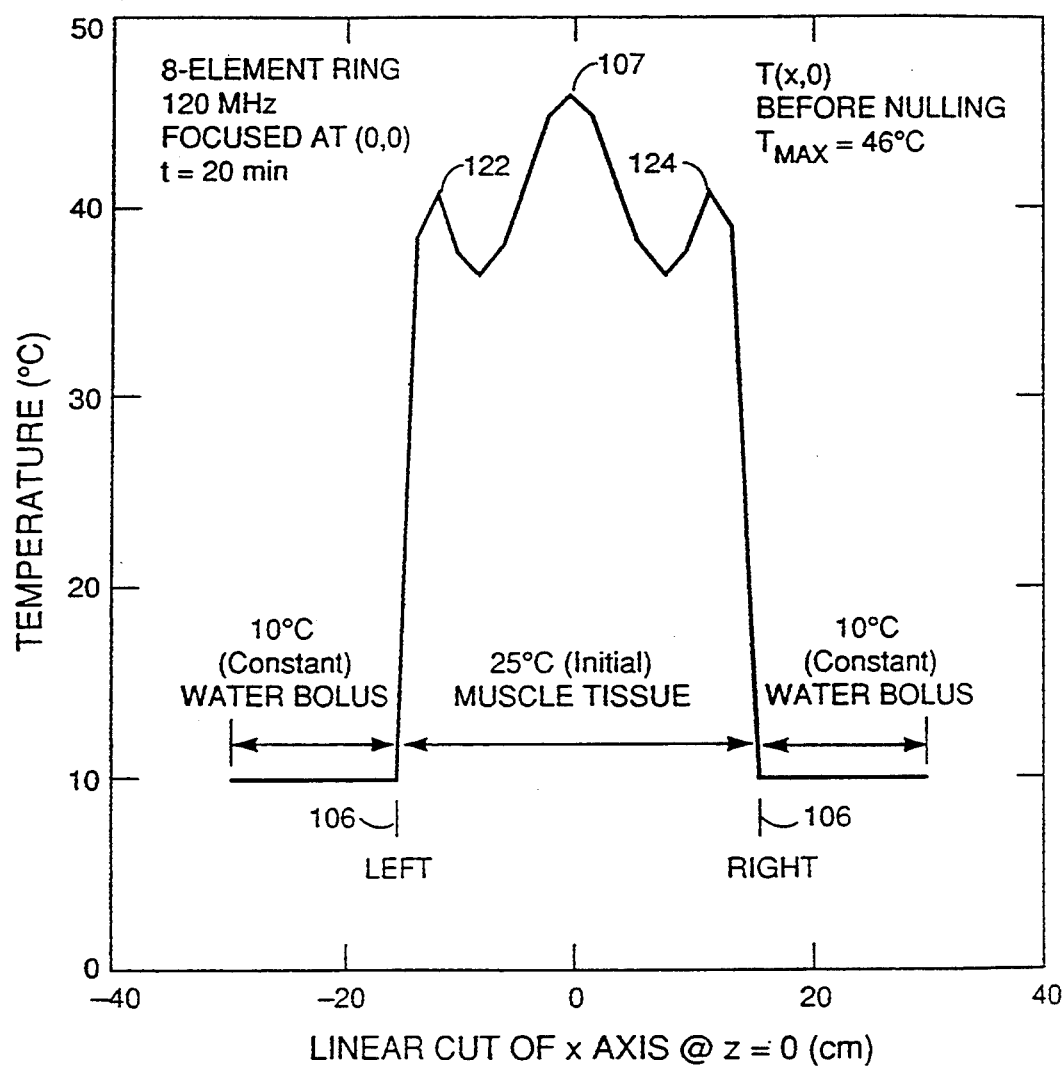
FIGS. 30 and 31 are diagrams of the temperature profile of FIG. 29 taken along the x- and z-axes, respectively.
Figure 31:
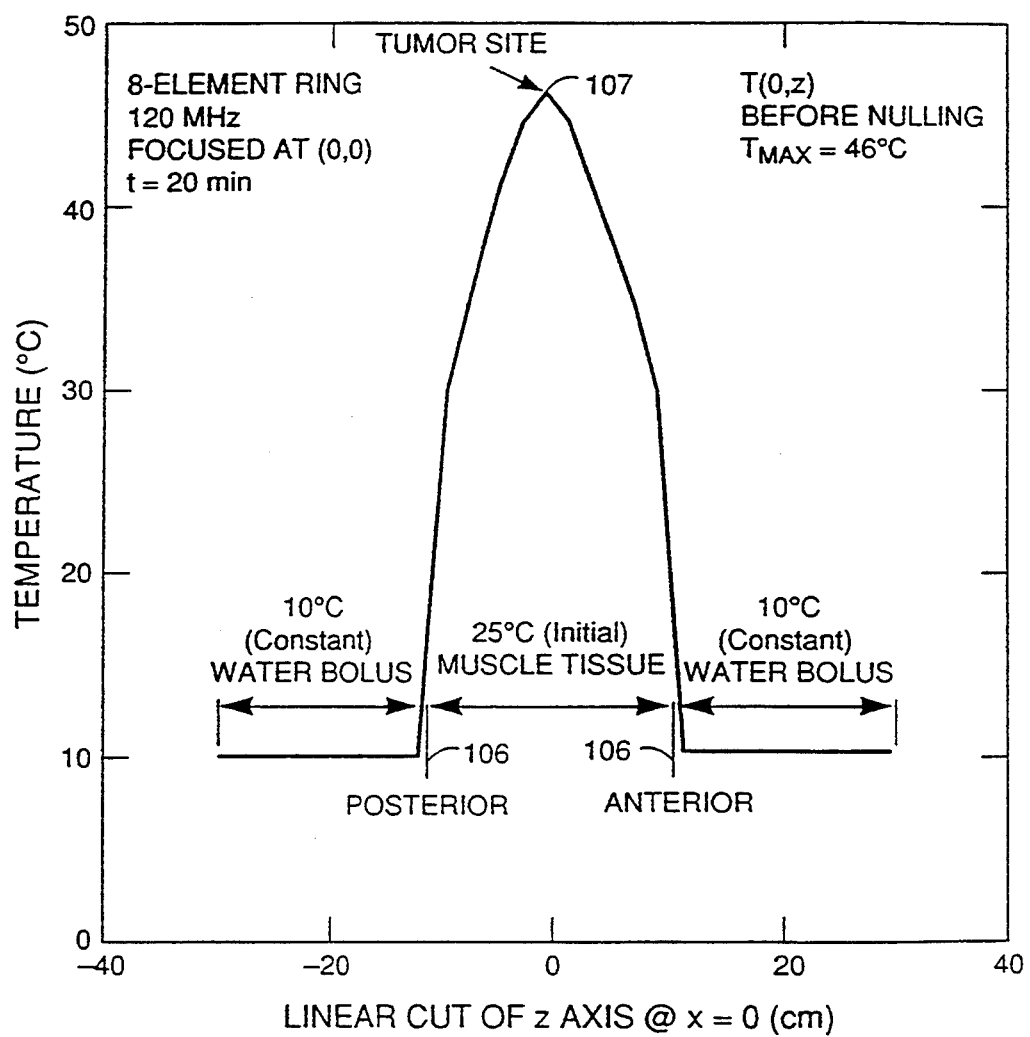

The scale factors used to convert the normalized E-field distributions to a power level that induces a 46° C. peak temperature at $t=20$ minutes are 94.1 dB and 96.0 dB for the quiescent and adaptive patterns, respectively. These scale factors are determined empirically. From Equations (68) through (73) and the parameter values given in Table 1, all resistors $R_{ij}$ in the phantom muscle tissue had a value of 96.5° C./W and all resistors $R_{ij}$ in the water bolus had a value of 87.2° C./W. The value of the capacitors $C_i$ in the phantom muscle tissue is 23.6 J/°C. Capacitors are not used in the water-bolus region in the input to the transient thermal analysis software. Instead, a constant temperature of 10° C. is enforced at each water-bolus node. With a 41×41 grid, a total of 3280 resistors and 1681 capacitors are used in the thermal simulation. The CPU time required to compute this temperature distribution is under four minutes. FIG. 29 shows the two-dimensional temperature distribution produced at time $t=20$ minutes in the elliptical phantom muscle tissue target 106 without adaptive nulling. To generate FIG. 29, the power source used in the transient thermal analysis is the quiescent radiation pattern given in FIG. 18. The initial temperature (at time $t=0$) is 25° C. Notice the occurrence of two hot spots 122 and 124 on the left and right sides of the elliptical phantom, respectively. The peak temperature at focus 107 is 46° C., which is achieved by scaling the normalized quiescent E-field as described earlier. The two hot spots 122 and 124 are quantified in the $z=0$ temperature pattern cut shown in FIG. 30, and have a peak temperature at each hot spot of approximately 41° C. The temperature profile for $x=0$ in FIG. 31 shows no hot spots. As any undesired hot spot is a potential source for compromising the therapy session, adaptive nulling is used to reduce the sidelobes corresponding to the hot spots.

Figure 32:
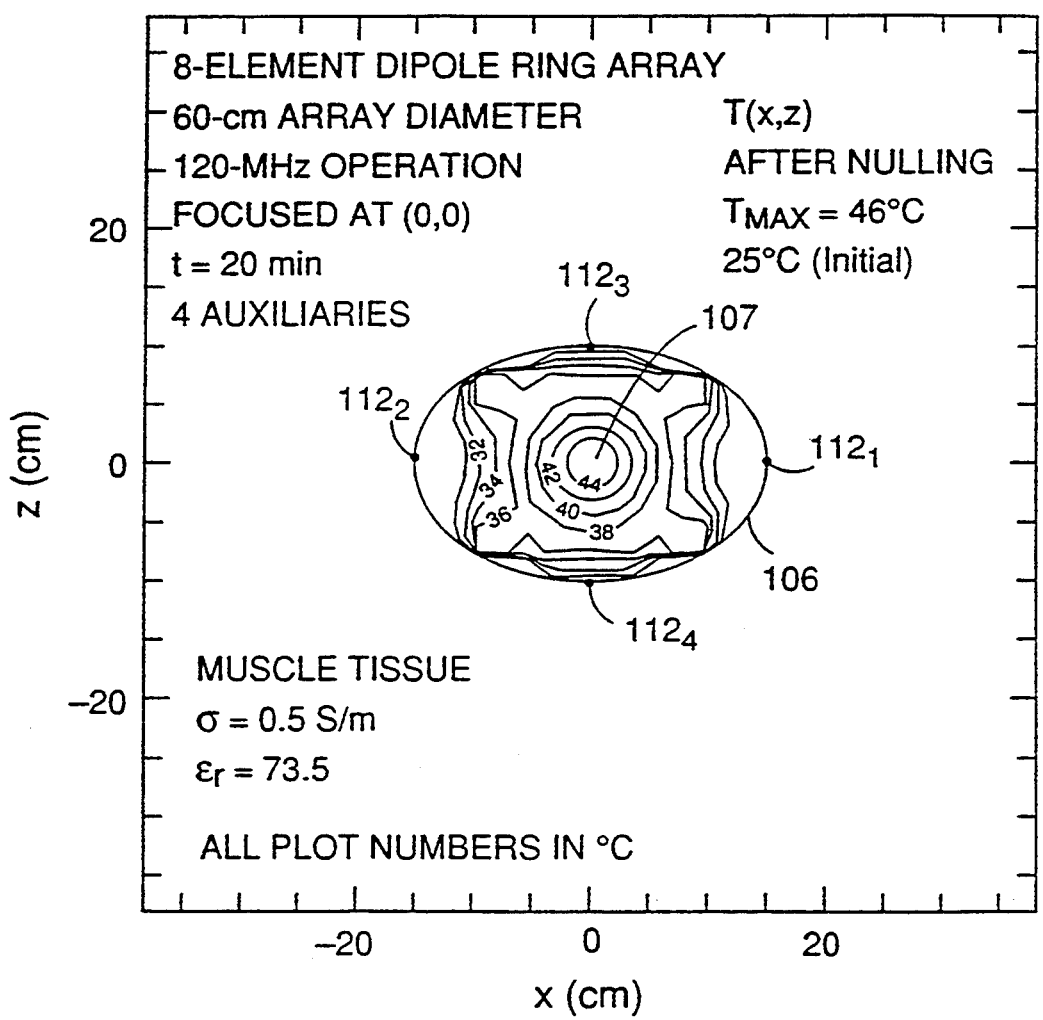
FIG. 32 is a diagram of the simulated target temperature profile for the E-field of FIG. 22 after adaptive nulling.
Figure 33:
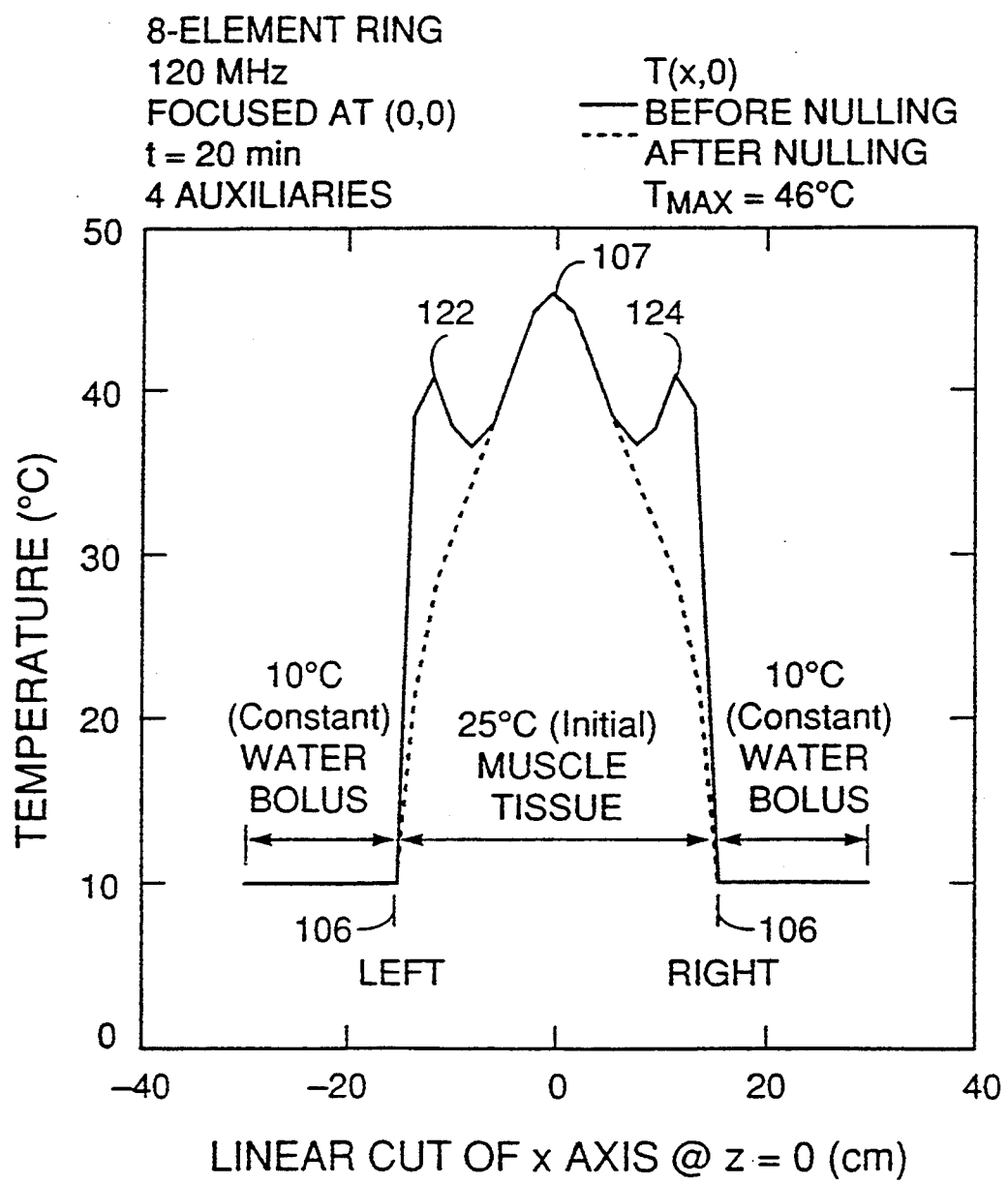
FIGS. 33 and 34 are diagrams of the temperature profile of FIGS. 29 and 32 taken along the x- and z-axes, respectively.
Figure 34:
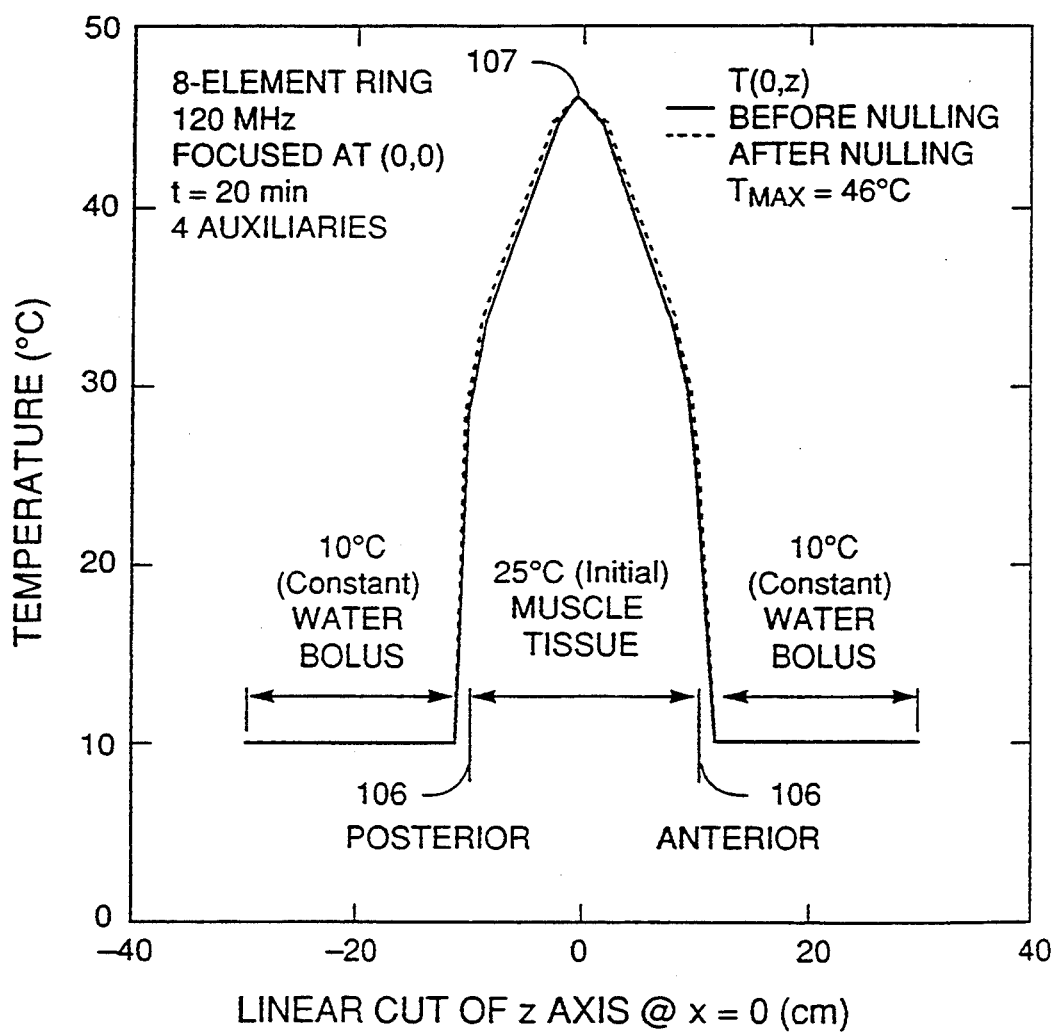

FIG. 32 shows the simulated two-dimensional thermal distribution at time $t=20$ minutes, with adaptive nulling at four auxiliary probes $112_1$ through $112_4$ in effect. The focal-spot diameter at focus 107 with adaptive nulling is equivalent to the focal-spot diameter before adaptive nulling, shown in FIG. 29. Hot spots on the left and right sides of the target 106 are eliminated. FIG. 33 shows a comparison of the temperature distribution before (solid line) and after (broken line) nulling along the major axis ($z=0$) of the target ellipse 106. Similarly, FIG. 34 shows the temperature distribution before (solid line) and after (broken line) nulling along the minor axis ($x=0$) of the target ellipse 106.

Figure 35:
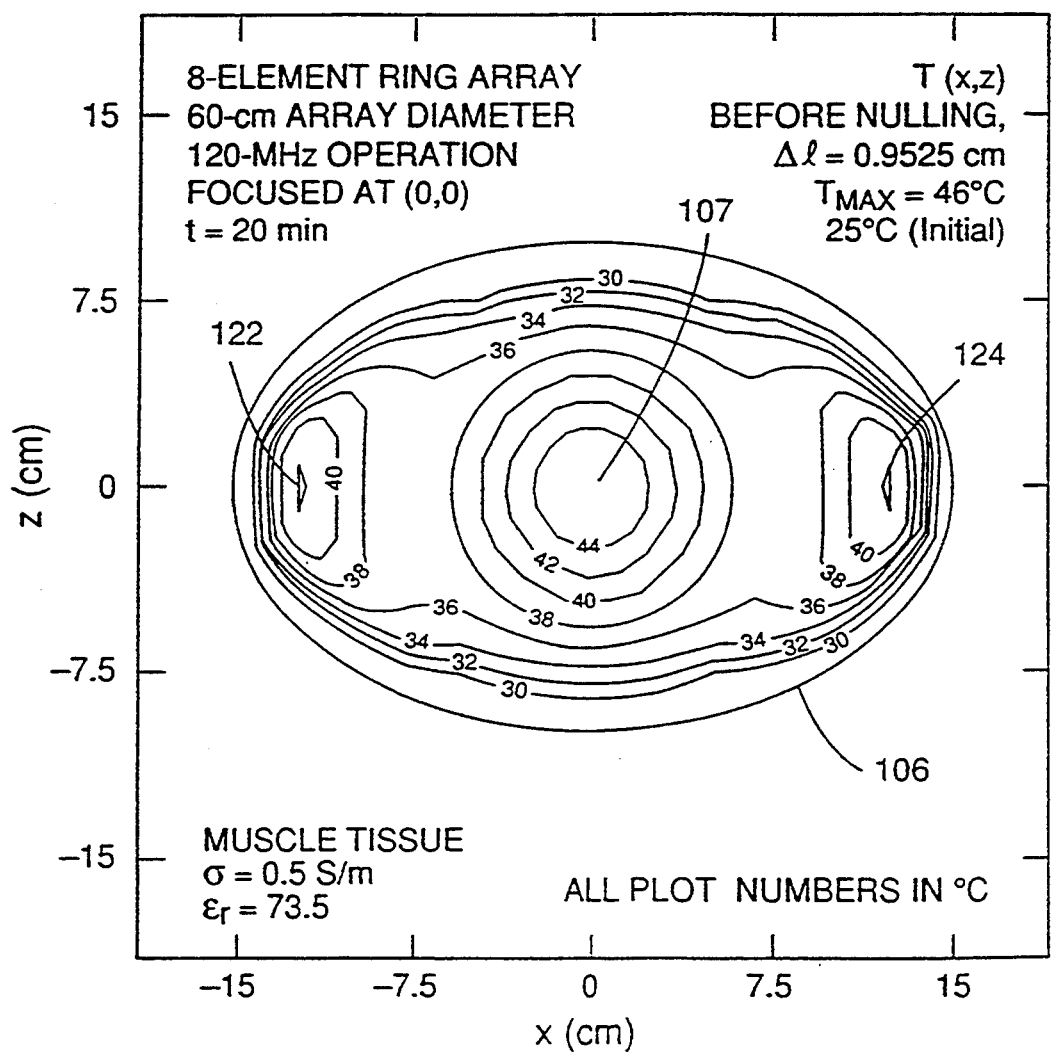
FIG. 35 is a diagram of the simulated target temperature profile for the E-field of FIG. 18 prior to adaptive nulling.
Figure 36:
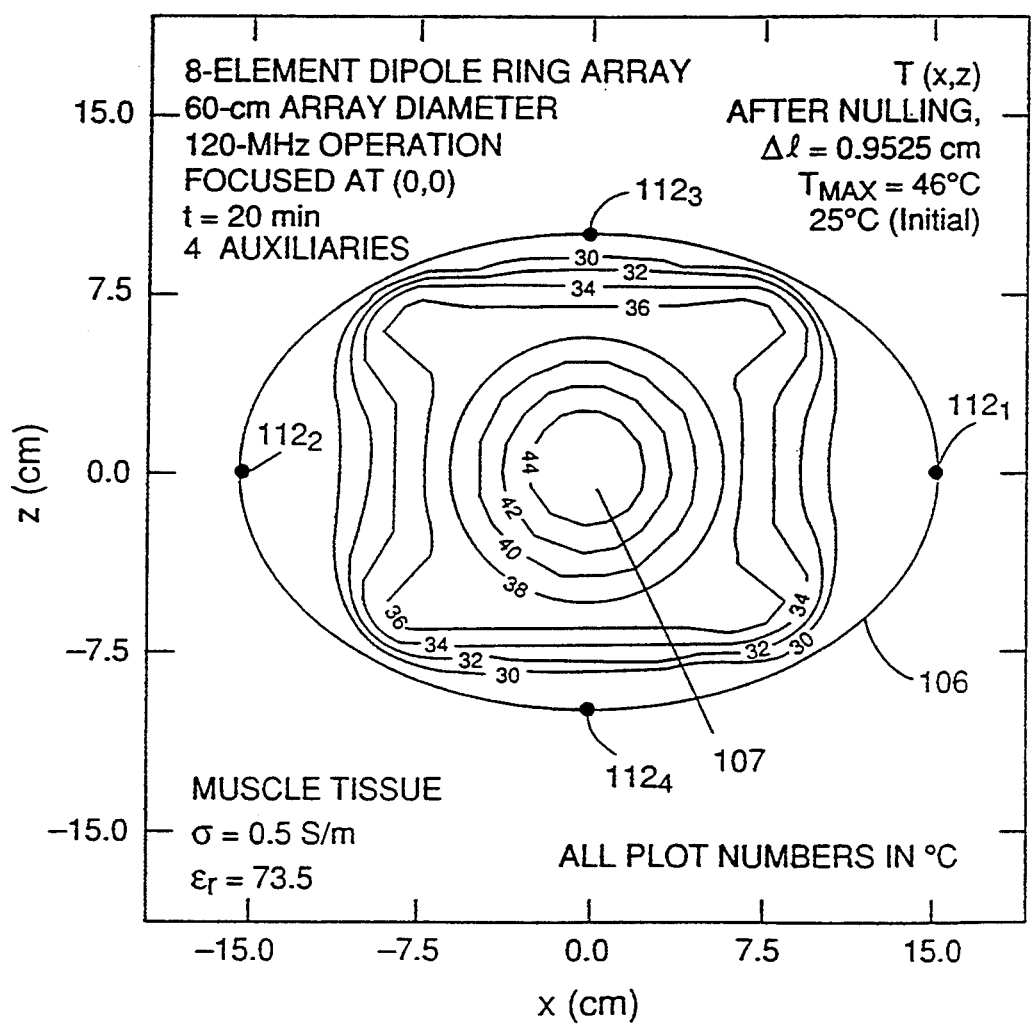
FIG. 36 is a diagram of the simulated target temperature profile for the E-field of FIG. 22 after adaptive nulling.
Figure 37:
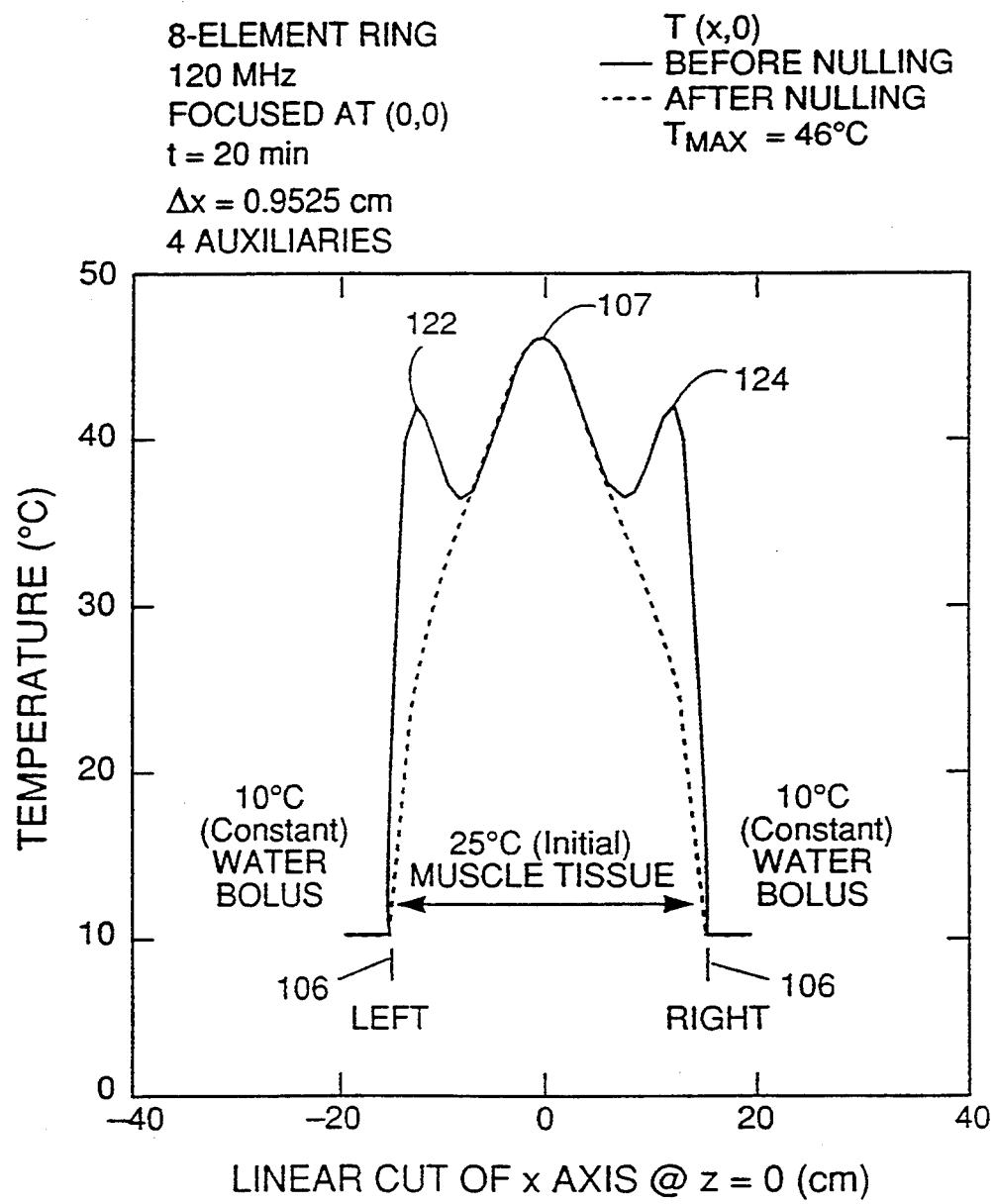
FIGS. 37 and 38 are diagrams of the temperature profile of FIG. 36 taken along the x- and z-axis, respectively.
Figure 38:
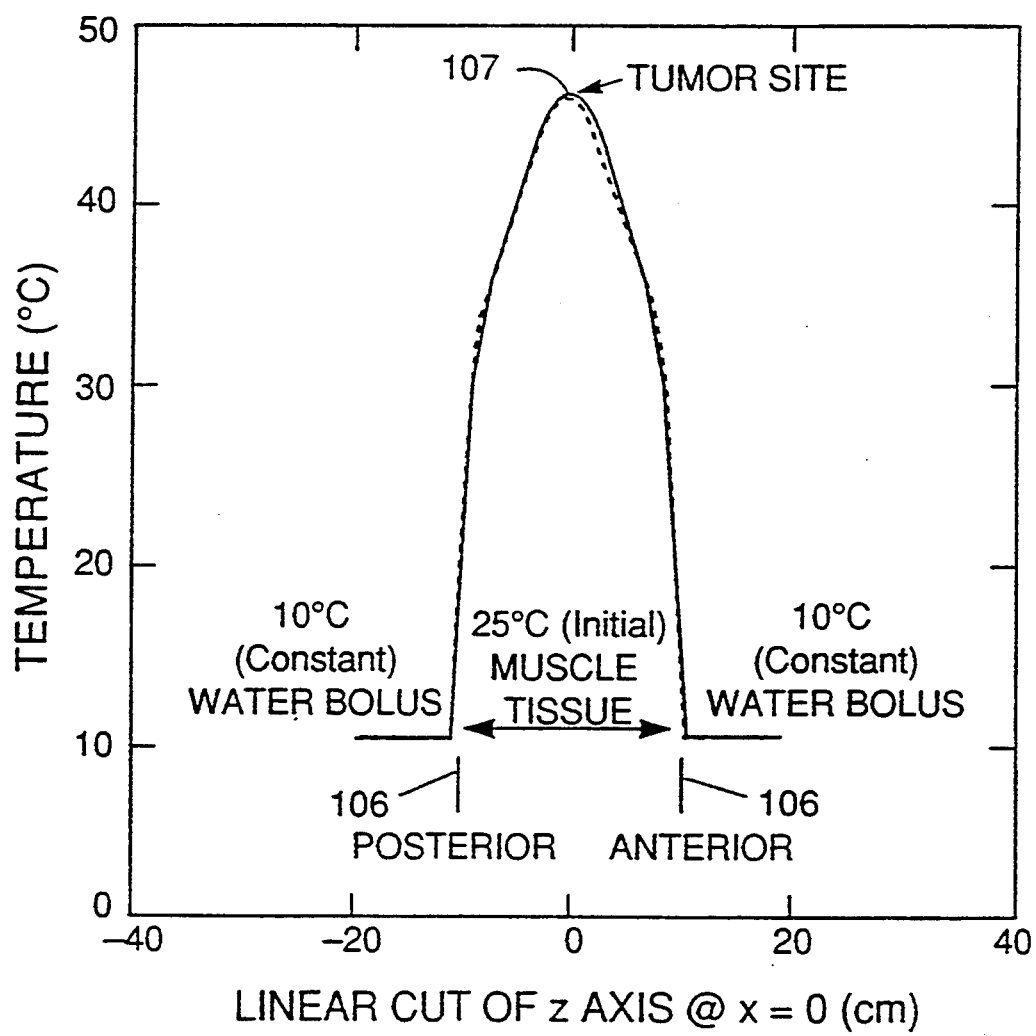

The convergence of the previous thermal simulations was verified by increasing the density of E-field observation probe positions by a factor of two, with a new spacing between points of 0.9525 cm, still with a 41×41 grid. The ring array operates as before at 120 MHz, and there are four auxiliary probes $112_1$ through $112_4$ laid out as shown in FIG. 17. As the auxiliary positions are the same, the adaptive weights and channel correlation matrix eigenvalues in FIGS. 27 and 28, respectively, remain the same. From the parameter values in Table 1, all resistors $R_{ij}$ in the finer-grid muscle-tissue phantom had a value of 193.0° C./W and all resistors $R_{ij}$ in the water bolus had a value of 174.4° C./W. The value of the capacitors $C_i$ in the phantom muscle-tissue is 2.95 J/°C. Again, a constant temperature of 10° C. is enforced at each water-bolus node. The E-field scaling factors to raise the focal-point temperature to 46° C. before and after nulling are 76.5 dB and 78.4 dB, respectively. The finer-grid two-dimensional thermal distributions before and after nulling are shown in FIGS. 35 and 34, respectively. Although the temperature contours are smoother, the general agreement between these patterns and the coarser-grid patterns in FIGS. 29 and 32 are evident. Similarly, one-dimensional thermal pattern cuts with the finer grid are shown in FIGS. 37 (x axis) and 38 (z axis), and good agreement with the coarse-grid patterns of FIGS. 33 and 35, respectively, is observed. In particular, the finer detail in FIG. 37 shows that the hot spots 122 and 124 are at approximately 42° C. compared to 41° C. observed for the coarse grid of FIG. 33. Thus, convergence of the coarse-grid thermal patterns is demonstrated.

Elliptical Array

An elliptical phased-array hyperthermia applicator, having a 70 cm major axis and a 60 cm minor axis, was also analyzed by computer simulation. The computer simulation parameters were the same as those applied to the analysis of the annular array. Generally, the computer simulations show that reduced hot spot temperatures are observed along the major axis of the elliptical phantom, without adaptive nulling, while small increases in hot spot temperatures occur along the minor axis. Certain tumor geometries may be heated more efficiently with an elliptical array than with an annular array.

EXPERIMENTAL RESULTS

Experimental data have been gathered from a commercial annular phased-array hyperthermia system modified to perform a gradient search algorithm to produce an adaptive null (or focus) at one or more auxiliary E-field probe positions. The results confirm that a strong null can be formed at the surface of the target body without significantly affecting the power delivered at the focus of the hyperthermia system.

Figure 39:
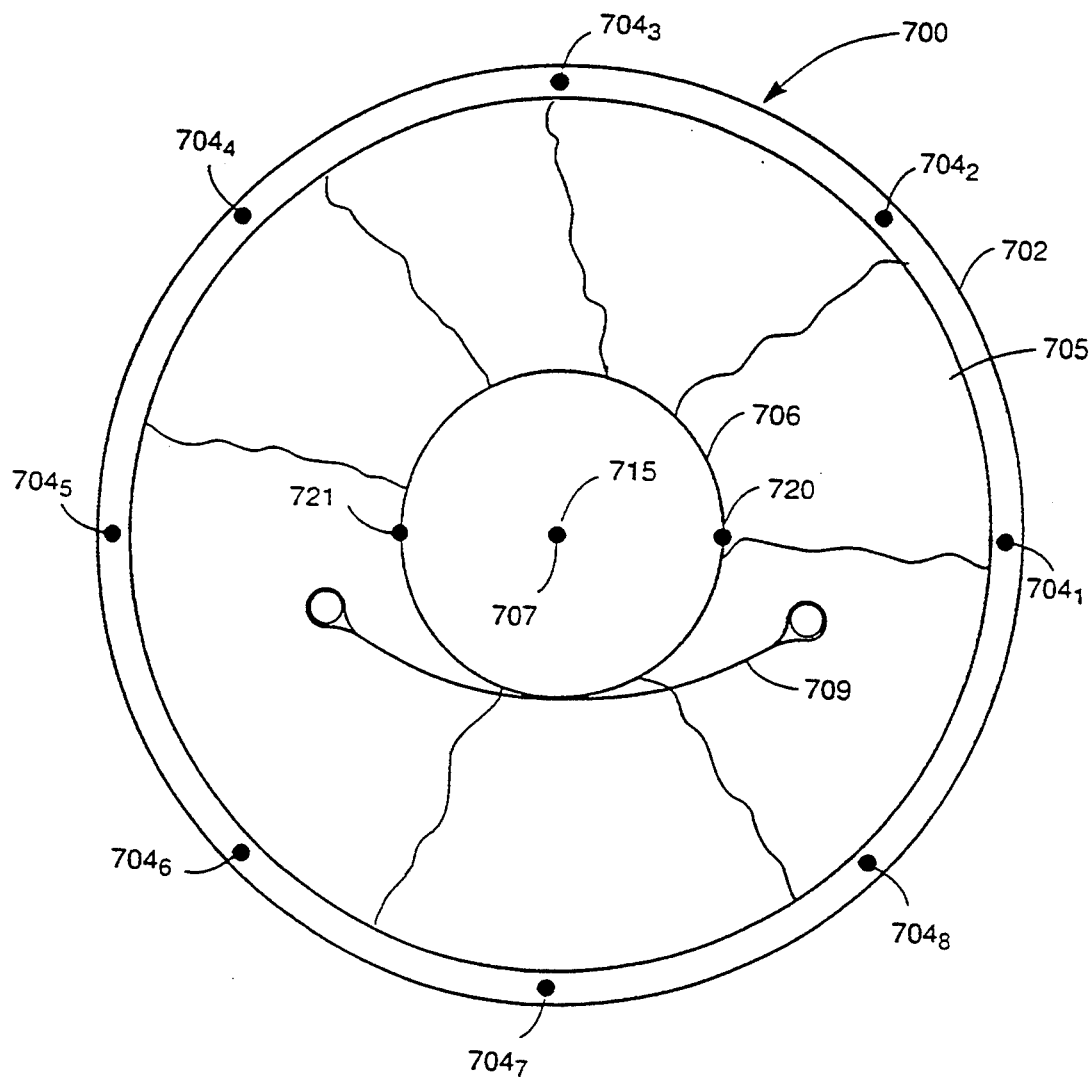
FIG. 39 is a cross-sectional view of an annular phased array hyperthermia system and saline phantom used for gathering experimental adaptive nulling and focusing data.

FIG. 39 shows a cross-sectional view of the experimental system 700, which is a modified BSD-2000 SIGMA-60 annular phased-array hyperthermia applicator, available from BSD Medical Corporation, Salt Lake City, Utah. The annular array antenna 702 of the system is 59 cm in diameter and includes eight uniformly spaced dipole antennas $704_1$ through $704_8$, excited with a four channel transmitter at 100 MHz. Each of the four transmit channel signals are distributed by separate coaxial cables from the hyperthermia controller (not shown) to a two-way power divider having two outputs. The two outputs of each two-way power divider drive a pair of dipole antenna elements through a pair of coaxial cables.

A cylindrical phantom target body 706 is supported by a patient sling 705 which centrally locates the phantom within the annular array so that the longitudinal axes of the phantom and the annular array correspond to each other. Phantom target 706 is a 28 cm diameter×40 cm long polymer bottle filled with saline solution (0.9% NaCl), which simulates a human subject. A deionized water-filled bladder 705 provides a water bolus between the annular array and the target phantom.

Single Adaptive Null

Three E-field probes are used to monitor the amplitude of the E-field at various sites in and around the phantom for this experiment. The first E-field probe 715 (BSD Medical Corp. Model EP-500) is located inside the phantom at the center, or focus, 707 of the array which simulates the tumor site. This probe monitors the amplitude of the E-field at the tumor site as the null is formed at the null site. The second E-field probe 720 (BSD Medical Corp. Model EP-100) is taped onto the outside surface of the phantom at the desired null location which simulates an E-field probe taped to a patient's skin. The probe is used to monitor the amplitude of the E-field at the null site as the null is formed by the gradient search algorithm. The third E-field probe 721 (BSD Medical Corp. Model EP-400) is taped onto the outside surface of the phantom diametrically opposite the location of the null site probe 720. This probe is used to monitor the amplitude of the E-field away from the null and focus sites and provides an E-field amplitude reference for the experiment.

The transmit array amplitude and phase control software and the electric field probe monitoring software supplied with the BSD-2000 system were modified to incorporate a gradient search feedback routine for adaptive nulling and adaptive focusing. Pascal source code listings and sample output of the adaptive nulling and focusing gradient search feedback routines are attached hereto as Appendicies C and D, respectively.

Figure 40:
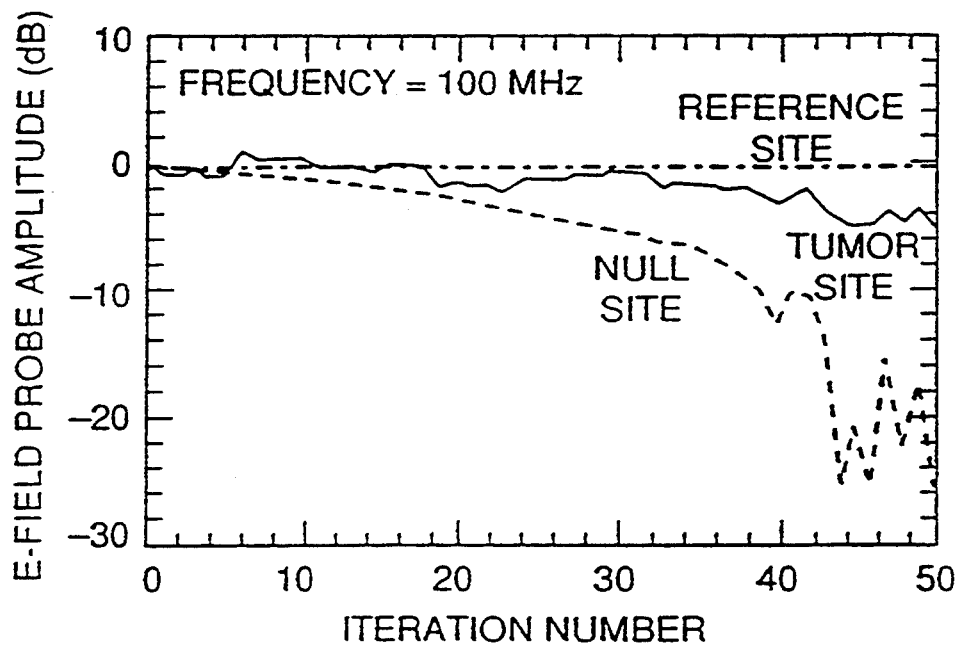
FIG. 40 is a diagram of the E-field amplitude measured at a single null site, the tumor site, and a reference site, versus gradient search iteration for the experimental hyperthermia system and phantom of FIG. 39.
Figure 40:
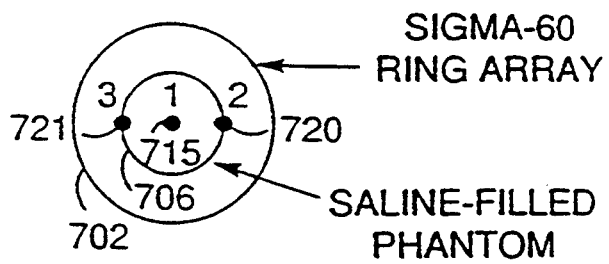
Figure 41:
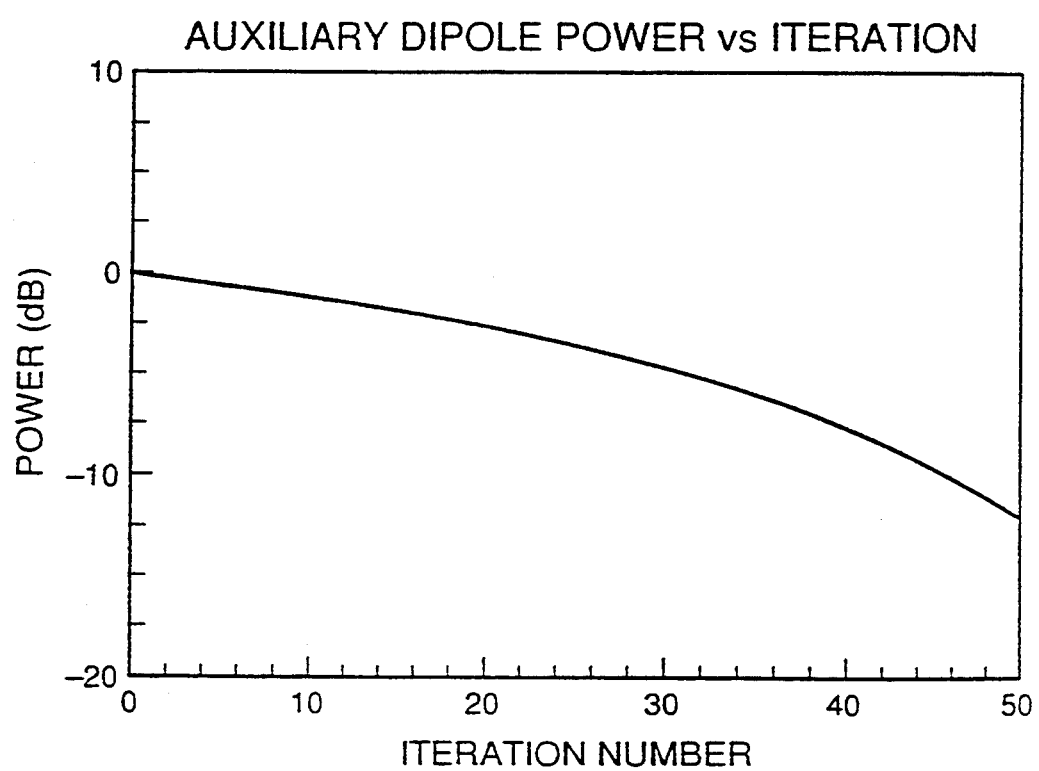
FIG. 41 is a diagram of the simulated E-field power versus gradient search iteration at the single null site of FIG. 40.

FIG. 40 graphically illustrates the results of this experiment, showing the measured E-field probe amplitude, in dB, versus the gradient search iteration number. The dB values are obtained by computing $10\log_{10}$(probe output signal) and normalizing the resulting values to 0 dB at iteration 0. It is evident from this graph that the gradient search formed a strong E-field amplitude null at the null site, on the order of $-15$ to $-20$ dB with respect to the reference site, in less than 50 iterations. (The apparent rise in the E-field amplitude at the null site between iterations 45 and 50 is most likely due to noise associated with the convergence calculations). Furthermore, the measured E-field amplitude at the tumor site was reduced by no more than $-5$ dB with respect to the initial reference level. FIG. 41 shows a graphic illustration of the power, in dB, calculated at the null site versus gradient search iteration. It is evident from this graph that the gradient search causes the null site power to monotonically decrease with each iteration, achieving an approximately 12 dB reduction in power within 50 iterations.

It should be noted that for at least the first 30 iterations of the gradient search, there is good agreement between the computer simulations, presented above, and these experimental measurements. After approximately 30 iterations, however, the results of the computer simulations differ from the experimental measurements. One reason for this difference is that the computer simulations herein described do not attempt to accurately model all the characteristics of the BSD-2000 system used for the experiments. For example, the simulations do not account for phase shifter non-linearities, A/D convertor errors, or D/A convertor errors associated with the system which will affect the experimental measurements, especially at the relatively low signal levels present after 30 iterations. Thus, it is not expected that the computer simulations and the experimental results will necessarily behave the same where the signals or computations are most affected by measurement system noise.

Single Adaptive Null—Beef Phantom

Figure 42:
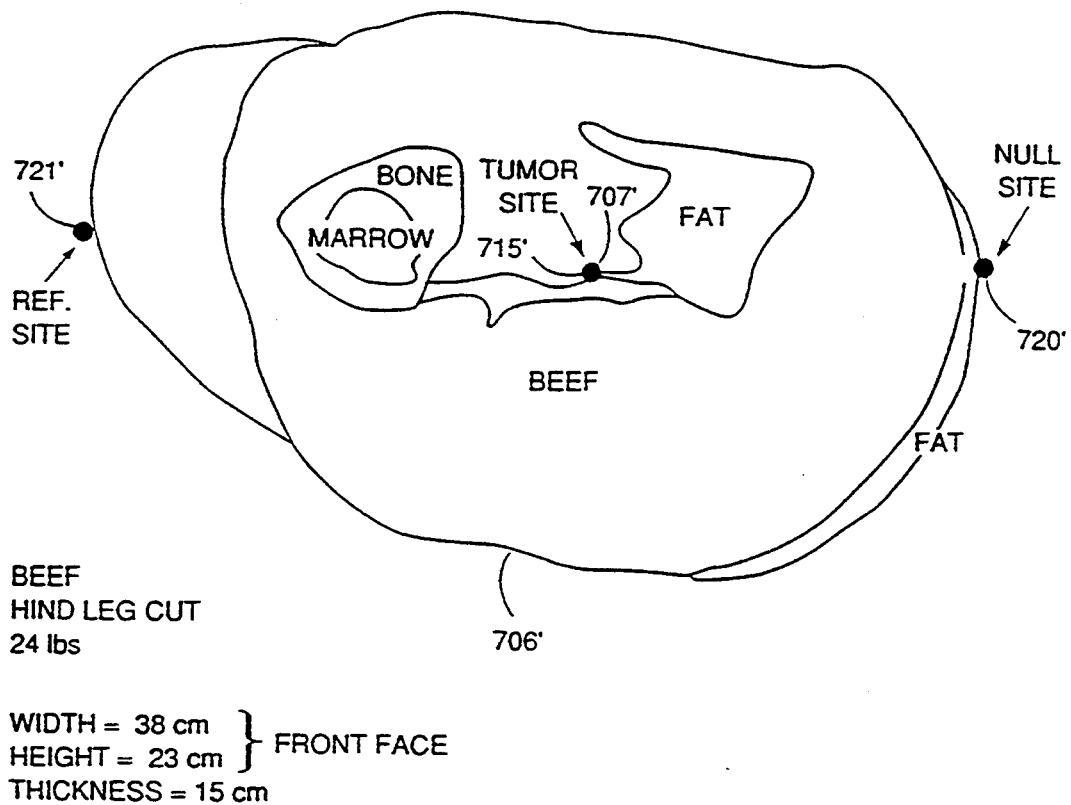
FIG. 42 is a cross-sectional view of a beef phantom used in place of the saline phantom in the experimental system of FIG. 39.

Referring to FIG. 42, in another experiment, a single adaptive null was produced in a beef phantom 706' used in place of the saline phantom 706 of FIG. 39 to better simulate human tissue. Beef phantom 706' was a 24 lbs.

hind leg cut having a front face width of 38 cm, a front face height of 23 cm and a thickness of 15 cm. The E-field probe positions used with the beef phantom are analogous to the E-field probe positions used with the saline phantom. That is, the first E-field probe 715' (BSD Medical Corp. Model EP-500) is located inside the beef phantom at the center, or focus, 707' of the array which simulates the tumor site. This probe monitors the amplitude of the E-field at the tumor site as the null is formed at the null site. The second E-field probe 720' (BSD Medical Corp. Model EP-100) is taped onto the outside surface of the beef phantom at the desired null location which simulates an E-field probe taped to a patient's skin. This probe is used to monitor the amplitude of the E-field at the null site as the null is formed by the gradient search algorithm. The third E-field probe 721' (BSD Medical Corp. Model EP-400) is taped onto the outside surface of the beef phantom diametrically opposite the location of the null site probe 720'. This probe is used to monitor the amplitude of the E-field away from the null and focus sites and provides an E-field amplitude reference for the experiment.

Figure 43:
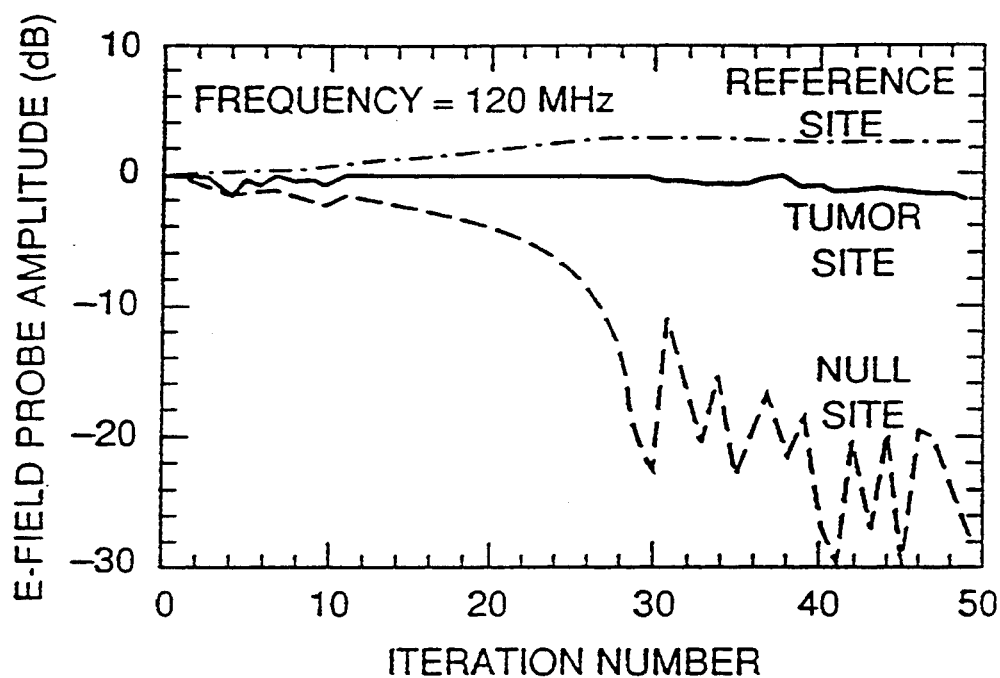
FIG. 43 is a diagram of the E-field amplitude measured at a single null site, the tumor site, and a reference site, versus gradient search iteration for the experimental hyperthermia system of FIG. 39 using the beef phantom of FIG. 42.
Figure 43:
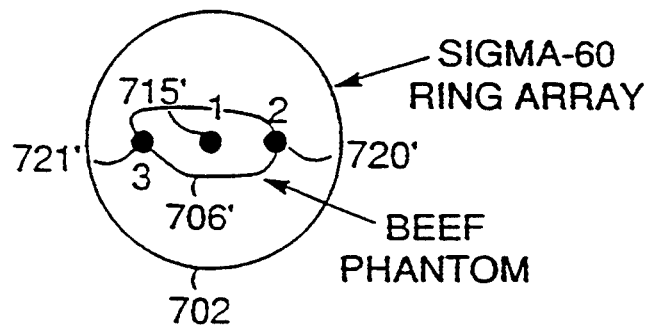

FIG. 43 graphically illustrates the results of the beef phantom experiment, showing the measured E-field probe amplitude, in dB, versus the gradient search iteration number. Again, the dB values are obtained by computing $10\log_{10}$(probe output signal) and normalizing the resulting values to 0 dB at iteration 0. It is evident from this graph that the gradient search formed a strong E-field amplitude null at the null site 720', on the order of $-18$ to $-20$ dB with respect to the reference site, in less than 50 iterations. Furthermore, the E-field amplitude at the tumor site was reduced by no more than $-2$ dB with respect to the initial reference level. It should be noted that these results are very similar to the results obtained with the saline phantom (FIG. 40).

Figure 44:
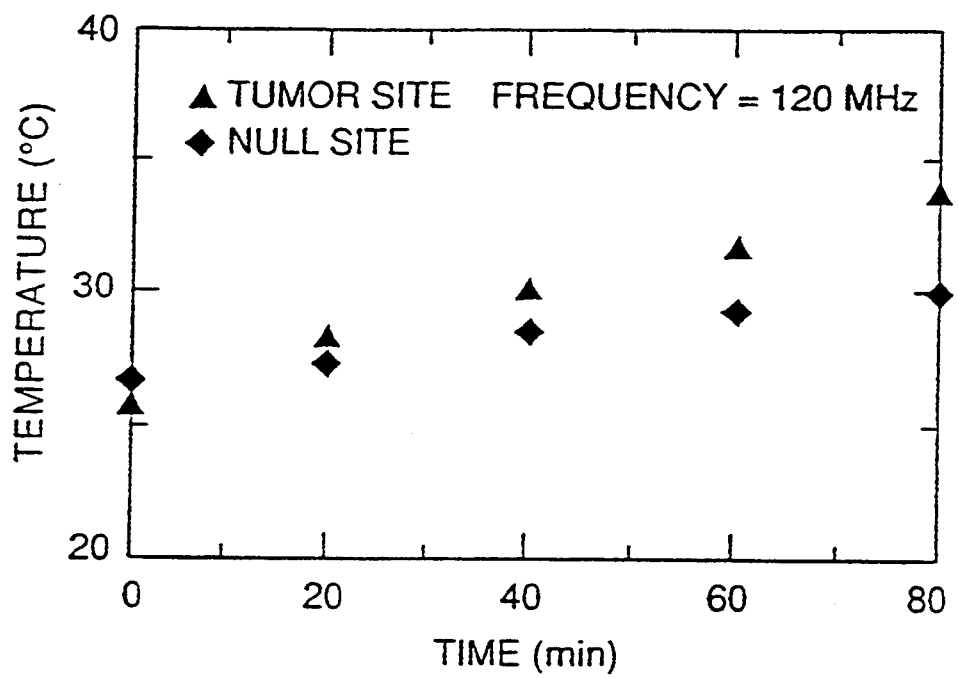
FIG. 44 is a diagram of the measured temperature versus time at the beef phantom tumor site and the single null site of FIG. 42.
Figure 44:
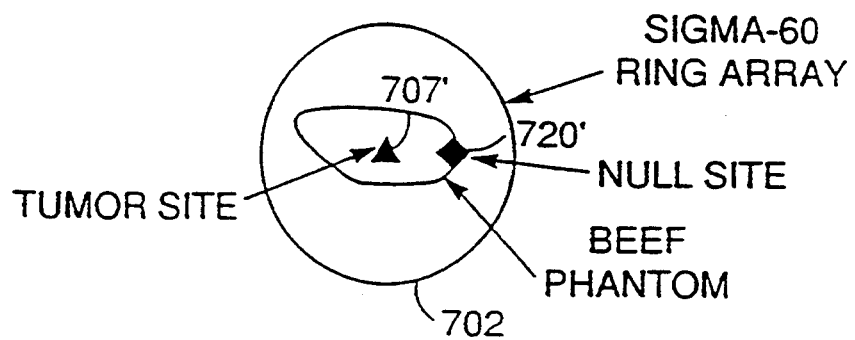

FIG. 44 shows a comparison between the temperature rise at the beef phantom tumor site 707' and the null site 720' during nulling. A thermocouple probe was located at each of the tumor and null sites, and the RF power was applied in four intervals of 15 minutes power on and 5 minutes power off for a total experiment time of 80 minutes. The gradient search performed 10 iterations during the 15 minute power on portion of each interval. Temperature measurements were taken during the 5 minute power off portion of each interval, i.e., one measurement for each 10 iterations. The experimental data shows that the tumor site was initially at about 26° C. and the null site was initially at about 27° C. before applying RF power. After 40 minutes (30 minutes power on and 10 minutes power off) the temperature of the tumor site has risen 4° C. to about 30° C., while the null site has risen only 1° C. to about 28° C. After 80 minutes (60 minutes power on and 20 minutes power off) the temperature of the tumor site has risen 8° C. to about 34° C., while the temperature of the null site has risen only 3° C. to about 30° C. Thus, an approximate differential of about 4° C. is attained between the tissue temperature of a deep-seated target and the temperature of a single surface null site in a beef phantom.

Two Adaptive Nulls

In another experiment, two adaptive nulls on the surface of the saline-filled cylindrical phantom were generated and measured. This experiment used the same configuration as shown in FIG. 39 with the one E-field probe 715 (BSD Medical Corp. Model EP-500) located inside the phantom 706 at the center, or focus, 707 of the array simulating the tumor site. Two E-field probes 720 and 721 (BSD Medical Corp. Model EP-100) were located on the outside surface of the phantom at diametrically opposite positions representing the two non-invasive null sites. Probe 715 monitored the E-field amplitude at the tumor site while probes 720 and 721 monitored the E-field amplitude at the null sites.

Figure 45:
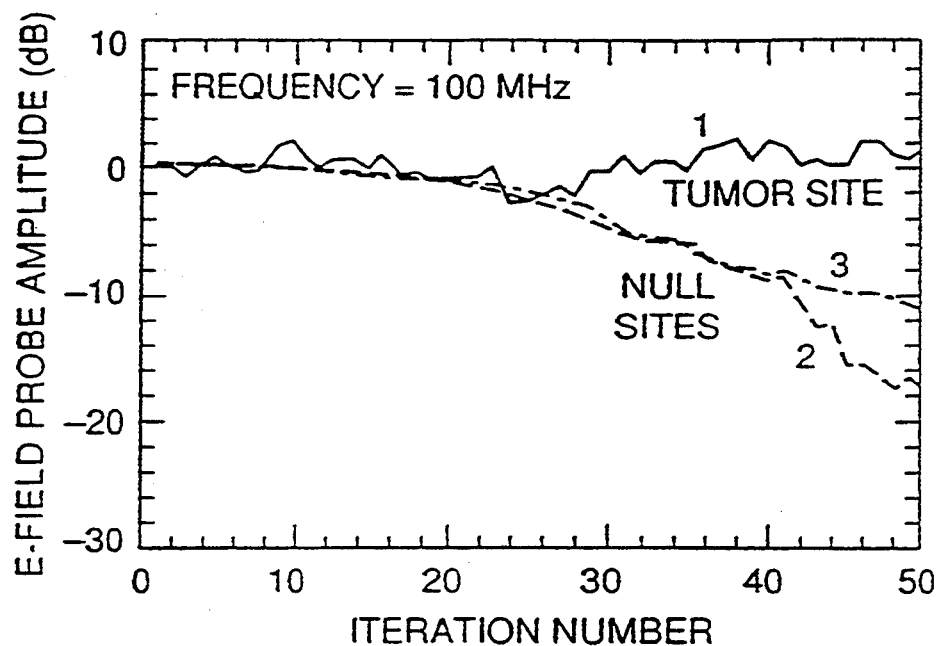
FIG. 45 is a diagram of the E-field amplitude measured at two null sites and the tumor site, versus gradient search iteration for the experimental hyperthermia system and phantom of FIG. 39.
Figure 45:
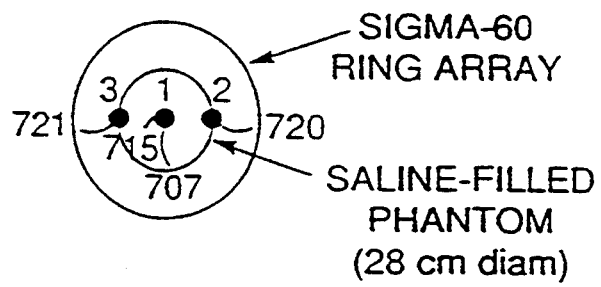

FIG. 45 graphically illustrates the results of this experiment, showing the measured E-field probe amplitude, in dB, versus the gradient search iteration number. Again, the dB values are obtained by computing $10\log_{10}$(probe output signal) and normalizing the resulting values to 0 dB at iteration 0. It is evident from this graph that the gradient search formed two strong adaptive E-field amplitude nulls at the null sites, on the order of $-10$ to $-20$ dB with respect to the reference site, in about 50 iterations. In particular, at iteration number 50 the null strength at probe 720 (probe site 2) is approximately $-18.0$ dB and the null strength at probe 721 (probe site 3) is approximately $-11.8$ dB. Furthermore, the E-field amplitude at the tumor site 715 (probe site 1) was held close to a constant value (0 dB) throughout the 50 iterations.

Adaptive Focusing

In another experiment, adaptive phase focusing was used to maximize the E-field amplitude at a selected location different from focus 707 of the saline-filled cylindrical phantom 706 of FIG. 39. In this case, the selected focus site was at E-field probe 720 (BSD Medical Corp. Model EP-100) located on the outside surface of the cylindrical phantom.

Figure 46:
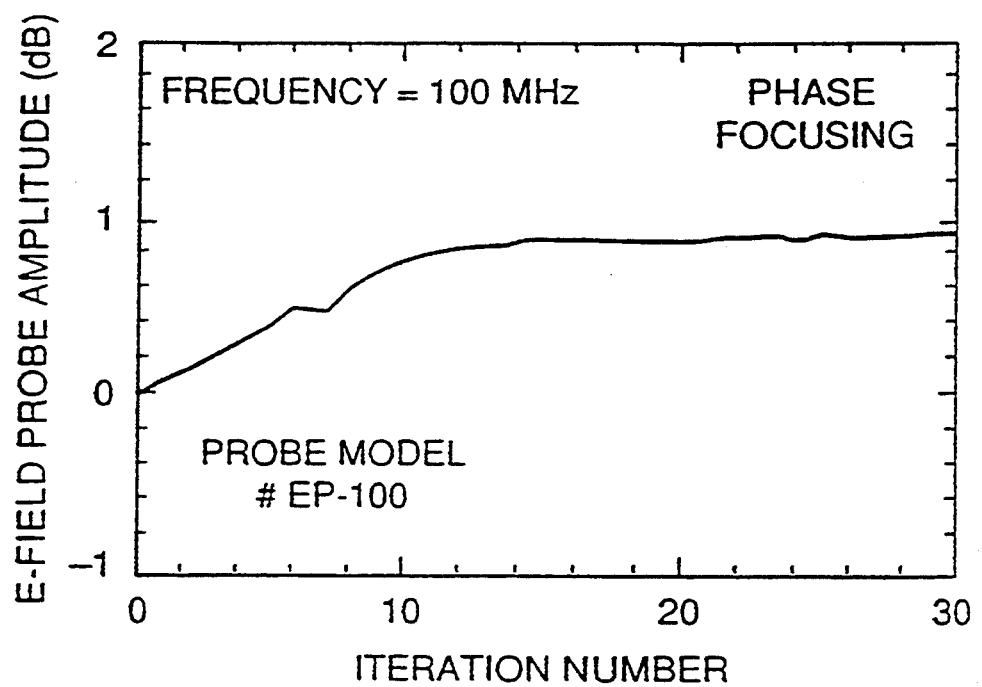
FIG. 46 is a diagram of the E-field amplitude measured at a focus on the surface of the saline phantom versus gradient search iteration for the experimental hyperthermia system and phantom of FIG. 39.
Figure 46:
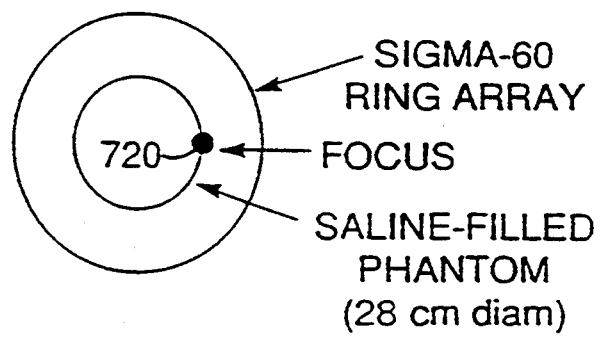

FIG. 46 graphically illustrates the results of this experiment, showing the measured E-field probe amplitude, in dB, versus the gradient search iteration number for 30 iterations. Again, the dB values are obtained by computing $10\log_{10}$(probe output signal) and normalizing the resulting values to 0 dB at iteration 0. The initial phase weights applied to the transmit elements of the array were equal, nominally producing an E-field focused at the center of the array 707. The gradient search was used to adjust the phases of the array transmit weights to maximize the E-field amplitude at probe site 720, i.e., refocus the array at probe 720. The transmit weight amplitudes were held constant over the 30 iterations. As shown, the gradient search converged in about 10 iterations and the power at probe 720 increased by about 0.9 dB compared to its initial value. This result demonstrates that adaptive focusing can be used successfully to optimize the peak power delivered to a tumor site.

Clinical Application

A modified BSD-2000 Sigma 60 system can be used as a clinical adaptive hyperthermia system for implementing the adaptive nulling and focusing techniques of this invention. An unmodified BSD-2000 hyperthermia system uses four transmit channels to energize the eight transmit elements (in pairs) of the annular array, and eight EP-400 (or EP-100) non-invasive E-field probes to monitor clinical hyperthermia treatments. The eight E-field probes can provide feedback signals to the controller performing the adaptive nulling and/or focusing algorithms. Theoretically, three independent adaptive nulls (and/or peaks) can be formed by adaptively adjusting the phases and gains of the four transmit channels. Any three of the eight E-field probes can provide the feedback signals required to produce a null (or peak) at the corresponding probe.

Various treatment protocols are possible for selecting desired null sites, depending on the particular patient and case history. One protocol would place the eight E-field probes around the circumference of the patient to measure the E-field strength at each probe before nulling and thereby identify the strongest electric fields on the surface of the patient indicating potentially serious hot spots. Adaptive nulling would then be applied to minimize the electric field at the three probes having the strongest electric fields before nulling. Alternatively, if the patient can localize a painful hot spot during treatment, adaptive nulling would be applied to minimize the electric field at the E-field probe closest to the identified hot spot.

The number of adaptive nulls required will vary with patient and pathology. In some situations it is possible that more than three independent adaptive nulls will be required to achieve a therapeutic thermal distribution in the patient. In such a case, an extension of the four transmit channel BSD-2000 system to an eight transmit channel configuration will allow up to seven independent adaptive nulls and an adaptive focus to be formed.

MONOPOLE ARRAY EMBODIMENT

Figure 47:
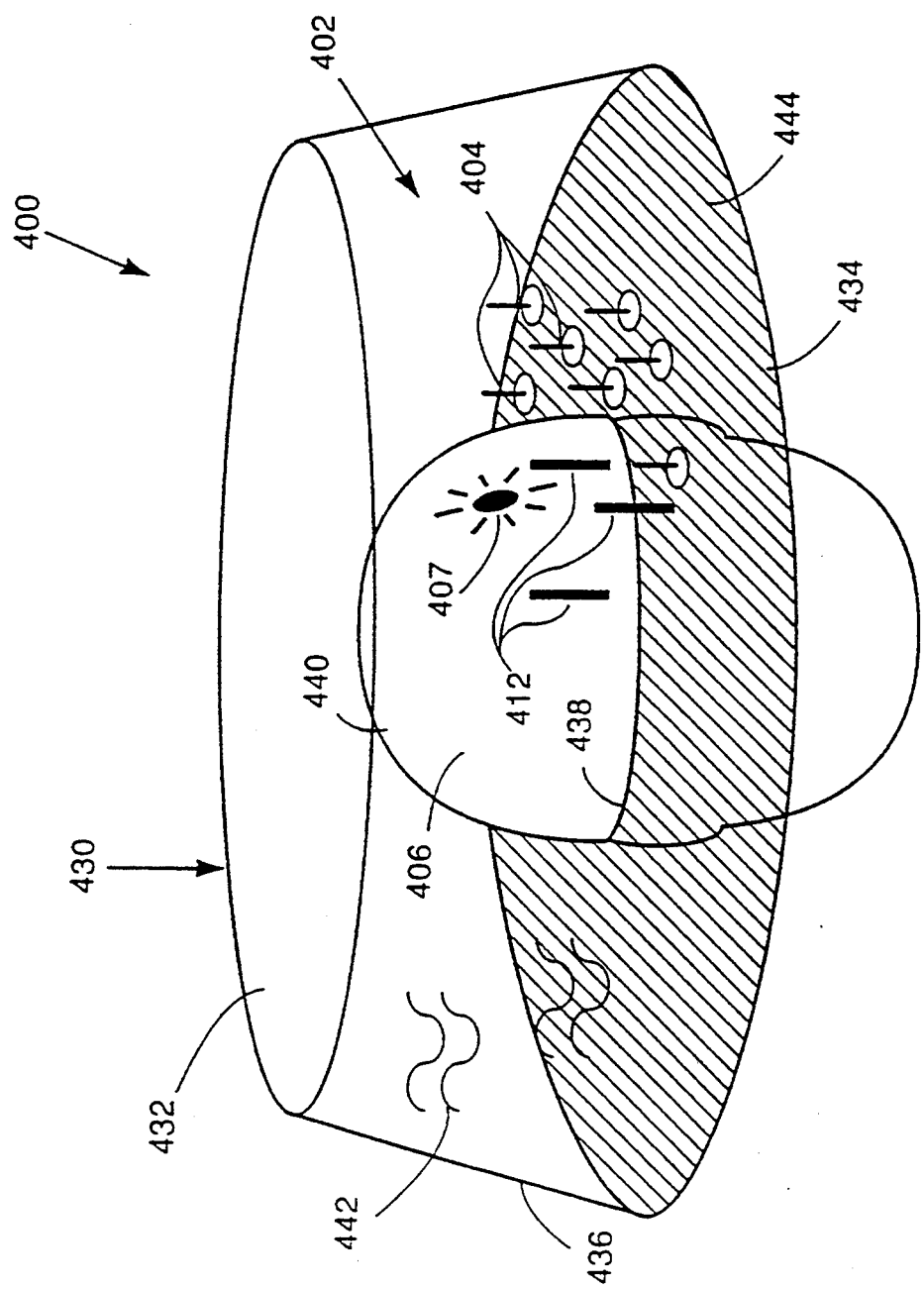
FIG. 47 is a perspective view of an RF monopole array hyperthermia system for treating brain tumors, featuring the adaptive focusing of this invention.
Figure 48:
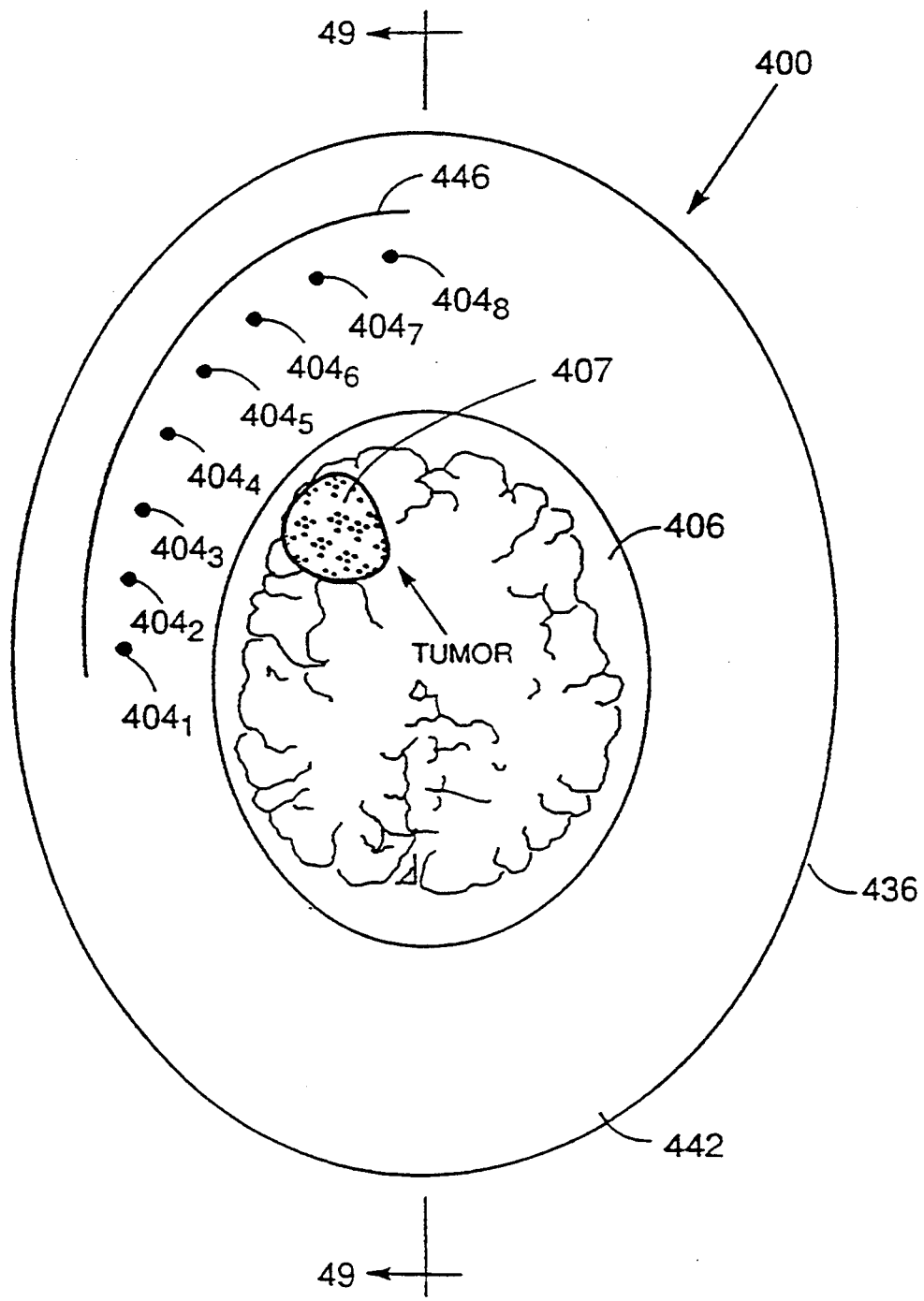
FIG. 48 is a top-view of the monopole phased array hyperthermia system of FIG. 47.
Figure 49:
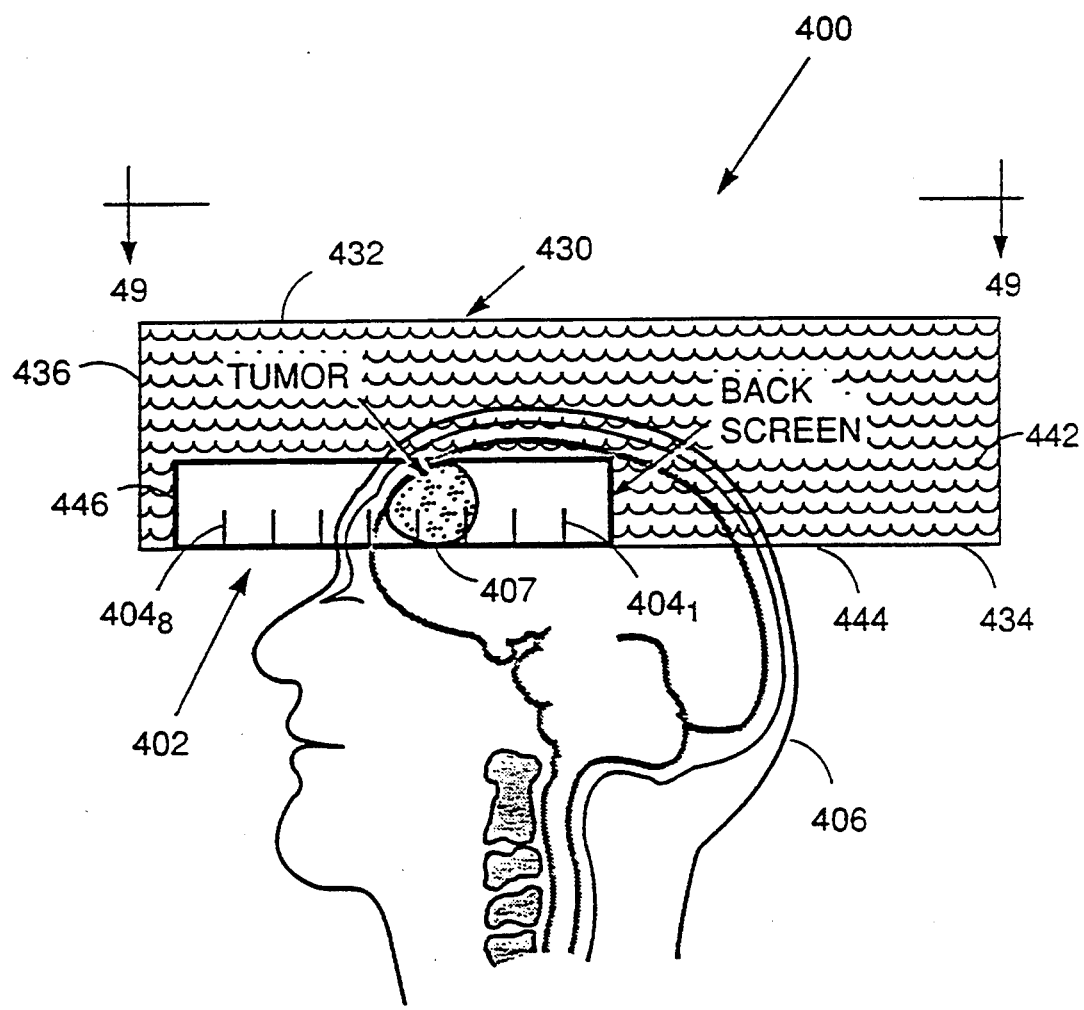
FIG. 49 is a cross-sectional side view of the RF monopole phased array hyperthermia system of FIG. 47.

FIGS. 47-49 show an embodiment of a non-invasive RF monopole phased-array hyperthermia system 400 for treating malignant brain tumors. Hyperthermia system 400 features a monopole phased-array transmit antenna 402 having a plurality of monopole transmit antenna elements 404 placed in proximity to the cranium 406 of a patient to be treated for a malignant brain tumor 407. Hyperthermia system 400 also features improved focusing characteristics through using one or more non-invasive electric field probes 412 placed on or near the patient's cranium, in conjunction with the near-field adaptive focusing and nulling apparatus and methods of this invention.

Monopole phased-array 402 is used to therapeutically heat the brain tumor 407, typically located 1-3 cm below the skin surface of the cranium 406, by adaptively focusing the RF electric field energy radiated by the monopole radiator elements 404 into the tumor 407. In practice, it is dangerous, and often impossible, to invasively place an E-field probe into the brain tumor site to facilitate adaptive focusing of the RF energy into the tumor. "Hot spots" are not typically a problem with the monopole hyperthermia array described since the side lobes generated by a phased-array in this near-field geometry are much lower than those generated by the annular phased-array described above. Thus, the monopole phased-array receives its major benefit by applying the adaptive focusing of this invention to more precisely focus energy into the tumor site. However, the adaptive nulling of this invention may also be used if "hot spots" do develop through the use of the monopole array.

The monopole phased array antenna 402 is mounted inside an water-tight enclosure 430 having a generally circular top and bottom surface 432 and 434, respectively, and a cylindrical or conical side surface 436 connecting the top and bottom surfaces. The enclosure is made from non-conductive plastic material, such as PLEXIGLAS TM brand plastic material, but may also be fashioned from any material which acts as an electrical insulator and will not interfere with the RF radiation patterns generated by the monopole phased-array inside the enclosure.

The bottom surface 434 has a central elliptical aperture 438 which accommodates a portion of the patient's cranium 406 to allow tumor 407 to be disposed within the interior of enclosure 430 adjacent to the monopole phased-array 402. A flexible silicone rubber membrane 440 covers the aperture to maintain the water-tight integrity of the enclosure. The enclosure 430 can be filled with chilled de-ionized water 442 for cooling the patient's skin during hyperthermia treatment. The de-ionized water can be temperature controlled and circulated through the enclosure 430 to maximize the cooling effect.

Bottom surface 434 also includes an RF conducting ground plane 444 mounted co-planar with the bottom surface and which acts as an RF reflector for monopole antenna elements 404. This ground plane may be fashioned out of a metal sheet, metal foil, metal mesh, or any other RF conductive material which can be fashioned to cover the area of bottom surface 434. The ground plane may also be imbedded into the bottom surface by, for instance, laminating the ground plane between two layers of insulating material.

The monopole radiator elements 404 are each mounted perpendicularly onto bottom surface 434 so that they may be energized from outside the enclosure, yet remain insulated from the ground plane 444. In one preferred embodiment, each monopole radiator element 404 is a $\frac{1}{4}$ wavelength long straight wire radiator threadably attached on one end into a connector mounted onto surface 434 and insulated from ground plane 444. It is understood that another form of a monopole antenna element, other than a straight wire radiator, can also be used. For instance, helical monopole, conical monopole, and sleeve monopole antenna elements are also appropriate for use as monopole array elements of the present invention.

Each monopole element is energized through a coaxial cable fed through the bottom surface 434 to the connector. The bottom surface may also be provided with extra monopole connectors which allow repositioning of the monopole radiator elements within the enclosure. Repositioning allows the user to change the geometry of the monopole phased-array antenna as well as position the antenna adjacent to the tumor location to maximize the therapeutic effect.

An RF reflecting screen 446 (FIGS. 48 and 49) can be placed behind the monopole antenna elements 404 to direct more of the radiated RF energy toward the cranium, i.e., energy which would otherwise be lost through the side of the water-tight enclosure. Reflecting screen 446 is typically positioned in the water bolus approximately $\frac{1}{4}$ wavelength behind the monopole antenna elements and has a cylindrical reflecting surface extending perpendicularly from the ground screen to a height of approximately twice the wavelength of the radiated energy. Alternatively, the reflecting surface of the screen can be curved toward the target to further enhance radiation of the target. The reflecting screen is constructed from high frequency RF conducting mesh which allows water to freely flow through it, and is electrically connected to the ground screen using good high frequency RF construction practices.

Each monopole radiator element 404 is configured as a $\frac{1}{4}$ wavelength radiator to resonate at approximately 915 MHz which is effective for heating tumors 1 to 3 cm, or more, beneath the surface of the patient's skull. The monopole phased-array can include a varying number of radiator elements spatially arranged in a variety of patterns. The spacing between the monopole antenna elements is typically between $\frac{1}{2}$ to 1 wavelength. Furthermore, the number and location of the non-invasive electric field probes 412 can also vary depending on the hyperthermia focusing patterns desired.

In the adaptive hyperthermia monopole phased-array of this invention, non-invasive E-field probes are used in conjunction with the adaptive focusing apparatus and techniques of this invention to maximize the RF power delivered to the tumor site inside the cranium. Computer simulations, presented herein, show that the optimum focused (e.g., with an invasive E-field probe) phased array can produce an RF energy pattern with maximum electric field strength at the tumor site and no undesired hot spots within the cranial target.

With the adaptive hyperthermia monopole phased-array described herein, RF energy peaks are adaptively formed to maximize the electric field energy delivered to the target focus. As shown, the focused energy peak achieved by the adaptive focusing apparatus of this invention is invasive to the cranial target extending into the tumor region.

Figure 50:
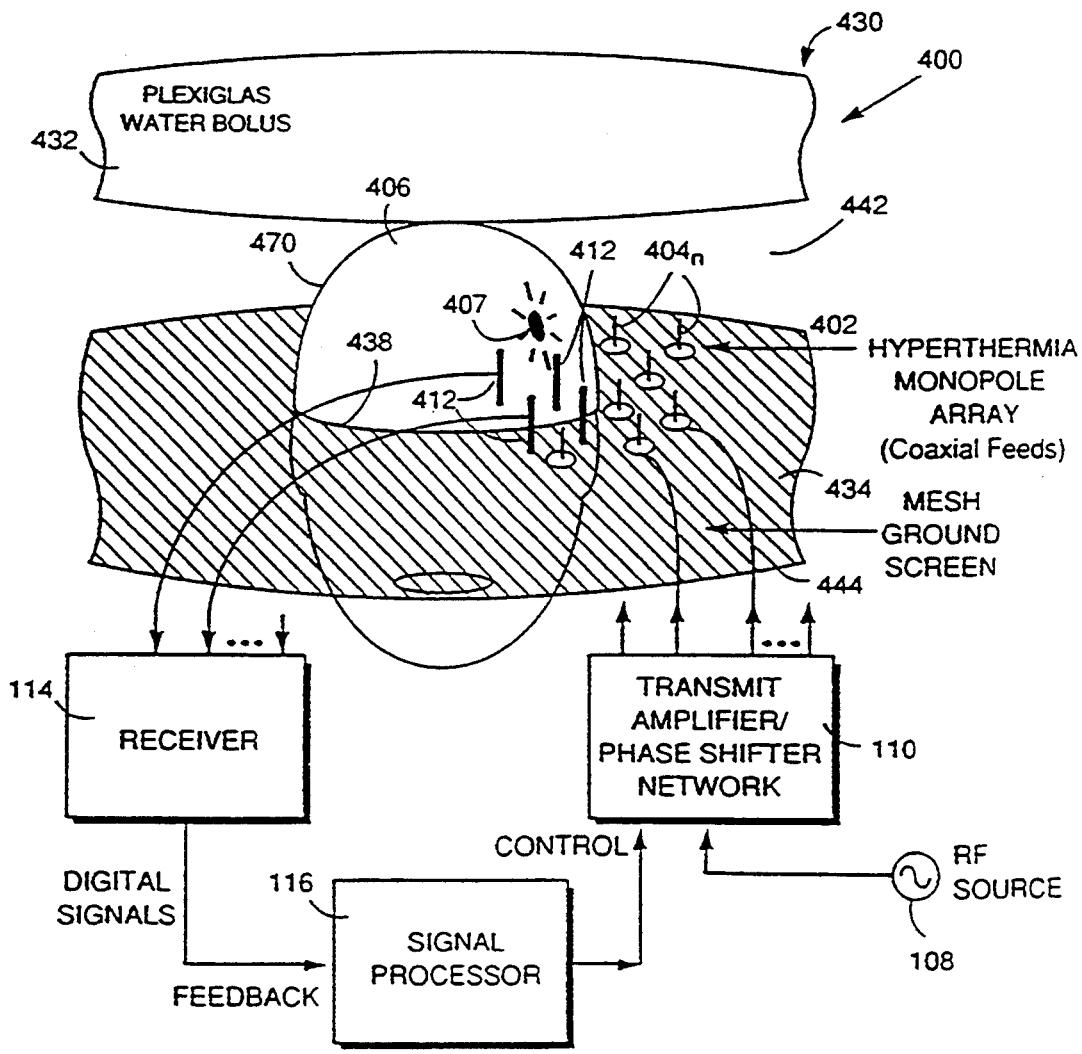
FIG. 50 is a schematic diagram of the monopole phased array hyperthermia system of FIG. 47 and an array controller.

Referring to FIG. 50, the adaptive-focusing monopole phased-array hyperthermia system of this invention can be described in terms corresponding to the generalized annular phased-array system schematic diagram of FIG. 6. Specifically, monopole transmit elements $404_n$ of hyperthermia transmitting antenna array 402 correspond respectively to the dipole transmit elements 1040 of annular phased array applicator 102 of FIG. 6. Furthermore, the plurality of E-field auxiliary probes $412_m$, correspond to the E-field probes $112_m$ of FIG. 6. It is apparent that the monopole phased-array hyperthermia system herein described does not take advantage of an electric field probe placed at the tumor 407, analogous to the receiving probe 115 used with the annular phased array applicator 102 of FIG. 6, to maximize the focus radiated energy into the tumor. Use of a probe at the focus would in most cases require a surgical procedure to invasively place the probe within the patient's brain.

The receiver 114, signal processor 116, RF source 108, and weighting functions $110_n$ (FIG. 6) operate with the monopole array as described above with regard to the annular array, except that the signal processor 116 performs an adaptive focusing algorithm described below, which is related to the adaptive nulling algorithm. That is, signal processor 116 performs either a sample matrix inversion (SMI) algorithm or a gradient search algorithm on the signals output from receiver 114 and updates the adaptive array weights w. (with gain g and phase $\phi$) to rapidly (within seconds) focus energy at the tumor 407.

Figure 51:
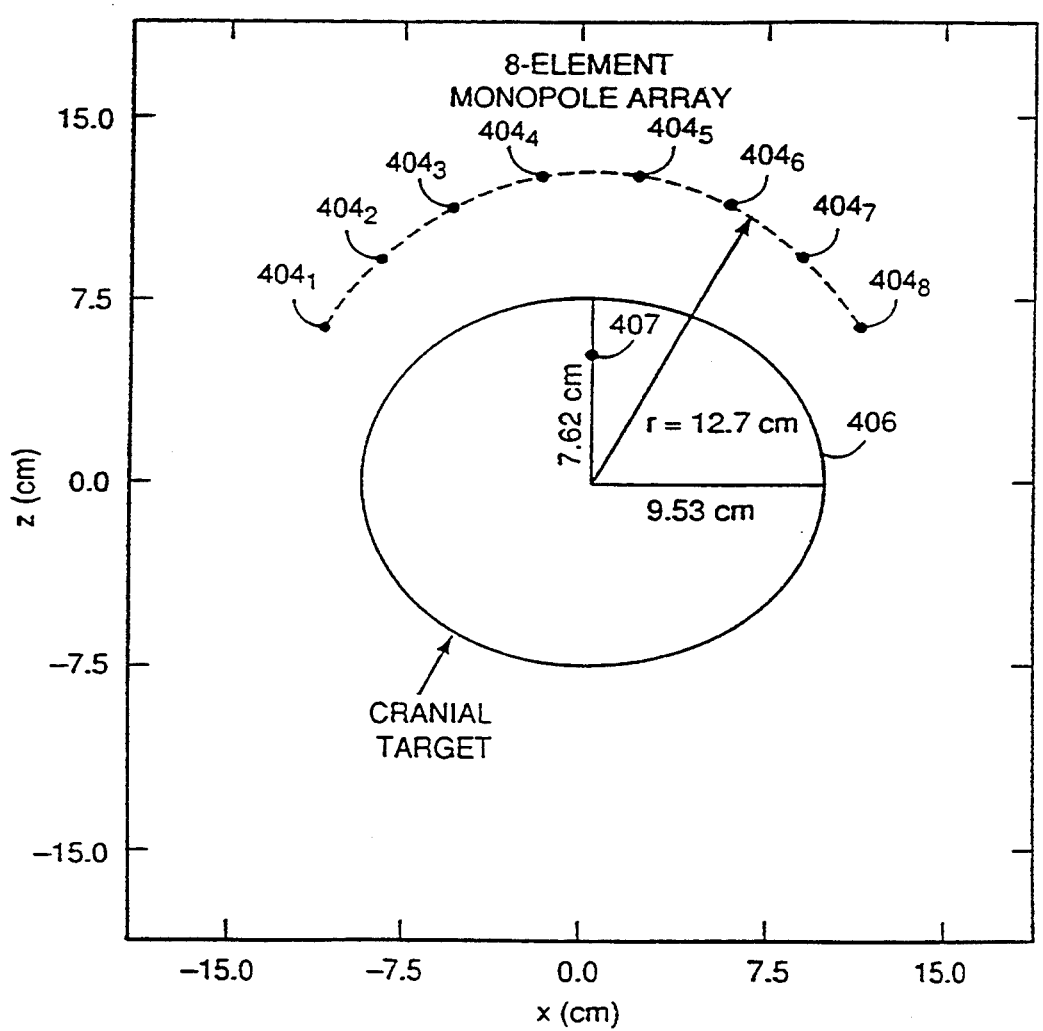
FIG. 51 is a schematic diagram of the monopole phased array geometries for the hyperthermia system of FIG. 47.
Figure 52:
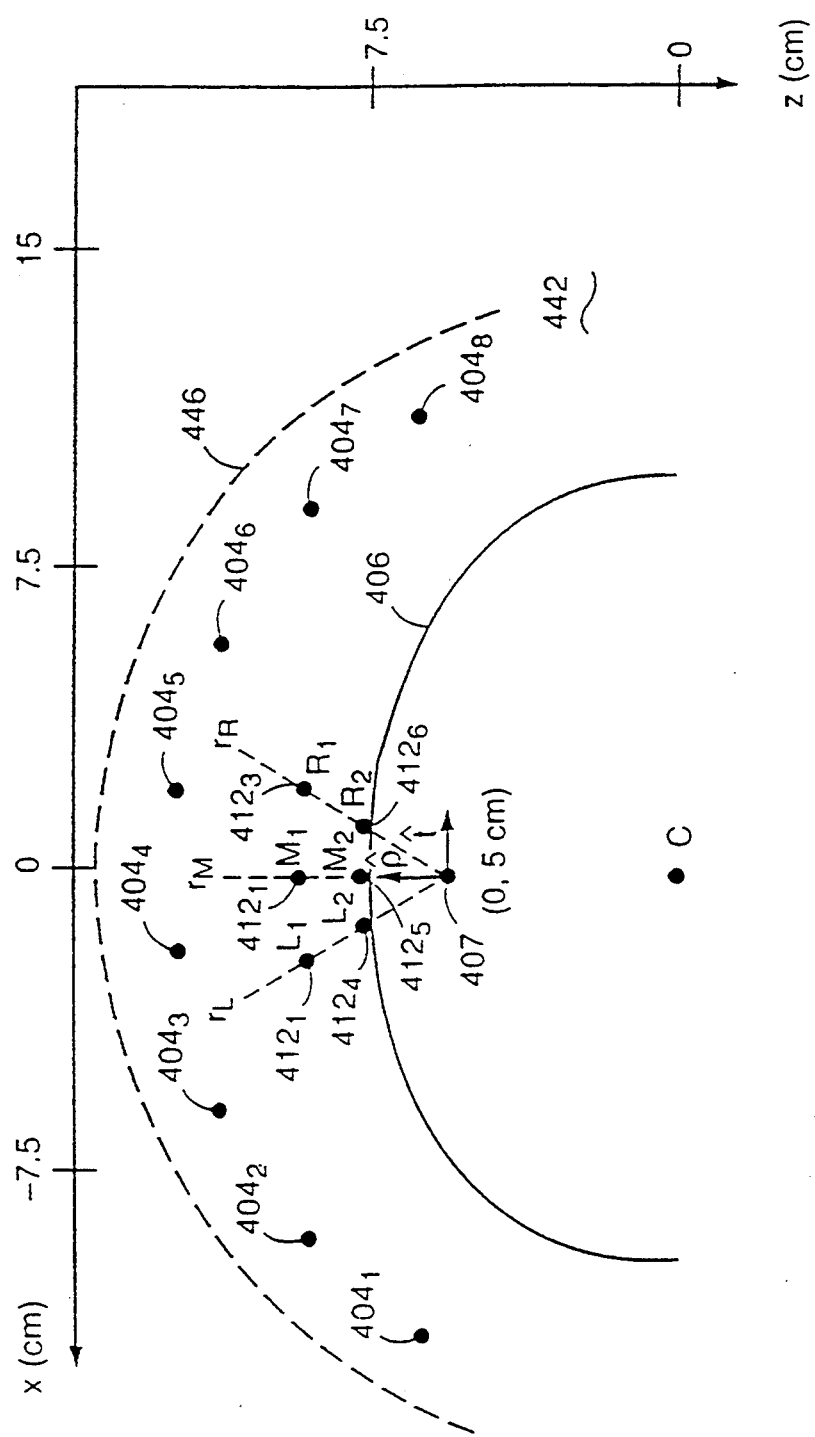
FIG. 52 is a schematic diagram of the monopole phased array and electric field probe array geometries for the hyperthermia system of FIG. 47.

Referring to FIGS. 51 and 52, there is shown an analytical model of an embodiment of an eight-element, 915 MHz hyperthermia monopole phased-array 402 of FIG. 47. Phased-array 402 has transmit antennas $404_1$ through $404_8$, arranged adjacent to an elliptical phantom target 406 representing the cross section of the human cranium at the tumor level. The focus 407 of the elliptical phantom models the location, approximately 2.0 cm below the surface of the cranium, of the brain tumor to receive hyperthermia treatment, i.e., the focus of RF energy for the phased array 402. Water bolus 442 is assumed to surround the target body 406, and is treated as a homogeneous medium for analysis purposes.

The monopole radiator elements $404_1$ through $404_8$ are arranged as a 120° circular arc array of uniformly spaced elements having a constant radius of 12.7 cm relative to the geometric center of the cranium C, i.e., at x=0.0 cm, z=0.0 cm. The tumor site, or focus 407 of the RF energy, is assumed to be at x=0.0 cm, z=5.08 cm for simulation purposes. (In an alternative preferred embodiment the monopole array elements form a circular arc having a geometric center at focus 407 (target) rather than at the center of the cranium C. This has the advantage that less phase focusing should be required to maximize the energy delivered to the focus, and thus the required number of gradient search iterations is reduced.)

Six auxiliary RF E-field probes, or sensors, $412_1$ through $412_6$ (i.e., receiving antennas) are placed on and near the perimeter of the elliptical target to model non-invasive E-field probes placed on and near the skin of the cranial target. Auxiliary probes $412_1$, $412_2$, and $412_3$ are uniformly spaced in an arc row, between the arc array and the cranial target, having a constant radius of approximately 4.0 cm relative to the desired focus 407. Auxiliary probes $412_4$, $412_5$ and $412_6$ are placed on the target skin adjacent to focus 407. Specifically, the first arc row of electric field probes $412_1$ through $412_3$ may be denoted as probes $L_1$, $M_1$, and $R_1$, respectively, and the row of electric field probes $412_4$ through $412_6$ may be denoted as probes $L_2$, $M_2$, and $R_2$, respectively. The electric field probes are arranged so that corresponding probes on the two rows are located along a radial line extending from the desired focus at tumor site 407 and are spaced $\frac{1}{4}$ to $\frac{1}{2}$ wavelength apart. That is, probe pair $(L_1, L_2)$ is located along radial $r_L$, probe pair $(M_1, M_2)$ is located along radial $r_M$ and, probe pair $(R_1, R_2)$ is located along radial $r_R$.

The gains and phases of the monopole elements are adaptively adjusted as described below to focus the energy output from the monopole phased-array into the tumor site 407 located several centimeters below the surface of the cranium. From the phased-array geometry of FIG. 52 it is observed that an electric field focused at tumor 407 will be balanced and symmetric with respect to the line x=0. Furthermore, the electric field is attenuated in the water bolus external to the cranium in the direction away from the transmit array. To achieve a focus interior to the cranium at the tumor site 407 it is assumed that the amplitude difference between the electric field adjacent to the skin surface of the cranium and the field approximately one quarter wavelength exterior to the skin surface of the cranium must be constrained to a desired value. This desired value is typically a minimum to avoid "hot spots" on the skin surface. Similarly the amplitude of the electric field in the transverse direction should be balanced to minimize the electric field variation between the left and right electric field probes with respect to the middle electric field probes, i.e., maintain electric field symmetry with respect to the x-axis. The electric field differences in the radial direction may be denoted by $$\Delta A_{L12} = |A_{L1} - A_{L2}|, \tag{74}$$

$$\Delta A_{M12} = |A_{M1} - A_{M2}|, \tag{75}$$

$$\Delta A_{R12} = |A_{R1} - A_{R2}|, \tag{76}$$

where A denotes the amplitude of the electric field measured by the specified field probe, $\hat{\rho}$ is a unit vector in the radial direction which bisects the transmit monopole array and $\hat{t}$ is a transverse unit vector as shown in FIG. 52. The electric field differences in the transverse direction for the first row may be denoted by $$\Delta A_{LM1} = |A_{L1} - A_{M1}|, \tag{77}$$

and, $$\Delta A_{RM1} = |A_{R1} - A_{M1}|, \quad (78)$$

and the electric field differences in the transverse direction for the second row may be denoted by $$\Delta A_{LM2} = |A_{L2} - A_{M2}|, \quad (79)$$

and, $$\Delta A_{RM2} = |A_{R2} - A_{M2}|. \quad (80)$$

A figure of merit F can be defined as $$F = \alpha(\Delta A_{L12} + \Delta A_{M12} + \Delta A_{R12}) + \Delta A_{LM1} + \Delta A_{RM1} + \Delta A_{LM2} + \Delta A_{RM2}, \quad (81)$$

where α is a scale factor used to adjust the effect of the electrical field gradient caused by attenuation in the radial direction between the phased-array antenna and the target. The figure of merit F involves seven constraints which are easily taken into account by the eight transmit element phased-array described. The gradient search algorithm described above is used to minimize the figure of merit F.

Figure 53:
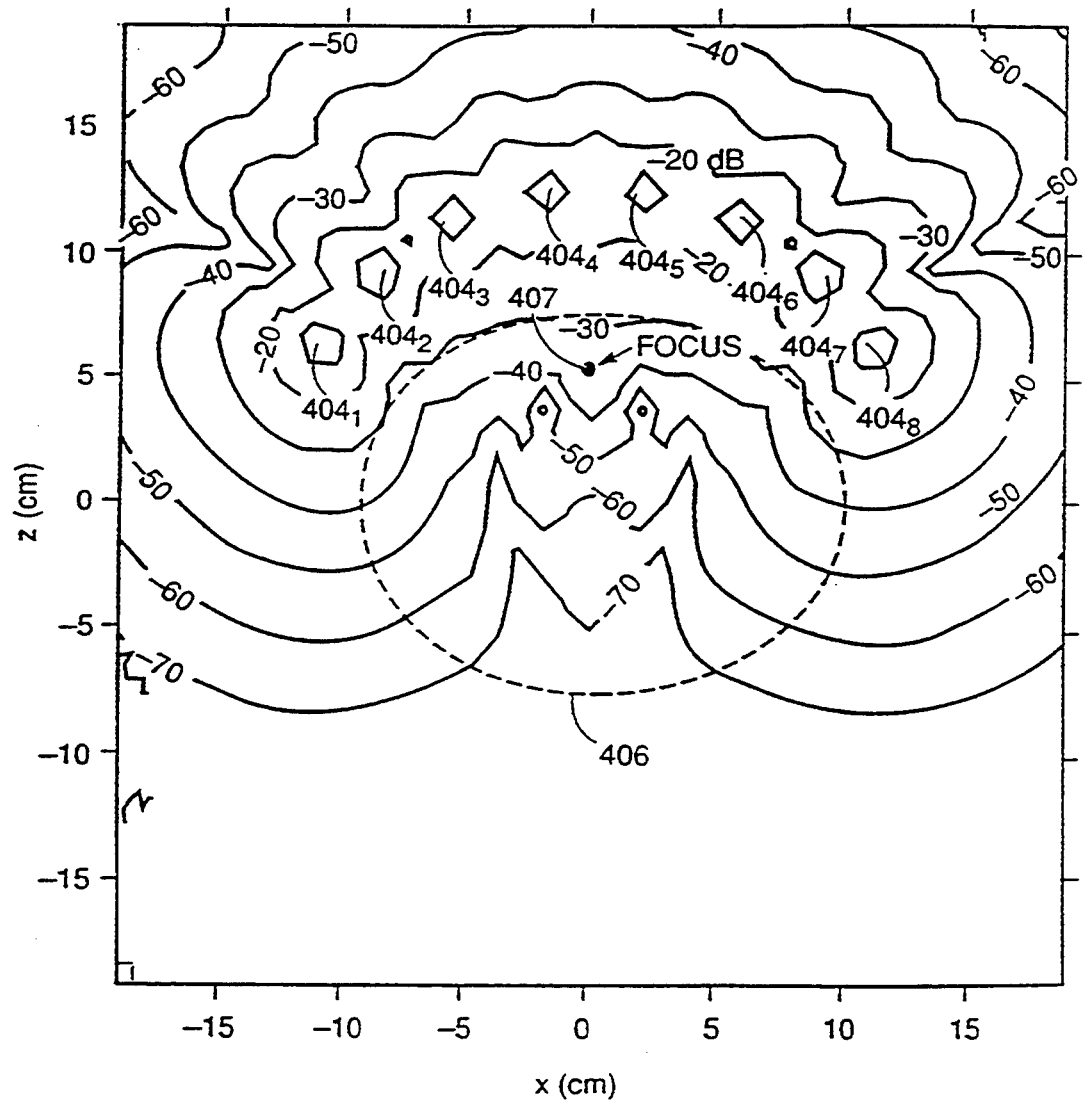
FIG. 53 is a diagram of a simulated E-field pattern for the monopole phased array geometry of FIG. 52.

FIG. 53 shows a simulated two-dimensional quiescent radiation pattern in the plane y=0 for the eight element monopole arc array of FIG. 52 operating at 915 MHz before adaptive focusing, i.e., with uniform amplitude and phase illumination. This radiation pattern was calculated using the moment-method described above, and the calculations assume an infinite homogeneous conducting medium simulating phantom brain tissue, i.e., $\epsilon_r = 50.0$, $\sigma = 1.3$. The focus of the array is at x=0.0, z=5.0 cm. The positions of the eight monopole radiators $404_1$ through $404_8$ are clearly evident by the −10 dB contours surrounding each element. The radiation pattern is symmetric because of the symmetry of the array and the assumed homogeneous medium.

Figure 54:
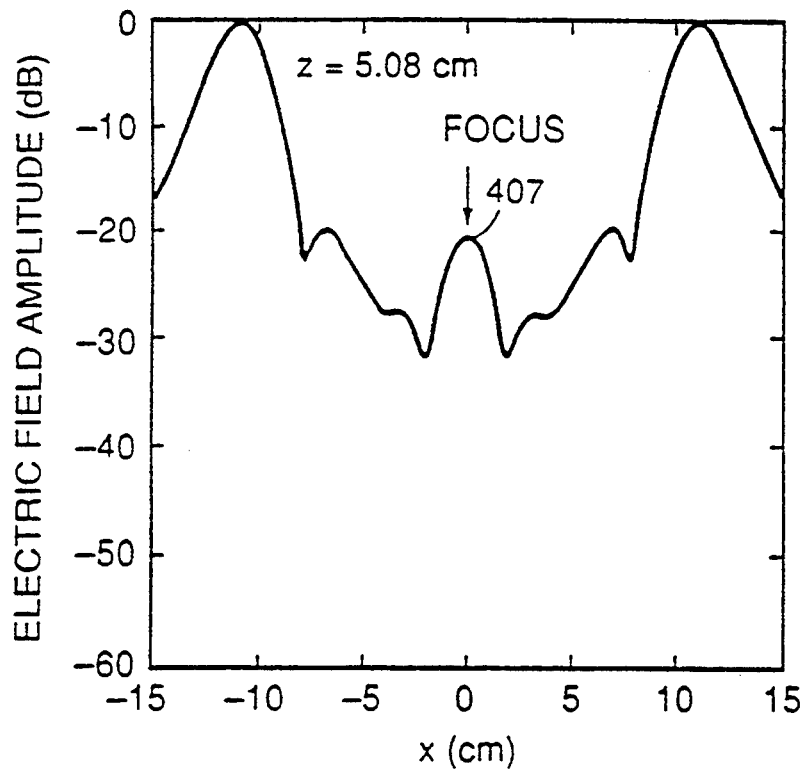
FIG. 54 is a diagram of the simulated E-field pattern of FIG. 53 taken parallel to the x-axis along the line z=5.08 cm.
Figure 54:
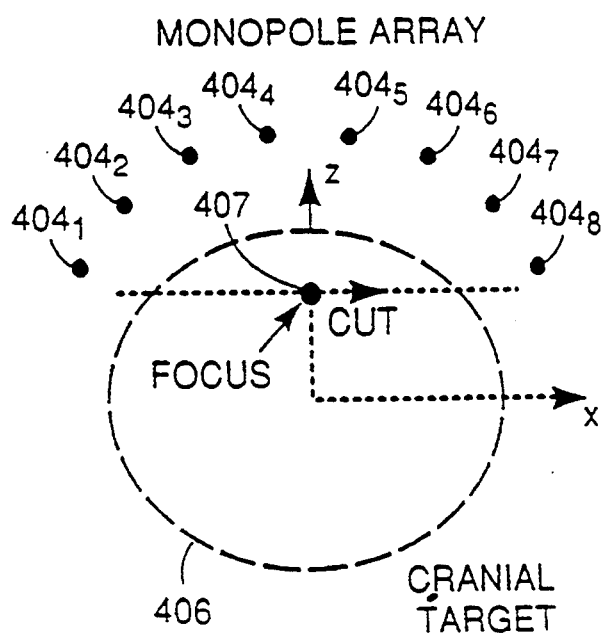

FIG. 54 shows the quiescent radiation pattern of FIG. 53 cut at z=5.0 cm, which is through the tumor site 407 assumed to be at x=0.0, z=5.0 cm. The focused main beam is centered at x=0.0 as desired. The half-power beamwidth is approximately 2.0 cm, which is close to ½ wavelength for the full ring array.

Figure 55:
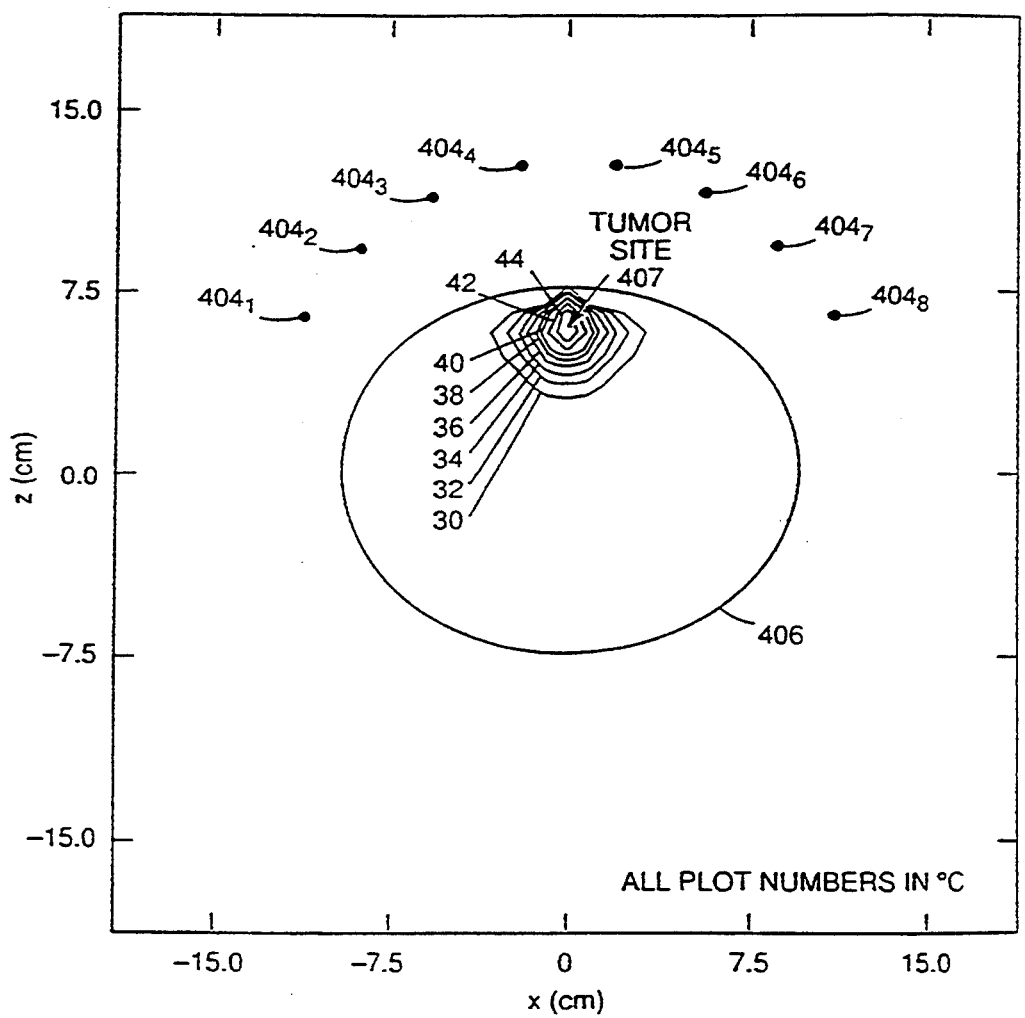
FIG. 55 is a diagram of the simulated temperature profile for the simulated E-field pattern of FIG. 53.

FIG. 55 shows a simulated two-dimensional thermal pattern expected for the quiescent radiation pattern of FIG. 53 at time t=20 minutes. This simulation assumes that the elliptical phantom brain tissue is surrounded by a 10° C. constant temperature water bolus and that the initial temperature of the brain tissue phantom is 25° C.

Figure 56:
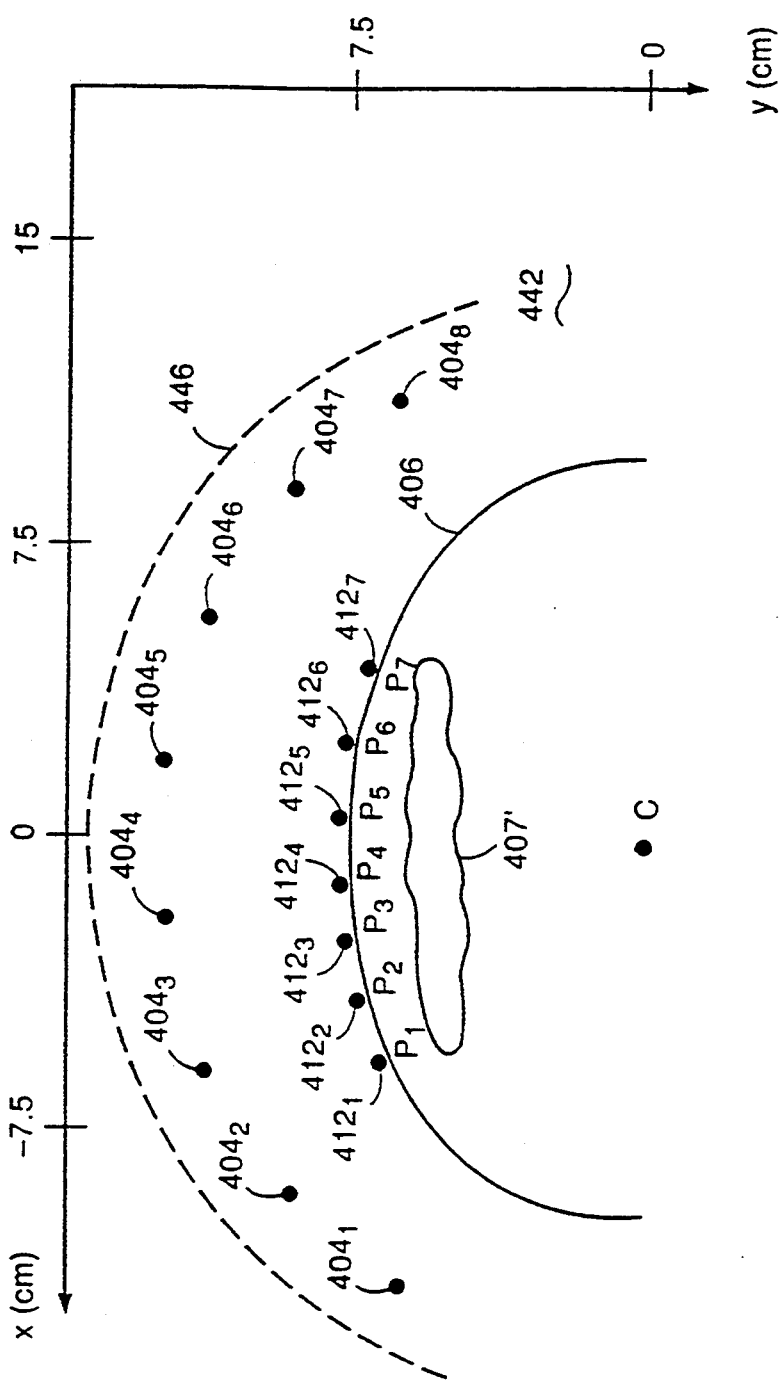
FIG. 56 is a schematic diagram of the monopole phased array hyperthermia system of FIG. 47 with an electric field probe array for generating uniform RF illumination over a large area of a target.

FIG. 56 shows a configuration of the monopole phased-array hyperthermia system of this invention configured to uniformly heat a large intra-cranial tumor target 407'. In this case, a set of auxiliary E-field probes 412 are uniformly spaced along the skin surface of the cranium between the monopole radiator elements 404 and the tumor site 407'. Here, seven E-field probes $412_1$ through $412_7$ are used, denoted $P_1$ through $P_7$ respectively, but the quantity of probes required will vary according to the tumor size and location. The gains and phases of the monopole elements are adaptively adjusted to uniformly distribute the electric field energy at the E-field probes $412_1$ through $412_7$. From the geometry of FIG. 56 it is observed that a uniform electric field at the E-field probes will produce a substantially uniform electric field inside tumor 407' to induce uniform heating of the tumor.

To achieve a uniform electric field distribution across all the E-field probes, and thus uniform heating of the tumor 407', the amplitude difference between any two adjacent E-field probes on the skin surface of the cranium must be minimized. The electric field differences between adjacent E-field probes may be written as $$\Delta A_{P12} | A_{P1} - A_{P2} |, \quad (82)$$

$$\Delta A_{P23} = | A_{P2} - A_{P3} |, \quad (83)$$

$$\Delta A_{P34} = | A_{P3} - A_{P4} |, \quad (84)$$

$$\Delta A_{P45} = | A_{P4} - A_{P5} |, \quad (85)$$

$$\Delta A_{P56} = | A_{P5} - A_{P6} |, \quad (86)$$

and, $$\Delta A_{P67} = | A_{P6} - A_{P7} |, \quad (87)$$

where A denotes the amplitude of the electric field measured by the specified field probe. A figure of merit F may be defined as $$F = \Delta A_{P12}^2 + \Delta A_{P23}^2 + \Delta A_{P45}^2 + \Delta A_{P56}^2 + \Delta A_{P67}^2. \quad (88)$$

The figure of merit F involves six constraints on measured differences and an additional constraint on total power radiated by the transmit array, all of which are easily taken into account by the eight transmit element phased-array described. The gradient search algorithm described above is used to minimize the figure of merit F and thereby achieve a uniform electric field distribution across the E-field probes.

It should be noted that this approach for achieving a uniform electric field distribution to effect uniform heating within a large mass is not limited to the monopole array heating of a brain tumor, and for example can be similarly implemented with the annular phased-array hyperthermia applicator of FIG. 1 for uniformly heating a large mass in other areas of the body.

Figure 57:
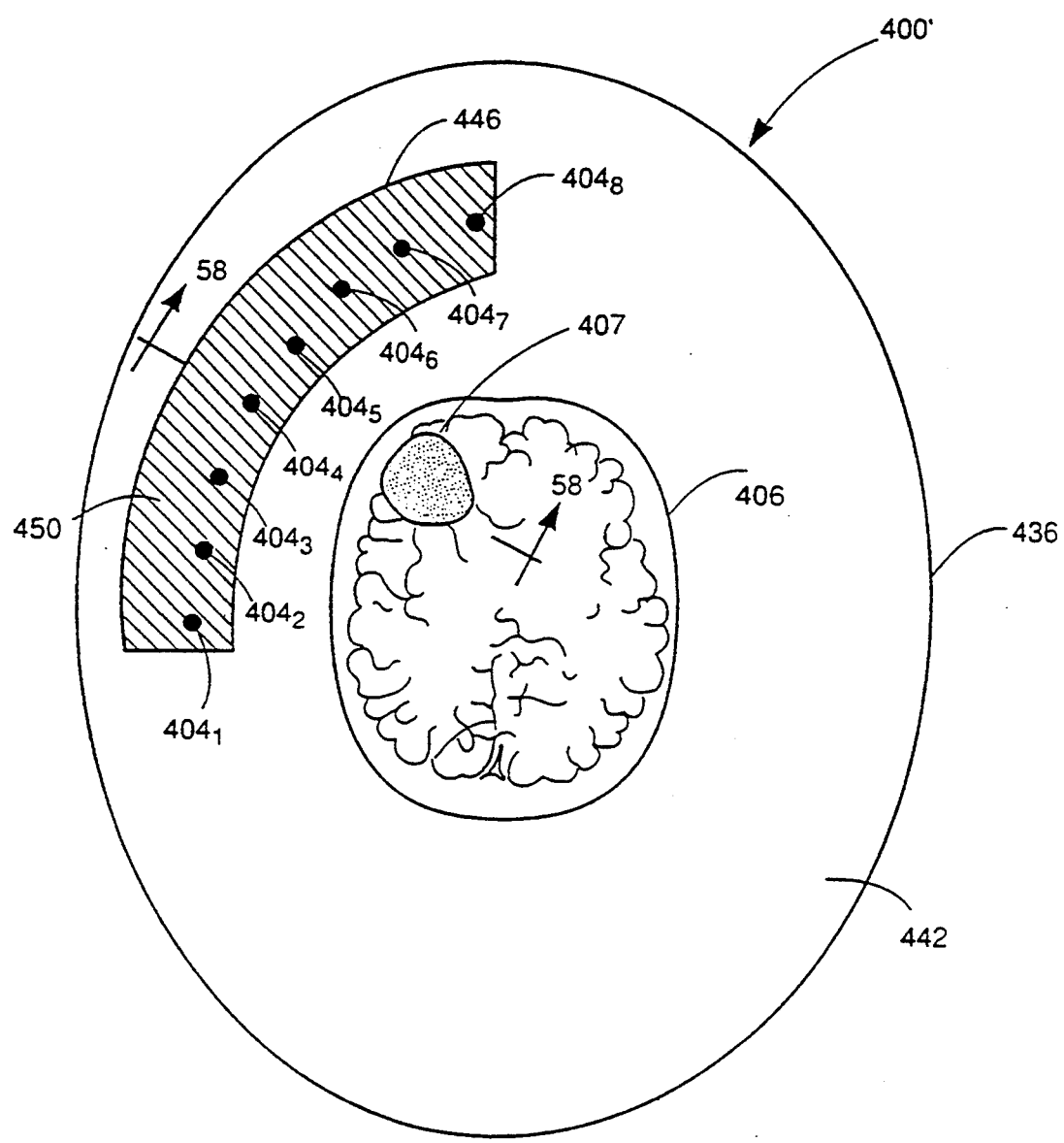
FIG. 57 show the monopole phased array system of FIG. 48 including the addition of a top ground plane surface forming a parallel plate waveguide.
Figure 58A:
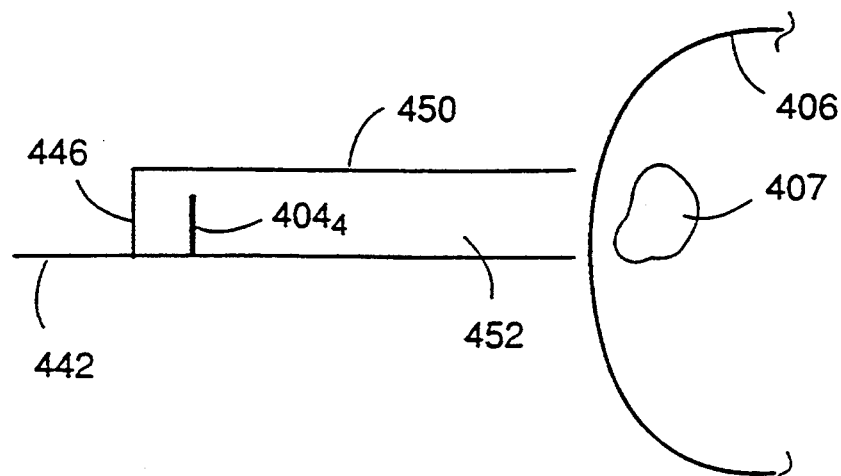
FIGS. 58A shows a cross-sectional view of the wave guide of FIG. 57.
Figure 58B:
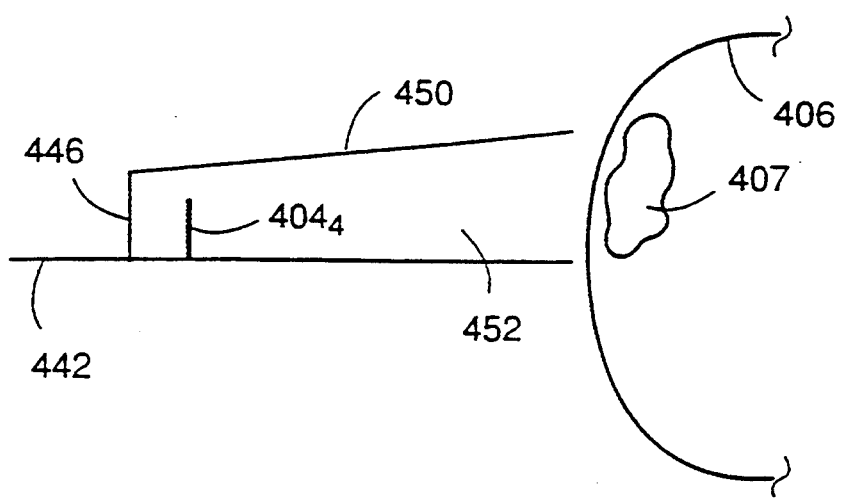
FIG. 58B shows a cross-sectional view of an alternative embodiment of the waveguide of FIG. 58A having diverging surfaces.
Figure 58C:
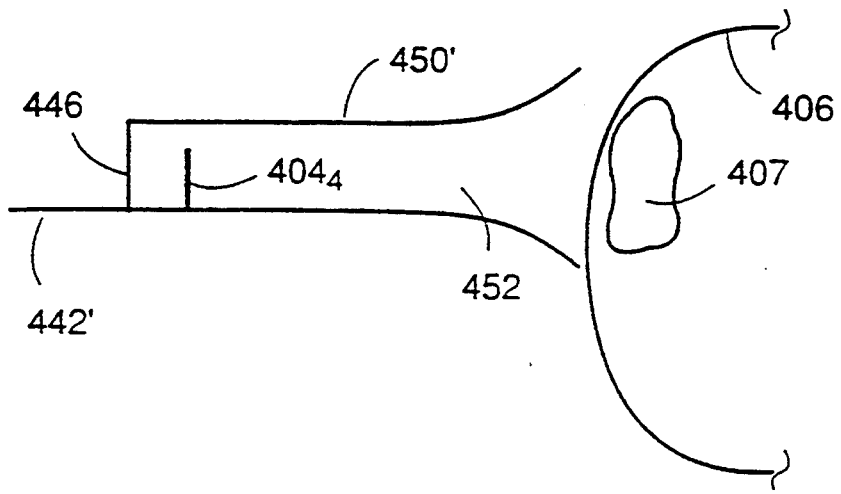
FIG. 58C shows a cross-sectional view of another alternative embodiment of the waveguide of FIG. 58A having flared surfaces forming a horn.

FIGS. 57 and 58A show an alternative preferred embodiment of the monopole phased array applicator 400 of FIG. 48 including the addition of a top ground plane surface 450 positioned above the monopole antenna elements $404_n$ and extending from the reflecting screen 446 toward the target body parallel to ground plane surface 442. The top ground plane surface 450 combines with ground plane surface 442 to form a parallel plate waveguide region 452 between the monopole antenna elements and the target body 406. The spacing between the parallel plates (i.e., between surfaces 442 and 450) can be used to adjust the radiation pattern in the direction perpendicular to the parallel plates. The spacing between the parallel plates is typically between ½ and 5 wavelengths. FIGS. 58B and 58C show alternative preferred embodiments of the parallel plate waveguide of FIG. 58A having non-parallel waveguide surfaces, and flared waveguide surface forming a horn, respectively.

Figure 59:
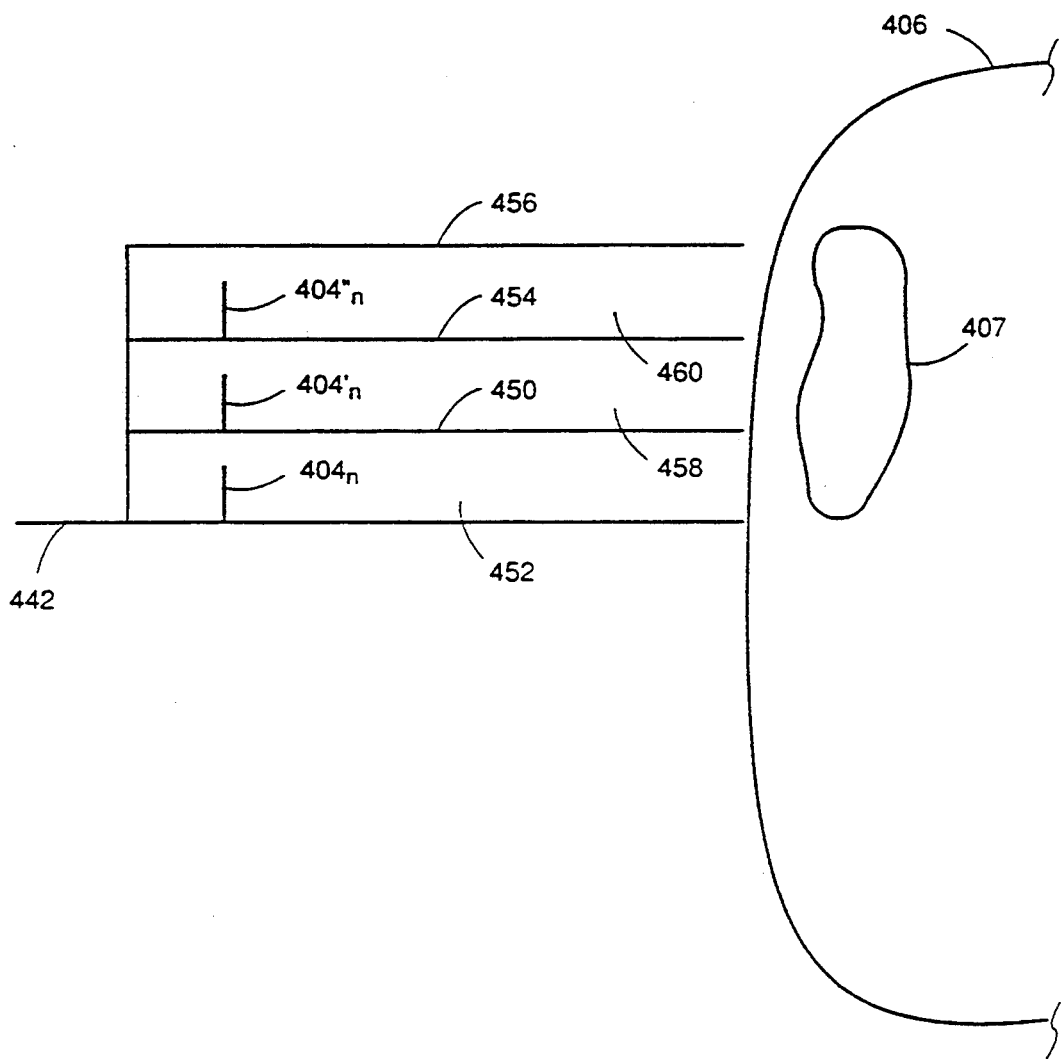
FIG. 59 shows a cross-sectional view of another alternative embodiment of the waveguide of FIG. 58A having multiple stacked monopole phased array antennas and associated stacked waveguides.

FIG. 59 shows a preferred embodiment of a stacked waveguide phased array applicator having multiple stacked parallel plates 450, 454, and 456 forming respective stacked waveguide regions 452, 458, and 460, each having a corresponding set of monopole phased array antenna elements $404_n$, $404_n'$, $404_n''$.

Figure 60:
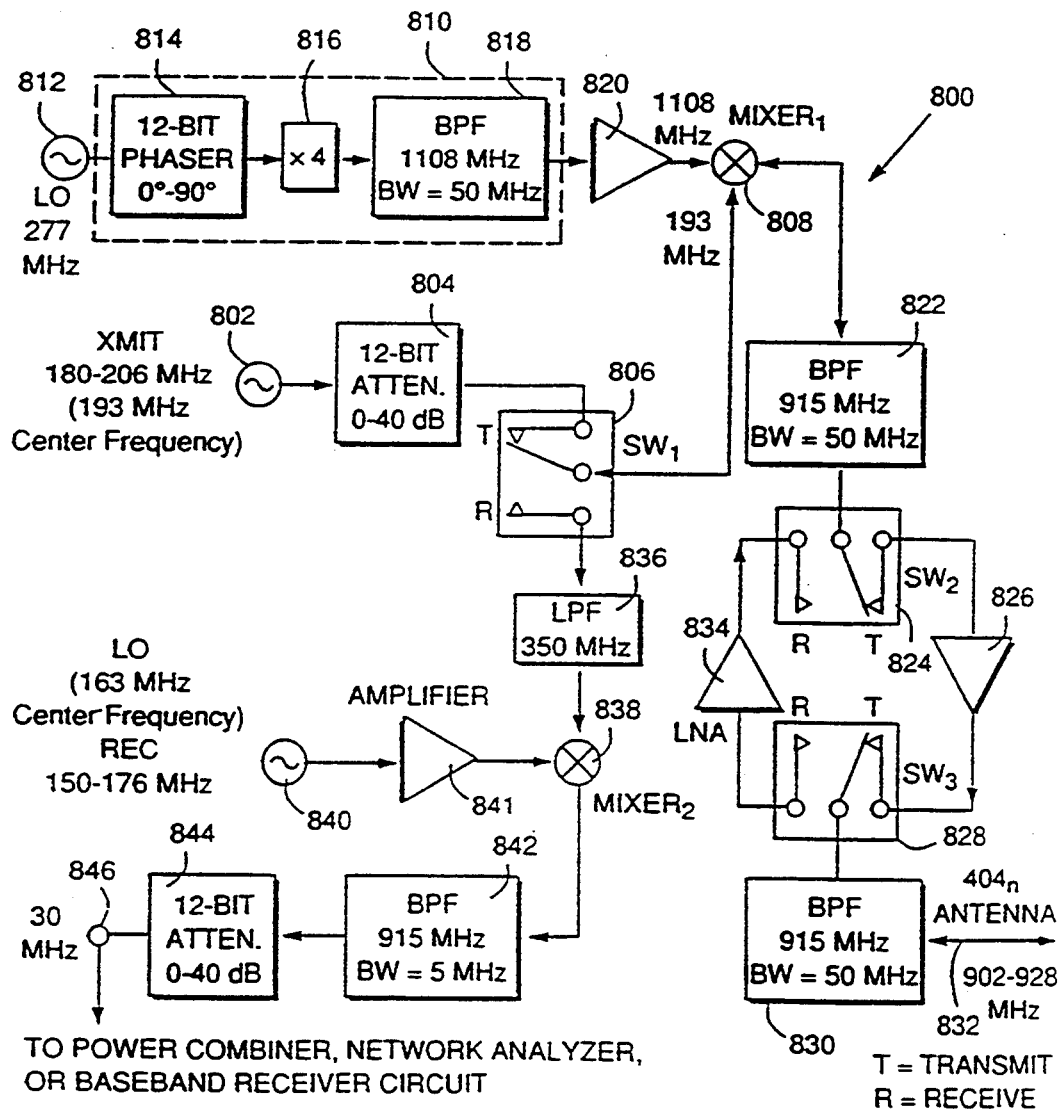
FIG. 60 is a block diagram of a microwave transmit and receive module for use with the monopole phased array system of FIG. 47.

FIG. 60 shows a block diagram of a preferred embodiment of a 915 MHz transmit and receive (T/R) module 800 for use with the monopole phased array hyperthermia system 400 (FIG. 47), specifically for use in transmit amplifier/phase shift network 110 of FIG. 50. Generally, the T/R module 800, as well as the monopole hyperthermia system 400, is not restricted to operate at 915 MHz, and is adaptable for operation anywhere within the industrial, scientific, medical (ISM) frequency band of 902 to 928 MHz.

The transmit function of the T/R module 800 is used to energize a monopole transmit antenna element 404. (FIG. 50) of the monopole hyperthermia array 402 with a 915 MHz signal, having controlled phase and gain, for the purposes of heating the target 407. Each monopole transmit antenna element $404_n$ of the array 402 is connected to a corresponding T/R module and therefore the quantity of T/R modules required depends on the quantity of monopole antenna elements $404_n$ in the array.

With regard to the generation of the 915 MHz transmit signal, having controlled phase and gain, a tunable oscillator 802, tunable from 180 to 206 MHz, is used to produce a transmit signal having a 193 MHz center frequency. The 193 MHz transmit signal is input to a dual-stage voltage-variable attenuator 804 which covers an attenuation range of 0 to −40 dB (−60 dB off state) determined by a 12 bit analog control voltage. The other port of mixer 808 is driven with a constant frequency 1108 MHz phase-controlled signal generated by a phase-controlled local oscillator 810.

Phase-controlled local oscillator 810 is excited with a 277 MHz signal generated by a fixed frequency local oscillator 812. The output of the 277 MHz local oscillator 812 is input to a voltage-variable phase shifter which shifts the phase of the 277 MHz signal from 0° to 90°, determined by a 12 bit analog control voltage. The phase-shifted 277 MHz signal is input to a ×4 frequency multiplier 816 which quadruples the signal to 1108 MHz and extends the phase control range to 0° to 360°. The output of the frequency multiplier passes through a 1108 MHz bandpass filter 818, having a 50 MHz bandwidth, to remove undesired harmonics. The 1108 MHz output of the bandpass filter is then amplified to saturation by an amplifier 820 to produce a relatively constant input power to the input port of mixer 808 independent of the commanded phase shift.

The upconverted, gain and phase-controlled 915 MHz signal output from mixer 808 passes through a 915 MHz bandpass filter 822, having a 50 MHz bandwidth, to remove undesired harmonics generated in mixer 808. The output signal of bandpass filter 822 passes through another T/R switch 824 which, when in the transmit position (T), connects the bandpass filter output signal to drive the input of a power amplifier 826 having an average CW output power of up to, or greater than, 100 watts. The output signal of the power amplifier 826 passes through another T/R switch 828 which, when in the transmit position (T), connects the amplified 915 MHz transmit signal to the input of another 915 MHz bandpass filter 830, having a 50 MHz bandwidth, which removes unwanted harmonics generated in the power amplifier. Finally, the 915 MHz transmit signal output from bandpass filter 830 is connected by a transmission line 832 to a monopole antenna element $404_n$ of the monopole hyperthermia array 402.

The receive function of the T/R module 800 can be used for passive microwave radiometry for non-invasively sensing the temperature of the target tissue 407 (FIG. 50) with the monopole antenna elements $404_n$ of array 402. To operate in a non-invasive microwave radiometry mode, the transmit power is turned off as desired for a period of several seconds during which the elements of the monopole hyperthermia array act as passive receive antennas.

In this case, the three T/R switches 806, 824, and 828 are set to the receive (R) position. The 915 MHz center-frequency passive signal received by the monopole antenna element $404_n$ is filtered by bandpass filter 830, amplified by a low-noise amplifier 834, and again filtered by bandpass filter 822. The output of bandpass filter 822 is mixed with the 1108 MHz controlled-phase local oscillator signal by mixer 808, the output of which is input to a lowpass filter 836. Lowpass filter 836 has a 350 MHz high frequency cutoff which provides a 193 MHz center frequency receive signal for input to a second mixer 838. A variable frequency local oscillator, tunable over a 150–176 MHz range, has an output signal tuned to 163 MHz which is amplified by an amplifier 841 and input to another port of mixer 838 to mix with the 193 MHz center frequency receive signal. The output of mixer 838 contains a 30 MHz center frequency receive signal which is input to a 30 MHz bandpass filter 842, having a 5 MHz bandwidth, to remove unwanted out of band signals. The filtered 30 MHz center frequency receive signal is then passed through a voltage controlled 0 to −40 dB attenuator 844 whose output signal 846 is controlled by a 12 bit analog voltage level.

The 30 MHz center frequency receive signal 846 can be analyzed with a commercial network analyzer, such as a Hewlett Packard 8510 analyzer, or can be combined with the output of the other T/R modules (i.e., receive signals from the other monopole antenna elements) in a commercial analog power combiner at the 30 MHz frequency. Alternatively, the 30 MHz receive signal 846 can be mixed with a 28.5 MHz local oscillator and downconverted to a baseband offset frequency of 1.5 MHz. The resulting baseband signal is lowpass filtered with a cutoff frequency of 2.0 MHz, and sampled with a high speed digital to analog convertor at 4.5 MHz (i.e., above the Nyquist sampling limit for the bandlimited signal). The frequency spectrum of the baseband signal is then computed using digital signal processing techniques (see, J. R. Johnson, et al., "An Experimental Adaptive Nulling Receiver Utilizing the Sample Matrix Inversion Algorithm with Channel Equalization", IEEE Transactions on Microwave Theory and Techniques, Vol. MTT-39, No. 5, pp. 798–808, May 1991). It should further be noted that the T/R module 800 can be used as a receiver 114 (FIG. 50) for the E-field probes 412 if the low-noise amplifier 834 is bypassed.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. For instance, the adaptive focusing and nulling apparatus and methods described herein are applicable to ultrasound hyperthermia systems. Further, although the RF hyperthermia systems are described herein with respect to a particular range of frequencies, the invention is applicable to RF hyperthermia systems operating from low RF frequencies to microwave frequencies. Although each of the preferred embodiments of the invention describes using a particular quantity of auxiliary probes, it is understood that a larger or smaller number of auxiliary probes may also be used with differing focused and nulled radiation patterns, e.g., more control over the radiation pattern with more probes and less control with fewer probes. Although each of the preferred embodiments describes applying hyperthermia radiation to a particular part of the body, it is understood that other parts of the body can be similarly treated with the same or similar embodiment, e.g., a monopole phased array can also be used to treat tumors located in the neck, arm, or leg. Still further, the invention is applicable to non-medical hyperthermia systems, such as those used for industrial materials heating.

APPENDIX A

```
*** Copyright MIT Lincoln Laboratory 1991.  All rights reserved.
****************makefile for moment method software*******
****file sdipjamhyperMake*****
EXECUTABLE = sdipjamhyper.out
OBJS = sdipjamhyper.o dzabgnloss.o \
        dpack2.o zabgenloss.o pack2.o fwgh.o \
        chebaf.o wwquan.o taylor.o \
        eigenv.o reordr.o ydipsubloss.o \
        plothyper.o contek.o plabel.o \
        conturek.o circsubloss.o
# use tabs for continues
IL = /usr/lib/f68881/libm.il
FLAGS = -O1 -v -f68881
$(EXECUTABLE): $(OBJS)
        dislink -lF77 $(FLAGS) -o $(EXECUTABLE) $(OBJS) $(IL)

sdipjamhyper.o: /home/ajf/hyperthermia/sdipjamhyper.f
        f77 $(FLAGS) -c /home/ajf/hyperthermia/sdipjamhyper.f $(IL)

plothyper.o: /home/ajf/hyperthermia/plothyper.f
        f77 $(FLAGS) -c /home/ajf/hyperthermia/plothyper.f $(IL)

dzabgnloss.o: /home/ajf/hyperthermia/dzabgnloss.f
        f77 $(FLAGS) -c /home/ajf/hyperthermia/dzabgnloss.f $(IL)

dpack2.o: /home/ajf/monjam/dpack2.f
        f77 $(FLAGS) -c /home/ajf/monjam/dpack2.f $(IL)

contek.o: /home/ajf/monjam/contek.f
        f77 $(FLAGS) -c /home/ajf/monjam/contek.f $(IL)

plabel.o: /home/ajf/monjtr/plabel.f
        f77 $(FLAGS) -c /home/ajf/monjtr/plabel.f $(IL)

conturek.o: /home/ajf/hyperthermia/conturek.f
        f77 $(FLAGS) -c /home/ajf/hyperthermia/conturek.f $(IL)
zabgenloss.o: /home/ajf/hyperthermia/zabgenloss.f
        f77 $(FLAGS) -c /home/ajf/hyperthermia/zabgenloss.f $(IL)

pack2.o: /home/ajf/monjam/pack2.f
        f77 $(FLAGS) -c /home/ajf/monjam/pack2.f $(IL)

fwgh.o: /home/ajf/monjam/fwgh.f
        f77 $(FLAGS) -c /home/ajf/monjam/fwgh.f $(IL)

chebaf.o: /home/ajf/monjam/chebaf.f
        f77 $(FLAGS) -c /home/ajf/monjam/chebaf.f $(IL)

wwquan.o: /home/ajf/monjam/wwquan.f
        f77 $(FLAGS) -c /home/ajf/monjam/wwquan.f $(IL)

taylor.o: /home/ajf/monjam/taylor.f
        f77 $(FLAGS) -c /home/ajf/monjam/taylor.f $(IL)

eigenv.o: /home/ajf/monjam/eigenv.f
        f77 $(FLAGS) -c /home/ajf/monjam/eigenv.f $(IL)
reordr.o: /home/ajf/monjam/reordr.f
        f77 $(FLAGS) -c /home/ajf/monjam/reordr.f $(IL)
```

```
ydipsubloss.o: /home/ajf/hyperthermia/ydipsubloss.f
        f77 $(FLAGS) -c /home/ajf/hyperthermia/ydipsubloss.f $(IL)

circsubloss.o: /home/ajf/hyperthermia/circsubloss.f
        f77 $(FLAGS) -c /home/ajf/hyperthermia/circsubloss.f $(IL)

******file sdipjamhyper.f*************
C***PROGRAM SDIPJAMHYPER.F ---  ANALYZES FINITE ARRAYS OF DIPOLES
C***IN LOSSY DIELECTRIC OR FREE SPACE.
C***THE DIPOLES ARE ASSUMED TO BE ORIENTED PARALLEL
C***TO THE PLANE OF THE GRID FOR A PLANAR ARRAY, OR THEY CAN BE
C***ARRANGED IN AN ANNULAR (RING) ARRAY CONFIGURATION.
C***RECEIVING CONDITIONS ARE ASSUMED.
C***DOUBLE-PRECISION VERSION
        PARAMETER (NUMCHN=8)
        PARAMETER (NUMAUX=8)
        PARAMETER (NUMJAM=7)
        PARAMETER (NUMELM=8)
        PARAMETER (NUMFRQ=5)
        PARAMETER (NUMNPT=1681)
        COMPLEX PS(1825),CZ(900),VA(NUMELM),Z(NUMELM,NUMELM)
        COMPLEX VTA(NUMELM),VREFA,VRECVA(NUMELM)
        COMPLEX VCW(NUMELM),VRECVX(NUMELM),CJ,CSUMA,VXA
CC***THE ABOVE MATRICES ARE DIMENSIONED BY THE NUMBER OF ELEMENTS
        COMPLEX *16 COVNF(NUMCHN,NUMCHN),COVNFI(NUMCHN,NUMCHN)
        COMPLEX *16 COVAAJ(NUMCHN,NUMCHN),CINVCN(NUMCHN,NUMCHN)
        COMPLEX *16 VCHA(NUMCHN,NUMFRQ)
        COMPLEX *16 VMAJMA(NUMJAM,NUMFRQ)
        COMPLEX *16 VAUXJA(NUMAUX,NUMJAM,NUMFRQ)
        COMPLEX *8 VAXCWA(NUMAUX,NUMNPT)
C***NOTE DIMENS.  VCHA(NCHAN,NFREQ),VMAJMA(NJAM,NFREQ)
C                 VAUXJA(NAUX,NJAM,NFREQ),VAXCWA(NAUX,NPTS)
        COMPLEX *8 VXMANA(NUMNPT),ETASP,GAMSP
        COMPLEX *16 EIGVAN(NUMCHN),EIGVEN(NUMCHN,NUMCHN)
        COMPLEX *16 WANA(NUMCHN,1)
        COMPLEX *16 WTCTR(1,NUMCHN),WQSLC(NUMCHN,1)
        COMPLEX *16 WQNA(NUMELM,1),CMPROD(1,NUMCHN),WAN(NUMCHN,1)
        COMPLEX *16 WANDMA(NUMELM,1)
        COMPLEX *16 CWTA(NUMELM,1),ETADP,GAMDP
        DIMENSION ACALPH(NUMELM),RWTA(NUMELM),RWTB(NUMELM)
        DIMENSION VXADB(NUMNPT),VXAPH(NUMNPT)
        DIMENSION XC(NUMNPT),YC(NUMNPT),ZC(NUMNPT)
        DIMENSION THSD(1),PHSD(1),THCT(1),PHCT(1)
        DIMENSION XJAMIN(NUMJAM),YJAMIN(NUMJAM),ZJAMIN(NUMJAM)
        DIMENSION XJAM(NUMJAM),YJAM(NUMJAM),ZJAM(NUMJAM)
        DIMENSION PWRJDB(NUMJAM)
        DIMENSION PCHADB(NUMNPT)
        REAL *8 CNDB,PHASEN,DPDCR,WKE(144),EVLDBN
        REAL *8 PREALN,PIMAGN
        REAL *8 QINRDB,AINRDB,CANCDB,EXCPCB
        REAL *8 QINRAA,AINRAA
        REAL *8 CNCLNA,ELSGDB,ELSGDG,AWSGDB,AWSGDG
        REAL *8 SUMC,SUMAA,AVECAN,AVCAA,SAVE,SAVESR
        REAL *4 RX(100),RY(100),RZ(100),FM(41,41),DMF(41,41)
        REAL *4 AUXADB(NUMAUX),VATENA(NUMAUX)
        INTEGER IAUXA(NUMAUX),LTMP(NUMCHN),MTMP(NUMCHN)
        CHARACTER DATNAM*35, OUTNAM*35
        COMMON/A/DX,DY,NCOLX,NROWY,NEL,HZ,HL,ARAD,ZLOAD,ZCHAR
        COMMON /B/ NGEN,IGEN,THETAS,PHIS,IMUT,IBLTSL,IPATRN
        COMMON /D/ FGHZ,RLAMDA,IWL,IS,NSCANS
        COMMON /DEG/ THDR,THDMIN
        COMMON /PLT/ INEAR,IPLOTM
        COMMON/XLYL/XL,YL
        COMMON/NEAR/IANTX,IANTY,NPOWER,IPCONN,IPCONF,IPCUTF
        COMMON/NEAR2/IPCFX,IPCFY,IPCFZ
        COMMON /P/XN,YN,ZN,RLSX,RLSY,RLSZ,NCOLXN,NROWYN,NCOLZN
        COMMON /P2/EDGET,ICOMB,PUNFLX,PUNFLY
        COMMON /CHEBY/ ICHEB,SLLDB
        COMMON /GROUND/ IGRNDP
        COMMON /NORM/ IENORM,BIGNDB
        COMMON /NORMAL/ INRNOR
        COMMON/PCENTR/PCDXIN
```

```
      COMMON /WRITE/ IWR
      COMMON /SPLOSS/ ETASP,GAMSP
      COMMON /DPLOSS/ ETADP,GAMDP
      COMMON /F/ FHZ,ER3,SIG3,TD3
      COMMON /CIRCLE/ ICIRC,RADIUS,HLS
      NAMELIST/DIPOLE/NCOLX,NROWY,HZIN,HLIN,ARADIN,ZLOAD,NGEN,IGEN,
     1DXIN,DYIN,IMUT,NSCANS,THSD,PHSD,THSINC,IBLTSL,IPATRN,ER3,SIG3,TD3,
     2NPHCT,PHCT,NTHPT,ZCHAR,IWL,FCHZ,BWFHZ,NFREQ,THDR,THDMIN,ICIRC,
     3XNIN,YNIN,ZNIN,NCOLXN,NROWYN,NCOLZN,INEAR,IPRCOM,IANGLP,CRADIN,
     4IANTX,IANTY,NPOWER,NFCOLX,NFROWY,IPCONN,IPCONF,IPOL,HLSIN,
     5IPCFX,IPCFY,IPCFZ,ITEK,IGRNDP,IGAIN,ICHEB,IWR,IENORM,BIGNDB,
     6NXDUM,NYDUM,NPDX,EDGTDB,RLSXIN,RLSYIN,RLSZIN,ISLC,INUNIF,
     7XFOCIN,ZFOCIN,XJAMIN,YJAMIN,ZJAMIN,IATTEN,AUXADB,INRNOR,
     8NJAMS,PWRCDB,PWRJDB,NAUX,IAUXA,IAUXB,ITLTPR,ITLTDP,
     9IQUAN,IRNERR,ELERDB,ELERDG,AWERDB,AWERDG,NBMOD,NBADWT,NRAN,SLLDB
C**NOTE; IF IWL=0 (INCHES), IWL=2 (METERS)
      WRITE(6,2959)
2959  FORMAT(1X,'ENTER INPUT DATA FILE NAME (typ. sdipjamhyper.data)')
      READ(5,*) DATNAM
      OPEN(4,FILE=DATNAM,FORM='FORMATTED')
      WRITE(6,3959)
3959  FORMAT(1X,'ENTER OUTPUT DATA FILE NAME (typ sdipjamhyper.output)')
      READ(5,*) OUTNAM
      OPEN(8,FILE=OUTNAM,FORM='FORMATTED')
      CALL GETCP2(CPU1)
      PI=3.141592654
      DCR=PI/180.
      DPDCR=DCR
      CJ=(0.,1.)
      CINMTR=0.0254
      IGRNDP=1
      IGAIN=0
      ZLOAD=0.0
      ICHEB=0
      IWR=0
      IENORM=1
      EXCPCB=-1.0D0
      IQUAN=0
      NRAN=1
      TILTPR=0.0
      TILTDP=0.0
      IATTEN=0
      IPOL=1
      ER3=1.0
      SIG3=0.0
      TD3=-1.0
      ICIRC=0
      CRADIN=0.0
      HLSIN=0.0
      ISLC=1
      INUNIF=0
      INRNOR=0
      READ(4,DIPOLE)
      IF(NFREQ.EQ.1) BWFHZ=0.0
      IF(ISLC.EQ.0) WRITE(6,81100)
81100 FORMAT(1X,'FULLY ADAPTIVE ARRAY')
      IF(ISLC.EQ.0.AND.ICHEB.EQ.0) INUNIF=1
      IF(ICIRC.EQ.1) WRITE(6,7000)
7000  FORMAT(1X,'RING ARRAY GEOMETRY')
      FHZ=FCHZ
      IXZ=0
      IXY=0
      IF(NROWYN.EQ.1) IXZ=1
      IF(NCOLZN.EQ.1) IXY=1
      IF(IPOL.EQ.2) IPRCOM=0
      IF(IPRCOM.EQ.0) WRITE(6,7898)
7898  FORMAT(1X,'NO PROBE COMPENSATION')
      WRITE(6,9276)IGRNDP
9276  FORMAT(1X'GROUND PLANE PARAMETER, IGRNDP=',I4)
CC    DO 1615 IX=1,NAUX
CC    IF(IATTEN.EQ.0) AUXADB(IX)=0.0
CC    WRITE(6,2318)IX,AUXADB(IX)
```

```
C2318   FORMAT(1X,'IX,AUXADB(IX)=',I4,2X,F12.2)
CC      VATENA(IX)=10.**(AUXADB(IX)/20.)
C1615   CONTINUE
        IF(NJAMS.GT.1) WRITE(8,2009)XJAMIN(1),YJAMIN(1),ZJAMIN(1)
2009    FORMAT(1X,'XJAMIN(1),YJAMIN(1),ZJAMIN(1)=',3F12.3)
        WRITE(6,6987) BWFHZ,NFREQ
6987    FORMAT(1X,'BWFHZ,NFREQ=',E12.5,2X,I5)
        IF(ITEK.EQ.0)CALL COMPRS
        IF(ITEK.EQ.1)CALL TEKALL(4014,480,0,1,0)
CC      IF(INEAR.EQ.0) CALL PRNTDA
        IF(IMUT.EQ.0) ZLOAD=1.0
        IF(ITLTPR.EQ.1) TILTPR=45.
        IF(ITLTDP.EQ.1) TILTDP=45.
        CTPR=COS(TILTPR*DCR)
        STPR=SIN(TILTPR*DCR)
        CTDP=COS(TILTDP*DCR)
        STDP=SIN(TILTDP*DCR)
        FGHZ=FCHZ/1.0E9
        NEL=NCOLX*NROWY
        RNEL=NEL
        XLIN=DXIN*(NCOLX-1)
        YLIN=DYIN*(NROWY-1)
        NACOLX=NCOLX-NPDX-2*NXDUM
        NAROWY=NROWY-2*NYDUM
        NAEL=NACOLX*NAROWY
        PCDXIN=NPDX*DXIN
        NAUXP1=NAUX+1
        NAUXP2=NAUX+2
        IF(ISLC.EQ.1) NMAX=NAUXP1
        IF(ISLC.EQ.0) NMAX=NEL
        NMAXP1=NMAX+1
        ELSGDB=ELERDB*SQRT(3.)
        ELSGDG=ELERDG*SQRT(3.)
        AWSGDB=AWERDB*SQRT(3.)
        AWSGDG=AWERDG*SQRT(3.)
        INITRN=1
        IF(ISLC.EQ.0) THEN
           NAUX=NEL
           NAUXP1=NAUX+1
           NAUXP2=NAUX+2
           DO 79130 I=1,NEL
           IAUXA(I)=I
           WRITE(6,76767)I,IAUXA(I)
76767      FORMAT(1X,'I,IAUXA(I)=',2I5)
79130      CONTINUE
        ENDIF
        DO 1615 IX=1,NAUX
        IF(IATTEN.EQ.0) AUXADB(IX)=0.0
        WRITE(6,2318)IX,AUXADB(IX)
2318    FORMAT(1X,'IX,AUXADB(IX)=',I4,2X,F12.2)
        VATENA(IX)=10.**(AUXADB(IX)/20.)
1615    CONTINUE
30      CONTINUE
        NR=1
        IF(NGEN.EQ.1) NSCANS=0
        ICC=NEL
        ICC1=ICC
        IF(IBLTSL.EQ.1) ICC1=NROWY
CC      IF(IWL.EQ.1)GO TO 50
        WRITE(8,40)FGHZ
40      FORMAT(/,1X,'FGHZ=',F15.7)
C*********************************************************************
C*****COMPUTE FREE SPACE LAMBDA*******
C*****ALL UNITS HAVE TO BE IN METERS
        RLAMDA=2.997925E10/FCHZ/2.54
C***PARAMETER CONVERSIONS TO PROPER UNITS
55      CONTINUE
        IF(IWL.EQ.2) GO TO 50
        DX=DXIN*CINMTR
        DY=DYIN*CINMTR
        HL=HLIN*CINMTR
        HLS=HLSIN*CINMTR
```

```
            ARAD=ARADIN*CINMTR
            HZ=HZIN*CINMTR
            RLSX=RLSXIN*CINMTR
            RLSY=RLSYIN*CINMTR
            RLSZ=RLSZIN*CINMTR
            XN=XNIN*CINMTR
            YN=YNIN*CINMTR
            ZN=ZNIN*CINMTR
            XFOC=XFOCIN*CINMTR
            ZFOC=ZFOCIN*CINMTR
            XL=XLIN*CINMTR
            YL=YLIN*CINMTR
            PCDX=PCDXIN*CINMTR
            RADIUS=CRADIN*CINMTR
50          CONTINUE
            WRITE(8,60)DX,DY,HL,ARAD
60          FORMAT(1X,'DX,DY,HL,ARAD=',2X,4F14.5)
C
C***COMPUTE CALIBRATION CONSTANTS (PHASE ONLY) TO
C***MAXIMIZE GAIN (FOCUS ANTENNA) TO NEAR FIELD RANGE
C
C***PHASE CENTER 'A' VOLTAGE EXCITATION
            X0A=-XL/2.+NXDUM*DX+(NACOLX-1)/2.*DX
            YP=0.0
            IF(ICIRC.EQ.0) WRITE(6,24690)
24690       FORMAT(1X,'CALLING NFDPX2')
            IF(ICIRC.EQ.0)
           2CALL NFDPX2(CTPR,STPR,CTDP,STDP,XFOC,YP,ZFOC,X0A,0,VA,VREFA)
            IF(ICIRC.EQ.1)
           2CALL NFDPC2(XFOC,YP,ZFOC,X0A,0,VA,VREFA)
C***SAVE INCIDENT VOLTAGES
            DO 65 IV=1,NEL
            VTA(IV)=VA(IV)
            WRITE(6,3757)IV,VTA(IV)
            WRITE(8,3757)IV,VTA(IV)
3757        FORMAT(1X,'IV,VTA=',I4,2X,2E12.4)
65          CONTINUE
            WRITE(6,9876)VTA(2)
9876        FORMAT(1X,'VTA(2)=',2E12.4)
            NB=NCOLX
            IDMB=NROWY
            IDM=NEL
            ICC=NEL
            IBLT=IBLTSL
            IDM1=IDMB
            IF(IBLT.EQ.0) IDM1=NEL
            I2=1
8889        CONTINUE
            CALL ZMATRX(CTDP,STDP,IBLTSL,ICC1,ICC,CZ,Z)
C***SOLVE SYSTEM OF EQUATIONS FOR THE UNKNOWN CURRENTS
            IF(IBLT.EQ.1) GO TO 240
            ISYM=0
            I12=1
            WRITE(6,9876)VTA(2)
            WRITE(6,6110)
6110        FORMAT(1X,'CALL CROUT')
            CALL CROUT(Z,VA,ICC1,ICC,ISYM,IWR,I12,NEL)
            I12=2
            WRITE(6,9876)VTA(2)
            GO TO 255
240         IENTRY=4
            CALL BLTSOL(CZ,VA,PS,NCOLX,IDMB,IENTRY)
            IENTRY=3
255         WRITE(8,270)
270         FORMAT(1X,'CURRENTS')
            IF(NEL.LT.40) CALL CNORM(VA,NEL)
            WRITE(6,280)
280         FORMAT(1X,'AFTER CURRENTS SOLUTION')
C***VA ARE CURRENTS (AMPERES) NOW
C*
C***COMPUTE RECEIVED VOLTAGES
            DO 285 IC=1,NEL
```

```
        WRITE(6,7531)ZLOAD
7531    FORMAT(1X,'ZLOAD=',F12.5)
        WRITE(6,1134)IC,VTA(IC)
        VRECVA(IC)=VA(IC)*ZLOAD
        WRITE(6,1174)IC,VRECVA(IC)
1134    FORMAT(1X,'IC,VTA=',I4,2X,2E12.4)
1174    FORMAT(1X,'IC,VRECVA=',I4,2X,2E12.4)
        WRITE(6,1135)IC,VA(IC)
1135    FORMAT(1X,'IC,VA=',I4,2X,2E12.4)
        VRADB=20.*ALOG10(CABS(VRECVA(IC)))
        VRAPH=ATAN2(AIMAG(VRECVA(IC)),REAL(VRECVA(IC)))/DCR
C***COMPUTE CALIBRATION CONSTANTS (PHASE ONLY)
        ACALPH(IC)=-VRAPH
285     CONTINUE
        DO 7777 IC=1,NEL
        WRITE(6,6667)IC,ACALPH(IC)
CC      WRITE(8,6667)IC,ACALPH(IC)
6667    FORMAT(1X,'IC,ACALPH=',I4,2X,F10.2,' DEGS')
7777    CONTINUE
C***COMPUTE NEAR FIELD PATTERN OF FOCUSED ARRAY
C
C***COMPUTE BEAMFORMER WEIGHTS (I.E. TAPER)
        IF(INUNIF.EQ.0)
       2CALL VRCVWT(NACOLX,NAROWY,NXDUM,NYDUM,EDGTDB,RWTA,RWTB)
        DO 1199 IC=1,NEL
        IF(INUNIF.EQ.1.AND.ISLC.EQ.0) RWTA(IC)=1./SQRT(RNEL)
        WRITE(6,5111)IC,RWTA(IC)
        WRITE(8,5111)IC,RWTA(IC)
5111    FORMAT(1X,'IC,RWTA=',I4,2X,E12.5)
1199    CONTINUE
        DO 5333 KC=1,NEL
        CWTA(KC,1)=RWTA(KC)*CEXP(CJ*ACALPH(KC)*DCR)
5333    CONTINUE
        IF(IQUAN.EQ.1)
       2CALL ADQUAN(NEL,CWTA,NBMOD,IRNERR,INITRN,ELSGDB,ELSGDG)
        BIGWDB=-299.0
        DO 91020 I=1,NEL
        WRITE(6,61910)I,CWTA(I,1)
        WRITE(8,61910)I,CWTA(I,1)
61910   FORMAT(1X,'I,CWTA(I,1)=',I4,2X,2E12.5)
        CWTADB=20.*DLOG10(CDABS(CWTA(I,1)))
        IF(CWTADB.GT.BIGWDB) BIGWDB=CWTADB
91020   CONTINUE
        DO 91120 I=1,NEL
        CWTADB=20.*DLOG10(CDABS(CWTA(I,1)))-BIGWDB
        CWTADG=DATAN2(DIMAG(CWTA(I,1)),DREAL(CWTA(I,1)))/DCR
        WRITE(6,35990)I,CWTADB,CWTADG
        WRITE(8,35990)I,CWTADB,CWTADG
35990   FORMAT(1X,'I=',I4,2X,'CWTADB,CWTADG=',1X,2F14.5)
91120   CONTINUE
        INITRN=2
C***PERFORM NEAR FIELD SCAN WITH CW RADIATING DIPOLE
        IF(INEAR.EQ.0) GO TO 390
        WRITE(6,350)
        WRITE(6,360)XNIN,YNIN,ZNIN,RLSXIN,RLSYIN,RLSZIN,NCOLXN,NROWYN,
       2NCOLZN
        WRITE(6,320)IWL
320     FORMAT(1X,'IWL=',I4)
        WRITE(6,330)
330     FORMAT(1X,'CHANGE NEAR FIELD SCAN PARAMETERS?, ICHANG=1')
        READ(5,*,END=370)ICHANG
        IF(ICHANG.EQ.0) GO TO 370
340     WRITE(6,350)
350     FORMAT(1X,'XN,YN,ZN,RLSXIN,RLSYIN,RLSZIN,NCOLXN,NROWYN,NCOLZN=')
        READ(5,*)XNIN,YNIN,ZNIN,RLSXIN,RLSYIN,RLSZIN,NCOLXN,NROWYN,NCOLZN
        WRITE(6,360)XNIN,YNIN,ZNIN,RLSXIN,RLSYIN,RLSZIN,NCOLXN,NROWYN,
       2NCOLZN
360     FORMAT(1X,6F10.3,2X,3I5)
        IF(IWL.EQ.2) GO TO 370
        XN=XNIN*CINMTR
        YN=YNIN*CINMTR
        ZN=ZNIN*CINMTR
```

```
        RLSX=RLSXIN*CINMTR
        RLSY=RLSYIN*CINMTR
        RLSZ=RLSZIN*CINMTR
370     CONTINUE
C**ALL DIMENSIONS IN METERS
        NELN=NCOLXN*NROWYN
        NPTSN=NELN*NCOLZN
C***SET DEFAULT VALUES FOR DXN,DYN,DZN
        DXN=0.0
        DYN=0.1
        DZN=0.0
        IF(NCOLXN.GT.1)DXN=RLSX/(NCOLXN-1)
        IF(NROWYN.GT.1)DYN=RLSY/(NROWYN-1)
        IF(NCOLZN.GT.1)DZN=RLSZ/(NCOLZN-1)
        IC=0
        BIGNDB=-299.0
        DO 3000 ICOLZN=1,NCOLZN
        ZPOS=ZN+DZN*(ICOLZN-1)
        DO 3000 IROWYN=1,NROWYN
        Y=YN+DYN*(IROWYN-1)
        DO 3000 ICOLXN=1,NCOLXN
        CALL GETCP2(CPU2)
        CPUSUB=CPU2-CPU1
        WRITE(6,7319)CPUSUB
7319    FORMAT(1X,'CPU SUBTOTAL=',F14.2)
        IC=IC+1
        X=XN+DXN*(ICOLXN-1)
        XC(IC)=X
        YC(IC)=Y
        ZC(IC)=ZPOS
        WRITE(6,6969)IC,XC(IC),YC(IC),ZC(IC)
6969    FORMAT(1X,'IC,XC,YC,ZC=',I4,2X,3F12.3)
        IF(ICIRC.EQ.0)
       2CALL NFDPX2(CTPR,STPR,CTDP,STDP,X,Y,ZPOS,0.0,0,VCW,VREFCW)
        IF(ICIRC.EQ.1)
       2CALL NFDPC2(X,Y,ZPOS,0.0,0,VCW,VREFCW)
        IF(IMUT.EQ.0) GO TO 4255
C***SOLVE EACH SYSTEM OF EQUATIONS FOR THE UNKNOWN CURRENTS
        IF(IBLT.EQ.1) GO TO 4040
        I12=2
        WRITE(6,6110)
        CALL CROUT(Z,VCW,ICC1,ICC,ISYM,IWR,I12,NEL)
        GO TO 4255
4040    IENTRY=3
        CALL BLTSOL(CZ,VCW,PS,NCOLX,IDMB,IENTRY)
4255    CONTINUE
C***COMPUTE RECEIVED VOLTAGES FOR PRESENT SCAN
        DO 3285 IIIC=1,NEL
        VRECVX(IIIC)=VCW(IIIC)*ZLOAD
3285    CONTINUE
C***STORE AUX. CHANNEL VOLTAGES
        DO 1681 IAX=1,NAUX
C**MODIFICATION TO INCLUDE AUX. ATTEN.
        VAXCWA(IAX,IC)=VRECVX(IAUXA(IAX))*VATENA(IAX)
CC      WRITE(6,3231)IAX,IC,XC(IC),VAXCWA(IAX,IC)
3231    FORMAT(1X,'IAX,IC,XC,VAXCWA(IAX,IC)=',2I4,2X,F12.3,2X,2E12.5)
1681    CONTINUE
C***PERFORM BEAM FORMATION
        CSUMA=(0.,0.)
        DO 5444 KC=1,NEL
        CSUMA=CSUMA+VRECVX(KC)*CWTA(KC,1)
5444    CONTINUE
        VXA=CSUMA
        IF(CABS(VXA).EQ.0.)VXA=(1.E-10,0.)
        VXADB(IC)=20.*ALOG10(CABS(VXA))
        IF(VXADB(IC).GT.BIGNDB) BIGNDB=VXADB(IC)
        VXAPH(IC)=ATAN2(AIMAG(VXA),REAL(VXA))/DCR
        VXMANA(IC)=10.**(VXADB(IC)/20.)*CEXP(CJ*VXAPH(IC)*DCR)
CC      WRITE(6,4457)IC,VXMANA(IC)
4457    FORMAT(1X,'IC,VXMANA=',I4,2X,2E12.5)
        WRITE(6,6429)IC,XC(IC),VXADB(IC)
6429    FORMAT(1X,'IC,X,VXADB=',I4,2X,F10.2,2X,F12.2)
```

```
3000   CONTINUE
       IF(IENORM.EQ.0) GO TO 2500
       WRITE(6,3765)BIGNDB
3765   FORMAT(1X,'BIGNDB=',F12.2)
       DO 3020 IC=1,NPTSN
CC     WRITE(6,3343)IC,VXADB(IC)
       VXADB(IC)=VXADB(IC)-BIGNDB
CC     WRITE(6,3343)IC,VXADB(IC)
3020   CONTINUE
2500   WRITE(6,3030)
3030   FORMAT(1X,'WANT TO PLOT NEAR FIELD CUTS, IPLOTN=1')
       READ(5,*)IPLOTN
C***NEXT LINE ADDED TO AVOID RUN TIME ERROR
       IF(IPCONN.EQ.1) IPLOTN=0
       IF(IPCONN.EQ.0) THEN
          WRITE(30,18889)
          WRITE(30,18888)XN,NCOLXN,DXN,ZN,NCOLZN,DZN
          WRITE(30,4547)
4547   FORMAT(1X,'IZ,IX,VXADB(IC)')
       ENDIF
       IPP=0
       DO 7788 IZ=1,NCOLZN
       DO 7788 IY=1,NROWYN
       DO 7788 IX=1,NCOLXN
       IPP=IPP+1
CC     DO 7788 IPP=1,NPTSN
CC     WRITE(6,3343)IPP,VXADB(IPP)
3343   FORMAT(1X,'IPP,VXADB=',I4,2X,F12.2)
       IF(IPCONN.EQ.0) WRITE(30,*) IZ,IX,VXADB(IPP)
7788   CONTINUE
3040   IF((NCOLXN.GT.1.OR.NROWYN.GT.1).AND.IPLOTN.EQ.1)
      1CALL PLOTTR(NCOLXN,NROWYN,NCOLZN,XC,YC,ZC,NPTSN,VXADB,VXAPH,
      2VXADB,VXAPH)
       IF(NELN.EQ.1.AND.IPLOTN.EQ.1)
      1CALL PLOTAX(NPTSN,ZC,VXADB,VXAPH,VXADB,VXAPH)
       IF(IPCONN.EQ.0) GO TO 3939
C***THIS SECTION FOR CONTOUR PLOTS
       NCLXN2=NCOLXN+2
       NRWYN2=NROWYN+2
       NCLZN2=NCOLZN+2
       DO 3777 IX=1,NCOLXN
       RX(IX)=(XN+DXN*(IX-1))/CINMTR
3777   CONTINUE
       DO 3008 IY=1,NROWYN
       RY(IY)=(YN+DYN*(IY-1))/CINMTR
3008   CONTINUE
       DO 3009 IZ=1,NCOLZN
       RZ(IZ)=(ZN+DZN*(IZ-1))/CINMTR
3009   CONTINUE
       IC=0
       IF(IXZ.EQ.1) WRITE(30,18889)
18889  FORMAT(1X,'XN,NCOLXN,DXN,ZN,NCOLZN,DZN=')
       IF(IXZ.EQ.1) WRITE(30,18888)XN,NCOLXN,DXN,ZN,NCOLZN,DZN
18888  FORMAT(1X,E14.5,I5,2X,E14.5,2X,E14.5,I5,2X,E14.5)
       IF(IXZ.EQ.1) WRITE(30,4546)
4546   FORMAT(1X,'IZ,IX,FM(IZ,IX)')
       DO 3022 IZ=1,NCOLZN
       DO 3022 IY=1,NROWYN
       DO 3022 IX=1,NCOLXN
       IC=IC+1
       IF(IXY.EQ.1) FM(IY,IX)=VXADB(IC)
       IF(IXZ.EQ.1) FM(IZ,IX)=VXADB(IC)
       IF(IXZ.EQ.1.AND.IPCONN.EQ.1) WRITE(30,*) IZ,IX,FM(IZ,IX)
3022   CONTINUE
       IF(IXY.EQ.1)
      2CALL PLCONT(NCOLXN,NROWYN,NCLXN2,NRWYN2,RX,RY,FM,DMF,-50.,
       310.,5,1)
       IF(IXZ.EQ.1)
      2CALL PLCONT(NCOLXN,NCOLZN,NCLXN2,NCLZN2,RX,RZ,FM,DMF,-50.,
       310.,5,1)
3939   CONTINUE
CC     WRITE(25,*)NCOLXN
```

```
           DO 1767 IDDD=1,NCOLXN
CC         WRITE(25,*)VXADB(IDDD)
1767       CONTINUE
           WRITE(6,3050)
3050       FORMAT(1X,'PLOT NEAR FIELD AGAIN?, IPLA=1')
           READ(5,*)IPLA
           IF(IPLA.EQ.1) GO TO 3040
390        CONTINUE
           ISTOP=0
           IF(ISTOP.EQ.1) GO TO 9999
C***CALL PRNTDA (PRINT PARAMETERS)
C370       CALL PRNTDA
           IF(IPATRN.EQ.0) GO TO 440
410        WRITE(6,420)
420        FORMAT(1X,'ISYLMBL FOR PLOTTING, LT. 0 THEN NOT USED')
           READ(5,*)ISYMBL
           WRITE(6,430)
430        FORMAT(1X,'WANT TO PLOT PATTERNS AGAIN?, IPFNA=1')
           READ(5,*)IPFNA
           IF(IPFNA.EQ.1) GO TO 410
440        CONTINUE
C***THIS SECTION FOR COVARIANCE MATRIX COMPUTATION
           IF(NJAMS.EQ.0) GO TO 9999
           DO 7999 ICH=1,NMAX
           DO 7999 JCH=1,NMAX
           COVNF(ICH,JCH)=DCMPLX(0.0D0,0.0D0)
7999       CONTINUE
8888       IF(NJAMS.EQ.0) GO TO 4444
C***THIS SECTION FOR JAMMER COVARIANCE MATRIX
           FMINHZ=FCHZ-BWFHZ/2.
           DELFHZ=0.0
           IF(NFREQ.GT.1) DELFHZ=BWFHZ/(NFREQ-1)
           DO 600 IFR=1,NFREQ
           FHZ=FMINHZ+DELFHZ*(IFR-1)
           FGHZ=FHZ/1.0E9
C***COMPUTE FREE SPACE WAVELENGTH AT EACH FREQUENCY
           RLAMDA=2.997925E10/FHZ/2.54
C***NOTE: GAMMA= ALPHA +J BETA
C***      AND RLAMDA=2 PI/ BETA    (REF. HAYT PG. 334)
C***THUS NEED TO COMPUTE GAMMA, AND ETA FOR EACH FREQ.
           IF(IWL.EQ.2) GO TO 8789
           DX=DXIN*CINMTR
           DY=DYIN*CINMTR
           HL=HLIN*CINMTR
           ARAD=ARADIN*CINMTR
           HZ=HZIN*CINMTR
8789       CONTINUE
           CALL ZMATRX(CTDP,STDP,IBLTSL,ICC1,ICC,CZ,Z)
C***COMPUTE ELEMENT INDUCED VOLTAGES DUE TO JAMMER SOURCES
           CALL VJAMMR(NJAMS,NEL,PWRJDB,ICC1,ICC,PS,CZ,Z,CWTA
          1,NB,IDMB,NAUX,IAUXA,ZLOAD,XJAMIN,YJAMIN,ZJAMIN,
          2IFR,NFREQ,CTPR,STPR,CTDP,STDP,VMAJMA,VAUXJA)
           WRITE(6,1234)IFR,VMAJMA(1,IFR),VAUXJA(1,1,IFR)
           WRITE(8,1234)IFR,VMAJMA(1,IFR),VAUXJA(1,1,IFR)
1234       FORMAT(1X,'IFR,VMAJMA,VAUXA=',I4,2X,4E11.4)
600        CONTINUE
C***FORM RECEIVED VOLTAGE MATRIX
C***VRECVM(MAIN A, AUX A1, AUX A2,... AUX AN :)
           DO 9001 IJAM=1,NJAMS
           DO 9002 IFR=1,NFREQ
           IF(ISLC.EQ.1) VCHA(1,IFR)=VMAJMA(IJAM,IFR)
CC         WRITE(6,6789)IJAM,IFR,VMAJMA(IJAM,IFR)
6789       FORMAT(1X,'IJAM,IFR,VMAJMA(IJAM,IFR)=',2I4,2X,2E12.5)
           DO 9003 IA=1,NAUX
           IAP1=IA+1
           IF(ISLC.EQ.1) VCHA(IAP1,IFR)=VAUXJA(IA,IJAM,IFR)*VATENA(IA)
           IF(ISLC.EQ.0) VCHA(IA,IFR)=VAUXJA(IA,IJAM,IFR)*VATENA(IA)
           WRITE(6,8876)IJAM,IFR,IA,VAUXJA(IA,IJAM,IFR)
           WRITE(8,8876)IJAM,IFR,IA,VAUXJA(IA,IJAM,IFR)
8876       FORMAT(1X,'IJAM,IFR,IA,VAUXJA=',3I4,2X,2E12.4)
9003       CONTINUE
9002       CONTINUE
```

```
            DO 5555 KKK=1,4
            DO 5555 LLL=1,NFREQ
CCC         WRITE(6,6655)KKK,LLL,VCHA(KKK,LLL)
5555        CONTINUE
            WRITE(6,5533)
5533        FORMAT(1X,'NOW COMPUTE JAMMER COVARIANCE MATRIX')
C***COMPUTE COVARIANCE MATRIX FOR JTH JAMMER SOURCE
            IF(NFREQ.GT.1) CALL COVSWC(VCHA,VCHA,NMAX,NFREQ,BWFHZ,COVAAJ)
            DO 9005 ICH=1,NMAX
            DO 9005 JCH=1,NMAX
            COVNF(ICH,JCH)=COVNF(ICH,JCH)+COVAAJ(ICH,JCH)
CC          WRITE(6,2299)ICH,JCH,COVNF(ICH,JCH)
9005        CONTINUE
9001        CONTINUE
C***ADD RECEIVER NOISE TO DIAGONAL ELEMENTS
4444        DO 8006 ICH=1,NMAX
            COVNF(ICH,ICH)=COVNF(ICH,ICH)+1.0D0
8006        CONTINUE
            DO 2727 I=1,NMAX
            DO 2727 J=1,NMAX
            IF(CDABS(COVNF(I,J)).EQ.0.0D0) GO TO 2727
            CNDB=10.*DLOG10(CDABS(COVNF(I,J)))
            PREALN=DREAL(COVNF(I,J))
            PIMAGN=DIMAG(COVNF(I,J))
            PHASEN=DATAN2(PIMAGN,PREALN)/DCR
            WRITE(8,4411)I,J,CNDB,PHASEN
            IF(I.EQ.1)WRITE(6,4411)I,J,CNDB,PHASEN
4411        FORMAT(1X,'I,J,CNDB,PHASEN=',2I4,2X,2F12.2)
2727        CONTINUE
C***COMPUTE COVARIANCE MATRIX INVERSE
            DO 8007 ICH=1,NMAX
            DO 8007 JCH=1,NMAX
            COVNFI(ICH,JCH)=COVNF(ICH,JCH)
8007        CONTINUE
            CALL DCMINV(COVNFI,LTMP,MTMP,NMAX,NMAX)
C***CHECK MATRIX INVERSION ACCURACY  (CINVERSE*C=I)
            CALL CMMULT(COVNFI,COVNF,NMAX,NMAX,NMAX,CINVCN)
            DO 8008 ICH=1,NMAX
            DO 8008 JCH=1,NMAX
            IF(ICH.EQ.1)WRITE(6,8009)ICH,JCH,CINVCN(ICH,JCH)
8009        FORMAT(1X,'ICH,JCH,CINVCN=',2I4,2X,2E12.5)
8008        CONTINUE
C***COMPUTE EIGENVALUES (ALSO EIGENVECTORS AND PERFORMANCE INDEX)
            IJOB=2
            CALL EIGCC(COVNF,NMAX,NMAX,IJOB,EIGVAN,EIGVEN,NMAX,WKE,IER)
            WRITE(6,155)IER
155         FORMAT(1X,'AFTER COMPUTE EIGENVALUES, IER=',I5)
            DO 200 I=1,NMAX
            WRITE(6,300)I,EIGVAN(I)
300         FORMAT(1X,'I,EIGVAN=',2X,I4,2E10.3)
200         CONTINUE
            DO 205 I=1,NMAX
            EVLDBN=10.*DLOG10(CDABS(EIGVAN(I)))
            WRITE(8,207)I,EVLDBN
            WRITE(6,207)I,EVLDBN
207         FORMAT(1X,'I,EVLDBN=',I4,2X,2F12.3)
205         CONTINUE
C***        CALL PRNTDA
C***FILL-IN SIDELOBE CANCELLER QUIESCENT WEIGHTS
            DO 8985 I=1,NMAX
            WQSLC(I,1)=DCMPLX(0.0D0,0.0D0)
8985        CONTINUE
            WQSLC(1,1)=DCMPLX(1.0D0,0.0D0)
            DO 7769 I=1,NMAX
            WRITE(6,1212)I,WQSLC(I,1)
            WRITE(8,1212)I,WQSLC(I,1)
1212        FORMAT(1X,'I,WQSLC=',I4,2X,2E12.5)
7769        CONTINUE
C***COMPUTE QUIESCENT INR
            IF(ISLC.EQ.1) CALL INRTIO(WQSLC,COVNF,NMAX,WTCTR,CMPROD,QINRDB)
            IF(ISLC.EQ.0) CALL INRTIO(CWTA,COVNF,NMAX,WTCTR,CMPROD,QINRDB)
            QINRAA=10.*DLOG10(CDABS(COVNF(1,1)))
```

```
C***COMPUTE AVERAGE CANCELLATION
      SUMC=0.0
      SUMAA=0.0
      DO 1829 IR=1,NRAN
C***ZERO-OUT ADAPTIVE WEIGHTS INITIALLY
      DO 57 I=1,NMAX
      WAN(I,1)=DCMPLX(0.0D0,0.0D0)
57    CONTINUE
C***COMPUTE ADAPTIVE ARRAY WEIGHTS
      IF(ISLC.EQ.1) CALL CMMULT(COVNFI,WQSLC,NMAX,NMAX,1,WAN)
      IF(ISLC.EQ.0) CALL CMMULT(COVNFI,CWTA,NMAX,NMAX,1,WAN)
C***QUANTIZE AND RANDOMIZE ADAPTIVE WEIGHT SETTINGS
      IF(IQUAN.EQ.1.AND.NBADWT.LT.20)
     2CALL ADQUAN(NMAX,WAN,NBADWT,IRNERR,INITRN,AWSGDB,AWSGDG)
C***NORMALIZE FULLY ADAPTIVE WEIGHTS
      IF(ISLC.EQ.0) THEN
         SAVE=0.0D0
         DO 33345 I=1,NEL
         SAVE=SAVE+CDABS(WAN(I,1))**2
33345    CONTINUE
         SAVESR=DSQRT(SAVE)
         DO 44456 I=1,NEL
         WAN(I,1)=WAN(I,1)/SAVESR
         WANDB=20.*DLOG10(CDABS(WAN(I,1)))
         IF(IR.EQ.1) WRITE(6,3599)I,WANDB
         IF(IR.EQ.1) WRITE(8,3599)I,WANDB
3599     FORMAT(1X,'I=',I4,2X,'WANDB=',1X,F12.3)
44456    CONTINUE
      ENDIF
C****TO PRINT NORMALIZED WEIGHTS
      BIGWDB=-299.0
      DO 9102 I=1,NMAX
      IF(IR.EQ.1) WRITE(6,6191)I,WAN(I,1)
      IF(IR.EQ.1) WRITE(8,6191)I,WAN(I,1)
6191  FORMAT(1X,'I,WAN(I,1)=',I4,2X,2E12.5)
      WANDBM=20.*DLOG10(CDABS(WAN(I,1)))
      IF(WANDBM.GT.BIGWDB) BIGWDB=WANDBM
9102  CONTINUE
      DO 9112 I=1,NMAX
      WANDB=20.*DLOG10(CDABS(WAN(I,1)))-BIGWDB
      WANDG=DATAN2(DIMAG(WAN(I,1)),DREAL(WAN(I,1)))/DCR
      IF(IR.EQ.1) WRITE(6,35991)I,WANDB,WANDG
      IF(IR.EQ.1) WRITE(8,35991)I,WANDB,WANDG
35991 FORMAT(1X,'I=',I4,2X,'WANDB,WANDG=',1X,2F14.5)
9112  CONTINUE
C***COMPUTE ADAPTED INR
      CALL INRTIO(WAN,COVNF,NMAX,WTCTR,CMPROD,AINRDB)
C***COMPUTE CANCELLATION
      CANCDB=AINRDB-QINRDB
      WRITE(6,3007)QINRDB,AINRDB,CANCDB
      WRITE(8,3007)QINRDB,AINRDB,CANCDB
3007  FORMAT(1X,'INR= QUI,ADAP ,CANCEL=',2X,3F10.3,2X,' DB')
      SUMC=SUMC+CANCDB
C***COMPUTE ADAPTED INR CH. A
      DO 2255 I=1,NMAX
      WANDMA(I,1)=WAN(I,1)
      IF(I.GT.NMAX) WANDMA(I,1)=(0.0D0,0.0D0)
2255  CONTINUE
      CALL INRTIO(WANDMA,COVNF,NMAX,WTCTR,CMPROD,AINRAA)
C***CANCELLATION CH. A
      CNCLNA=AINRAA-QINRAA
      WRITE(6,3738)QINRAA,AINRAA,CNCLNA
      WRITE(8,3738)QINRAA,AINRAA,CNCLNA
3738  FORMAT(1X,'SIDELOBE CANCELLER CH. A INR= QUI,ADAP,CAN=',2X,3F10.3)
      SUMAA=SUMAA+CNCLNA
1829  CONTINUE
      AVECAN=SUMC/NRAN
      WRITE(6,4456)CANCDB,NRAN,AVECAN
4456  FORMAT(1X,'CANCDB,NRAN,AVECAN=',F12.5,2X,I5,2X,F12.5)
      WRITE(8,4456)CANCDB,NRAN,AVECAN
      AVECAA=SUMAA/NRAN
      WRITE(6,2220)AVECAA
```

```
        WRITE(8,2220)AVECAA
 2220   FORMAT(1X,'AVE. CANEL, CH. A, =',2X,F12.5)
C***SECTION TO COMPUTE ADAPTIVE ARRAY RADIATION PATTERNS
CC      IF(INEAR.EQ.0.OR.IANGLP.EQ.0) GO TO 9990
        IF(INEAR.EQ.0) GO TO 9990
        BIGADB=-299.
        IC=0
        DO 8919 IZ=1,NCOLZN
        DO 8919 IY=1,NROWYN
        DO 8919 IX=1,NCOLXN
        IC=IC+1
        CSUMA=(0.,0.)
        IF(ISLC.EQ.1) CSUMA=CSUMA+DCONJG(WAN(1,1))*VXMANA(IC)
        DO 7921 IAX=1,NAUX
        IAXP1=IAX+1
        IF(ISLC.EQ.1) CSUMA=CSUMA+DCONJG(WAN(IAXP1,1))*VAXCWA(IAX,IC)
        IF(ISLC.EQ.0) CSUMA=CSUMA+DCONJG(WAN(IAX,1))*VAXCWA(IAX,IC)
 7921   CONTINUE
        IF(CABS(CSUMA).EQ.0.) CSUMA=(1.E-10,0.)
        PCHADB(IC)=20.*ALOG10(CABS(CSUMA))
        IF(PCHADB(IC).GT.BIGADB) BIGADB=PCHADB(IC)
CC      WRITE(6,4999)IC,PCHADB(IC)
 8919   CONTINUE
C***NORMALIZE ADAPTIVE PATTERNS
        IF(IXZ.EQ.1) WRITE(31,18889)
        IF(IXZ.EQ.1) WRITE(31,18888)XN,NCOLXN,DXN,ZN,NCOLZN,DZN
        IF(IXZ.EQ.1) WRITE(31,4546)
        IC=0
        DO 3459 IZ=1,NCOLZN
        DO 3459 IY=1,NROWYN
        DO 3459 IX=1,NCOLXN
        IC=IC+1
        PCHADB(IC)=PCHADB(IC)-BIGADB
        IF(IPCONN.EQ.0) WRITE(31,*)IZ,IX,PCHADB(IC)
        IF(IPCONN.EQ.0) GO TO 3459
        IF(IXY.EQ.1) FM(IY,IX)=PCHADB(IC)
        IF(IXZ.EQ.1) FM(IZ,IX)=PCHADB(IC)
        IF(IXZ.EQ.1.AND.IPCONN.EQ.1) WRITE(31,*) IZ,IX,FM(IZ,IX)
 3459   CONTINUE
        WRITE(25,*)NCOLXN
        DO 1879 IDDD=1,NCOLXN
        WRITE(25,*)PCHADB(IDDD)
 1879   CONTINUE
        IF((NCOLXN.GT.1.OR.NROWYN.GT.1).AND.IPLOTN.EQ.1.AND.IANGLP.EQ.0)
       2CALL PLOTTR(NCOLXN,NROWYN,NCOLZN,XC,YC,ZC,NPTSN,PCHADB,PCHADB,
       3PCHADB,PCHADB)
        IF(IPCONN.EQ.1.AND.IXY.EQ.1)
       2CALL PLCONT(NCOLXN,NROWYN,NCLXN2,NRWYN2,RX,RY,
       3FM,DMF,-50.,10.,5,1)
        IF(IPCONN.EQ.1.AND.IXZ.EQ.1)
       2CALL PLCONT(NCOLXN,NCOLZN,NCLXN2,NCLZN2,RX,RZ,
       3FM,DMF,-50.,10.,5,1)
 9990   CONTINUE
 9999   CONTINUE
        CALL DONEPL
        CALL GETCP2(CPUL)
        CPUTOT=CPUL-CPU1
        WRITE(6,2006)CPUTOT
 2006   FORMAT(1X,'TOTAL CPU TIME=',F15.2)
        STOP
        END
C***SUBROUTINE TO COMPUTE IMPEDANCE MATRIX
        SUBROUTINE ZMATRX(CTDP,STDP,IBLTSL,ICC1,ICC,CZ,Z)
        COMPLEX Z(ICC1,ICC),CZ(1)
        COMMON/A/DX,DY,NCOLX,NROWY,NEL,HZ,HL,ARAD,ZLOAD,ZCHAR
        COMMON /GROUND/ IGRNDP
        COMMON /CIRCLE/ ICIRC,RADIUS,HLS
        NB=NCOLX
        IDMB=NROWY
C***COMPUTE MUTUAL IMPEDANCES Z(1,1),Z(1,2),Z(1,3),...,Z(1,NEL).
CC      CALL RGDZMN(IGRNDP,ICC1,ICC,Z)
CC      CALL RGDZAB(CTDP,STDP,IGRNDP,ICC1,ICC,Z)
```

```
      IF(ICIRC.EQ.0) CALL RGDZA2(CTDP,STDP,IGRNDP,ICC1,ICC,Z)
      IF(ICIRC.EQ.1) CALL CADZA2(CTDP,STDP,IGRNDP,ICC1,ICC,Z)
      WRITE(8,10) NEL,NCOLX,NROWY
10    FORMAT(1X,'NEL,NCOLX,NROWY=',3I5)
      ICOUNT=0
      DO 20 I=1,NCOLX
      DO 20 J=1,NROWY
      ICOUNT=ICOUNT+1
      WRITE(6,80) I,J,Z(1,ICOUNT)
80    FORMAT(1X,'I,J,Z(1,ICOUNT)=',2I4,2X,2E12.5)
20    CONTINUE
      IDM=NEL
      ICC=NEL
C***FILL THE IMPEDANCE MATRIX
      IF(NCOLX.LE.1) GO TO 70
      IBLT=IBLTSL
      IDM1=IDMB
      IF(IBLT.EQ.0) IDM1=NEL
      IF(NROWY.GT.1) GO TO 40
C***FILL TOEPLITZ MATRIX
      DO 30 I=2,NEL
      DO 30 J=I,NEL
      K=1+J-I
      Z(I,J)=Z(1,K)
30    CONTINUE
      GO TO 50
40    CALL BTOEPL(IBLT,NB,IDMB,IDM1,IDM,Z)
50    CONTINUE
      IF(IBLT.EQ.0) GO TO 70
      DO 60 I=1,IDMB
      DO 60 J=1,IDM
        IC=(J-1)*IDMB+I
        CZ(IC)=Z(I,J)
CC    WRITE(8,7878)I,J,Z(I,J)
7878  FORMAT(1X,'I,J,Z(I,J)=',2I4,2X,2E12.5)
60    CONTINUE
70    CONTINUE
      RETURN
      END
C***SUBROUTINE TO COMPUTE RECEIVE BEAMFORMER WEIGHTS
      SUBROUTINE VRCVWT(NACOLX,NAROWY,NXDUM,NYDUM,EDGTDB,WA,WB)
      DIMENSION WA(1),WB(1)
      DIMENSION WT(180)
      COMMON/A/DX,DY,NCOLX,NROWY,NEL,HZ,HL,ARAD,ZLOAD,ZCHAR
      COMMON /CHEBY/ ICHEB,SLLDB
      PI=3.141592654
      TPI=2.*PI
      DCR=PI/180.
CC    SLLDB=40.
      TAP=10.**(EDGTDB/20.)
      WRITE(6,*)TAP
      AMP=(1.-TAP)/2.
      NPDX=NCOLX-NACOLX-2*NXDUM
      AXL=DX*(NACOLX-1)
      AYL=DY*(NAROWY-1)
      IF(TAP.NE.1.0)FX=AXL/2.*PI/ACOS(TAP)
      IF(TAP.NE.1.0)FY=AYL/2.*PI/ACOS(TAP)
      WRITE(6,20)
20    FORMAT(1X,'BEFORE CALL CHEBWT')
      WRITE(6,30)SLLDB
30    FORMAT(1X,'SLLDB=',2X,F10.2)
      IF(ICHEB.EQ.1)CALL CHEBWT(NACOLX,SLLDB,WT,RLOSS)
      WRITE(6,40)
40    FORMAT(1X,'AFTER CHEBWT')
      DO 1000 IC=1,NEL
      WA(IC)=0.0
      WB(IC)=0.0
1000  CONTINUE
C***COMPUTE EFFECTIVE DIPOLE CENTER COORDS. FOR BOTH PHASE CENTERS
      X0=-AXL/2.
      Y0=-AYL/2.
      IC=0
```

```
            DO 80 I=1,NACOLX
            DO 80 J=1,NAROWY
            IC=IC+1
            X=X0+DX*(I-1)
            Y=Y0+DY*(J-1)
            TAPERX=1.0
            TAPERY=1.0
            IF(ICHEB.EQ.1) GO TO 70
            IF(TAP.NE.1.0)TAPERX=COS(PI*X/FX)
            IF(TAP.NE.1.0.AND.FY.NE.0.0)TAPERY=COS(PI*Y/FY)
60          TAPER=TAPERX*TAPERY
            WT(IC)=TAPER
70          CONTINUE
80          CONTINUE
C***TRANSFORM FROM SUB-APERTURES TO FULL ARRAY
            IBGNA=NXDUM*NROWY+NYDUM
            IBGNB=IBGNA+NPDX*NROWY
            IC=0
            DO 1010 IX=1,NACOLX
            DO 1010 IY=1,NAROWY
            IC=IC+1
            IA=IBGNA+(IX-1)*NROWY+IY
            IB=IBGNB+(IX-1)*NROWY+IY
            WA(IA)=WT(IC)
            WB(IB)=WT(IC)
1010        CONTINUE
            RETURN
            END
C***SUBROUTINE TO COVARIANCE MATRIX BASED ON NUMERICAL INTEGRATION
C***IN THE FREQUENCY DOMAIN ACCORDING TO SIMPSON'S RULE
            SUBROUTINE COVSWC(VA,VB,NCHAN,NFREQ,BWFHZ,COVAB)
            COMPLEX *16 VA(NCHAN,NFREQ),VB(NCHAN,NFREQ)
            COMPLEX *16 COVAB(NCHAN,NCHAN),CSUM,DCABF
            REAL *8 SWC(101)
            DELTAF=BWFHZ/(NFREQ-1)
            CALL SIMWC(NFREQ,SWC)
            DO 10 ICH=1,NCHAN
            DO 10 JCH=1,NCHAN
            CSUM=(0.0D0,0.0D0)
            DO 20 IFR=1,NFREQ
            DCABF=VA(ICH,IFR)*DCONJG(VB(JCH,IFR))
            CSUM=CSUM+DCABF*SWC(IFR)
CC          WRITE(6,6767)IFR,CSUM
6767        FORMAT(1X,'IFR,CSUM=',I4,2X,2E12.5)
20          CONTINUE
            COVAB(ICH,JCH)=DELTAF/2.*CSUM
C***NEW LINE TO NORMALIZE COVAB
            COVAB(ICH,JCH)=COVAB(ICH,JCH)/BWFHZ
CC          WRITE(6,4567)ICH,JCH,COVAB(ICH,JCH)
4567        FORMAT(1X,'ICH,JCH,COVAB(ICH,JCH)=',2I4,2X,2E12.5)
10          CONTINUE
            RETURN
            END
C***SUBROUTINE TO GENERATE SIMPSON'S 1/3 RULE WEIGHTING COEF.
C***INTGERAL F(X)DX=(DELTAX/3.)*(F(1)+4*F(2)+2*F(3)+4*F(4)+...+F(OOD))
C*** THE SERIES 1 4 2 4 2 4 .....1 ARE SIMPSON'S COEF.
            SUBROUTINE SIMWC(NCOEF,SWC)
            REAL *8 SWC(NCOEF)
            DO 10 N=1,NCOEF
            XNN=FLOAT(N)
            NN=N/2
            TT=XNN/2.
            DIF=TT-FLOAT(NN)
            NC=2
            IF(DIF.EQ.0.) NC=4
            IF(N.EQ.1.OR.N.EQ.NCOEF) NC=1
            SWC(N)=NC
10          CONTINUE
            RETURN
            END
C***SUBROUTINE TO COMPUTE RECEIVED VOLTAGES DUE TO JAMMER SOURCES
            SUBROUTINE VJAMMR(NJM,NEL,PWRJDB,ICC1,ICC,PS,CZ,Z,CWTA
```

```
      1,NB,IDMB,NAUX,IAUXA,ZLOAD,XJAMIN,YJAMIN,ZJAMIN,
      2IFR,NFR,CTPR,STPR,CTDP,STDP,VMAINA,VAUXA)
      COMPLEX *16 CWTA(NEL,1)
      COMPLEX PS(1),CZ(1),Z(ICC1,ICC)
      COMPLEX VJM(180),VREFJM
      COMPLEX CJ,CSUMA
      COMPLEX *16 VMAINA(NJM,NFR)
      COMPLEX *16 VAUXA(NAUX,NJM,NFR)
      DIMENSION PWRJDB(1),PWRJ(10)
      DIMENSION XJAMIN(1),YJAMIN(1),ZJAMIN(1)
      INTEGER IAUXA(1)
      COMMON/PCENTR/PCDXIN
      COMMON /B/ NGEN,IGEN,THETAS,PHIS,IMUT,IBLTSL,IPATRN
      COMMON /D/ FGHZ,RLAMDA,IWL,IS,NSCANS
      COMMON /WRITE/ IWR
      COMMON /CIRCLE/ ICIRC,RADIUS,HLS
      PI=3.141592654
      DCR=PI/180.
      CJ=(0.,1.)
      CINMTR=0.0254
      ISYM=0
C***CONVERT DB TO POWER (RELATIVE TO NOISE)
      DO 10 II=1,NJM
      PWRJ(II)=10.**(PWRJDB(II)/10.)
      WRITE(6,66)II,PWRJ(II)
      WRITE(8,66)II,PWRJ(II)
66    FORMAT(1X,'II,PWRJ IN POWER=',I4,2X,E12.5)
10    CONTINUE
      IF(IFR.GT.1) GO TO 55
      WRITE(6,20)IWL
      DO 5544 IJAM=1,NJM
      WRITE(6,40)
      WRITE(6,50)XJAMIN(IJAM),YJAMIN(IJAM),ZJAMIN(IJAM)
5544  CONTINUE
20    FORMAT(1X,'IWL=',I4)
      WRITE(6,30)
30    FORMAT(1X,'CHANGE NEAR FIELD JAMMER POSITIONS (INCHES)?, ICH=1')
      READ(5,*)ICH
      IF(ICH.EQ.0) GO TO 55
      DO 8887 IJAM=1,NJM
      WRITE(6,40)
40    FORMAT(1X,'XJAMIN,YJAMIN,ZJAMIN,=')
      READ(5,*,END=55)XJAMIN(IJAM),YJAMIN(IJAM),ZJAMIN(IJAM)
      WRITE(6,50)XJAMIN(IJAM),YJAMIN(IJAM),ZJAMIN(IJAM)
50    FORMAT(1X,5F10.3,2X,2I5)
8887  CONTINUE
55    CONTINUE
      PCDX=PCDXIN*CINMTR
      WRITE(6,4757)IFR
4757  FORMAT(1X,'FREQ. INDEX, IFR=',I4)
60    CONTINUE
C**ALL DIMENSIONS IN METERS
      DO 180 IPHACN=1,1
      WRITE(6,2223)IPHACN
2223  FORMAT(1X,'IPHACN=',I4)
      XREFDP=-PCDX/2.+(IPHACN-1)*PCDX
C***PERFORM JAMMER SOURCE SCAN
      DO 180 IJAM=1,NJM
      X=XJAMIN(IJAM)*CINMTR+PCDX*(IPHACN-1)
      Y=YJAMIN(IJAM)*CINMTR
      ZPOS=ZJAMIN(IJAM)*CINMTR
      WRITE(6,6688)X,Y,ZPOS,XREFDP
6688  FORMAT(1X,'X,Y,ZPOS,XREFDP (METERS)=',4F12.4)
      IF(ICIRC.EQ.0)
     2CALL NFDPX2(CTPR,STPR,CTDP,STDP,X,Y,ZPOS,XREFDP,1,VJM,VREFJM)
      IF(ICIRC.EQ.1)
     2CALL NFDPC2(X,Y,ZPOS,XREFDP,1,VJM,VREFJM)
C***NORMALIZE INCIDENT JAMMER POWER
      DO 70 INORM=1,NEL
      VJM(INORM)=VJM(INORM)/VREFJM*SQRT(PWRJ(IJAM))
      WRITE(6,77)INORM,VJM(INORM)
77    FORMAT(1X,'INORM,VJM(INORM) VOLTAGE=',I4,2X,2E12.5)
```

```
70      CONTINUE
        IF(IMUT.EQ.0) GO TO 90
C***SOLVE EACH SYSTEM OF EQUATIONS FOR THE UNKNOWN CURRENTS
        IF(IBLTSL.EQ.1) GO TO 80
        I12=1
        IF(IJAM.GT.1.OR.IPHACN.GT.1) I12=2
        WRITE(6,6110)
6110    FORMAT(1X,'CALL CROUT IN VJAMMER')
        CALL CROUT(Z,VJM,ICC1,ICC,ISYM,IWR,I12,NEL)
        GO TO 90
80      IENTRY=4
        IF(IJAM.GT.1.OR.IPHACN.GT.1) IENTRY=3
        CALL BLTSOL(CZ,VJM,PS,NB,IDMB,IENTRY)
        IF(NEL.LT.40) CALL CNORM(VJM,NEL)
90      CONTINUE
C***COMPUTE RECEIVED VOLTAGES FOR PRESENT SOURCE POSITION
        DO 100 IEL=1,NEL
        VJM(IEL)=VJM(IEL)*ZLOAD
CC      WRITE(6,4456)IEL,VJM(IEL)
4456    FORMAT(1X,'IEL,VJM(IEL) RECEIVED VOLT.=',I4,2X,2E12.5)
100     CONTINUE
C***PERFORM BEAM FORMATION FOR MAIN A
C***PHASE CENTER A
        CSUMA=(0.0D0,0.0D0)
        DO 110 KC=1,NEL
        CSUMA=CSUMA+VJM(KC)*CWTA(KC,1)
110     CONTINUE
        VMAINA(IJAM,IFR)=CSUMA
        WRITE(6,2222)IJAM,IFR,VMAINA(IJAM,IFR)
2222    FORMAT(1X,'IJAM,IFR,VMAINA= (AFTER B.F.)',2I4,2X,2E12.5)
C***COMPUTE AUXILIARY CHANNEL VOLTAGES
        DO 7000 IAUX=1,NAUX
        VAUXA(IAUX,IJAM,IFR)=VJM(IAUXA(IAUX))
7000    CONTINUE
180     CONTINUE
        DO 9000 IJAM=1,NJAMS
CCC     WRITE(6,4433)IJAM,IFR,VMAINA(IJAM,IFR)
4433    FORMAT(1X,'VJAMMR:IJAM,IFR,VMAINA=',2I4,2X,2E12.5)
        DO 9001 IAUX=1,NAUX
        WRITE(6,3333)IAUX,IJAM,IFR,VAUXA(IAUX,IJAM,IFR)
3333    FORMAT(1X,'VJAMMR:IAUX,IJAM,IFR,VAUXA=',3I4,2X,2E12.5)
9001    CONTINUE
9000    CONTINUE
        RETURN
        END
C***SUBROUTINE TO COMPUTE INTERFERENCE TO NOISE RATIO
        SUBROUTINE INRTIO(WT,COV,NEL,WTCTR,CMPROD,DBINR)
        IMPLICIT REAL *8 (A-H,O-Z)
        COMPLEX *16 WT(NEL,1),COV(NEL,NEL),WTCTR(1,NEL)
        COMPLEX *16 CMPROD(1,NEL),CPROD1(1,1),CPROD2(1,1),CINR
        COMMON /NORMAL/ INRNOR
        WRITE(12,2222)
2222    FORMAT(1X,'INSIDE INRTIO SUBROUTINE')
        DO 110 I=1,NEL
CC      WRITE(12,445)I,WT(I,1)
445     FORMAT(1X,'I,WT(I,1)=',2X,I4,2X,2E12.5)
110     CONTINUE
        CALL CONJTR(WT,NEL,1,WTCTR)
        DO 111 I=1,NEL
CC      WRITE(12,666)I,WT(I,1),WTCTR(1,I)
666     FORMAT(1X,'I,WT,WTCTR=',2X,I4,2X,4E12.5)
111     CONTINUE
        CALL CMMULT(WTCTR,COV,1,NEL,NEL,CMPROD)
        CALL CMMULT(CMPROD,WT,1,NEL,1,CPROD1)
        CALL CMMULT(WTCTR,WT,1,NEL,1,CPROD2)
        WRITE(6,333)CPROD1(1,1),CPROD2(1,1)
        WRITE(8,333)CPROD1(1,1),CPROD2(1,1)
333     FORMAT(1X,'CPROD1,CPROD2=',4E12.5)
C***INR NORMALIZED
CC      INRNOR=0
        WRITE(6,7739)INRNOR
        WRITE(8,7739)INRNOR
```

```
7739  FORMAT(1X,'INR NORMALIZATION PARAMETER, INRNOR=',I4)
      IF(INRNOR.EQ.1) CINR=CPROD1(1,1)/CPROD2(1,1)
C***INR NOT NORMALIZED FOR INRNOR=0
      IF(INRNOR.EQ.0) CINR=CPROD1(1,1)
      DBINR=10.*DLOG10(CDABS(CINR))
      RETURN
      END
      SUBROUTINE CMMULT(A,B,L,M,N,C)
      COMPLEX *16 A(L,M),B(M,N),C(L,N)
      DO 20 I=1,L
      DO 20 J=1,N
      C(I,J)=DCMPLX(0.0D0,0.0D0)
      DO 20 K=1,M
      C(I,J)=C(I,J)+(A(I,K)*B(K,J))
20    CONTINUE
      RETURN
      END
C***SUBROUTINE TO COMPUTE CONJUGATE TRANSPOSE OF A MATRIX
      SUBROUTINE CONJTR(A,L,M,ACTR)
      COMPLEX *16 A(L,M),ACTR(M,L)
      DO 10 I=1,M
      DO 10 J=1,L
      ACTR(I,J)=DCONJG(A(J,I))
CC    WRITE(12,7766)I,J,A(J,I),ACTR(I,J)
7766  FORMAT(1X,'I,J,A(J,I),ACTR(I,J)=',2X,2I4,2X,4E12.5)
10    CONTINUE
      RETURN
      END
      SUBROUTINE DCMINV(A,L,M,IDM,NEQ)
      COMPLEX *16 A(IDM,IDM),BIGA,HOLD,DET
      INTEGER L(IDM),M(IDM)
      N=NEQ
      DET=DCMPLX(1.0D0,0.0D0)
      DO 80 K=1,N
      L(K)=K
      M(K)=K
      BIGA=A(K,K)
      DO 20 J=K,N
      DO 20 I=K,N
10    IF(CDABS(BIGA)-CDABS(A(I,J)))15,19,19
15    BIGA=A(I,J)
      L(K)=I
      M(K)=J
19    CONTINUE
20    CONTINUE
      J=L(K)
      IF(J-K)35,35,25
25    CONTINUE
      DO 30 I=1,N
      HOLD=-A(K,I)
      A(K,I)=A(J,I)
30    A(J,I)=HOLD
35    I=M(K)
      IF(I-K) 45,45,38
38    CONTINUE
      DO 40 J=1,N
      HOLD=-A(J,K)
      A(J,K)=A(J,I)
40    A(J,I)=HOLD
45    CONTINUE
      DO 55 I=1,N
      IF(I-K)50,55,50
50    A(I,K)=A(I,K)/(-BIGA)
55    CONTINUE
      DO 65 I=1,N
      DO 65 J=1,N
      IF(I-K)60,64,60
60    IF(J-K)62,64,62
62    A(I,J)=A(I,K)*A(K,J)+A(I,J)
64    CONTINUE
65    CONTINUE
      DO 75 J=1,N
```

```
            IF(J-K)70,75,70
70      A(K,J)=A(K,J)/BIGA
75      CONTINUE
        DET=DET*BIGA
        A(K,K)=1.0D0/BIGA
80      CONTINUE
        K=N
100     K=K-1
        IF(K)150,150,105
105     I=L(K)
        IF(I-K)120,120,108
108     CONTINUE
        DO 110 J=1,N
        HOLD=A(J,K)
        A(J,K)=-A(J,I)
110     A(J,I)=HOLD
120     J=M(K)
        IF(J-K)100,100,125
125     CONTINUE
        DO 130 I=1,N
        HOLD=A(K,I)
        A(K,I)=-A(J,I)
130     A(J,I)=HOLD
        GO TO 100
150     RETURN
        END
C***SUBROUTINE CNORM
C***COMPUTES A NORMALIZED COMPLEX COLUMN VECTOR SUCH THAT THE
C***MAXIMUM ELEMENT HAS UNITY MAGNITUDE.
C
C***PRINTS MAGNITUDE AND PHASE OF NORMALIZED VECTOR
C
        SUBROUTINE CNORM(V,N)
C***    V IS THE INPUT COMPLEX COLUMN VECTOR
C***    N IS THE LENGTH OF V
        COMPLEX V(1),SS
        CNOR=0.0
        DO 10 K=1,N
        SA=CABS(V(K))
        IF(SA.GT.CNOR) CNOR=SA
10      CONTINUE
        IF(CNOR.LE.0.) CNOR=1.0
        DO 30 K=1,N
        SS=V(K)
        SA=CABS(SS)
        SNOR=SA/CNOR
        PHR=0.
        IF(SA.GT.0.) PHR=ATAN2(AIMAG(SS),REAL(SS))
        PH=57.29578*PHR
        WRITE(8,20) K,SNOR,SA,PH
20      FORMAT(1X,I5,F10.6,3X,E15.3,F10.0)
30      CONTINUE
        RETURN
        END
        SUBROUTINE GETCP2(RCPU)
        REAL ETIME,TARRAY(2),RCPU
        TIME=ETIME(TARRAY)
        RCPU=TARRAY(1)
        RETURN
        END
C***SUBROUTINE TO COMPUTE INDUCED VOLTAGE BETWEEN PROBE AND
C***DIPOLE ARRAY ELEMENTS
C***RING ARRAY
        SUBROUTINE NFDPC2(XP,YP,ZP,XREF,IREF,V,VREF)
C***DISTANCES ARE IN METERS
        COMPLEX V(1),VD,VR1,VREF
        COMPLEX *16 DZABG
        COMMON/A/DX,DY,NCOLX,NROWY,NEL,HZ,HL,ARAD,ZLOAD,ZCHAR
        COMMON /CIRCLE/ ICIRC,RADIUS,HLS
C***NOTE: AA,BB,... FOR PROBE     11,22,... FOR DIPOLE
        PI=3.1415926535
        DCR=PI/180.
```

```
C***PROBE DIMENSIONS
      XAA=XP
      XBB=XP
      XCC=XP
      YAA=YP-HLS
      YBB=YP
      YCC=YP+HLS
785   ZAA=ZP
      ZBB=ZP
      ZCC=ZP
      IC=0
C****CIRCULAR DIPOLE ARRAY ELEMENTS
      DELPHI=360./NEL
      DO 10 IX=1,NEL
      PHI=DELPHI*(IX-1)
      XD=RADIUS*COS(PHI*DCR)
      ZD=RADIUS*SIN(PHI*DCR)
      DIST=SQRT((XP-XD)**2+(ZP-ZD)**2)
      IF(DIST.LT.ARAD) XD=XD+ARAD
      X11=XD
      X22=XD
      X33=XD
      Y11=YP-HL
      Y22=YP
      Y33=YP+HL
      Z11=ZD
      Z22=ZD
      Z33=ZD
9446  IC=IC+1
CC    WRITE(6,2233)IX,IY,XD,YD
2233  FORMAT(1X,'IX,IY,XD,YD=',2X,2I4,2X,2F12.5)
CC    WRITE(6,7854)XAA,XBB,XCC,YAA,YBB,YCC,ZAA,ZBB,ZCC
7854  FORMAT(1X,'XYZABC=',9E12.5)
CC    WRITE(6,7855)X11,X22,X33,Y11,Y22,Y33,Z11,Z22,Z33
7855  FORMAT(1X,'XYZ123=',9E12.5)
      CALL DSZABG(XAA,XBB,XCC,YAA,YBB,YCC,ZAA,ZBB,ZCC,X11,X22,X33,
     2Y11,Y22,Y33,Z11,Z22,Z33,DZABG)
      VD=DZABG
CC    WRITE(6,33)IC,VD
33    FORMAT(1X,'IC,VD=',2X,I5,2E12.5)
      V(IC)=VD
      VAMPDB=20.*ALOG10(CABS(V(IC)))
      VPHASE=ATAN2(AIMAG(V(IC)),REAL(V(IC)))*180./3.141592654
CC    WRITE(6,4455)IC,VAMPDB,VPHASE
4455  FORMAT(1X,'IC,VAMDB,VPHASE=',2X,I4,2X,2F12.2)
10    CONTINUE
C***COMPUTE REFERENCE VOLTAGE (FICTITIOUS ELEMENT AT XREF, Y=0)
C***SET XREF=RADIUS, THIS MAKES ELEMENT 1 THE REFERENCE
      XREF=RADIUS
C***SET XREF=ARAD, (REF. CLOSE TO THE ORIGIN)
      XREF=ARAD
      X11=XREF
      X22=XREF
      X33=XREF
      Y11=-HL
      Y22=0.0
      Y33=HL
      Z11=0.0
      Z22=0.0
      Z33=0.0
9267  CALL DSZABG(XAA,XBB,XCC,YAA,YBB,YCC,ZAA,ZBB,ZCC,X11,X22,X33,
     2Y11,Y22,Y33,Z11,Z22,Z33,DZABG)
      VR1=DZABG
      VREF=VR1
99    RETURN
      END
C***SUBROUTINE TO COMPUTE MUT. IMPED. BETWEEN STRAIGHT DIPOLES
C***ARRANGED IN A RING ARRAY (CIRCLE)
      SUBROUTINE CADZA2(CTDP,STDP,IGRNDP,ICC1,ICC,Z)
      COMPLEX ZMA,ZABG,Z(ICC1,ICC)
      COMMON /A/ DX,DY,NCOLX,NROWY,NEL,HZ,HL,ARAD,ZLOAD,ZCHAR
      COMMON /CIRCLE/ ICIRC,RADIUS,HLS
```

```
C***ALL DIMENSIONS IN METERS
      PI=3.1415926535
      DCR=PI/180.
C***FIXED POSITION FOR ELEMENT 1
      XAA=RADIUS
      XBB=RADIUS
      XCC=RADIUS
      YAA=-HL
      YBB=0.0
      YCC=HL
      ZAA=0.0
      ZBB=0.0
      ZCC=0.0
      Y11=YAA
      Y22=YBB
      Y33=YCC
C***VARIABLE POSITION FOR RING ARRAY ELEMENTS
      DELPHI=360./NEL
      IC=0
      DO 20 I=1,NEL
      IC=IC+1
      PHI=DELPHI*(I-1)*DCR
      XD=RADIUS*COS(PHI)
      ZD=RADIUS*SIN(PHI)
      X11=XD
      X22=XD
      X33=XD
      IF(I.EQ.1) X11=X11+ARAD
      IF(I.EQ.1) X22=X22+ARAD
      IF(I.EQ.1) X33=X33+ARAD
      Z11=ZD
      Z22=ZD
      Z33=ZD
CC    WRITE(6,87)IC
87    FORMAT(1X,'IC=',I5)
CC    WRITE(6,88)XAA,XBB,XCC,YAA,YBB,YCC,ZAA,ZBB,ZCC
88    FORMAT(1X,'XYZABC=',9E12.4)
CC    WRITE(6,89)X11,X22,X33,Y11,Y22,Y33,Z11,Z22,Z33
89    FORMAT(1X,'XYZ123=',9E12.4)
      ZMA=ZABG(XAA,XBB,XCC,YAA,YBB,YCC,ZAA,ZBB,ZCC,X11,X22,X33,
     2Y11,Y22,Y33,Z11,Z22,Z33)
      Z(1,IC)=ZMA
      IF(IC.EQ.1) Z(1,1)=Z(1,1)+ZLOAD
20    CONTINUE
      DO 40 I=1,NEL
      IF(I.LT.9)WRITE(6,30)I,Z(1,I)
      WRITE(8,30)I,Z(1,I)
30    FORMAT(1X,'Z(1,',I4,')=',2E12.5)
40    CONTINUE
      RETURN
      END
*********file zabgenloss.f********************
C***PROGRAM TO CALCULATE MUTUAL IMPEDANCE BETWEEN TWO DIPOLES
C***WITH ARBITRARY LENGTH AND ORIENTATION.  A PIECEWISE-
C***SINUSOIDAL CURRENT DISTRIBUTION IS ASSUMED.
                 C O M P L E X      F U N C T I O N
     ZABG(X1,X2,X3,Y1,Y2,Y3,Z1,Z2,Z3,XA,XB,XC,YA,YB,YCZAB00040
     2,ZA,ZB,ZC)
      COMPLEX P11,P12,P21,P22,Q11,Q12,Q21,Q22,R11,R12,R21,R22
      COMPLEX S11,S12,S21,S22,JCOM,GAM,CGDS,SGDS,SGDT,ETA,EP3
      COMPLEX EGDS,EGDT
      COMMON /F/ FHZ,ER3,SIG3,TD3
C***ALL DIMENSIONS IN METERS
      PI=3.141592654
      TPI=2.*PI
      B=TPI
      JCOM=(0.,1.)
      E0=8.854E-12
      U0=1.2566E-6
      OMEGA=TPI*FHZ
      IF(SIG3.LT.0.)EP3=ER3*E0*CMPLX(1.,-TD3)
      IF(TD3.LT.0.)EP3=CMPLX(ER3*E0,-SIG3/OMEGA)
```

```
          ETA=CSQRT(U0/EP3)
          GAM=OMEGA*CSQRT(-U0*EP3)
          AM=0.0001
          IF(CABS(GAM*AM).GT.0.06) WRITE(6,7923)AM
 7923     FORMAT(1X,'CABS(GAM*AM) IS GREATER THAN 0.06, AM=',E14.5)
          INT=0
          XBA=XB-XA
          YBA=YB-YA
          ZBA=ZB-ZA
          X21=X2-X1
          Y21=Y2-Y1
          Z21=Z2-Z1
          DS=SQRT(XBA*XBA+YBA*YBA+ZBA*ZBA)
          DT=SQRT(X21*X21+Y21*Y21+Z21*Z21)
CC        DSK=B*DS
CC        DTK=B*DT
CC        CGDS=CMPLX(COS(DSK),0.0)
CC        SGDS=CMPLX(0.0,SIN(DSK))
CC        SGDT=CMPLX(0.0,SIN(DTK))
C***FOR LOSSY MEDIUM THE NEXT LINES ARE APPROPRIATE
          EGDS=CEXP(GAM*DS)
          EGDT=CEXP(GAM*DT)
          CGDS=(EGDS+1./EGDS)/2.
          SGDS=(EGDS-1./EGDT)/2.
          SGDT=(EGDT-1./EGDT)/2.
CC        WRITE(6,1345)XA,XB,YA,YB,ZA,ZB
 1345     FORMAT(1X,'XYZAB=',6E14.5)
CC        WRITE(6,1346)X1,X2,Y1,Y2,Z1,Z2
 1346     FORMAT(1X,'XYZ12=',6E14.5)
          CALL GGS(XA,YA,ZA,XB,YB,ZB,X1,Y1,Z1,X2,Y2,Z2,AM,
         2DS,CGDS,SGDS,DT,SGDT,INT,ETA,GAM,P11,P12,P21,P22)
          CALL GGS(XA,YA,ZA,XB,YB,ZB,X2,Y2,Z2,X3,Y3,Z3,AM,
         2DS,CGDS,SGDS,DT,SGDT,INT,ETA,GAM,Q11,Q12,Q21,Q22)
          CALL GGS(XB,YB,ZB,XC,YC,ZC,X1,Y1,Z1,X2,Y2,Z2,AM,
         2DS,CGDS,SGDS,DT,SGDT,INT,ETA,GAM,R11,R12,R21,R22)
          CALL GGS(XB,YB,ZB,XC,YC,ZC,X2,Y2,Z2,X3,Y3,Z3,AM,
         2DS,CGDS,SGDS,DT,SGDT,INT,ETA,GAM,S11,S12,S21,S22)
          ZABG=P22+Q21+R12+S11
CC        WRITE(6,7898)ZABG
 7898     FORMAT(1X,'EXITING ZABG WITH ZABG=',2E14.5)
          RETURN
          END
**********file dzabgnloss.f*******
C****DOUBLE PRECISION VERSION
C***PROGRAM TO CALCULATE MUTUAL IMPEDANCE BETWEEN TWO DIPOLES
C***WITH ARBITRARY LENGTH AND ORIENTATION.  A PIECEWISE-
C***SINUSOIDAL CURRENT DISTRIBUTION IS ASSUMED.
          SUBROUTINE DSZABG(SX1,SX2,SX3,SY1,SY2,SY3,SZ1,SZ2,SZ3,
         2SXA,SXB,SXC,SYA,SYB,SYC,SZA,SZB,SZC,DZABG)
          IMPLICIT REAL*8 (A-H,O-Z)
          COMPLEX*16 P11,P12,P21,P22,Q11,Q12,Q21,Q22,R11,R12,R21,R22
          COMPLEX*16 S11,S12,S21,S22,JCOM,GAM,CGDS,SGDS,SGDT,ETA
          COMPLEX*16 DZABG,EP3,EGDS,EGDT
          REAL*4 SX1,SX2,SX3,SY1,SY2,SY3,SZ1,SZ2,SZ3
          REAL*4 SXA,SXB,SXC,SYA,SYB,SYC,SZA,SZB,SZC
          REAL*4 FHZ,ER3,SIG3,TD3
          COMMON /F/ FHZ,ER3,SIG3,TD3
          JCOM=(0.D0,1.D0)
          PI=3.1415926535898D0
          TPI=2.0D0*PI
          B=TPI
          E0=8.854D-12
          U0=1.2566D-6
          OMEGA=TPI*FHZ
CC        WRITE(6,2843)OMEGA
 2843     FORMAT(1X,'OMEGA=',E12.5)
          IF(SIG3.LT.0.0D0)EP3=ER3*E0*DCMPLX(1.0D0,-TD3)
          IF(TD3.LT.0.0D0)EP3=DCMPLX(ER3*E0,-SIG3/OMEGA)
CC        WRITE(6,7755)ER3,E0,EP3
 7755     FORMAT(1X,'ER3,E0,EP3=',4E12.5)
          ETA=CDSQRT(U0/EP3)
          GAM=OMEGA*CDSQRT(-U0*EP3)
```

```
C**COMPUTE GAMMA BY EQUATION IN HAYT PAGE 333
CC      GAM=JCOM*OMEGA*CDSQRT(U0*EP3)*CDSQRT(1.D0-JCOM*SIG3/(OMEGA*EP3))
CC      WRITE(6,8888)GAM
8888    FORMAT(1X,'HYAT GAM=',2E12.5)
        AM=0.0001D0
        INT=0
        X1=SX1
        X2=SX2
        X3=SX3
        Y1=SY1
        Y2=SY2
        Y3=SY3
        Z1=SZ1
        Z2=SZ2
        Z3=SZ3
        XA=SXA
        XB=SXB
        XC=SXC
        YA=SYA
        YB=SYB
        YC=SYC
        ZA=SZA
        ZB=SZB
        ZC=SZC
        XBA=XB-XA
        YBA=YB-YA
        ZBA=ZB-ZA
        X21=X2-X1
        Y21=Y2-Y1
        Z21=Z2-Z1
        DS=DSQRT(XBA*XBA+YBA*YBA+ZBA*ZBA)
        DT=DSQRT(X21*X21+Y21*Y21+Z21*Z21)
CC      DSK=B*DS
CC      DTK=B*DT
CC      CGDS=DCMPLX(DCOS(DSK),0.0D0)
CC      SGDS=DCMPLX(0.0D0,DSIN(DSK))
CC      SGDT=DCMPLX(0.0D0,DSIN(DTK))
        EGDS=CDEXP(GAM*DS)
        EGDT=CDEXP(GAM*DT)
        CGDS=(EGDS+1.0D0/EGDS)/2.0D0
        SGDS=(EGDS-1.0D0/EGDS)/2.0D0
        SGDT=(EGDT-1.0D0/EGDT)/2.0D0
        CALL DGGS(XA,YA,ZA,XB,YB,ZB,X1,Y1,Z1,X2,Y2,Z2,AM,
       2DS,CGDS,SGDS,DT,SGDT,INT,ETA,GAM,P11,P12,P21,P22)
        CALL DGGS(XA,YA,ZA,XB,YB,ZB,X2,Y2,Z2,X3,Y3,Z3,AM,
       2DS,CGDS,SGDS,DT,SGDT,INT,ETA,GAM,Q11,Q12,Q21,Q22)
        CALL DGGS(XB,YB,ZB,XC,YC,ZC,X1,Y1,Z1,X2,Y2,Z2,AM,
       2DS,CGDS,SGDS,DT,SGDT,INT,ETA,GAM,R11,R12,R21,R22)
        CALL DGGS(XB,YB,ZB,XC,YC,ZC,X2,Y2,Z2,X3,Y3,Z3,AM,
       2DS,CGDS,SGDS,DT,SGDT,INT,ETA,GAM,S11,S12,S21,S22)
        DZABG=P22+Q21+R12+S11
CC      WRITE(6,8899)DZABG
8899    FORMAT(1X,'EXITING DZABG, DZABG=',2E14.5)
        RETURN
        END
```

APPENDIX B

```
*** Copyright MIT Lincoln Laboratory 1991. All rights reserved.
***Input data file for adaptive nulling with four auxiliary probes.
***sdipjamhyper data file, filename sdipjamhyper.datacirconicrr4
 &DIPOLE NCOLX=8,NROWY=1,HZIN=0.001,HLIN=2.6,
  DXIN=6.888,DYIN=6.888,ARADIN=0.0039,
  ICIRC=1,CRADIN=11.81,HLSIN=0.25,
  IWL=0,FCHZ=120.0E6,BWFHZ=1.0E0,NFREQ=5,IWR=0,
  NPDX=0,NXDUM=0,NYDUM=0,ER3=73.5,SIG3=0.5,TD3=-1.0,
  ZLOAD=50.0,ZCHAR=0.0,NGEN=8,IGEN=0,

NSCANS=1,
 THSINC=5.0,
```

```
IMUT=1,IBLTSL=0,

IENORM=1,ICHEB=0,SLLDB=20.,EDGTDB=0.,

IPATRN=1,IPRCOM=1,IANGLP=0,
NPHCT=0,NTHPT=499,
THDR=180.,THDMIN=-90.,

NCOLXN=121,NROWYN=1,NCOLZN=1,
RLSYIN=0.0,RLSZIN=0.0,

NCOLXN=117,NROWYN=1,NCOLZN=1,

INEAR=1,

IPOL=2,IGRNDP=0,

ITLTPR=0,ITLTDP=0,

NFCOLX=1,NFROWY=1,

IANTX=1,IANTY=0,NPOWER=0,

IPCONN=1,IPCONF=0,IPCUTF=0,IPCFX=0,IPCFY=0,IPCFZ=0,

ITEK=0,

IQUAN=0,IRNERR=0,ELERDB=0.02,ELERDG=0.2,NBMOD=12,

NRAN=1,NBADWT=32,AWERDB=0.0,AWERDG=0.0,

NAUX=7,IAUXA(1)=1,2,3,4,5,6,7,

IATTEN=1,
NJAMS=7,ISLC=0,AUXADB(1)=8*0.0,
PWRJDB(1)=40.,40.,15.,15.,3*-99.0,
YJAMIN(1)=7*0.0,
XFOCIN=0.0,ZFOCIN=0.0,
XJAMIN(1)=5.9,-5.9,2*0.0,3*-0.0,
ZJAMIN(1)=0.0,0.0,4.0,-4.0,3*0.0
YNIN=0.0,
NCOLXN=101,NTHPT=101,
XNIN=-15.,ZNIN=-15.,RLSXIN=30.,RLSZIN=30.,NCOLXN=41,NCOLZN=41,
&END

***Output data file for adaptive nulling with four auxiliary probes.
***sdipjamhyper data file, filename sdipjamhyper.datacirconicrr4
  XJAMIN(1),YJAMIN(1),ZJAMIN(1)=      5.900      0.000      0.000
  FGHZ=      0.1200000
  DX,DY,HL,ARAD=          0.17496       0.17496      0.06604      0.00010
  IV,VTA=    1    0.5916E-02   0.2211E-02
  IV,VTA=    2    0.5916E-02   0.2211E-02
  IV,VTA=    3    0.5916E-02   0.2211E-02
  IV,VTA=    4    0.5916E-02   0.2211E-02
  IV,VTA=    5    0.5916E-02   0.2211E-02
  IV,VTA=    6    0.5916E-02   0.2211E-02
  IV,VTA=    7    0.5916E-02   0.2211E-02
  IV,VTA=    8    0.5916E-02   0.2211E-02
 *******array mutual impedance matrix (first row)*****
  Z(1,   1)= 0.91705E+02 0.12403E+02
  Z(1,   2)=-0.33552E-01 0.19136E+00
  Z(1,   3)=-0.14488E-01-0.54125E-02
  Z(1,   4)= 0.29420E-02 0.13780E-02
  Z(1,   5)= 0.15283E-02-0.11371E-02
  Z(1,   6)= 0.29420E-02 0.13780E-02
  Z(1,   7)=-0.14488E-01-0.54125E-02
  Z(1,   8)=-0.33552E-01 0.19136E+00
  NEL,NCOLX,NROWY=       8     8    1
  CURRENTS
      1   1.000000         0.683E-04      13.
      2   1.000000         0.683E-04      13.
```

```
     3  1.000000         0.683E-04      13.
     4  1.000000         0.683E-04      13.
     5  1.000000         0.683E-04      13.
     6  1.000000         0.683E-04      13.
     7  1.000000         0.683E-04      13.
     8  1.000000         0.683E-04      13.
IC,RWTA=    1    0.35355E+00
IC,RWTA=    2    0.35355E+00
IC,RWTA=    3    0.35355E+00
IC,RWTA=    4    0.35355E+00
IC,RWTA=    5    0.35355E+00
IC,RWTA=    6    0.35355E+00
IC,RWTA=    7    0.35355E+00
IC,RWTA=    8    0.35355E+00
I,CWTA(I,1)=    1    0.34510E+00-0.76830E-01
I,CWTA(I,1)=    2    0.34510E+00-0.76830E-01
I,CWTA(I,1)=    3    0.34510E+00-0.76830E-01
I,CWTA(I,1)=    4    0.34510E+00-0.76830E-01
I,CWTA(I,1)=    5    0.34510E+00-0.76830E-01
I,CWTA(I,1)=    6    0.34510E+00-0.76830E-01
I,CWTA(I,1)=    7    0.34510E+00-0.76830E-01
I,CWTA(I,1)=    8    0.34510E+00-0.76830E-01
******ring array weights before nulling (amp,phase)*************
I=   1   CWTADB,CWTADG=       0.00000      -12.55098
I=   2   CWTADB,CWTADG=       0.00000      -12.55099
I=   3   CWTADB,CWTADG=       0.00000      -12.55098
I=   4   CWTADB,CWTADG=       0.00000      -12.55097
I=   5   CWTADB,CWTADG=       0.00000      -12.55098
I=   6   CWTADB,CWTADG=       0.00000      -12.55097
I=   7   CWTADB,CWTADG=       0.00000      -12.55098
I=   8   CWTADB,CWTADG=       0.00000      -12.55097
Z(1,  1)= 0.91705E+02 0.12403E+02
Z(1,  2)=-0.33552E-01 0.19136E+00
Z(1,  3)=-0.14488E-01-0.54125E-02
Z(1,  4)= 0.29420E-02 0.13780E-02
Z(1,  5)= 0.15283E-02-0.11371E-02
Z(1,  6)= 0.29420E-02 0.13780E-02
Z(1,  7)=-0.14488E-01-0.54125E-02
Z(1,  8)=-0.33552E-01 0.19136E+00
NEL,NCOLX,NROWY=    8    8    1
II,PWRJ IN POWER=    1    0.10000E+05
II,PWRJ IN POWER=    2    0.10000E+05
II,PWRJ IN POWER=    3    0.31623E+02
II,PWRJ IN POWER=    4    0.31623E+02
II,PWRJ IN POWER=    5    0.12589E-09
II,PWRJ IN POWER=    6    0.12589E-09
II,PWRJ IN POWER=    7    0.12589E-09
******covariance matrix*************************
I,J,CNDB,PHASEN=    1    1       36.35         0.00
I,J,CNDB,PHASEN=    1    2       31.68        91.33
I,J,CNDB,PHASEN=    1    3       24.99      -117.95
I,J,CNDB,PHASEN=    1    4       20.88         6.26
I,J,CNDB,PHASEN=    1    5       20.72        -0.14
I,J,CNDB,PHASEN=    1    6       20.88         6.26
I,J,CNDB,PHASEN=    1    7       24.99      -117.95
I,J,CNDB,PHASEN=    1    8       31.68        91.33
I,J,CNDB,PHASEN=    2    1       31.68       -91.33
I,J,CNDB,PHASEN=    2    2       27.05         0.00
I,J,CNDB,PHASEN=    2    3       20.23       155.55
I,J,CNDB,PHASEN=    2    4        8.12       177.91
I,J,CNDB,PHASEN=    2    5       20.90        -6.14
I,J,CNDB,PHASEN=    2    6        8.28       177.98
I,J,CNDB,PHASEN=    2    7       20.24       155.46
I,J,CNDB,PHASEN=    2    8       27.04         0.00
I,J,CNDB,PHASEN=    3    1       24.99       117.95
I,J,CNDB,PHASEN=    3    2       20.23      -155.55
I,J,CNDB,PHASEN=    3    3       16.67         0.00
I,J,CNDB,PHASEN=    3    4       20.26      -155.49
I,J,CNDB,PHASEN=    3    5       25.01       117.95
I,J,CNDB,PHASEN=    3    6       20.27      -155.41
I,J,CNDB,PHASEN=    3    7       16.52         0.00
I,J,CNDB,PHASEN=    3    8       20.24      -155.46
```

| | | | |
|---|---|---|---|
| I,J,CNDB,PHASEN= | 4 1 | 20.88 | -6.26 |
| I,J,CNDB,PHASEN= | 4 2 | 8.12 | -177.91 |
| I,J,CNDB,PHASEN= | 4 3 | 20.26 | 155.49 |
| I,J,CNDB,PHASEN= | 4 4 | 27.08 | 0.00 |
| I,J,CNDB,PHASEN= | 4 5 | 31.71 | -91.33 |
| I,J,CNDB,PHASEN= | 4 6 | 27.07 | 0.00 |
| I,J,CNDB,PHASEN= | 4 7 | 20.27 | 155.41 |
| I,J,CNDB,PHASEN= | 4 8 | 8.28 | -177.98 |
| I,J,CNDB,PHASEN= | 5 1 | 20.72 | 0.14 |
| I,J,CNDB,PHASEN= | 5 2 | 20.90 | 6.14 |
| I,J,CNDB,PHASEN= | 5 3 | 25.01 | -117.95 |
| I,J,CNDB,PHASEN= | 5 4 | 31.71 | 91.33 |
| I,J,CNDB,PHASEN= | 5 5 | 36.38 | 0.00 |
| I,J,CNDB,PHASEN= | 5 6 | 31.71 | 91.33 |
| I,J,CNDB,PHASEN= | 5 7 | 25.01 | -117.95 |
| I,J,CNDB,PHASEN= | 5 8 | 20.90 | 6.14 |
| I,J,CNDB,PHASEN= | 6 1 | 20.88 | -6.26 |
| I,J,CNDB,PHASEN= | 6 2 | 8.28 | -177.98 |
| I,J,CNDB,PHASEN= | 6 3 | 20.27 | 155.41 |
| I,J,CNDB,PHASEN= | 6 4 | 27.07 | 0.00 |
| I,J,CNDB,PHASEN= | 6 5 | 31.71 | -91.33 |
| I,J,CNDB,PHASEN= | 6 6 | 27.08 | 0.00 |
| I,J,CNDB,PHASEN= | 6 7 | 20.26 | 155.49 |
| I,J,CNDB,PHASEN= | 6 8 | 8.12 | -177.91 |
| I,J,CNDB,PHASEN= | 7 1 | 24.99 | 117.95 |
| I,J,CNDB,PHASEN= | 7 2 | 20.24 | -155.46 |
| I,J,CNDB,PHASEN= | 7 3 | 16.52 | 0.00 |
| I,J,CNDB,PHASEN= | 7 4 | 20.27 | -155.41 |
| I,J,CNDB,PHASEN= | 7 5 | 25.01 | 117.95 |
| I,J,CNDB,PHASEN= | 7 6 | 20.26 | -155.49 |
| I,J,CNDB,PHASEN= | 7 7 | 16.67 | 0.00 |
| I,J,CNDB,PHASEN= | 7 8 | 20.23 | -155.55 |
| I,J,CNDB,PHASEN= | 8 1 | 31.68 | -91.33 |
| I,J,CNDB,PHASEN= | 8 2 | 27.04 | 0.00 |
| I,J,CNDB,PHASEN= | 8 3 | 20.24 | 155.46 |
| I,J,CNDB,PHASEN= | 8 4 | 8.28 | 177.98 |
| I,J,CNDB,PHASEN= | 8 5 | 20.90 | -6.14 |
| I,J,CNDB,PHASEN= | 8 6 | 8.12 | 177.91 |
| I,J,CNDB,PHASEN= | 8 7 | 20.23 | 155.55 |
| I,J,CNDB,PHASEN= | 8 8 | 27.05 | 0.00 |

*******eigenvalues******************
```
I,EVLDBN=    1      37.437
I,EVLDBN=    2      37.195
I,EVLDBN=    3       2.771
I,EVLDBN=    4       3.103
I,EVLDBN=    5       0.000
I,EVLDBN=    6       0.000
I,EVLDBN=    7       0.000
I,EVLDBN=    8       0.000
CPROD1,CPROD2= 0.13839E+04-0.85265E-13 0.10000E+01 0.00000E+00
INR NORMALIZATION PARAMETER, INRNOR=   1
I=    1   WANDB=       -12.318
I=    2   WANDB=        -8.734
I=    3   WANDB=        -7.602
I=    4   WANDB=        -8.734
I=    5   WANDB=       -12.318
I=    6   WANDB=        -8.734
I=    7   WANDB=        -7.602
I=    8   WANDB=        -8.734
I,WAN(I,1)=    1    0.11307E+00-0.21414E+00
I,WAN(I,1)=    2    0.34937E+00 0.10851E+00
I,WAN(I,1)=    3    0.32832E+00-0.25671E+00
I,WAN(I,1)=    4    0.34937E+00 0.10851E+00
I,WAN(I,1)=    5    0.11307E+00-0.21414E+00
I,WAN(I,1)=    6    0.34937E+00 0.10851E+00
I,WAN(I,1)=    7    0.32832E+00-0.25671E+00
I,WAN(I,1)=    8    0.34937E+00 0.10851E+00
```
*******adaptive array weights (amp.,phase)*******
```
I=    1   WANDB,WANDG=       -4.71576       -62.16515
I=    2   WANDB,WANDG=       -1.13211        17.25469
I=    3   WANDB,WANDG=        0.00000       -38.02192
```

```
I=   4  WANDB,WANDG=         -1.13210       17.25474
I=   5  WANDB,WANDG=         -4.71576      -62.16529
I=   6  WANDB,WANDG=         -1.13210       17.25474
I=   7  WANDB,WANDG=          0.00000      -38.02193
I=   8  WANDB,WANDG=         -1.13210       17.25469
*********cancellation******************
 CPROD1,CPROD2= 0.12271E+01 0.12185E-13 0.10000E+01 0.00000E+00
 INR NORMALIZATION PARAMETER, INRNOR=   1
 INR= QUI, ADAP ,CANCEL=       31.411      0.889    -30.522   DB
 CANCDB,NRAN,AVECAN=    -30.52207         1      -30.52207
***Input data file for adaptive nulling with two auxiliary probes.
***sdipjamhyper data file, filename sdipjamhyper.datacirconicrr3
 &DIPOLE NCOLX=8,NROWY=1,HZIN=0.001,HLIN=2.6,
 DXIN=6.888,DYIN=6.888,ARADIN=0.0039,
 ICIRC=1,CRADIN=11.81,HLSIN=0.25,
 IWL=0,FCHZ=120.0E6,BWFHZ=1.0E0,NFREQ=5,IWR=0,
 NPDX=0,NXDUM=0,NYDUM=0,ER3=73.5,SIG3=0.5,TD3=-1.0,
 ZLOAD=50.0,ZCHAR=0.0,NGEN=8,IGEN=0,

NSCANS=1,
 THSINC=5.0,

IMUT=1,IBLTSL=0,

IENORM=1,ICHEB=0,SLLDB=20.,EDGTDB=0.,

IPATRN=1,IPRCOM=1,IANGLP=0,
 NPHCT=0,NTHPT=499,
 THDR=180.,THDMIN=-90.,

RLSYIN=0.0,RLSZIN=0.0,

NCOLXN=117,NROWYN=1,NCOLZN=1,

INEAR=1,

IPOL=2,IGRNDP=0,

ITLTPR=0,ITLTDP=0,

NFCOLX=1,NFROWY=1,

IANTX=1,IANTY=0,NPOWER=0,

IPCONN=1,IPCONF=0,IPCUTF=0,IPCFX=0,IPCFY=0,IPCFZ=0,

ITEK=0,

IQUAN=0,IRNERR=0,ELERDB=0.02,ELERDG=0.2,NBMOD=12,

NRAN=1,NBADWT=32,AWERDB=0.0,AWERDG=0.0,

NAUX=7,IAUXA(1)=1,2,3,4,5,6,7,

IATTEN=1,
 INRNOR=1,
 NJAMS=7,ISLC=0,AUXADB(1)=8*0.0,
 PWRJDB(1)=40.,40.,5*-99.0,
 YJAMIN(1)=7*0.0,
 XFOCIN=0.0,ZFOCIN=0.0,
 XJAMIN(1)=5.9,-5.9,2*0.0,2*-4.0,1*0.0,
 ZJAMIN(1)=0.0,0.0,4.0,-4.0,3.0,-3.0,1*0.0
 YNIN=0.0,
 NCOLXN=101,NTHPT=101,
 XNIN=-15.,ZNIN=-15.,RLSXIN=30.,RLSZIN=30.,NCOLXN=41,NCOLZN=41,
 &END

***Output data file for adadptive nulling with two auxiliary probes.
***sdipjamhyper data file, filename sdipjamhyper.datacirconicrr3
 XJAMIN(1),YJAMIN(1),ZJAMIN(1)=       5.900       0.000       0.000
```

```
FGHZ=        0.1200000
DX,DY,HL,ARAD=              0.17496        0.17496        0.06604        0.00010
IV,VTA=    1    0.5916E-02   0.2211E-02
IV,VTA=    2    0.5916E-02   0.2211E-02
IV,VTA=    3    0.5916E-02   0.2211E-02
IV,VTA=    4    0.5916E-02   0.2211E-02
IV,VTA=    5    0.5916E-02   0.2211E-02
IV,VTA=    6    0.5916E-02   0.2211E-02
IV,VTA=    7    0.5916E-02   0.2211E-02
IV,VTA=    8    0.5916E-02   0.2211E-02
*******array mutual impedance matrix (first row)*****
Z(1,   1)= 0.91705E+02 0.12403E+02
Z(1,   2)=-0.33552E-01 0.19136E+00
Z(1,   3)=-0.14488E-01-0.54125E-02
Z(1,   4)= 0.29420E-02 0.13780E-02
Z(1,   5)= 0.15283E-02-0.11371E-02
Z(1,   6)= 0.29420E-02 0.13780E-02
Z(1,   7)=-0.14488E-01-0.54125E-02
Z(1,   8)=-0.33552E-01 0.19136E+00
NEL,NCOLX,NROWY=    8    8    1
CURRENTS
     1   1.000000           0.683E-04         13.
     2   1.000000           0.683E-04         13.
     3   1.000000           0.683E-04         13.
     4   1.000000           0.683E-04         13.
     5   1.000000           0.683E-04         13.
     6   1.000000           0.683E-04         13.
     7   1.000000           0.683E-04         13.
     8   1.000000           0.683E-04         13.
IC,RWTA=   1    0.35355E+00
IC,RWTA=   2    0.35355E+00
IC,RWTA=   3    0.35355E+00
IC,RWTA=   4    0.35355E+00
IC,RWTA=   5    0.35355E+00
IC,RWTA=   6    0.35355E+00
IC,RWTA=   7    0.35355E+00
IC,RWTA=   8    0.35355E+00
I,CWTA(I,1)=   1    0.34510E+00-0.76830E-01
I,CWTA(I,1)=   2    0.34510E+00-0.76830E-01
I,CWTA(I,1)=   3    0.34510E+00-0.76830E-01
I,CWTA(I,1)=   4    0.34510E+00-0.76830E-01
I,CWTA(I,1)=   5    0.34510E+00-0.76830E-01
I,CWTA(I,1)=   6    0.34510E+00-0.76830E-01
I,CWTA(I,1)=   7    0.34510E+00-0.76830E-01
I,CWTA(I,1)=   8    0.34510E+00-0.76830E-01
******ring array weights before nulling (amp,phase)*************
I=   1   CWTADB,CWTADG=         0.00000     -12.55098
I=   2   CWTADB,CWTADG=         0.00000     -12.55099
I=   3   CWTADB,CWTADG=         0.00000     -12.55098
I=   4   CWTADB,CWTADG=         0.00000     -12.55097
I=   5   CWTADB,CWTADG=         0.00000     -12.55098
I=   6   CWTADB,CWTADG=         0.00000     -12.55097
I=   7   CWTADB,CWTADG=         0.00000     -12.55098
I=   8   CWTADB,CWTADG=         0.00000     -12.55097
Z(1,   1)= 0.91705E+02 0.12403E+02
Z(1,   2)=-0.33552E-01 0.19136E+00
Z(1,   3)=-0.14488E-01-0.54125E-02
Z(1,   4)= 0.29420E-02 0.13780E-02
Z(1,   5)= 0.15283E-02-0.11371E-02
Z(1,   6)= 0.29420E-02 0.13780E-02
Z(1,   7)=-0.14488E-01-0.54125E-02
Z(1,   8)=-0.33552E-01 0.19136E+00
NEL,NCOLX,NROWY=    8    8    1
II,PWRJ IN POWER=   1    0.10000E+05
II,PWRJ IN POWER=   2    0.10000E+05
II,PWRJ IN POWER=   3    0.12589E-09
II,PWRJ IN POWER=   4    0.12589E-09
II,PWRJ IN POWER=   5    0.12589E-09
II,PWRJ IN POWER=   6    0.12589E-09
II,PWRJ IN POWER=   7    0.12589E-09
******covariance matrix*************************
```

```
I,J,CNDB,PHASEN=    1   1      36.35        0.00
I,J,CNDB,PHASEN=    1   2      31.68       91.33
I,J,CNDB,PHASEN=    1   3      24.98     -117.94
I,J,CNDB,PHASEN=    1   4      20.88        6.28
I,J,CNDB,PHASEN=    1   5      20.72       -0.14
I,J,CNDB,PHASEN=    1   6      20.88        6.28
I,J,CNDB,PHASEN=    1   7      24.98     -117.94
I,J,CNDB,PHASEN=    1   8      31.68       91.33
I,J,CNDB,PHASEN=    2   1      31.68      -91.33
I,J,CNDB,PHASEN=    2   2      27.05        0.00
I,J,CNDB,PHASEN=    2   3      20.24      155.47
I,J,CNDB,PHASEN=    2   4       8.24      177.97
I,J,CNDB,PHASEN=    2   5      20.90       -6.17
I,J,CNDB,PHASEN=    2   6       8.24      177.97
I,J,CNDB,PHASEN=    2   7      20.24      155.47
I,J,CNDB,PHASEN=    2   8      27.04        0.00
I,J,CNDB,PHASEN=    3   1      24.98      117.94
I,J,CNDB,PHASEN=    3   2      20.24     -155.47
I,J,CNDB,PHASEN=    3   3      16.62        0.00
I,J,CNDB,PHASEN=    3   4      20.27     -155.41
I,J,CNDB,PHASEN=    3   5      25.01      117.93
I,J,CNDB,PHASEN=    3   6      20.27     -155.41
I,J,CNDB,PHASEN=    3   7      16.52        0.00
I,J,CNDB,PHASEN=    3   8      20.24     -155.47
I,J,CNDB,PHASEN=    4   1      20.88       -6.28
I,J,CNDB,PHASEN=    4   2       8.24     -177.97
I,J,CNDB,PHASEN=    4   3      20.27      155.41
I,J,CNDB,PHASEN=    4   4      27.08        0.00
I,J,CNDB,PHASEN=    4   5      31.71      -91.33
I,J,CNDB,PHASEN=    4   6      27.07        0.00
I,J,CNDB,PHASEN=    4   7      20.27      155.41
I,J,CNDB,PHASEN=    4   8       8.24     -177.97
I,J,CNDB,PHASEN=    5   1      20.72        0.14
I,J,CNDB,PHASEN=    5   2      20.90        6.17
I,J,CNDB,PHASEN=    5   3      25.01     -117.93
I,J,CNDB,PHASEN=    5   4      31.71       91.33
I,J,CNDB,PHASEN=    5   5      36.38        0.00
I,J,CNDB,PHASEN=    5   6      31.71       91.33
I,J,CNDB,PHASEN=    5   7      25.01     -117.93
I,J,CNDB,PHASEN=    5   8      20.90        6.17
I,J,CNDB,PHASEN=    6   1      20.88       -6.28
I,J,CNDB,PHASEN=    6   2       8.24     -177.97
I,J,CNDB,PHASEN=    6   3      20.27      155.41
I,J,CNDB,PHASEN=    6   4      27.07        0.00
I,J,CNDB,PHASEN=    6   5      31.71      -91.33
I,J,CNDB,PHASEN=    6   6      27.08        0.00
I,J,CNDB,PHASEN=    6   7      20.27      155.41
I,J,CNDB,PHASEN=    6   8       8.24     -177.97
I,J,CNDB,PHASEN=    7   1      24.98      117.94
I,J,CNDB,PHASEN=    7   2      20.24     -155.47
I,J,CNDB,PHASEN=    7   3      16.52        0.00
I,J,CNDB,PHASEN=    7   4      20.27     -155.41
I,J,CNDB,PHASEN=    7   5      25.01      117.93
I,J,CNDB,PHASEN=    7   6      20.27     -155.41
I,J,CNDB,PHASEN=    7   7      16.62        0.00
I,J,CNDB,PHASEN=    7   8      20.24     -155.47
I,J,CNDB,PHASEN=    8   1      31.68      -91.33
I,J,CNDB,PHASEN=    8   2      27.04        0.00
1 I,J,CNDB,PHASEN=   8   3      20.24      155.47
I,J,CNDB,PHASEN=    8   4       8.24      177.97
I,J,CNDB,PHASEN=    8   5      20.90       -6.17
I,J,CNDB,PHASEN=    8   6       8.24      177.97
I,J,CNDB,PHASEN=    8   7      20.24      155.47
I,J,CNDB,PHASEN=    8   8      27.05        0.00
*********eigenvalues********************
I,EVLDBN=     1       37.195
I,EVLDBN=     2       37.437
I,EVLDBN=     3        0.000
I,EVLDBN=     4        0.000
I,EVLDBN=     5        0.000
I,EVLDBN=     6        0.000
I,EVLDBN=     7        0.000
I,EVLDBN=     8        0.000
```

```
CPROD1,CPROD2= 0.13835E+04-0.56843E-13 0.10000E+01 0.00000E+00
INR NORMALIZATION PARAMETER, INRNOR=   1
  I=   1  WANDB=         -14.003
  I=   2  WANDB=          -8.939
  I=   3  WANDB=          -6.886
  I=   4  WANDB=          -8.939
  I=   5  WANDB=         -14.003
  I=   6  WANDB=          -8.939
  I=   7  WANDB=          -6.886
  I=   8  WANDB=          -8.939
 I,WAN(I,1)=    1   0.48427E-01-0.19349E+00
 I,WAN(I,1)=    2   0.35635E+00 0.26440E-01
 I,WAN(I,1)=    3   0.43481E+00-0.12564E+00
 I,WAN(I,1)=    4   0.35635E+00 0.26441E-01
 I,WAN(I,1)=    5   0.48427E-01-0.19349E+00
 I,WAN(I,1)=    6   0.35635E+00 0.26441E-01
 I,WAN(I,1)=    7   0.43481E+00-0.12564E+00
 I,WAN(I,1)=    8   0.35635E+00 0.26441E-01
*********adaptive array weights (amp.,phase)*********
  I=   1  WANDB,WANDG=       -7.11720       -75.94859
  I=   2  WANDB,WANDG=       -2.05298         4.24348
  I=   3  WANDB,WANDG=        0.00000       -16.11658
  I=   4  WANDB,WANDG=       -2.05297         4.24352
  I=   5  WANDB,WANDG=       -7.11719       -75.94872
  I=   6  WANDB,WANDG=       -2.05298         4.24352
  I=   7  WANDB,WANDG=        0.00000       -16.11658
  I=   8  WANDB,WANDG=       -2.05297         4.24348
*********cancellation******************
CPROD1,CPROD2= 0.10001E+01-0.63768E-14 0.10000E+01 0.00000E+00
INR NORMALIZATION PARAMETER, INRNOR=   1
 INR= QUI,ADAP ,CANCEL=       31.410        0.000     -31.410   DB
  CANCDB,NRAN,AVECAN=   -31.40966       1      -31.40966
```

APPENDIX C

```
{ COPYRIGHT M.I.T. LINCOLN LABORATORY 1991, ALL RIGHTS RESERVED}
{   PROGRAM NULLGS.P (PASCAL VERSION BY ALAN J. FENN)}
{   THIS SUBROUTINE PERFORMS A GRADIENT SEARCH FOR THE}
{   ADAPTIVE NULLING WEIGHTS (AMPLITUDE AND PHASE)}
{   BASED ON MINIMIZING THE POWER RECEIVED BY AN E-FIELD PROBE}
{   AT A DESIRED NULLING POSITION. }
PROGRAM NULLGS (INPUT,OUTPUT) ;
{   PROGRAM INPUT OR FIXED PARAMETERS}

{       NCHAN IS THE NUMBER OF ADAPTIVE TRANSMIT CHANNELS (=4)}
{       NETUMOR IS THE NUMBER OF E-FIELD TUMOR-SITE PROBES (=1)}
{       NEPROBE IS THE NUMBER OF E-FIELD NULLING PROBES (=1)}
{       JSMAX IS THE MAXIMUM NUMBER OF GRADIENT ITERATIONS (=200)}
{       NBSETWT IS THE NUMBER OF BITS USED IN SETTING THE TRANSMIT WEIGHTS (=8)}
{       NBMEAWT IS THE NUMBER OF BITS USED IN MEASURING THE TRANSMIT WEIGHTS (=12)}
{       NBPROBE IS THE NUMBER OF BITS USED IN MEASURING THE E-FIELD PROBE POWER (=12)}

{   PROGRAM OUTPUT}

{       IWTAMP8 IS THE ADAPTIVE NULLING WEIGHT VECTOR AMPLITUDE}
{       IWTPHA8 IS THE ADAPTIVE NULLING WEIGHT VECTOR PHASE}

{ This computer program is intended to be used in the following manner:}

{ Initially, the hyperthermia phased array should be turned on and the}
{ transmit weights are set to some nominal values.  Assume that there are}
{ two E-field probes, one invasive at the desired tumor position and}
{ one noninvasive on the skin surface.  The output power of the two E-field}
{ probes should be measured and be printed, saved, or displayed on the screen }
{ for reference purposes.}

{ DECLARE INTEGER AND REAL ARRAYS WITH APPROPRIATE DIMENSIONS}

VAR
    IWTAMP12 : ARRAY [1..4] OF INTEGER;
    IWTPHA12 : ARRAY [1..4] OF INTEGER;
    IWTAMP8  : ARRAY [1..4] OF INTEGER;
    IWTPHA8  : ARRAY [1..4] OF INTEGER;
    IWORKAM8 : ARRAY [1..4] OF INTEGER;
    IWORKPH8 : ARRAY [1..4] OF INTEGER;

DFANJ    : ARRAY [1..4] OF REAL;
```

```
    DFPNJ       : ARRAY [1..4] OF REAL;
    RANJ        : ARRAY [1..4] OF REAL;
    RPNJ        : ARRAY [1..4] OF REAL;

{   DECLARE INTEGER AND REAL VARIABLES}

MAXAMP8,NBSETWT,NBMEAWT,NBPROBE         : INTEGER;
    MSBMEAWT,MSBSETWT,MSBPROBE              : INTEGER;
    I,K,N,MDELAMP,MDELPHA,ITER,JSMAX        : INTEGER;
    NCHAN,IAMPP8,IPHAP8,IAMPM8,IPHAM8       : INTEGER;
    NAMPINC,NPHAINC,NEWMAXA8                : INTEGER;
    NETUMOR,NEPROBE                         : INTEGER;

FAC12TO8,FACDEN,SUMDF                   : REAL;
    TPOWER,DNPOWER,TAPOWER,DNAPOWER         : REAL;
    PWR_TPA,PWR_NPA,PWR_TMA,PWR_NMA         : REAL;
    PWR_TPP,PWR_NPP,PWR_TMP,PWR_NMP         : REAL;
    RMSBMEAW,RMSBSETW,RNAMPINC,RNPHAINC     : REAL;

RMAXAMP8                                : REAL;

{   NOTE: Define MEASUREPOWER Procedure}

PROCEDURE MEASUREP (IA1,IA2,IA3,IA4,IP1,IP2,IP3,IP4 : INTEGER ;
              VAR  POWER : REAL) ; {E-FIELD PROBE POWER MEASUREMENT PROCEDURE}

VAR
    IA01,IA02,IA03,IA04,IP01,IP02,IP03,IP04 : INTEGER ;
    POWERA,POWERP                           : REAL    ;

BEGIN

{8-bit weight data}

IA01 :=  71 ;
   IA02 :=  85 ;
   IA03 :=  91 ;
   IA04 := 125 ;

IP01 :=   1 ;
   IP02 := 100 ;
   IP03 :=  74 ;
   IP04 :=  42 ;

{ Polynomial Function Definition }

POWERA := SQR(IA1-IA01)+SQR(IA2-IA02)+SQR(IA3-IA03)+SQR(IA4-IA04) ;
POWERP := SQR(IP1-IP01)+SQR(IP2-IP02)+SQR(IP3-IP03)+SQR(IP4-IP04) ;

POWER  := POWERA + POWERP       {   ;   }

END;

PROCEDURE MEASIW (VAR  IWA1,IWA2,IWA3,IWA4,IWP1,IWP2,IWP3,IWP4 : INTEGER) ;

{THIS PROCEDURE MEASURES THE INITIAL WEIGHTS}
{artificially sets them for now}

BEGIN

{12-bit data}

IWA1 := 2000 ;
   IWA2 := 2000 ;
   IWA3 := 2000 ;
   IWA4 := 2000 ;

IWP1 :=    1 ;
   IWP2 :=    1 ;
   IWP3 :=    1 ;
   IWP4 :=    1       {   ;   }

END;

PROCEDURE SETWTS ;    {procedure to set weights}

BEGIN

{NON-FUNCTIONING FOR NOW}
```

END;

BEGIN    {BEGIN THE MAIN PROGRAM}

{   FIXED DATA FOR SYSTEM}

NCHAN := 4 ;

{   NUMBER OF BITS TO SET WEIGHTS, MEASURE WEIGHTS, MEASURE E-FIELD PROBE}
    NBSETWT:=8 ;
    NBMEAWT:=12 ;
    NBPROBE:=12 ;

NETUMOR:=1 ;
    NEPROBE:=1 ;
    JSMAX  :=25 ;    {number of iterations in gradient search}

WRITELN('enter number of iterations in gradient search') ;

READLN (JSMAX) ;

WRITELN('JSMAX=',JSMAX) ;

{   END OF DATA}

{   MEASURE INITIAL E-FIELD POWER AT TUMOR SITE (RECEIVE PROBE CHANNEL 1)}
{     CALL MEASUREPOWER(  measure TPOWER, the E-field probe power at the tumor site)}
{   MEASURE INITIAL E-FIELD POWER AT DESIRED NULL POSITION (RECEIVE PROBE CHANNEL 2)}
{     CALL MEASUREPOWER(  measure DNPOWER, the E-field probe power at the desired null pos.)}

{   MEASURE TRANSMIT WEIGHTS AMPLITUDE (IWTAMP12) AND PHASE (IWTPHA12) FOR EACH TRANSMIT CH.}
{   NOTE: THE 12 IN IWTAMP12 AND IWTPHA12 REFERS TO 12 BITS}

{FOR I:=1 TO NCHAN  DO}
    {CALL MEASUREWEIGHT(  IWTAMP12[I], IWTPHA12[I]  ) ;}

MEASIW (IWTAMP12[1],IWTAMP12[2],IWTAMP12[3],IWTAMP12[4],
        IWTPHA12[1],IWTPHA12[2],IWTPHA12[3],IWTPHA12[4] ) ;

{   CONVERT 12 BIT MEASUREMENTS TO 8 BIT RANGE FOR PURPOSES OF SETTING WEIGHTS}
{   WITH 8-BIT DIGITAL TO ANALOG CONVERTERS}

{   NOTE: 12 BIT RANGE IS STATES    1,2,3,............,4096}
{          8 BIT RANGE IS STATES    1,2,3,...256}

{   THE MOST SIGNIFICANT BIT FOR THE TRANSMIT WEIGHT MEASUREMENTS IS (MSBMEAWT=4096)}

{ RMSBMEAW := EXP(NBMEAWT * (LN (2.) ) ) ; }
    RMSBMEAW := 4096 ;
    MSBMEAWT := round(RMSBMEAW) ;

{   THE MOST SIGNIFICANT BIT FOR THE TRANSMIT WEIGHT SETTINGS IS (MSBSETWT=256)}

{   RMSBSETW := EXP(NBSETWT * (LN (2.) ) ) ; }
    RMSBSETW := 256 ;
    MSBSETWT := round(RMSBSETW) ;

{   COMPUTE SCALE FACTOR TO CONVERT 12-BIT RANGE TO 8-BIT RANGE}

FAC12TO8 := RMSBSETW / MSBMEAWT ;

{   CONVERT THE 12-BIT TRANSMIT WEIGHT DATA TO 8-BIT DATA AND PRINT-OUT}

FOR I:= 1 TO NCHAN  DO

BEGIN

IWTAMP8[I] := round( IWTAMP12[I] * FAC12TO8) ;

IF IWTAMP8[I] < 1 THEN   IWTAMP8[I] := 1 ;

IWTPHA8[I] := round( IWTPHA12[I] * FAC12TO8) ;

IF IWTPHA8[I] < 1 THEN   IWTPHA8[I] := 1 ;

WRITELN('CHANNEL', I, ' AMPLITUDE=', IWTAMP8[I],' PHASE=', IWTPHA8[I]) ;

{   STORE THE 8-BIT DATA IN TEMPORARY WORK ARRAYS}
    IWORKAM8[I] := IWTAMP8[I] ;
    IWORKPH8[I] := IWTPHA8[I]     {     ;     }

END;

```
{       DETERMINE MAXIMUM WEIGHT AMPLITUDE BEFORE NULLING }

MAXAMP8 :=0 ;

FOR I := 1 TO NCHAN  DO
                BEGIN
                    IF IWTAMP8[I] > MAXAMP8  THEN
                        MAXAMP8 :=IWTAMP8[I]    {  ;  }
                END;
{       COPY MAXAMP8 TO A REAL VARIABLE (RMAXAMP8)}

RMAXAMP8 := MAXAMP8 ;

{       PRINT-OUT THE MAXIMUM WEIGHT AMPLITUDE OVER 8-BIT RANGE}

WRITELN('MAXIMUM WEIGHT AMPLITUDE OVER 8-BIT RANGE=', RMAXAMP8) ;

{   MEASURE INITIAL E-FIELD POWER AT DESIRED NULL POSITION (RECEIVE PROBE CHANNEL 2)}

MEASUREP (IWTAMP8[1],IWTAMP8[2],IWTAMP8[3],IWTAMP8[4],
        IWTPHA8[1],IWTPHA8[2],IWTPHA8[3],IWTPHA8[4], DNPOWER)  ;

WRITELN('INITIAL E-FIELD POWER AT DESIRED NULL POSITION=',DNPOWER) ;

{       READ-IN THE MAXIMUM NUMBER OF STATES TO DITHER TRANSMIT WEIGHT AMPLITUDE}

WRITELN('ENTER MAXIMUM NUMBER OF STATES TO DITHER TRANSMIT WEIGHT AMPLITUDE');

READLN (MDELAMP) ;

{       READ-IN THE MAXIMUM NUMBER OF STATES TO DITHER TRANSMIT WEIGHT PHASE}

WRITELN('ENTER MAXIMUM NUMBER OF STATES TO DITHER TRANSMIT WEIGHT PHASE');

READLN (MDELPHA) ;

writeln('MDELAMP=',MDELAMP,'   MDELPHA=',MDELPHA) ;

{   BEGIN GRADIENT SEARCH: }

FOR ITER := 1 TO JSMAX  DO    {Start ITER Loop}
            BEGIN

SUMDF :=0.0 ;

WRITELN ('ITERATION NUMBER=',ITER);

{       COMPUTE WEIGHT-DITHERING STATES +-AMPLITUDE,  +-PHASE}

FOR K := 1 TO NCHAN  DO    {Start K Loop For Weight Dithering}
                    BEGIN

{   AMPLITUDE SECTION: }

IAMPP8 := IWTAMP8[K] + MDELAMP ;

writeln('IAMPP8=',IAMPP8)  ;

{   MAKE SURE WEIGHT AMPLITUDE DOES NOT EXCEED MOST SIGNIFICANT BIT (256) }

IF IAMPP8 > MSBSETWT THEN
                            BEGIN

IAMPP8 := MSBSETWT ;

END;

IAMPM8 := IWTAMP8[K] - MDELAMP ;

writeln('IAMPM8=',IAMPM8)  ;

{   MAKE SURE WEIGHT AMPLITUDE STATE IS NOT LESS THAN THE LEAST SIGNIFICANT BIT [1]}

IF IAMPM8 < 1  THEN
                            BEGIN

IAMPM8 := 1 ;
```

```
                            END;

{ PHASE SECTION:}
                IPHAP8 := IWTPHA8[K] + MDELPHA ;

{  MAKE SURE WEIGHT PHASE DOES NOT EXCEED MOST SIGNIFICANT BIT (256)}

IF IPHAP8 > MSBSETWT  THEN

BEGIN

IPHAP8 := MSBSETWT ;

END;

writeln('IPHAP8=',IPHAP8) ;

IPHAM8 := IWTPHA8[K] - MDELPHA ;

{  MAKE SURE WEIGHT PHASE STATE IS NOT LESS THAN THE LEAST SIGNIFICANT BIT [1]}

IF IPHAM8 <  1  THEN

BEGIN

IPHAM8 := 1 ;

END;

writeln('IPHAM8=',IPHAM8) ;

{   NOW, DITHER THE TRANSMIT WEIGHTS UP AND DOWN IN AMPLITUDE AND PHASE}

{ AMPLITUDE SECTION:}

{ DITHER WEIGHT AMPLITUDE UP:}

IWTAMP8[K] := IAMPP8 ;

{ SET THE TRANSMIT WEIGHTS WITH KTH WEIGHT DITHERED UP IN AMPLITUDE}

{   CALL SETWEIGHTS( IWTAMP8(1 2 3 ... NCHAN) , IWTPHA8(1 2 3 ... NCHAN) }

{   *MEASURE CURRENT E-FIELD POWER AT TUMOR SITE (RECEIVE PROBE CHANNEL 1)}
{    notation in PWR_TPA for example is PA for +Amplitude}
{    CALL MEASUREPOWER(  measure PWR_TPA, the E-field probe power at the tumor site)}
{   *MEASURE INITIAL E-FIELD POWER AT DESIRED NULL POSITION (RECEIVE PROBE CHANNEL 2)}
{    CALL MEASUREPOWER(  measure PWR_NPA, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_NPA) ;

WRITELN('POWER WITH KTH WEIGHT DITHERED UP IN AMPLITUDE=',PWR_NPA) ;

{  DITHER WEIGHT AMPLITUDE DOWN:}

IWTAMP8[K] := IAMPM8 ;

{ SET THE TRANSMIT WEIGHTS WITH KTH WEIGHT DITHERED DOWN IN AMPLITUDE}

{CALL SETWEIGHTS( IWTAMP8(1 2 3 ... NCHAN) , IWTPHA8(1 2 3 ... NCHAN)}

{   *MEASURE CURRENT E-FIELD POWER AT TUMOR SITE (RECEIVE PROBE CHANNEL 1)}
{    notation in PWR_TMA for example is MA for -Amplitude}
{    CALL MEASUREPOWER(  measure PWR_TMA, the E-field probe power at the tumor site) }
{   *MEASURE INITIAL E-FIELD POWER AT DESIRED NULL POSITION (RECEIVE PROBE CHANNEL 2)}
{    CALL MEASUREPOWER(  measure PWR_NMA, the E-field probe power at the desired null pos.) }
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_NMA) ;

WRITELN('POWER WITH KTH WEIGHT DITHERED DOWN IN AMPLITUDE=',PWR_NMA) ;

{   RESET KTH WEIGHT AMPLITUDE BACK TO STATE SET BEFORE THIS DITHERING WAS PERFORMED}

IWTAMP8[K] := IWORKAM8[K] ;

{ PHASE SECTION:}

{ DITHER WEIGHT PHASE UP:}

IWTPHA8[K] := IPHAP8 ;

{ SET THE TRANSMIT WEIGHTS WITH KTH WEIGHT DITHERED UP IN PHASE}
```

```
{ CALL SETWEIGHTS( IWTAMP8(1 2 3 ... NCHAN) , IWTPHA8(1 2 3 ... NCHAN) }

{   *MEASURE CURRENT E-FIELD POWER AT TUMOR SITE (RECEIVE PROBE CHANNEL 1)}
{   notation in PWR_TPP for example is PP for +Phase}
{     CALL MEASUREPOWER(  measure PWR_TPP, the E-field probe power at the tumor site)}
{   *MEASURE INITIAL E-FIELD POWER AT DESIRED NULL POSITION (RECEIVE PROBE CHANNEL 2)}
{     CALL MEASUREPOWER(  measure PWR_NPP, the E-field probe power at the desired null pos.)}

MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_NPP) ;

WRITELN('POWER WITH KTH WEIGHT DITHERED UP IN PHASE=',PWR_NPP) ;

{  DITHER WEIGHT PHASE DOWN:}

IWTPHA8[K] := IPHAM8 ;

{ SET THE TRANSMIT WEIGHTS WITH KTH WEIGHT DITHERED DOWN IN PHASE}

{   CALL SETWEIGHTS( IWTAMP8(1 2 3 ... NCHAN) , IWTPHA8(1 2 3 ... NCHAN) }

{   *MEASURE CURRENT E-FIELD POWER AT TUMOR SITE (RECEIVE PROBE CHANNEL 1) }
{   notation in PWR_TMP for example is MP for -Phase}
{    CALL MEASUREPOWER(  measure PWR_TMP, the E-field probe power at the tumor site)}
{   *MEASURE INITIAL E-FIELD POWER AT DESIRED NULL POSITION (RECEIVE PROBE CHANNEL 2)}
{    CALL MEASUREPOWER(  measure PWR_NMP, the E-field probe power at the desired null pos.)}

MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_NMP) ;

WRITELN('POWER WITH KTH WEIGHT DITHERED DOWN IN PHASE=',PWR_NMP) ;

{  RESET KTH WEIGHT PHASE BACK TO STATE SET BEFORE THIS DITHERING WAS PERFORMED} writeln('reset kth phase weight') ;

IWTPHA8[K] := IWORKPH8[K] ;

writeln('KTH PHASE WEIGHT IS NOW=',IWTPHA8[K]) ;

{ COMPUTE POWER DIFFERENCES DUE TO WEIGHT DITHERING } writeln('compute power differences') ;

DFANJ[K] := PWR_NPA - PWR_NMA ;

DFPNJ[K] := PWR_NPP - PWR_NMP ;

writeln('DFANJ[K]=',DFANJ[K],'  DFPNJ[K]=',DFPNJ[K]) ;

{ COMPUTE NORMALIZING FACTOR } writeln('MDELAMP=',MDELAMP,'  MDELPHA=',MDELPHA) ;
               SUMDF := SUMDF + SQR(DFANJ[K]/MDELAMP) + SQR(DFPNJ[K]/MDELPHA) ;
      writeln('SUMDF=',SUMDF)

END;      {End of K Loop For Weight Dithering}

{ END OF WEIGHT DITHERING AND POWER DIFFERENCING LOOP}

FACDEN := SQRT(SUMDF) ;

{ END OF WEIGHT DITHERING AND POWER DIFFERENCING SECTION}

{ COMPUTE GRADIENT SEARCH DIRECTIONS}

{ START GRADIENT SEARCH DIRECTION LOOP}

FOR N :=1 TO NCHAN DO

BEGIN    {Begin N Loop For Computing Search Directions}

{ THE NEXT TWO LINES ARE FOR FIGURE OF MERIT (POWER) MINIMIZATION}

RANJ[N] := -DFANJ[N]/MDELAMP/FACDEN ;

RPNJ[N] := -DFPNJ[N]/MDELPHA/FACDEN ;

writeln('N=',N,'  RANJ[N]=',RANJ[N],'  RPNJ[N]=',RPNJ[N]) ;

{ COMPUTE ACTUAL WEIGHT INCREMENTS (NUMBER OF STATES)}

RNAMPINC := MDELAMP * RANJ[N] ;
     NAMPINC  := round(RNAMPINC) ;
```

```
            RNPHAINC := MDELPHA * RPNJ[N] ;
            NPHAINC  := round(RNPHAINC) ;

writeln('N=',N,' NAMPINC=',NAMPINC,' NPHAINC=',NPHAINC) ;

{   COMPUTE UPDATED WEIGHTS:}
{   AMPLITUDE SECTION:}
         IWTAMP8[N] := IWTAMP8[N] + NAMPINC ;
{    MAKE SURE WEIGHT AMPLITUDE DOES NOT EXCEED MOST SIGNIFICANT BIT (256)}
         IF IWTAMP8[N] > MSBSETWT   THEN
            BEGIN
             IWTAMP8[N] := MSBSETWT ;
            END;
{    MAKE SURE WEIGHT AMPLITUDE STATE IS NOT LESS THAN THE LEAST SIGNIFICANT BIT [1] }
         IF IWTAMP8[N] < 1  THEN
            BEGIN
            IWTAMP8[N] := 1 ;
            END;

PHASE SECTION: }
         IWTPHA8[N] := IWTPHA8[N] + NPHAINC ;
: MAKE SURE WEIGHT PHASE DOES NOT EXCEED MOST SIGNIFICANT BIT (256)}
         IF IWTPHA8[N] > MSBSETWT   THEN
            BEGIN
            IWTPHA8[N] := MSBSETWT ;
            END;
{ MAKE SURE WEIGHT PHASE STATE IS NOT LESS THAN THE LEAST SIGNIFICANT BIT [1] }
         IF IWTPHA8[N] < 1  THEN
            BEGIN
            IWTPHA8[N] := 1 ;
            END;
{  END GRADIENT SEARCH DIRECTIONS LOOP}
         END;   {End N Loop For Gradient Search Directions}

{   FIND NEW MAXIMUM AMPLITUDE}
         NEWMAXA8 := 0 ;
            FOR K:= 1 TO NCHAN  DO
               BEGIN
                  IF IWTAMP8[K] > NEWMAXA8   THEN
                     BEGIN
                     NEWMAXA8 := IWTAMP8[K] ;
                     END;
               END;
{   MAKE SURE TRANSMIT WEIGHT AMPLITUDES DO NOT EXCEED INITIAL MAXIMUM AMPLITUDE}
            FOR  K:= 1 TO NCHAN  DO
               BEGIN
```

```
                IWTAMP8[K] := round( IWTAMP8[K] * RMAXAMP8 / NEWMAXA8) {  ;  }
            END;

{ SET THE UPDATED (ADAPTIVE) TRANSMIT WEIGHTS AT ITERATION NUMBER ITER}

{ CALL SETWEIGHTS( IWTAMP8(1 2 3 ... NCHAN) , IWTPHA8(1 2 3 ... NCHAN) }
{ MEASURE ADAPTIVE E-FIELD POWER AT TUMOR SITE (RECEIVE PROBE CHANNEL 1)}
{ CALL MEASUREPOWER( measure TAPOWER, the E-field probe power at the tumor site)}
{ MEASURE ADAPTIVE E-FIELD POWER AT DESIRED NULL POSITION (RECEIVE PROBE CHANNEL 2)}
{ CALL MEASUREPOWER( measure DNAPOWER, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], DNAPOWER ) ;

WRITELN('ITERATION no.=',ITER,'  POWER=',DNAPOWER)  ;

{   PRINT OUT ADAPTIVE WEIGHTS }

FOR K:= 1 TO NCHAN  DO

BEGIN

WRITELN('CH. no.',K,'  AMP=',IWTAMP8[K],'  PHASE=',IWTPHA8[K]) {  ;  }

END;

{FILL-IN NEW VALUES FOR WORK ARRAYS}

FOR K := 1 TO NCHAN  DO

BEGIN

IWORKAM8[K] := IWTAMP8[K]  ;

IWORKPH8[K] := IWTPHA8[K]

END

{END OF GRADIENT SEARCH LOOP}

END;     {End ITER loop}
{   END OF GRADIENT SEARCH} writeln('final adaptive weights')  ;

{   PRINT OUT ADAPTIVE WEIGHTS }

FOR K:= 1 TO NCHAN  DO

BEGIN

WRITELN('CH. no.',K,'  AMP=',IWTAMP8[K],'  PHASE=',IWTPHA8[K]) {  ;  }

END;

END.
```

SAMPLE OUTPUT

```
enter number of iterations in gradient search
JSMAX=          5
CHANNEL         1   AMPLITUDE=        125  PHASE=          1
CHANNEL         2   AMPLITUDE=        125  PHASE=          1
CHANNEL         3   AMPLITUDE=        125  PHASE=          1
CHANNEL         4   AMPLITUDE=        125  PHASE=          1
MAXIMUM WEIGHT AMPLITUDE OVER 8-BIT RANGE= 1.2500000000000E+0002
INITIAL E-FIELD POWER AT DESIRED NULL POSITION= 2.2483000000000E+0004
ENTER MAXIMUM NUMBER OF STATES TO DITHER TRANSMIT WEIGHT AMPLITUDE
ENTER MAXIMUM NUMBER OF STATES TO DITHER TRANSMIT WEIGHT PHASE
MDELAMP=        20  MDELPHA=          20
ITERATION NUMBER=        1
IAMPP8=        145
IAMPM8=        105
IPHAP8=         21
IPHAM8=          1
POWER WITH KTH WEIGHT DITHERED UP IN AMPLITUDE= 2.5043000000000E+0004
```

POWER WITH KTH WEIGHT DITHERED DOWN IN AMPLITUDE= 2.0723000000000E+0004
POWER WITH KTH WEIGHT DITHERED UP IN PHASE= 2.2883000000000E+0004
POWER WITH KTH WEIGHT DITHERED DOWN IN PHASE= 2.2483000000000E+0004
reset kth phase weight
KTH PHASE WEIGHT IS NOW=          1
compute power differences
DFANJ[K]= 4.3200000000000E+0003   DFPNJ[K]= 4.0000000000000E+0002
MDELAMP=          20  MDELPHA=          20
SUMDF= 4.7055999999999E+0004
IAMPP8=         145
IAMPM8=         105
IPHAP8=          21
IPHAM8=           1
POWER WITH KTH WEIGHT DITHERED UP IN AMPLITUDE= 2.4483000000000E+0004
POWER WITH KTH WEIGHT DITHERED DOWN IN AMPLITUDE= 2.1283000000000E+0004
POWER WITH KTH WEIGHT DITHERED UP IN PHASE= 1.8923000000000E+0004
POWER WITH KTH WEIGHT DITHERED DOWN IN PHASE= 2.2483000000000E+0004
reset kth phase weight
KTH PHASE WEIGHT IS NOW=          1
compute power differences
DFANJ[K]= 3.2000000000000E+0003   DFPNJ[K]=-3.5600000000000E+0003
MDELAMP=          20  MDELPHA=          20
SUMDF= 1.0434000000000E+0005
IAMPP8=         145
IAMPM8=         105
IPHAP8=          21
IPHAM8=           1
POWER WITH KTH WEIGHT DITHERED UP IN AMPLITUDE= 2.4243000000000E+0004
POWER WITH KTH WEIGHT DITHERED DOWN IN AMPLITUDE= 2.1523000000000E+0004
POWER WITH KTH WEIGHT DITHERED UP IN PHASE= 1.9963000000000E+0004
POWER WITH KTH WEIGHT DITHERED DOWN IN PHASE= 2.2483000000000E+0004
reset kth phase weight
KTH PHASE WEIGHT IS NOW=          1
compute power differences
DFANJ[K]= 2.7200000000000E+0003   DFPNJ[K]=-2.5200000000000E+0003
MDELAMP=          20  MDELPHA=          20
SUMDF= 1.3871200000000E+0005
IAMPP8=         145
IAMPM8=         105
IPHAP8=          21
IPHAM8=           1
POWER WITH KTH WEIGHT DITHERED UP IN AMPLITUDE= 2.2883000000000E+0004
POWER WITH KTH WEIGHT DITHERED DOWN IN AMPLITUDE= 2.2883000000000E+0004
POWER WITH KTH WEIGHT DITHERED UP IN PHASE= 2.1243000000000E+0004
POWER WITH KTH WEIGHT DITHERED DOWN IN PHASE= 2.2483000000000E+0004
reset kth phase weight
KTH PHASE WEIGHT IS NOW=          1
compute power differences
DFANJ[K]= 0.0000000000000E+0000   DFPNJ[K]=-1.2400000000000E+0003
MDELAMP=          20  MDELPHA=          20
SUMDF= 1.4255600000000E+0005
N=        1   RANJ[N]=-5.7208557949563E-0001   RPNJ[N]=-5.2970886990336E-0002
N=        1   NAMPINC=         -11  NPHAINC=          -1
N=        2   RANJ[N]=-4.2376709592269E-0001   RPNJ[N]= 4.7144089421399E-0001
N=        2   NAMPINC=          -8  NPHAINC=           9
N=        3   RANJ[N]=-3.6020203153428E-0001   RPNJ[N]= 3.3371658803912E-0001
N=        3   NAMPINC=          -7  NPHAINC=           7
N=        4   RANJ[N]= 0.0000000000000E+0000   RPNJ[N]= 1.6420974967004E-0001
N=        4   NAMPINC=           0  NPHAINC=           3
ITERATION no.=         1   POWER= 1.7502000000000E+0004
CH. no.           1   AMP=         114   PHASE=           1
CH. no.           2   AMP=         117   PHASE=          10
CH. no.           3   AMP=         118   PHASE=           8
CH. no.           4   AMP=         125   PHASE=           4
ITERATION NUMBER=            2
IAMPP8=         134
IAMPM8=          94
IPHAP8=          21
IPHAM8=           1
POWER WITH KTH WEIGHT DITHERED UP IN AMPLITUDE= 1.9622000000000E+0004
POWER WITH KTH WEIGHT DITHERED DOWN IN AMPLITUDE= 1.6182000000000E+0004

```
POWER WITH KTH WEIGHT DITHERED UP IN PHASE= 1.7902000000000E+0004
POWER WITH KTH WEIGHT DITHERED DOWN IN PHASE= 1.7502000000000E+0004
reset kth phase weight
KTH PHASE WEIGHT IS NOW=            1
compute power differences
DFANJ[K]= 3.4400000000000E+0003   DFPNJ[K]= 4.0000000000000E+0002
MDELAMP=          20   MDELPHA=          20
SUMDF= 2.9984000000000E+0004
IAMPP8=         137
IAMPM8=          97
IPHAP8=          30
IPHAM8=           1
POWER WITH KTH WEIGHT DITHERED UP IN AMPLITUDE= 1.9182000000000E+0004
POWER WITH KTH WEIGHT DITHERED DOWN IN AMPLITUDE= 1.6622000000000E+0004
POWER WITH KTH WEIGHT DITHERED UP IN PHASE= 1.4302000000000E+0004
POWER WITH KTH WEIGHT DITHERED DOWN IN PHASE= 1.9203000000000E+0004
reset kth phase weight
KTH PHASE WEIGHT IS NOW=           10
compute power differences
DFANJ[K]= 2.5600000000000E+0003   DFPNJ[K]=-4.9010000000000E+0003
MDELAMP=          20   MDELPHA=          20
SUMDF= 1.0641750250000E+0005
IAMPP8=         138
IAMPM8=          98
IPHAP8=          28
IPHAM8=           1
POWER WITH KTH WEIGHT DITHERED UP IN AMPLITUDE= 1.8982000000000E+0004
POWER WITH KTH WEIGHT DITHERED DOWN IN AMPLITUDE= 1.6822000000000E+0004
POWER WITH KTH WEIGHT DITHERED UP IN PHASE= 1.5262000000000E+0004
POWER WITH KTH WEIGHT DITHERED DOWN IN PHASE= 1.8475000000000E+0004
reset kth phase weight
KTH PHASE WEIGHT IS NOW=            8
compute power differences
DFANJ[K]= 2.1600000000000E+0003   DFPNJ[K]=-3.2130000000000E+0003
MDELAMP=          20   MDELPHA=          20
SUMDF= 1.4388992500000E+0005
IAMPP8=         145
IAMPM8=         105
IPHAP8=          24
IPHAM8=           1
POWER WITH KTH WEIGHT DITHERED UP IN AMPLITUDE= 1.7902000000000E+0004
POWER WITH KTH WEIGHT DITHERED DOWN IN AMPLITUDE= 1.7902000000000E+0004
POWER WITH KTH WEIGHT DITHERED UP IN PHASE= 1.6382000000000E+0004
POWER WITH KTH WEIGHT DITHERED DOWN IN PHASE= 1.7739000000000E+0004
reset kth phase weight
KTH PHASE WEIGHT IS NOW=            4
compute power differences
DFANJ[K]= 0.0000000000000E+0000   DFPNJ[K]=-1.3570000000000E+0003
MDELAMP=          20   MDELPHA=          20
SUMDF= 1.4849354750000E+0005
N=           1   RANJ[N]=-4.4634909195497E-0001   RPNJ[N]=-5.1901057204067E-0002
N=           1   NAMPINC=          -9   NPHAINC=          -1
N=           2   RANJ[N]=-3.3216676610603E-0001   RPNJ[N]= 6.3591770339283E-0001
N=           2   NAMPINC=          -7   NPHAINC=          13
N=           3   RANJ[N]=-2.8026570890196E-0001   RPNJ[N]= 4.1689524199167E-0001
N=           3   NAMPINC=          -6   NPHAINC=           8
N=           4   RANJ[N]= 0.0000000000000E+0000   RPNJ[N]= 1.7607433656480E-0001
N=           4   NAMPINC=           0   NPHAINC=           4
ITERATION no.=           2   POWER= 1.2671000000000E+0004
CH. no.           1   AMP=        105   PHASE=           1
CH. no.           2   AMP=        110   PHASE=          23
CH. no.           3   AMP=        112   PHASE=          16
CH. no.           4   AMP=        125   PHASE=           8
ITERATION NUMBER=           3
IAMPP8=         125
IAMPM8=          85
IPHAP8=          21
IPHAM8=           1
POWER WITH KTH WEIGHT DITHERED UP IN AMPLITUDE= 1.4431000000000E+0004
POWER WITH KTH WEIGHT DITHERED DOWN IN AMPLITUDE= 1.1711000000000E+0004
POWER WITH KTH WEIGHT DITHERED UP IN PHASE= 1.3071000000000E+0004
POWER WITH KTH WEIGHT DITHERED DOWN IN PHASE= 1.2671000000000E+0004
```

```
reset kth phase weight
KTH PHASE WEIGHT IS NOW=          1
compute power differences
DFANJ[K]= 2.7200000000000E+0003   DFPNJ[K]= 4.0000000000000E+0002
MDELAMP=        20 MDELPHA=        20
SUMDF= 1.8896000000000E+0004
IAMPP8=        130
IAMPM8=         90
IPHAP8=         43
IPHAM8=          3
POWER WITH KTH WEIGHT DITHERED UP IN AMPLITUDE= 1.4071000000000E+0004
POWER WITH KTH WEIGHT DITHERED DOWN IN AMPLITUDE= 1.2071000000000E+0004
POWER WITH KTH WEIGHT DITHERED UP IN PHASE= 9.9910000000000E+0003
POWER WITH KTH WEIGHT DITHERED DOWN IN PHASE= 1.6151000000000E+0004
reset kth phase weight
KTH PHASE WEIGHT IS NOW=         23
compute power differences
DFANJ[K]= 2.0000000000000E+0003   DFPNJ[K]=-6.1600000000000E+0003
MDELAMP=        20 MDELPHA=        20
SUMDF= 1.2376000000000E+0005
IAMPP8=        132
IAMPM8=         92
IPHAP8=         36
IPHAM8=          1
POWER WITH KTH WEIGHT DITHERED UP IN AMPLITUDE= 1.3911000000000E+0004
POWER WITH KTH WEIGHT DITHERED DOWN IN AMPLITUDE= 1.2231000000000E+0004
POWER WITH KTH WEIGHT DITHERED UP IN PHASE= 1.0751000000000E+0004
POWER WITH KTH WEIGHT DITHERED DOWN IN PHASE= 1.4636000000000E+0004
reset kth phase weight
KTH PHASE WEIGHT IS NOW=         16
compute power differences
DFANJ[K]= 1.6800000000000E+0003   DFPNJ[K]=-3.8850000000000E+0003
MDELAMP=        20 MDELPHA=        20
SUMDF= 1.6854906250000E+0005
IAMPP8=        145
IAMPM8=        105
IPHAP8=         28
IPHAM8=          1
POWER WITH KTH WEIGHT DITHERED UP IN AMPLITUDE= 1.3071000000000E+0004
POWER WITH KTH WEIGHT DITHERED DOWN IN AMPLITUDE= 1.3071000000000E+0004
POWER WITH KTH WEIGHT DITHERED UP IN PHASE= 1.1711000000000E+0004
POWER WITH KTH WEIGHT DITHERED DOWN IN PHASE= 1.3196000000000E+0004
reset kth phase weight
KTH PHASE WEIGHT IS NOW=          8
compute power differences
DFANJ[K]= 0.0000000000000E+0000   DFPNJ[K]=-1.4850000000000E+0003
MDELAMP=        20 MDELPHA=        20
SUMDF= 1.7406212500000E+0005
N=       1  RANJ[N]=-3.2597685677754E-0001  RPNJ[N]=-4.7937773055521E-0002
N=       1  NAMPINC=       -7  NPHAINC=       -1
N=       2  RANJ[N]=-2.3968886527760E-0001  RPNJ[N]= 7.3824170505502E-0001
N=       2  NAMPINC=       -5  NPHAINC=       15
N=       3  RANJ[N]=-2.0133864683319E-0001  RPNJ[N]= 4.6559562080175E-0001
N=       3  NAMPINC=       -4  NPHAINC=        9
N=       4  RANJ[N]= 0.0000000000000E+0000  RPNJ[N]= 1.7796898246862E-0001
N=       4  NAMPINC=        0  NPHAINC=        4
ITERATION no.=        3   POWER= 8.5630000000000E+0003
CH. no.       1  AMP=        98  PHASE=         1
CH. no.       2  AMP=       105  PHASE=        38
CH. no.       3  AMP=       108  PHASE=        25
CH. no.       4  AMP=       125  PHASE=        12
ITERATION NUMBER=        4
IAMPP8=        118
IAMPM8=         78
IPHAP8=         21
IPHAM8=          1
POWER WITH KTH WEIGHT DITHERED UP IN AMPLITUDE= 1.0043000000000E+0004
POWER WITH KTH WEIGHT DITHERED DOWN IN AMPLITUDE= 7.8830000000000E+0003
POWER WITH KTH WEIGHT DITHERED UP IN PHASE= 8.9630000000000E+0003
POWER WITH KTH WEIGHT DITHERED DOWN IN PHASE= 8.5630000000000E+0003
reset kth phase weight
KTH PHASE WEIGHT IS NOW=          1
``` compute power differences
DFANJ[K]= 2.1600000000000E+0003  DFPNJ[K]= 4.0000000000000E+0002
MDELAMP=        20  MDELPHA=        20
SUMDF= 1.2064000000000E+0004
IAMPP8=        125
IAMPM8=         85
IPHAP8=         58
IPHAM8=         18
POWER WITH KTH WEIGHT DITHERED UP IN AMPLITUDE= 9.7630000000000E+0003
POWER WITH KTH WEIGHT DITHERED DOWN IN AMPLITUDE= 8.1630000000000E+0003
POWER WITH KTH WEIGHT DITHERED UP IN PHASE= 6.4830000000000E+0003
POWER WITH KTH WEIGHT DITHERED DOWN IN PHASE= 1.1443000000000E+0004
reset kth phase weight
KTH PHASE WEIGHT IS NOW=         38
compute power differences
DFANJ[K]= 1.6000000000000E+0003  DFPNJ[K]=-4.9600000000000E+0003
MDELAMP=        20  MDELPHA=        20
SUMDF= 7.9967999999999E+0004
IAMPP8=        128
IAMPM8=         88
IPHAP8=         45
IPHAM8=          5
POWER WITH KTH WEIGHT DITHERED UP IN AMPLITUDE= 9.6430000000000E+0003
POWER WITH KTH WEIGHT DITHERED DOWN IN AMPLITUDE= 8.2830000000000E+0003
POWER WITH KTH WEIGHT DITHERED UP IN PHASE= 7.0030000000000E+0003
POWER WITH KTH WEIGHT DITHERED DOWN IN PHASE= 1.0923000000000E+0004
reset kth phase weight
KTH PHASE WEIGHT IS NOW=         25
compute power differences
DFANJ[K]= 1.3600000000000E+0003  DFPNJ[K]=-3.9200000000000E+0003
MDELAMP=        20  MDELPHA=        20
SUMDF= 1.2300800000000E+0005
IAMPP8=        145
IAMPM8=        105
IPHAP8=         32
IPHAM8=          1
POWER WITH KTH WEIGHT DITHERED UP IN AMPLITUDE= 8.9630000000000E+0003
POWER WITH KTH WEIGHT DITHERED DOWN IN AMPLITUDE= 8.9630000000000E+0003
POWER WITH KTH WEIGHT DITHERED UP IN PHASE= 7.7630000000000E+0003
POWER WITH KTH WEIGHT DITHERED DOWN IN PHASE= 9.3440000000000E+0003
reset kth phase weight
KTH PHASE WEIGHT IS NOW=         12
compute power differences
DFANJ[K]= 0.0000000000000E+0000  DFPNJ[K]=-1.5810000000000E+0003
MDELAMP=        20  MDELPHA=        20
SUMDF= 1.2925690250000E+0005
N=         1  RANJ[N]=-3.0039789378774E-0001  RPNJ[N]=-5.5629239590322E-0002
N=         1  NAMPINC=         -6  NPHAINC=         -1
N=         2  RANJ[N]=-2.2251695836129E-0001  RPNJ[N]= 6.8980257091999E-0001
N=         2  NAMPINC=         -4  NPHAINC=         14
N=         3  RANJ[N]=-1.8913941460710E-0001  RPNJ[N]= 5.4516654798516E-0001
N=         3  NAMPINC=         -4  NPHAINC=         11
N=         4  RANJ[N]= 0.0000000000000E+0000  RPNJ[N]= 2.1987456948075E-0001
N=         4  NAMPINC=          0  NPHAINC=          4
ITERATION no.=          4  POWER= 5.2900000000000E+0003
CH. no.          1  AMP=         92  PHASE=          1
CH. no.          2  AMP=        101  PHASE=         52
CH. no.          3  AMP=        104  PHASE=         36
CH. no.          4  AMP=        125  PHASE=         16
ITERATION NUMBER=          5
IAMPP8=        112
IAMPM8=         72
IPHAP8=         21
IPHAM8=          1
POWER WITH KTH WEIGHT DITHERED UP IN AMPLITUDE= 6.5300000000000E+0003
POWER WITH KTH WEIGHT DITHERED DOWN IN AMPLITUDE= 4.8500000000000E+0003
POWER WITH KTH WEIGHT DITHERED UP IN PHASE= 5.6900000000000E+0003
POWER WITH KTH WEIGHT DITHERED DOWN IN PHASE= 5.2900000000000E+0003
reset kth phase weight
KTH PHASE WEIGHT IS NOW=          1
compute power differences
DFANJ[K]= 1.6800000000000E+0003  DFPNJ[K]= 4.0000000000000E+0002

```
MDELAMP=            20  MDELPHA=         20
SUMDF= 7.4559999999999E+0003
IAMPP8=            121
IAMPM8=             81
IPHAP8=             72
IPHAM8=             32
POWER WITH KTH WEIGHT DITHERED UP IN AMPLITUDE=   6.3300000000000E+0003
POWER WITH KTH WEIGHT DITHERED DOWN IN AMPLITUDE= 5.0500000000000E+0003
POWER WITH KTH WEIGHT DITHERED UP IN PHASE=       3.7700000000000E+0003
POWER WITH KTH WEIGHT DITHERED DOWN IN PHASE=     7.6100000000000E+0003
reset kth phase weight
KTH PHASE WEIGHT IS NOW=           52
compute power differences
DFANJ[K]= 1.2800000000000E+0003   DFPNJ[K]=-3.8400000000000E+0003
MDELAMP=            20  MDELPHA=         20
SUMDF= 4.8415999999999E+0004
IAMPP8=            124
IAMPM8=             84
IPHAP8=             56
IPHAM8=             16
POWER WITH KTH WEIGHT DITHERED UP IN AMPLITUDE=   6.2100000000000E+0003
POWER WITH KTH WEIGHT DITHERED DOWN IN AMPLITUDE= 5.1700000000000E+0003
POWER WITH KTH WEIGHT DITHERED UP IN PHASE=       4.1700000000000E+0003
POWER WITH KTH WEIGHT DITHERED DOWN IN PHASE=     7.2100000000000E+0003
reset kth phase weight
KTH PHASE WEIGHT IS NOW=           36
compute power differences
DFANJ[K]= 1.0400000000000E+0003   DFPNJ[K]=-3.0400000000000E+0003
MDELAMP=            20  MDELPHA=         20
SUMDF= 7.4223999999999E+0004
IAMPP8=            145
IAMPM8=            105
IPHAP8=             36
IPHAM8=              1
POWER WITH KTH WEIGHT DITHERED UP IN AMPLITUDE=   5.6900000000000E+0003
POWER WITH KTH WEIGHT DITHERED DOWN IN AMPLITUDE= 5.6900000000000E+0003
POWER WITH KTH WEIGHT DITHERED UP IN PHASE=       4.6500000000000E+0003
POWER WITH KTH WEIGHT DITHERED DOWN IN PHASE=     6.2950000000000E+0003
reset kth phase weight
KTH PHASE WEIGHT IS NOW=           16
compute power differences
DFANJ[K]= 0.0000000000000E+0000   DFPNJ[K]=-1.6450000000000E+0003
MDELAMP=            20  MDELPHA=         20
SUMDF= 8.0989062499999E+0004
N=         1  RANJ[N]=-2.9516584387132E-0001   RPNJ[N]=-7.0277581874123E-0002
N=         1  NAMPINC=            -6  NPHAINC=        -1
N=         2  RANJ[N]=-2.2488826199720E-0001   RPNJ[N]= 6.7466478599158E-0001
N=         2  NAMPINC=            -4  NPHAINC=        13
N=         3  RANJ[N]=-1.8272171287272E-0001   RPNJ[N]= 5.3410962224334E-0001
N=         3  NAMPINC=            -4  NPHAINC=        11
N=         4  RANJ[N]= 0.0000000000000E+0000   RPNJ[N]= 2.8901655545733E-0001
N=         4  NAMPINC=             0  NPHAINC=         6
ITERATION no.=        5  POWER= 2.8040000000000E+0003
CH. no.         1   AMP=         86   PHASE=             1
CH. no.         2   AMP=         97   PHASE=            65
CH. no.         3   AMP=        100   PHASE=            47
CH. no.         4   AMP=        125   PHASE=            22
final adaptive weights
CH. no.         1   AMP=         86   PHASE=             1
CH. no.         2   AMP=         97   PHASE=            65
CH. no.         3   AMP=        100   PHASE=            47
CH. no.         4   AMP=        125   PHASE=            22
```

APPENDIX D

```
{ COPYRIGHT M.I.T. LINCOLN LABORATORY 1991, ALL RIGHTS RESERVED}
{   PROGRAM FOCUSGS.P (PASCAL VERSION BY ALAN J. FENN)}
{   THIS SUBROUTINE PERFORMS A GRADIENT SEARCH FOR THE}
{   ADAPTIVE FOCUSING WEIGHTS (PHASE ONLY)}
{   BASED ON MAXIMIZING THE POWER RECEIVED BY AN E-FIELD PROBE}
{   AT A DESIRED FOCUS (TUMOR) POSITION. }
PROGRAM FOCUSGS (INPUT,OUTPUT) ;
{   PROGRAM INPUT OR FIXED PARAMETERS}
```

```
{       NCHAN IS THE NUMBER OF ADAPTIVE TRANSMIT CHANNELS (=4)}
{       NETUMOR IS THE NUMBER OF E-FIELD TUMOR-SITE PROBES (=1)}
{       NEPROBE IS THE NUMBER OF E-FIELD NULLING PROBES (=1)}
{       JSMAX IS THE MAXIMUM NUMBER OF GRADIENT ITERATIONS (=200)}
{       NBSETWT IS THE NUMBER OF BITS USED IN SETTING THE TRANSMIT WEIGHTS (=8)}
{       NBMEAWT IS THE NUMBER OF BITS USED IN MEASURING THE TRANSMIT WEIGHTS (=12)}
{       NBPROBE IS THE NUMBER OF BITS USED IN MEASURING THE E-FIELD PROBE POWER (=12)}

{   PROGRAM OUTPUT}

{       IWTAMP8 IS THE ADAPTIVE NULLING WEIGHT VECTOR AMPLITUDE}
{       IWTPHA8 IS THE ADAPTIVE NULLING WEIGHT VECTOR PHASE}

{  This computer program is intended to be used in the following manner:}

{  Initially, the phased array should be turned on and the}
{  transmit weights are set to some nominal values.  Assume that there are}
{  two E-field probes, one invasive at the desired tumor position and}
{  one noninvasive on the skin surface. The output power of the two E-field}
{  probes should be measured and be printed, saved, or displayed on the screen }
{  for reference purposes.}
{  This focusing program can do both amplitude and phase dithering if }
{  desired by uncommenting the read statement for the amplitude dither}
{  parameter and then commenting the line of code where the amplitude}
{  dither parameter.is set equal to zero}
{  Currently, this program will only dither the transmit phase weights}

{  DECLARE INTEGER AND REAL ARRAYS WITH APPROPRIATE DIMENSIONS}

VAR
    IWTAMP12 : ARRAY [1..4] OF INTEGER;
    IWTPHA12 : ARRAY [1..4] OF INTEGER;
    IWTAMP8  : ARRAY [1..4] OF INTEGER;
    IWTPHA8  : ARRAY [1..4] OF INTEGER;
    IWORKAM8 : ARRAY [1..4] OF INTEGER;
    IWORKPH8 : ARRAY [1..4] OF INTEGER;

DFANJ    : ARRAY [1..4] OF REAL;
    DFPNJ    : ARRAY [1..4] OF REAL;
    RANJ     : ARRAY [1..4] OF REAL;
    RPNJ     : ARRAY [1..4] OF REAL;

{  DECLARE INTEGER AND REAL VARIABLES}

MAXAMP8,NBSETWT,NBMEAWT,NBPROBE        : INTEGER;
    MSBMEAWT,MSBSETWT,MSBPROBE             : INTEGER;
    I,K,N,MDELAMP,MDELPHA,ITER,JSMAX       : INTEGER;
    NCHAN,IAMPP8,IPHAP8,IAMPM8,IPHAM8      : INTEGER;
    NAMPINC,NPHAINC,NEWMAXA8               : INTEGER;
    NETUMOR,NEPROBE                        : INTEGER;
    FAC12TO8,FACDEN,SUMDF                  : REAL;
    TPOWER,DNPOWER,TAPOWER,DNAPOWER        : REAL;
    PWR_TPA,PWR_NPA,PWR_TMA,PWR_NMA        : REAL;
    PWR_TPP,PWR_NPP,PWR_TMP,PWR_NMP        : REAL;
    RMSBMEAW,RMSBSETW,RNAMPINC,RNPHAINC    : REAL;
    RMAXAMP8                               : REAL;

{   NOTE: Define MEASUREPOWER Procedure}

PROCEDURE MEASUREP (IA1,IA2,IA3,IA4,IP1,IP2,IP3,IP4 : INTEGER ;
            VAR POWER : REAL) ; {E-FIELD PROBE POWER MEASUREMENT PROCEDURE}

VAR
    IA01,IA02,IA03,IA04,IP01,IP02,IP03,IP04 : INTEGER ;
    POWERA,POWERP                           : REAL    ;

BEGIN

{8-bit weight data}

IA01 :=  71 ;
    IA02 :=  85 ;
    IA03 :=  91 ;
    IA04 := 125 ;

IP01 :=   1 ;
    IP02 := 100 ;
    IP03 :=  74 ;
    IP04 :=  42 ;

{ Polynomial Function Definition }

POWERA := SQR(IA1-IA01)+SQR(IA2-IA02)+SQR(IA3-IA03)+SQR(IA4-IA04) ;
POWERP := SQR(IP1-IP01)+SQR(IP2-IP02)+SQR(IP3-IP03)+SQR(IP4-IP04) ;
```

```
POWER := -POWERA - POWERP     {  ;  }

END;

PROCEDURE MEASIW (VAR  IWA1,IWA2,IWA3,IWA4,IWP1,IWP2,IWP3,IWP4 : INTEGER) ;

{THIS PROCEDURE MEASURES THE INITIAL WEIGHTS}
{artificially sets them for now}

BEGIN

{12-bit data}

IWA1 :=  2000 ;
   IWA2 :=  2000 ;
   IWA3 :=  2000 ;
   IWA4 :=  2000 ;

IWP1 :=    1 ;
   IWP2 :=    1 ;
   IWP3 :=    1 ;
   IWP4 :=    1       {  ;  }

END;

PROCEDURE SETWTS ;   {procedure to set weights}

BEGIN

{NON-FUNCTIONING FOR NOW}

END;

BEGIN   {BEGIN THE MAIN PROGRAM}

{   FIXED DATA FOR SYSTEM}

NCHAN := 4 ;

{   NUMBER OF BITS TO SET WEIGHTS, MEASURE WEIGHTS, MEASURE E-FIELD PROBE}
      NBSETWT:=8 ;
      NBMEAWT:=12 ;
      NBPROBE:=12 ;

NETUMOR:=1 ;
      NEPROBE:=1 ;
      JSMAX  :=25 ;    {number of iterations in gradient search}

WRITELN('enter number of iterations in gradient search') ;

READLN (JSMAX) ;

WRITELN('JSMAX=',JSMAX) ;

{   END OF DATA}

{   MEASURE INITIAL E-FIELD POWER AT TUMOR SITE (RECEIVE PROBE CHANNEL 1)}
{     CALL MEASUREPOWER(  measure TPOWER, the E-field probe power at the tumor site)}
{   MEASURE INITIAL E-FIELD POWER AT DESIRED NULL POSITION (RECEIVE PROBE CHANNEL 2)}
{     CALL MEASUREPOWER(  measure DNPOWER, the E-field probe power at the desired null pos.)}

{   MEASURE TRANSMIT WEIGHTS AMPLITUDE (IWTAMP12) AND PHASE (IWTPHA12) FOR EACH TRANSMIT CH.}
{   NOTE: THE 12 IN IWTAMP12 AND IWTPHA12 REFERS TO 12 BITS}

{FOR I:=1 TO NCHAN  DO}
      {CALL MEASUREWEIGHT(  IWTAMP12[I], IWTPHA12[I]  ) ;}

MEASIW (IWTAMP12[1],IWTAMP12[2],IWTAMP12[3],IWTAMP12[4],
        IWTPHA12[1],IWTPHA12[2],IWTPHA12[3],IWTPHA12[4] ) ;

{   CONVERT 12 BIT MEASUREMENTS TO 8 BIT RANGE FOR PURPOSES OF SETTING WEIGHTS}
{   WITH 8-BIT DIGITAL TO ANALOG CONVERTERS}

{   NOTE: 12 BIT RANGE IS STATES   1,2,3,............,4096}
{            8 BIT RANGE IS STATES   1,2,3,...256}

{    THE MOST SIGNIFICANT BIT FOR THE TRANSMIT WEIGHT MEASUREMENTS IS (MSBMEAWT=4096)}

{ RMSBMEAW := EXP(NBMEAWT * (LN (2.) ) ) ; }
        RMSBMEAW := 4096 ;
```

```
        MSBMEAWT := round(RMSBMEAW) ;

{   THE MOST SIGNIFICANT BIT FOR THE TRANSMIT WEIGHT SETTINGS IS (MSBSETWT=256)}

{   RMSBSETW := EXP(NBSETWT * (LN (2.) ) )   ; }
        RMSBSETW := 256 ;
        MSBSETWT := round(RMSBSETW) ;

{   COMPUTE SCALE FACTOR TO CONVERT 12-BIT RANGE TO 8-BIT RANGE}

FAC12TO8 := RMSBSETW / MSBMEAWT ;

{   CONVERT THE 12-BIT TRANSMIT WEIGHT DATA TO 8-BIT DATA AND PRINT-OUT}

FOR I:= 1 TO NCHAN  DO

BEGIN

IWTAMP8[I] := round( IWTAMP12[I] * FAC12TO8) ;

IF IWTAMP8[I] < 1 THEN  IWTAMP8[I] := 1 ;

IWTPHA8[I] := round( IWTPHA12[I] * FAC12TO8) ;

IF IWTPHA8[I] < 1 THEN  IWTPHA8[I] := 1 ;

WRITELN('CHANNEL', I, '  AMPLITUDE=', IWTAMP8[I],'  PHASE=', IWTPHA8[I]) ;

{   STORE THE 8-BIT DATA IN TEMPORARY WORK ARRAYS}
        IWORKAM8[I] := IWTAMP8[I] ;
        IWORKPH8[I] := IWTPHA8[I]       {    ;    }

END;

{   DETERMINE MAXIMUM WEIGHT AMPLITUDE BEFORE FOCUSING}

MAXAMP8 :=0 ;

FOR I := 1 TO NCHAN  DO

BEGIN

IF IWTAMP8[I] > MAXAMP8  THEN

MAXAMP8 :=IWTAMP8[I]    {   ;   }

END;

{   COPY MAXAMP8 TO A REAL VARIABLE (RMAXAMP8)}

RMAXAMP8 := MAXAMP8 ;

{   PRINT-OUT THE MAXIMUM WEIGHT AMPLITUDE OVER 8-BIT RANGE}

WRITELN('MAXIMUM WEIGHT AMPLITUDE OVER 8-BIT RANGE=', RMAXAMP8) ;

{MEASURE INITIAL E-FIELD POWER AT DESIRED FOCUS (TUMOR) POSITION (RECEIVE PROBE CHANNEL 2)}

MEASUREP (IWTAMP8[1],IWTAMP8[2],IWTAMP8[3],IWTAMP8[4],
          IWTPHA8[1],IWTPHA8[2],IWTPHA8[3],IWTPHA8[4], TPOWER)  ;

WRITELN('INITIAL E-FIELD POWER AT DESIRED FOCUS (TUMOR) POSITION=',TPOWER) ;

{    READ-IN THE MAXIMUM NUMBER OF STATES TO DITHER TRANSMIT WEIGHT AMPLITUDE}

WRITELN('A BASIC ASSUMPTION IS THAT NO AMPLITUDE FOCUSING IS NEEDED,') ;
        WRITELN('SO THE NUMBER OF STATES TO DITHER AMPLITUDE IS EQUAL TO ZERO (0)') ;

{WRITELN('ENTER MAXIMUM NUMBER OF STATES TO DITHER TRANSMIT WEIGHT AMPLITUDE');}

{   READLN (MDELAMP) ;  }

MDELAMP := 0 ;     {set amplitude dither to zero}

{    READ-IN THE MAXIMUM NUMBER OF STATES TO DITHER TRANSMIT WEIGHT PHASE}

WRITELN('ENTER MAXIMUM NUMBER OF STATES TO DITHER TRANSMIT WEIGHT PHASE');

READLN (MDELPHA) ;

writeln('MDELAMP=',MDELAMP,'  MDELPHA=',MDELPHA) ;

{   BEGIN GRADIENT SEARCH: }
```

```
        FOR ITER := 1 TO JSMAX  DO    {Start ITER Loop}
           BEGIN
         SUMDF :=0.0 ;
             WRITELN ('ITERATION NUMBER=',ITER);
{     COMPUTE WEIGHT-DITHERING STATES +-AMPLITUDE,  +-PHASE}
               FOR K := 1 TO NCHAN  DO    {Start K Loop For Weight Dithering}
                  BEGIN
{  AMPLITUDE SECTION: }
                 IAMPP8 := IWTAMP8[K] + MDELAMP ;
        writeln('IAMPP8=',IAMPP8)  ;
{    MAKE SURE WEIGHT AMPLITUDE DOES NOT EXCEED MOST SIGNIFICANT BIT (256) }
                    IF IAMPP8 > MSBSETWT THEN
                       BEGIN
                       IAMPP8 := MSBSETWT ;
                       END;
                  IAMPM8 := IWTAMP8[K] - MDELAMP ;
     writeln('IAMPM8=',IAMPM8)  ;
{    MAKE SURE WEIGHT AMPLITUDE STATE IS NOT LESS THAN THE LEAST SIGNIFICANT BIT [1]}
                    IF IAMPM8 <  1  THEN
                       BEGIN
                       IAMPM8 := 1 ;
                       END;

{  PHASE SECTION:}
                 IPHAP8 := IWTPHA8[K] + MDELPHA ;
{    MAKE SURE WEIGHT PHASE DOES NOT EXCEED MOST SIGNIFICANT BIT (256)}
                    IF IPHAP8 > MSBSETWT  THEN
                       BEGIN
                       IPHAP8 := MSBSETWT ;
                       END;
     writeln('IPHAP8=',IPHAP8) ;
                 IPHAM8 := IWTPHA8[K] - MDELPHA ;
{   MAKE SURE WEIGHT PHASE STATE IS NOT LESS THAN THE LEAST SIGNIFICANT BIT [1]}
                    IF IPHAM8 <  1  THEN
                       BEGIN
                       IPHAM8 := 1 ;
                       END;
     writeln('IPHAM8=',IPHAM8) ;

{   NOW, DITHER THE TRANSMIT WEIGHTS UP AND DOWN IN AMPLITUDE AND PHASE}
{  AMPLITUDE SECTION:}
{  DITHER WEIGHT AMPLITUDE UP:}
                   IWTAMP8[K] := IAMPP8 ;
{  SET THE TRANSMIT WEIGHTS WITH KTH WEIGHT DITHERED UP IN AMPLITUDE}
     {   CALL SETWEIGHTS( IWTAMP8(1 2 3 ... NCHAN) , IWTPHA8(1 2 3 ... NCHAN) }
```

```
{   *MEASURE CURRENT E-FIELD POWER AT TUMOR SITE (RECEIVE PROBE CHANNEL 1)}
{    notation in PWR_TPA for example is PA for +Amplitude}
{      CALL MEASUREPOWER(  measure PWR_TPA, the E-field probe power at the tumor site)}
{   *MEASURE INITIAL E-FIELD POWER AT DESIRED NULL POSITION (RECEIVE PROBE CHANNEL 2)}
{      CALL MEASUREPOWER(  measure PWR_NPA, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_TPA) ;

WRITELN('POWER WITH KTH WEIGHT DITHERED UP IN AMPLITUDE=',PWR_TPA) ;

{  DITHER WEIGHT AMPLITUDE DOWN:}

IWTAMP8[K] := IAMPM8 ;

{ SET THE TRANSMIT WEIGHTS WITH KTH WEIGHT DITHERED DOWN IN AMPLITUDE}

{CALL SETWEIGHTS( IWTAMP8(1 2 3 ... NCHAN) , IWTPHA8(1 2 3 ... NCHAN)}
{   *MEASURE CURRENT E-FIELD POWER AT TUMOR SITE (RECEIVE PROBE CHANNEL 1)}
{    notation in PWR_TMA for example is MA for -Amplitude}
{      CALL MEASUREPOWER(  measure PWR_TMA, the E-field probe power at the tumor site) }
{   *MEASURE INITIAL E-FIELD POWER AT DESIRED NULL POSITION (RECEIVE PROBE CHANNEL 2)}
{      CALL MEASUREPOWER(  measure PWR_NMA, the E-field probe power at the desired null pos.) }
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_TMA) ;

WRITELN('POWER WITH KTH WEIGHT DITHERED DOWN IN AMPLITUDE=',PWR_TMA) ;

{  RESET KTH WEIGHT AMPLITUDE BACK TO STATE SET BEFORE THIS DITHERING WAS PERFORMED}

IWTAMP8[K] := IWORKAM8[K] ;

{ PHASE SECTION:}

{ DITHER WEIGHT PHASE UP:}

IWTPHA8[K] := IPHAP8 ;

{ SET THE TRANSMIT WEIGHTS WITH KTH WEIGHT DITHERED UP IN PHASE}

{ CALL SETWEIGHTS( IWTAMP8(1 2 3 ... NCHAN) , IWTPHA8(1 2 3 ... NCHAN) }

{   *MEASURE CURRENT E-FIELD POWER AT TUMOR SITE (RECEIVE PROBE CHANNEL 1)}
{    notation in PWR_TPP for example is PP for +Phase}
{      CALL MEASUREPOWER(  measure PWR_TPP, the E-field probe power at the tumor site)}
{   *MEASURE INITIAL E-FIELD POWER AT DESIRED NULL POSITION (RECEIVE PROBE CHANNEL 2)}
{      CALL MEASUREPOWER(  measure PWR_NPP, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_TPP) ;

WRITELN('POWER WITH KTH WEIGHT DITHERED UP IN PHASE=',PWR_TPP) ;

{  DITHER WEIGHT PHASE DOWN:}

IWTPHA8[K] := IPHAM8 ;

{ SET THE TRANSMIT WEIGHTS WITH KTH WEIGHT DITHERED DOWN IN PHASE}

{ CALL SETWEIGHTS( IWTAMP8(1 2 3 ... NCHAN) , IWTPHA8(1 2 3 ... NCHAN) }

{   *MEASURE CURRENT E-FIELD POWER AT TUMOR SITE (RECEIVE PROBE CHANNEL 1) }
{    notation in PWR_TMP for example is MP for -Phase}
{     CALL MEASUREPOWER(  measure PWR_TMP, the E-field probe power at the tumor site)}
{   *MEASURE INITIAL E-FIELD POWER AT DESIRED NULL POSITION (RECEIVE PROBE CHANNEL 2)}
{     CALL MEASUREPOWER(  measure PWR_NMP, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], PWR_TMP) ;

WRITELN('POWER WITH KTH WEIGHT DITHERED DOWN IN PHASE=',PWR_TMP) ;

{  RESET KTH WEIGHT PHASE BACK TO STATE SET BEFORE THIS DITHERING WAS PERFORMED} writeln('reset kth phase weight') ;

IWTPHA8[K] := IWORKPH8[K] ;

writeln('KTH PHASE WEIGHT IS NOW=',IWTPHA8[K]) ;
{ COMPUTE POWER DIFFERENCES DUE TO WEIGHT DITHERING } writeln('compute power differences') ;
```

```
                    DFANJ[K] := PWR_TPA - PWR_TMA ;

DFPNJ[K] := PWR_TPP - PWR_TMP ;

writeln('DFANJ[K]=',DFANJ[K],'  DFPNJ[K]=',DFPNJ[K]) ;

{ COMPUTE NORMALIZING FACTOR } writeln('MDELAMP=',MDELAMP,'  MDELPHA=',MDELPHA) ;

IF MDELAMP > 0 THEN
                BEGIN
                  SUMDF := SUMDF + SQR(DFANJ[K]/MDELAMP) + SQR(DFPNJ[K]/MDELPHA) ;
                END
         ELSE
                BEGIN
                  SUMDF := SUMDF + SQR(DFPNJ[K]/MDELPHA) ;
                END;
   writeln('SUMDF=',SUMDF)

END;        {End of K Loop For Weight Dithering}

{  END OF WEIGHT DITHERING AND POWER DIFFERENCING LOOP}

FACDEN := SQRT(SUMDF) ;

{  END OF WEIGHT DITHERING AND POWER DIFFERENCING SECTION}

{  COMPUTE GRADIENT SEARCH DIRECTIONS}

{  START GRADIENT SEARCH DIRECTION LOOP}

FOR N :=1 TO NCHAN  DO

BEGIN    {Begin N Loop For Computing Search Directions}

{  THE NEXT TWO LINES ARE FOR FIGURE OF MERIT (POWER) MAXIMIZATION}

IF MDELAMP > 0 THEN
                BEGIN
                   RANJ[N] := DFANJ[N]/MDELAMP/FACDEN ;
                END
         ELSE
                BEGIN
                   RANJ[N] := 0.0
                END;

RPNJ[N] := DFPNJ[N]/MDELPHA/FACDEN ;

writeln('N=',N,'  RANJ[N]=',RANJ[N],'  RPNJ[N]=',RPNJ[N]) ;

{  COMPUTE ACTUAL WEIGHT INCREMENTS (NUMBER OF STATES)}

RNAMPINC := MDELAMP * RANJ[N] ;
      NAMPINC  := round(RNAMPINC) ;

RNPHAINC := MDELPHA * RPNJ[N] ;
      NPHAINC  := round(RNPHAINC) ;

writeln('N=',N,'  NAMPINC=',NAMPINC,'  NPHAINC=',NPHAINC) ;

{  COMPUTE UPDATED WEIGHTS:}

{  AMPLITUDE SECTION:}

IWTAMP8[N] := IWTAMP8[N] + NAMPINC ;

{   MAKE SURE WEIGHT AMPLITUDE DOES NOT EXCEED MOST SIGNIFICANT BIT (256)}

IF IWTAMP8[N] > MSBSETWT  THEN

BEGIN

IWTAMP8[N] := MSBSETWT ;

END;

{   MAKE SURE WEIGHT AMPLITUDE STATE IS NOT LESS THAN THE LEAST SIGNIFICANT BIT [1] }

IF IWTAMP8[N] < 1  THEN

BEGIN

IWTAMP8[N] := 1 ;

END;
```

```
{ PHASE SECTION: }

IWTPHA8[N] := IWTPHA8[N] + NPHAINC ;

{ MAKE SURE WEIGHT PHASE DOES NOT EXCEED MOST SIGNIFICANT BIT (256)}

IF IWTPHA8[N] > MSBSETWT  THEN

BEGIN

IWTPHA8[N] := MSBSETWT ;

END;

{ MAKE SURE WEIGHT PHASE STATE IS NOT LESS THAN THE LEAST SIGNIFICANT BIT [1] }

IF IWTPHA8[N] < 1  THEN

BEGIN

IWTPHA8[N] := 1 ;

END;

{   END GRADIENT SEARCH DIRECTIONS LOOP}

END;   {End N Loop For Gradient Search Directions}

{   FIND NEW MAXIMUM AMPLITUDE}

NEWMAXA8 := 0 ;

FOR K:= 1 TO NCHAN  DO

BEGIN

IF IWTAMP8[K] > NEWMAXA8  THEN

BEGIN

NEWMAXA8 := IWTAMP8[K] ;

END;

END;

{   MAKE SURE TRANSMIT WEIGHT AMPLITUDES DO NOT EXCEED INITIAL MAXIMUM AMPLITUDE}

FOR  K:= 1 TO NCHAN  DO

BEGIN

IWTAMP8[K] := round( IWTAMP8[K] * RMAXAMP8 / NEWMAXA8) {   ;   }

END;

{ SET THE UPDATED (ADAPTIVE) TRANSMIT WEIGHTS AT ITERATION NUMBER ITER}

{  CALL SETWEIGHTS( IWTAMP8(1 2 3 ... NCHAN) , IWTPHA8(1 2 3 ... NCHAN) }

{   MEASURE ADAPTIVE E-FIELD POWER AT TUMOR SITE (RECEIVE PROBE CHANNEL 1)}
{   CALL MEASUREPOWER( measure TAPOWER, the E-field probe power at the tumor site)}
{   MEASURE ADAPTIVE E-FIELD POWER AT DESIRED NULL POSITION (RECEIVE PROBE CHANNEL 2)}
{   CALL MEASUREPOWER( measure DNAPOWER, the E-field probe power at the desired null pos.)}
MEASUREP (IWTAMP8[1],IWTAMP8[2],IWTAMP8[3],IWTAMP8[4],
         IWTPHA8[1],IWTPHA8[2],IWTPHA8[3],IWTPHA8[4], TAPOWER ) ;

WRITELN('ITERATION no.=',ITER,' POWER=',TAPOWER)   ;

{   PRINT OUT ADAPTIVE WEIGHTS }

FOR K:= 1 TO NCHAN  DO

BEGIN

WRITELN('CH. no.',K,' AMP=',IWTAMP8[K],' PHASE=',IWTPHA8[K]) {   ;   }

END;

{FILL-IN NEW VALUES FOR WORK ARRAYS}

FOR K := 1 TO NCHAN  DO
```

```
      BEGIN

IWORKAM8[K] := IWTAMP8[K] ;

IWORKPH8[K] := IWTPHA8[K]

END

{END OF GRADIENT SEARCH LOOP}

END;   {End ITER loop}
{  END OF GRADIENT SEARCH} writeln('final adaptive weights') ;

{  PRINT OUT ADAPTIVE WEIGHTS }

FOR K:= 1 TO NCHAN  DO

BEGIN

WRITELN('CH. no.',K,' AMP=',IWTAMP8[K],' PHASE=',IWTPHA8[K]) {  ;   }

END;

END.
```

SAMPLE OUTPUT

```
enter number of iterations in gradient search
JSMAX=          5
CHANNEL         1   AMPLITUDE=        125  PHASE=           1
CHANNEL         2   AMPLITUDE=        125  PHASE=           1
CHANNEL         3   AMPLITUDE=        125  PHASE=           1
CHANNEL         4   AMPLITUDE=        125  PHASE=           1
MAXIMUM WEIGHT AMPLITUDE OVER 8-BIT RANGE= 1.2500000000000E+0002
INITIAL E-FIELD POWER AT DESIRED FOCUS (TUMOR) POSITION=-2.2483000000000E+0004
A BASIC ASSUMPTION IS THAT NO AMPLITUDE FOCUSING IS NEEDED,
SO THE NUMBER OF STATES TO DITHER AMPLITUDE IS EQUAL TO ZERO (0)
ENTER MAXIMUM NUMBER OF STATES TO DITHER TRANSMIT WEIGHT PHASE
MDELAMP=        0   MDELPHA=         20
ITERATION NUMBER=         1
IAMPP8=         125
IAMPM8=         125
IPHAP8=         21
IPHAM8=          1
POWER WITH KTH WEIGHT DITHERED UP IN AMPLITUDE=-2.2483000000000E+0004
POWER WITH KTH WEIGHT DITHERED DOWN IN AMPLITUDE=-2.2483000000000E+0004
POWER WITH KTH WEIGHT DITHERED UP IN PHASE=-2.2883000000000E+0004
POWER WITH KTH WEIGHT DITHERED DOWN IN PHASE=-2.2483000000000E+0004
reset kth phase weight
KTH PHASE WEIGHT IS NOW=          1
compute power differences
DFANJ[K]= 0.0000000000000E+0000  DFPNJ[K]=-4.0000000000000E+0002
MDELAMP=        0   MDELPHA=        20
SUMDF= 4.0000000000000E+0002
IAMPP8=         125
IAMPM8=         125
IPHAP8=         21
IPHAM8=          1
POWER WITH KTH WEIGHT DITHERED UP IN AMPLITUDE=-2.2483000000000E+0004
POWER WITH KTH WEIGHT DITHERED DOWN IN AMPLITUDE=-2.2483000000000E+0004
POWER WITH KTH WEIGHT DITHERED UP IN PHASE=-1.8923000000000E+0004
POWER WITH KTH WEIGHT DITHERED DOWN IN PHASE=-2.2483000000000E+0004
reset kth phase weight
KTH PHASE WEIGHT IS NOW=          1
compute power differences
DFANJ[K]= 0.0000000000000E+0000  DFPNJ[K]= 3.5600000000000E+0003
MDELAMP=        0   MDELPHA=        20
SUMDF= 3.2084000000000E+0004
IAMPP8=         125
IAMPM8=         125
IPHAP8=         21
```

```
IPHAM8=                      1
POWER WITH KTH WEIGHT DITHERED UP IN AMPLITUDE=-2.2483000000000E+0004
POWER WITH KTH WEIGHT DITHERED DOWN IN AMPLITUDE=-2.2483000000000E+0004
POWER WITH KTH WEIGHT DITHERED UP IN PHASE=-1.9963000000000E+0004
POWER WITH KTH WEIGHT DITHERED DOWN IN PHASE=-2.2483000000000E+0004
reset kth phase weight
KTH PHASE WEIGHT IS NOW=                  1
compute power differences
DFANJ[K]= 0.0000000000000E+0000   DFPNJ[K]= 2.5200000000000E+0003
MDELAMP=             0  MDELPHA=         20
SUMDF= 4.7959999999999E+0004
IAMPP8=            125
IAMPM8=            125
IPHAP8=             21
IPHAM8=              1
POWER WITH KTH WEIGHT DITHERED UP IN AMPLITUDE=-2.2483000000000E+0004
POWER WITH KTH WEIGHT DITHERED DOWN IN AMPLITUDE=-2.2483000000000E+0004
POWER WITH KTH WEIGHT DITHERED UP IN PHASE=-2.1243000000000E+0004
POWER WITH KTH WEIGHT DITHERED DOWN IN PHASE=-2.2483000000000E+0004
reset kth phase weight
KTH PHASE WEIGHT IS NOW=                  1
compute power differences
DFANJ[K]= 0.0000000000000E+0000   DFPNJ[K]= 1.2400000000000E+0003
MDELAMP=             0  MDELPHA=         20
SUMDF= 5.1803999999999E+0004
N=        1   RANJ[N]= 0.0000000000000E+0000   RPNJ[N]=-8.7871562373828E-0002
N=        1   NAMPINC=             0  NPHAINC=        -2
N=        2   RANJ[N]= 0.0000000000000E+0000   RPNJ[N]= 7.8205690512707E-0001
N=        2   NAMPINC=             0  NPHAINC=        16
N=        3   RANJ[N]= 0.0000000000000E+0000   RPNJ[N]= 5.5359084295511E-0001
N=        3   NAMPINC=             0  NPHAINC=        11
N=        4   RANJ[N]= 0.0000000000000E+0000   RPNJ[N]= 2.7240184335887E-0001
N=        4   NAMPINC=             0  NPHAINC=         5
ITERATION no.=          1   POWER=-1.7701000000000E+0004
CH. no.            1   AMP=       125   PHASE=        1
CH. no.            2   AMP=       125   PHASE=       17
CH. no.            3   AMP=       125   PHASE=       12
CH. no.            4   AMP=       125   PHASE=        6
ITERATION NUMBER=               2
IAMPP8=            125
IAMPM8=            125
IPHAP8=             21
IPHAM8=              1
POWER WITH KTH WEIGHT DITHERED UP IN AMPLITUDE=-1.7701000000000E+0004
POWER WITH KTH WEIGHT DITHERED DOWN IN AMPLITUDE=-1.7701000000000E+0004
POWER WITH KTH WEIGHT DITHERED UP IN PHASE=-1.8101000000000E+0004
POWER WITH KTH WEIGHT DITHERED DOWN IN PHASE=-1.7701000000000E+0004
reset kth phase weight
KTH PHASE WEIGHT IS NOW=                  1
compute power differences
DFANJ[K]= 0.0000000000000E+0000   DFPNJ[K]=-4.0000000000000E+0002
MDELAMP=             0  MDELPHA=         20
SUMDF= 4.0000000000000E+0002
IAMPP8=            125
IAMPM8=            125
IPHAP8=             37
IPHAM8=              1
POWER WITH KTH WEIGHT DITHERED UP IN AMPLITUDE=-1.7701000000000E+0004
POWER WITH KTH WEIGHT DITHERED DOWN IN AMPLITUDE=-1.7701000000000E+0004
POWER WITH KTH WEIGHT DITHERED UP IN PHASE=-1.4781000000000E+0004
POWER WITH KTH WEIGHT DITHERED DOWN IN PHASE=-2.0613000000000E+0004
reset kth phase weight
KTH PHASE WEIGHT IS NOW=                 17
compute power differences
DFANJ[K]= 0.0000000000000E+0000   DFPNJ[K]= 5.8320000000000E+0003
MDELAMP=             0  MDELPHA=         20
SUMDF= 8.5430559999999E+0004
IAMPP8=            125
IAMPM8=            125
IPHAP8=             32
IPHAM8=              1
POWER WITH KTH WEIGHT DITHERED UP IN AMPLITUDE=-1.7701000000000E+0004
```

```
POWER WITH KTH WEIGHT DITHERED DOWN IN AMPLITUDE=-1.7701000000000E+0004
POWER WITH KTH WEIGHT DITHERED UP IN PHASE=-1.5621000000000E+0004
POWER WITH KTH WEIGHT DITHERED DOWN IN PHASE=-1.9186000000000E+0004
reset kth phase weight
KTH PHASE WEIGHT IS NOW=             12
compute power differences
DFANJ[K]= 0.0000000000000E+0000   DFPNJ[K]= 3.5650000000000E+0003
MDELAMP=        0   MDELPHA=       20
SUMDF= 1.1720362250000E+0005
IAMPP8=         125
IAMPM8=         125
IPHAP8=          26
IPHAM8=           1
POWER WITH KTH WEIGHT DITHERED UP IN AMPLITUDE=-1.7701000000000E+0004
POWER WITH KTH WEIGHT DITHERED DOWN IN AMPLITUDE=-1.7701000000000E+0004
POWER WITH KTH WEIGHT DITHERED UP IN PHASE=-1.6661000000000E+0004
POWER WITH KTH WEIGHT DITHERED DOWN IN PHASE=-1.8086000000000E+0004
reset kth phase weight
KTH PHASE WEIGHT IS NOW=              6
compute power differences
DFANJ[K]= 0.0000000000000E+0000   DFPNJ[K]= 1.4250000000000E+0003
MDELAMP=        0   MDELPHA=       20
SUMDF= 1.2228018500000E+0005
N=          1   RANJ[N]= 0.0000000000000E+0000   RPNJ[N]=-5.7194195048731E-0002
N=          1   NAMPINC=         0   NPHAINC=       -1
N=          2   RANJ[N]= 0.0000000000000E+0000   RPNJ[N]= 8.3389136381050E-0001
N=          2   NAMPINC=         0   NPHAINC=       17
N=          3   RANJ[N]= 0.0000000000000E+0000   RPNJ[N]= 5.0974326337182E-0001
N=          3   NAMPINC=         0   NPHAINC=       10
N=          4   RANJ[N]= 0.0000000000000E+0000   RPNJ[N]= 2.0375431986110E-0001
N=          4   NAMPINC=         0   NPHAINC=        4
ITERATION no.=              2   POWER=-1.3756000000000E+0004
CH. no.          1   AMP=       125   PHASE=           1
CH. no.          2   AMP=       125   PHASE=          34
CH. no.          3   AMP=       125   PHASE=          22
CH. no.          4   AMP=       125   PHASE=          10
ITERATION NUMBER=             3
IAMPP8=         125
IAMPM8=         125
IPHAP8=          21
IPHAM8=           1
POWER WITH KTH WEIGHT DITHERED UP IN AMPLITUDE=-1.3756000000000E+0004
POWER WITH KTH WEIGHT DITHERED DOWN IN AMPLITUDE=-1.3756000000000E+0004
POWER WITH KTH WEIGHT DITHERED UP IN PHASE=-1.4156000000000E+0004
POWER WITH KTH WEIGHT DITHERED DOWN IN PHASE=-1.3756000000000E+0004
reset kth phase weight
KTH PHASE WEIGHT IS NOW=              1
compute power differences
DFANJ[K]= 0.0000000000000E+0000   DFPNJ[K]=-4.0000000000000E+0002
MDELAMP=        0   MDELPHA=       20
SUMDF= 4.0000000000000E+0002
IAMPP8=         125
IAMPM8=         125
IPHAP8=          54
IPHAM8=          14
POWER WITH KTH WEIGHT DITHERED UP IN AMPLITUDE=-1.3756000000000E+0004
POWER WITH KTH WEIGHT DITHERED DOWN IN AMPLITUDE=-1.3756000000000E+0004
POWER WITH KTH WEIGHT DITHERED UP IN PHASE=-1.1516000000000E+0004
POWER WITH KTH WEIGHT DITHERED DOWN IN PHASE=-1.6796000000000E+0004
reset kth phase weight
KTH PHASE WEIGHT IS NOW=             34
compute power differences
DFANJ[K]= 0.0000000000000E+0000   DFPNJ[K]= 5.2800000000000E+0003
MDELAMP=        0   MDELPHA=       20
SUMDF= 7.0095999999999E+0004
IAMPP8=         125
IAMPM8=         125
IPHAP8=          42
IPHAM8=           2
POWER WITH KTH WEIGHT DITHERED UP IN AMPLITUDE=-1.3756000000000E+0004
POWER WITH KTH WEIGHT DITHERED DOWN IN AMPLITUDE=-1.3756000000000E+0004
POWER WITH KTH WEIGHT DITHERED UP IN PHASE=-1.2076000000000E+0004
POWER WITH KTH WEIGHT DITHERED DOWN IN PHASE=-1.6236000000000E+0004
```

```
reset kth phase weight
KTH PHASE WEIGHT IS NOW=            22
compute power differences
DFANJ[K]= 0.0000000000000E+0000   DFPNJ[K]= 4.1600000000000E+0003
MDELAMP=           0  MDELPHA=           20
SUMDF= 1.1336000000000E+0005
IAMPP8=         125
IAMPM8=         125
IPHAP8=          30
IPHAM8=           1
POWER WITH KTH WEIGHT DITHERED UP IN AMPLITUDE=-1.3756000000000E+0004
POWER WITH KTH WEIGHT DITHERED DOWN IN AMPLITUDE=-1.3756000000000E+0004
POWER WITH KTH WEIGHT DITHERED UP IN PHASE=-1.2876000000000E+0004
POWER WITH KTH WEIGHT DITHERED DOWN IN PHASE=-1.4413000000000E+0004
reset kth phase weight
KTH PHASE WEIGHT IS NOW=            10
compute power differences
DFANJ[K]= 0.0000000000000E+0000   DFPNJ[K]= 1.5370000000000E+0003
MDELAMP=           0  MDELPHA=           20
SUMDF= 1.1926592250000E+0005
N=       1  RANJ[N]= 0.0000000000000E+0000   RPNJ[N]=-5.7912432871831E-0002
N=       1  NAMPINC=           0  NPHAINC=           -1
N=       2  RANJ[N]= 0.0000000000000E+0000   RPNJ[N]= 7.6444411390817E-0001
N=       2  NAMPINC=           0  NPHAINC=           15
N=       3  RANJ[N]= 0.0000000000000E+0000   RPNJ[N]= 6.0228930186705E-0001
N=       3  NAMPINC=           0  NPHAINC=           12
N=       4  RANJ[N]= 0.0000000000000E+0000   RPNJ[N]= 2.2252852331001E-0001
N=       4  NAMPINC=           0  NPHAINC=            4
ITERATION no.=        3  POWER=-1.0657000000000E+0004
CH. no.      1  AMP=      125  PHASE=        1
CH. no.      2  AMP=      125  PHASE=       49
CH. no.      3  AMP=      125  PHASE=       34
CH. no.      4  AMP=      125  PHASE=       14
ITERATION NUMBER=           4
IAMPP8=         125
IAMPM8=         125
IPHAP8=          21
IPHAM8=           1
POWER WITH KTH WEIGHT DITHERED UP IN AMPLITUDE=-1.0657000000000E+0004
POWER WITH KTH WEIGHT DITHERED DOWN IN AMPLITUDE=-1.0657000000000E+0004
POWER WITH KTH WEIGHT DITHERED UP IN PHASE=-1.1057000000000E+0004
POWER WITH KTH WEIGHT DITHERED DOWN IN PHASE=-1.0657000000000E+0004
reset kth phase weight
KTH PHASE WEIGHT IS NOW=             1
compute power differences
DFANJ[K]= 0.0000000000000E+0000   DFPNJ[K]=-4.0000000000000E+0002
MDELAMP=           0  MDELPHA=           20
SUMDF= 4.0000000000000E+0002
IAMPP8=         125
IAMPM8=         125
IPHAP8=          69
IPHAM8=          29
POWER WITH KTH WEIGHT DITHERED UP IN AMPLITUDE=-1.0657000000000E+0004
POWER WITH KTH WEIGHT DITHERED DOWN IN AMPLITUDE=-1.0657000000000E+0004
POWER WITH KTH WEIGHT DITHERED UP IN PHASE=-9.0170000000000E+0003
POWER WITH KTH WEIGHT DITHERED DOWN IN PHASE=-1.3097000000000E+0004
reset kth phase weight
KTH PHASE WEIGHT IS NOW=            49
compute power differences
DFANJ[K]= 0.0000000000000E+0000   DFPNJ[K]= 4.0800000000000E+0003
MDELAMP=           0  MDELPHA=           20
SUMDF= 4.2015999999999E+0004
IAMPP8=         125
IAMPM8=         125
IPHAP8=          54
IPHAM8=          14
POWER WITH KTH WEIGHT DITHERED UP IN AMPLITUDE=-1.0657000000000E+0004
POWER WITH KTH WEIGHT DITHERED DOWN IN AMPLITUDE=-1.0657000000000E+0004
POWER WITH KTH WEIGHT DITHERED UP IN PHASE=-9.4570000000000E+0003
POWER WITH KTH WEIGHT DITHERED DOWN IN PHASE=-1.2657000000000E+0004
reset kth phase weight
KTH PHASE WEIGHT IS NOW=            34
```

```
compute power differences
DFANJ[K]= 0.0000000000000E+0000   DFPNJ[K]= 3.2000000000000E+0003
MDELAMP=        0  MDELPHA=         20
SUMDF= 6.7615999999999E+0004
IAMPP8=         125
IAMPM8=         125
IPHAP8=          34
IPHAM8=           1
POWER WITH KTH WEIGHT DITHERED UP IN AMPLITUDE=-1.0657000000000E+0004
POWER WITH KTH WEIGHT DITHERED DOWN IN AMPLITUDE=-1.0657000000000E+0004
POWER WITH KTH WEIGHT DITHERED UP IN PHASE=-9.9370000000000E+0003
POWER WITH KTH WEIGHT DITHERED DOWN IN PHASE=-1.1554000000000E+0004
reset kth phase weight
KTH PHASE WEIGHT IS NOW=         14
compute power differences
DFANJ[K]= 0.0000000000000E+0000   DFPNJ[K]= 1.6170000000000E+0003
MDELAMP=        0  MDELPHA=         20
SUMDF= 7.4152722499999E+0004
N=       1  RANJ[N]= 0.0000000000000E+0000  RPNJ[N]=-7.3445711997549E-0002
N=       1  NAMPINC=        0  NPHAINC=         -1
N=       2  RANJ[N]= 0.0000000000000E+0000  RPNJ[N]= 7.4914626237500E-0001
N=       2  NAMPINC=        0  NPHAINC=         15
N=       3  RANJ[N]= 0.0000000000000E+0000  RPNJ[N]= 5.8756569598039E-0001
N=       3  NAMPINC=        0  NPHAINC=         12
N=       4  RANJ[N]= 0.0000000000000E+0000  RPNJ[N]= 2.9690429075009E-0001
N=       4  NAMPINC=        0  NPHAINC=          6
ITERATION no.=         4  POWER=-8.2360000000000E+0003
CH. no.         1  AMP=       125  PHASE=           1
CH. no.         2  AMP=       125  PHASE=          64
CH. no.         3  AMP=       125  PHASE=          46
CH. no.         4  AMP=       125  PHASE=          20
ITERATION NUMBER=         5
IAMPP8=         125
IAMPM8=         125
IPHAP8=          21
IPHAM8=           1
POWER WITH KTH WEIGHT DITHERED UP IN AMPLITUDE=-8.2360000000000E+0003
POWER WITH KTH WEIGHT DITHERED DOWN IN AMPLITUDE=-8.2360000000000E+0003
POWER WITH KTH WEIGHT DITHERED UP IN PHASE=-8.6360000000000E+0003
POWER WITH KTH WEIGHT DITHERED DOWN IN PHASE=-8.2360000000000E+0003
reset kth phase weight
KTH PHASE WEIGHT IS NOW=          1
compute power differences
DFANJ[K]= 0.0000000000000E+0000   DFPNJ[K]=-4.0000000000000E+0002
MDELAMP=        0  MDELPHA=         20
SUMDF= 4.0000000000000E+0002
IAMPP8=         125
IAMPM8=         125
IPHAP8=          84
IPHAM8=          44
POWER WITH KTH WEIGHT DITHERED UP IN AMPLITUDE=-8.2360000000000E+0003
POWER WITH KTH WEIGHT DITHERED DOWN IN AMPLITUDE=-8.2360000000000E+0003
POWER WITH KTH WEIGHT DITHERED UP IN PHASE=-7.1960000000000E+0003
POWER WITH KTH WEIGHT DITHERED DOWN IN PHASE=-1.0076000000000E+0004
reset kth phase weight
KTH PHASE WEIGHT IS NOW=         64
compute power differences
DFANJ[K]= 0.0000000000000E+0000   DFPNJ[K]= 2.8800000000000E+0003
MDELAMP=        0  MDELPHA=         20
SUMDF= 2.1136000000000E+0004
IAMPP8=         125
IAMPM8=         125
IPHAP8=          66
IPHAM8=          26
POWER WITH KTH WEIGHT DITHERED UP IN AMPLITUDE=-8.2360000000000E+0003
POWER WITH KTH WEIGHT DITHERED DOWN IN AMPLITUDE=-8.2360000000000E+0003
POWER WITH KTH WEIGHT DITHERED UP IN PHASE=-7.5160000000000E+0003
POWER WITH KTH WEIGHT DITHERED DOWN IN PHASE=-9.7560000000000E+0003
reset kth phase weight
KTH PHASE WEIGHT IS NOW=         46
compute power differences
DFANJ[K]= 0.0000000000000E+0000   DFPNJ[K]= 2.2400000000000E+0003
```

```
MDELAMP=           0  MDELPHA=         20
SUMDF=  3.3680000000000E+0004
IAMPP8=          125
IAMPM8=          125
IPHAP8=           40
IPHAM8=            1
POWER WITH KTH WEIGHT DITHERED UP IN AMPLITUDE=-8.2360000000000E+0003
POWER WITH KTH WEIGHT DITHERED DOWN IN AMPLITUDE=-8.2360000000000E+0003
POWER WITH KTH WEIGHT DITHERED UP IN PHASE=-7.7560000000000E+0003
POWER WITH KTH WEIGHT DITHERED DOWN IN PHASE=-9.4330000000000E+0003
reset kth phase weight
KTH PHASE WEIGHT IS NOW=          20
compute power differences
DFANJ[K]= 0.0000000000000E+0000   DFPNJ[K]= 1.6770000000000E+0003
MDELAMP=           0  MDELPHA=         20
SUMDF=  4.0710822499999E+0004
N=      1    RANJ[N]= 0.0000000000000E+0000    RPNJ[N]=-9.9123141423090E-0002
N=      1    NAMPINC=           0   NPHAINC=       -2
N=      2    RANJ[N]= 0.0000000000000E+0000    RPNJ[N]= 7.1368661824625E-0001
N=      2    NAMPINC=           0   NPHAINC=       14
N=      3    RANJ[N]= 0.0000000000000E+0000    RPNJ[N]= 5.5508959196930E-0001
N=      3    NAMPINC=           0   NPHAINC=       11
N=      4    RANJ[N]= 0.0000000000000E+0000    RPNJ[N]= 4.1557377041630E-0001
N=      4    NAMPINC=           0   NPHAINC=        8
ITERATION no.=           5   POWER=-6.6410000000000E+0003
CH. no.        1   AMP=      125    PHASE=          1
CH. no.        2   AMP=      125    PHASE=         78
CH. no.        3   AMP=      125    PHASE=         57
CH. no.        4   AMP=      125    PHASE=         28
final adaptive weights
CH. no.        1   AMP=      125    PHASE=          1
CH. no.        2   AMP=      125    PHASE=         78
CH. no.        3   AMP=      125    PHASE=         57
CH. no.        4   AMP=      125    PHASE=         28
```

I claim:

1. A hyperthermia applicator for inducing a temperature rise in a target within a body, comprising
a plurality of electric field radiators, each for transmitting electric field radiation, comprising a phased-array of monopole antenna elements;
an RF reflecting groundplane surface for mounting the monopole antenna elements, wherein the monopole antenna elements are substantially perpendicularly mounted on a side of the RF reflecting groundplane surface, wherein the body containing the target is adapted to be disposed on the same side of the groundplane surface as the monopole antenna elements;
a plurality of controllable transmit weighting networks, each such network coupled to a respective electric field radiator, each weighting network controlling the phase and amplitude of the electric field radiation transmitted by the respective electric field radiator in response to a respective feedback signal;
a source of electric field radiation coupled to each electric field radiator through a respective weighting network;
at least one electric field probe adapted to be disposed outside the body for detecting electric field radiation from the plurality of radiators; and
a controller coupled to the electric field probe for receiving the detected electric field radiation outside the body and generating the respective feedback signals, and for adjusting the feedback signals in response to the detected electric field radiation outside the body so that the electric field radiation is controlled at the target inside the body.

2. The apparatus of claim 1 wherein the groundplane surface comprises an aperture through which the body containing the target is adapted to be disposed to allow positioning the target on the same side of the groundplane surface as the monopole antenna elements.

3. The apparatus of claim 2 wherein the monopole antenna elements are arranged in a circular arc of substantially constant radius, the body containing the target is a cranium and the radius is substantially the distance from the monopole antenna elements to the center of the aperture.

4. The apparatus of claim 2 wherein the monopole antenna elements are arranged in a circular arc of substantially constant radius, the body containing the target is a cranium and the radius is substantially the distance from the monopole antenna elements to a target position within the aperture.

5. The apparatus of claim 1 further comprising an RF reflecting screen mounted perpendicular to the groundplane surface behind the monopole antenna elements to reflect RF energy from the monopole antenna elements toward the target.

6. The apparatus of claim 5 wherein the RF reflecting screen is positioned between $\frac{1}{8}$ to $\frac{1}{2}$ wavelength from the monopole antenna elements.

7. The apparatus of claim 6 wherein the RF reflecting screen is positioned about $\frac{1}{4}$ wavelength from the monopole antenna elements.

8. The apparatus of claim 1 further comprising an enclosure surrounding the monopole antenna elements and providing a vessel for enclosing a bolus of fluid between the monopole antenna elements and the body.

9. The apparatus of claim 8 wherein the vessel comprises a bolus of deionized water.

10. The apparatus of claim 1 wherein the monopole antenna elements are arranged in a circular arc of substantially constant radius.

11. The appratus of claim 10 wherein the radius is between 5 and 20 cm.

12. The apparatus of claim 11 wherein the radius is between 10 and 15 cm.

13. The apparatus of claim 10 wherein the monopole antenna elements resonate at between 800 and 1000 MHz.

14. The apparatus of claim 13 wherein the monopole antenna elements resonate at substantially 915 MHz.

15. A hyperthermia applicator for inducing a temperature rise in a target within a body, comprising
   a plurality of electric field radiators, each for transmitting electric field radiation;
   a plurality of controllable transmit weighting networks, each such network coupled to a respective electric field radiator, each weighting network controlling the phase and amplitude of the electric field radiation transmitted by the respective electric field radiator in response to a respective feedback signal;
   a source of electric field radiation coupled to each electric field radiator through a respective weighting network;
   a plurality of electric field probe elements adapted to be disposed noninvasively along the perimeter of the body between the electric field radiators and the target for detecting electric field radiation from the plurality of radiators; and
   a controller coupled to the electric field probe elements for receiving the detected electric field radiation outside the body and generating the respective feedback signals, and for adjusting the feedback signals in response to the detected electric field radiation outside the body so that the electric field radiation is controlled at the target inside the body;
   wherein the controller comprises means for adjusting the feedback signals to minimize the difference in the electric field detected by adjacent electric field probe elements and thereby provide uniform electric field radiation into the body.

16. The apparatus of claim 15, wherein the adjusting means performs a gradient search algorithm to adjust the feedback signals.

17. The apparatus of claim 15, wherein the adjusting means performs a matrix inversion algorithm to adjust the feedback signals.

18. A hyperthermia applicator for inducing a temperature rise in a target within a body, comprising
   a plurality of electric field radiators, each for transmitting electric field radiation, comprising a phased array of antenna elements;
   a plurality of controllable transmit weighting networks, each such network coupled to a respective electric field radiator, each weighting network controlling the phase and amplitude of the electric field radiation transmitted by the respective electric field radiator in response to a respective feedback signal;
   a source of electric field radiation coupled to each electric field radiator through a respective weighting network;
   a plurality of electric field probe elements adapted to be disposed non-invasively in an electric field probe array between elements of the phased array and the target for detecting electric field radiation from the plurality of electric field radiators; and
   a controller coupled to the electric field probe elements for receiving the detected electric field radiation and generating the respective feedback signals, and for adjusting the feedback signals in response to the detected electric field radiation to provide a particular electric field pattern across the electric field probe array and thereby focus radiation into the target,
   wherein the elements of the phased array are adapted to be disposed symmetrically with respect to a bisector line going from the target to the phased array which bisects the elements of the phased array into symmetric right and left halves, the electric field probe elements of the electric field probe array are adapted to be disposed symmetrically with respect to the bisector line which bisects the electric field probe array into symmetric right and left halves, and the controller adjusts the feedback signals to minimize the difference in the electric field detected by electric field probe elements in the left and right halves of the electric field probe array to balance the electric field pattern with respect to the bisector line, and to minimize the difference in the electric field detected by the electric field probe elements in a direction along the bisector line.

19. The apparatus of claim 18, wherein the controller performs a gradient search algorithm to adjust the feedback signals.

20. The apparatus of claim 18, wherein the controller performs a matrix inversion algorithm to adjust the feedback signals.

21. The apparatus of claim 18 wherein the antenna elements of the phased array are arranged in a circular arc of substantially constant radius.

22. The apparatus of claim 21 wherein the phased array comprises an array of monopole antenna elements resonating at between 800 and 1000 MHz, and the radius of the circular arc is between 5 and 20 cm.

23. A hyperthermia applicator for inducing a temperature rise in a target located within a living body, comprising
   a phased array of monopole antenna elements,
   a source of electric field radiation coupled to each monopole antenna element,
   and
   an RF reflecting groundplane surface for mounting the monopole antenna elements, the monopole antenna elements being perpendicularly mounted to one side of the RF reflecting groundplane surface, and
   the groundplane surface having an aperture adapted to accommodate a portion of the body to allow positioning the target proximate to the monopole antenna elements.

24. The applicator of claim 23 wherein the target is located within the cranium of the living body and the applicator further comprises an RF reflecting screen mounted perpendicular to the groundplane surface behind the monopole antenna elements to reflect RF energy from the monopole antenna elements toward the target.

25. The applicator of claim 24 wherein the RF reflecting screen is positioned between ⅛ to ½ wavelength from the monopole antenna elements.

26. The applicator of claim 25 wherein the RF reflecting screen is positioned about ¼ wavelength from the monopole antenna elements.

27. The applicator of claim 23 wherein the target is located within the cranium of the living body and further comprising an enclosure surrounding the monopole antenna elements and providing a vessel for enclosing a bolus of fluid between the monopole antenna elements and the cranium.

28. The applicator of claim 27 wherein the vessel comprises a bolus of deionized water.

29. The applicator of claim 23 wherein the monopole antenna elements are arranged in a circular arc of substantially constant radius.

30. The applicator of claim 29 wherein the radius is between 5 and 20 cm.

31. The applicator of claim 30 wherein the radius is between 10 and 15 cm.

32. The applicator of claim 29 wherein the monopole antenna elements resonate at between 800 and 1000 MHz.

33. The applicator of claim 32 wherein the monopole antenna elements resonate at substantially 915 MHz.

34. The applicator of claim 23 wherein the monopole antenna elements are arranged in a circular arc of substantially constant radius and the radius is substantially the distance from the monopole antenna array to the center of the aperture.

35. The applicator of claim 23 wherein the monopole antenna elements are arranged in a circular arc of substantially constant radius and the radius is substantially the distance from the monopole antenna array to a target position within the aperture.

36. The applicator of claim 33 wherein the monopole antenna elements are ¼ wavelength vertical antennas.

37. The applicator of claim 33 wherein the monopole antenna elements are helical antennas.

38. A method for inducing a temperature rise in a target within a body, comprising the steps of:
providing a plurality of monopole phased array electric field radiators mounted on a side of an RF reflecting groundplane surface;
positioning the body containing the target through an aperture in the ground plane surface so that the target is on the same side of the groundplane surface as the electric field radiators;
coupling a source of electric field radiation to each electric field radiator through a controllable transmit weighting network coupled to a respective electric field radiator;
controlling the phase and amplitude of the electric field radiation transmitted by the respective electric field radiator with each weighting network in response to a respective feedback signal;
detecting electric field radiation from the phased array of radiators with a plurality of electric field probe elements disposed noninvasively between the phased array of radiators and the target; and
receiving the detected electric field radiation and generating the respective feedback signals for adjusting the controllable transmit weighting network in response to the detected electric field radiation so that the electric field radiation is controlled at the target inside the body.

39. The method of claim 38 further comprising the step of positioning an RF reflecting screen behind the electric field radiators to direct RF energy from the electric field radiators toward the target.

40. The method of claim 38 further comprising the step of surrounding the electric field radiators with an enclosed vessel for containing a bolus of fluid between the electric field radiators and the body.

41. The method of claim 38 further comprising the step of arranging the electric field radiators in a circular arc of substantially constant radius.

42. A method for inducing a temperature rise in a target within a body, comprising the steps of:
positioning a phased array of electric field radiators nearby a target;
coupling a source of electric field radiation to each electric field radiator through a controllable transmit weighting network coupled to a respective electric field radiator;
controlling the phase and amplitude of the electric field radiation transmitted by the respective electric field radiator with each weighting network in response to a respective feedback signal;
detecting electric field radiation from the phased array of radiators with a plurality of electric field probe elements disposed non-invasively between the phased array of radiators and the target; and
receiving the detected electric field radiation and generating the respective feedback signals for adjusting the controllable transmit weighting network in response to the detected electric field radiation to minimize the difference in the electric field detected by adjacent electric field probe elements and thereby provide uniform electric field radiation into the body.

43. The method of claim 42, further comprising the step of positioning the electric field probe elements non-invasively along the perimeter of the body between the electric field radiators and the target.

44. The method of claim 42, wherein the receiving step further comprises performing a gradient search algorithm to adjust the feedback signals.

45. The method of claim 42, wherein the receiving step further comprises performing a matrix inversion algorithm to adjust the feedback signals.

46. A method for inducing a temperature rise in a target within a body, comprising the steps of:
arranging a plurality of electric field radiators of a hyperthermia phased array symmetrically with respect to a bisector line going from the target to the phased array which bisects the radiators of the phased array into symmetric right and left halves;
coupling a source of electric field radiation to each electric field radiator through a controllable transmit weighting network coupled to a respective electric field radiator;
controlling the phase and amplitude of the electric field radiation transmitted by the respective electric field radiator with each weighting network in response to a respective feedback signal;
detecting electric field radiation from the phased array of electric field radiators with an electric field probe array comprising a plurality of electric field probe elements disposed noninvasively between the phased array of electric field radiators and the target;

arranging electric field probe elements of the electric field probe array symmetrically with respect to the bisector line which bisects the electric field probe array into symmetric right and left halves; and receiving the detected electric field radiation and generating the respective feedback signals for adjusting the controllable transmit weighting network in response to the detected electric field radiation so that the electric field radiation is controlled at the target inside the body by adjusting the feedback signals to minimize the difference in the electric field detected by electric field probe elements in the left and right halves of the electric field probe array to balance the electric field pattern with respect to the bisector line, and to minimize the difference in the electric field detected by the electric field probe elements in a direction along the bisector line.

47. The method of claim 46, wherein adjusting the feedback signals comprises performing a gradient search algorithm.

48. The method of claim 46, wherein adjusting the feedback signals comprises performing a matrix inversion algorithm.

49. A hyperthermia applicator for inducing a temperature rise in a target within a body, comprising
- a first plurality of electric field radiators, each for transmitting electric field radiation, comprising a phased-array of monopole antenna elements;
- a first RF reflecting groundplane surface disposed adjacent and substantially perpendicular to the monopole antenna elements, the monopole antenna elements being disposed on a side of the RF reflecting groundplane surface;
- a plurality of controllable transmit weighting networks, each such network coupled to a respective monopole antenna element, each weighting network controlling the phase and amplitude of the electric field radiation transmitted by the respective monopole antenna element in response to a respective feedback signal;
- a source of electric field radiation coupled to each monopole antenna element through a respective weighting network;
- at least one electric field probe for detecting electric field radiation from the plurality of monopole antenna elements; and
- a controller coupled to the electric field probe for receiving the detected electric field radiation and generating the respective feedback signals, and for adjusting the feedback signals in response to the detected electric field radiation so that the electric field radiation is controlled at the target inside the body.

50. The hyperthermia applicator of claim 49, further comprising a second RF reflecting groundplane surface disposed opposite to the first RF reflecting groundplane surface such that the monopole antenna elements are disposed between the first and second RF reflecting groundplane surfaces.

51. The hyperthermia applicator of claim 50, further comprising
an RF reflecting screen mounted substantially perpendicular to the first and second groundplane surfaces behind the monopole antenna elements to form a waveguide for directing RF energy from the monopole antenna elements toward the target.

52. The hyperthermia applicator of claim 51, wherein the first and second groundplane surfaces are substantially parallel to each other.

53. The hyperthermia applicator of claim 51, wherein the first and second groundplane surfaces are disposed at an angle to one another forming a waveguide horn.

54. The hyperthermia applicator of claim 50, further comprising
a second plurality of electric field radiators comprising a second phased array of monopole antenna elements disposed adjacent and substantially perpendicular to the second RF reflecting groundplane surface on the side of the second RF reflecting groundplane surface opposite the first phased array of monopole antenna elements; and
a third RF reflecting groundplane surface disposed opposite to the second RF reflecting groundplane surface such that the second phased array of monopole antenna elements are disposed between the second and third RF reflecting groundplane surfaces.

55. The hyperthermia applicator of claim 49, wherein the electric field probe comprises an invasive probe for placement inside the target within the body.

56. The hyperthermia applicator of claim 49, wherein the electric field probe comprises a non-invasive probe for placement outside the body.

* * * * *